(12) United States Patent
Killary et al.

(10) Patent No.: US 7,169,384 B2
(45) Date of Patent: Jan. 30, 2007

(54) TUMOR SUPPRESSOR CAR-1

(75) Inventors: Ann Killary, West University Place, TX (US); Steve Lott, Palo Alto, CA (US); Dawn Chandler, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/153,238

(22) Filed: Jun. 15, 2005

(65) Prior Publication Data
US 2006/0019281 A1    Jan. 26, 2006

Related U.S. Application Data

(62) Division of application No. 09/927,091, filed on Aug. 9, 2001, now Pat. No. 6,943,245.

(60) Provisional application No. 60/227,560, filed on Aug. 23, 2000, provisional application No. 60/225,033, filed on Aug. 10, 2000.

(51) Int. Cl.
A61K 48/00    (2006.01)
A01N 63/00    (2006.01)

(52) U.S. Cl. .................................. 424/93.2

(58) Field of Classification Search ............... 424/93.2
See application file for complete search history.

(56) References Cited

U.S. PATENT DOCUMENTS

| | | | |
|---|---|---|---|
| 5,872,237 A | 2/1999 | Feder et al. | 536/23.5 |
| 5,932,210 A * | 8/1999 | Gregory et al. | 424/93.2 |
| 6,312,926 B1 | 11/2001 | Shatkin et al. | 435/91.1 |
| 6,551,828 B1 * | 4/2003 | Clark | 435/462 |
| 2002/0048763 A1 | 4/2002 | Penn et al. | 701/19 |
| 2002/0198371 A1 | 12/2002 | Wang et al. | 536/23.1 |

FOREIGN PATENT DOCUMENTS

| | | |
|---|---|---|
| EP | 1 074 617 | 2/2001 |
| WO | WO 98/42739 | 10/1998 |
| WO | WO 01 57182 | 9/2001 |

OTHER PUBLICATIONS

Anderson et al., Nature, vol. 392, pp. 25-30, 1998.*
Verma, Nature, vol. 389, pp. 239-242, 1997.*
Vile et al., Gene Therapy, vol. 7, pp. 2-8, 2000.*
McNeish et al., Gene Therapy 2004, vol. 7, 1-7.*
Attwood, Science, 290:471-473, 2000.
Avela et al., "Gene encoding a new RING-B-box-Coiled-coil protein is mutated in mulibrey nanism," Nature Genetics, 25:298-301, 2000.
Baker et al., Science, 294:93-96, 2001.
Bieche et al., "Deletion mapping in breast tumor cell lines point to two distinct tumor-suppressor genes in the 1p32-ter region, one of deleted regions (1p36.2) being located within the consensus region of LOH in neuroblastoma," Oncology Reports, 5:167-172, 1998.
Bieche et al., "Two distinct regions involved in 1p deletion in human primary breast cancer," Cancer Research, 53:1990-1994, 1993.
Borden, "RING domains: master builders of molecular scaffolds?" J. Mol. Biol., 295:1103-1112, 2000.
Borg et al., Chromosome 1 alterations in breast cancer: allelic loss on 1p and 1q is related to lymphogenic metastases and poor prognosis, Genes, Chromosomes, and Cancer, 5:311-320, 1992.
Couch et al., "Mutations and polymorphisms in the familial early-onset breast cancer (BRCA1) gene: Breast Cancer Information Care," Human Mutation, 8:8-18, 1996.
Cox et al., "New mutations in MID 1 provide support for loss of function as the cause of X-linked Opitz syndrome," Human Molecular Genetics, 9(17):2553-2562, 2000.
EMBL Database Accession No. AK001621, Feb. 22, 2000.
EMBL Database Accession No. BE258134, Jul. 14, 2000.
GenBank Accession No. AC022262.
GenBank Accession No. R71654.
Gerhold et al., BioEssays, 18:973-981, 1996.
Han et al., "Infrequent somatic mutations of the p73 gene in various human cancers," Euro. J. Surgical Oncology, 25:194-198, 1999.
Ichimiya et al., "p73 at chromosome 1p36.3 is lost in advanced stage neuroblastoma but its mutation is infrequent," Oncogene, 18:1061-1066, 1999.
Isomura et al., "RFP is a DNA binding protein associated with the nuclear matrix," Nucleic Acids Res., 20:5305-5310, 1992.
Kovacs et al., "Consistent chromosome 3p deletion and loss of heterozygosity in renal cell carcinoma," Proc. Nat'l Acad. Sci. USA, 85:1571-1575, 1988.
Le Douarin et al., "The N-terminal part of TIF1, a putative mediator of the ligand-dependent activation function (AF-2) of nuclear receptors, is fused to B-raf in the oncogenic protein T18," EMBO J., 14:2020-2033, 1995.
Lee et al., "The retinoblastoma susceptibility gene encodes a nuclear phosphoprotein associated with DNA binding activity," Nature, 329:642-645, 1987.
Lo Cunsolo et al., "Neuroblastoma on two siblings supports the role of 1p36 deletion in tumor development," Cancer, Genetics, & Cytogenetics, 109:126-130, 1999.
Loft et al., "Physical and functional mapping of a tumor suppressor locus for renal cell carcinoma within chromosome 3p12," Cancer Research, 58: 3533-3537, 1998.
Lovell et al., The genetic locus NRC-1 within chromosome 3p12 mediates tumor suppression in renal cell carcinoma independently of histological type, tumor microenvironment and VHL mutation, Cancer Research, 59: 2182-2189, 1999.

(Continued)

Primary Examiner—Brian Whiteman
(74) Attorney, Agent, or Firm—Fulbright & Jaworski

(57) ABSTRACT

The present invention relates to a new tumor suppressor, designated CAR-1, the gene for which is located on the short arm of human chromosome 1. This gene is directly implicated in colon, kidney and breast cancers, and the CAR-1 ubiquitous expression of the corresponding transcript suggests that it may be involved in yet others. Thus, one aspect of the invention is the diagnosis of CAR-1-related malignancies. The full length cDNA for CAR-1, as well as oligonucleotides derived therefrom, are disclosed. Screening methods for modulators of CAR-1 function and expression, as well as methods for cancer therapy, are described.

18 Claims, 6 Drawing Sheets

OTHER PUBLICATIONS

Matsuzaki et al., "Detailed deletion mapping on chromosome 1p32-p36 in human colorectal cancer: Identification of three distinct regions of common allelic loss," *Int. J. Oncology*, 13:1229-1233, 1998.

McCluskey et al., "Anhydride modified cantharidin analogues: synthesis, inhibition of protein phosphatases 1 and 2A and anticancer activity," *Bioorganic & Medicinal Chemistry Letters*, 10:1687-1690, 2000.

Miki et al., "A strong candidate for the breast and ovarian-cancer susceptibility gene BRCA1," *Science*, 266:66-71, 1994.

Millikan et al., "Linkage analysis and loss of heterozygosity for chromosome Arm 1p in familial breast cancer," *Genes, Chromosomes, and Cancer*, 25:354-361, 1999.

Ngo et al., "The protein folding problem and tertiary structure prediction," Merz et al., ed., Birkhauswer, Boston, MA, pp. 433 and 492-495, 1994.

Ogunbiyi et al., "Prognostic value of chromosome 1p allelic loss in colon cancer," *Gastroenterology*, 113:761-766, 1997.

Pandolfi, PML, PLZF, and NPM genes in the molecular pathogenesis of acute promyelocytic leukemia, *Haematologica*, 81:472-482, 1996.

Ragnarsson et al., "Loss of heterozygosity at chromosome ip in different solid human tumours: association with survival," *British J. of Cancer*, 79:1468-1474, 1999.

Rasio et al., "Characterization of the human homologue of RAD54: a gene located on chromosome 1p32 at a region of high loss of heterozygousity in breast tumors," *Cancer Research*, 57:2378-2383, 1997.

Russell et al., *J of Molecular Biology*, 244:332-350, 1994.

Sambrook et al., Molecular Cloning, a Laboratory Manual, Second Edition, Cold Spring Harbor Laboratory, Cold Spring Harbor, NY, p. 11.47, 1989.

Sanchez et al., "A tumor suppressor locus within 3p14-p12 mediates rapid cell death of renal cell carcinom *in vivo.,*" *Proc. Nat'l Acad. Sci.*, 91:3383-3387, 1994.

Saurin et al., "Does this have a familiar RING?" *TIBS*, 21:208-214, 1996.

Shimono et al., "RET finger protein is a transcriptional repressor and interacts with enhancer of polycomb that has dual transcriptional functions," *J. Biol. Chem.*, 275(50):39411-39419, 2000.

Somme et al., "Clonal karyotypic abnormalities in colorectal adenomas: clues to the early genetic events in the adenoma-carcinoma sequence," *Genes, Chromosomes and Cancer*, 10:190-196, 1994.

Steck et al., "Identification of a candidate tumour suprressor gene, MMAC1, at chromosome 10q23.3 that is mutated in multiple advanced cancers," *Nature Genetics*, 15:356-362, 1997.

Szabo and King, "Inherited breast and ovarian cancer," *Human Molecular Genetics*, 4:1811-1817, 1995.

Tanaka et al., "Suppresson of tumorigenicity in human colon carcinoma cells by introduction of normal chromosome 1p36 region," *Oncogene*, 8:2253-2258, 1993.

Tsukamato et al., "Allelic loss on chromosome 1p is associated with progression and lymph node metastasis of primary breast carcinoma," *Cancer*, 82:317-322, 1998.

Vogelstein, "Cancer. A deadly inheritance," *Nature*. 348:681-682, 1990.

Wallace et al., *Methods Enzymol*, 152:432-443, 1987.

Weinberg, "Positive and negative controls on cell growth," *Biochemistry*, 28:8263-8269, 1989.

Wells et al., *J of Leukocyte Biology*, 61:545-550, 1997.

Wu et al., "Identification of A RING protein that can interact in vivo with the BRCA1 gene product," *Nature Genetics*, 14:430-440, 1996.

* cited by examiner

TUMOR SUPPRESSOR CAR-1

This application is a divisional of U.S. patent application Ser. No. 09/927,091 filed on Aug. 9, 2001 now U.S. Pat. No. 6,943,245, which claims priority to U.S. Provisional Application No. 60/225,033 filed on Aug. 10, 2000, and U.S. Provisional Application No. 60/227,560, filed on Aug. 23, 2000, the entire contents of each which are incorporated herein by reference.

BACKGROUND OF THE INVENTION

I. Field of the Invention

The present invention relates to the fields of oncology, genetics and molecular biology. More particular the invention relates to the identification, on human chromosome 1, of a tumor suppressor gene. Defects in this gene are associated with the development of cancer.

II. Related Art

Oncogenesis was described as a multistep biological process, which is presently known to occur by the accumulation of genetic damage. On a molecular level, the multistep process of tumorigenesis involves the disruption of both positive and negative regulatory effectors (Weinberg, 1989). The molecular basis for human colon carcinomas has been postulated, by Vogelstein and coworkers (1990), to involve a number of oncogenes, tumor suppressor genes and repair genes. Similarly, defects leading to the development of retinoblastoma have been linked to another tumor suppressor gene (Lee et al., 1987). Still other oncogenes and tumor suppressors have been identified in a variety of other malignancies. Unfortunately, there remains an inadequate number of treatable cancers, and the effects of cancer are catastrophic—over half a million deaths per year in the United States alone.

Cytogenetic aberrations, as well as high frequency loss of heterozygosity (LOH), have been observed within the short arm of human chromosome 1 (Bomme et al., 1994; Bieche et al., 1994; Kovacs et al., 1988; Bieche et al., 1998). In a cytogenetic analysis of colorectal adenomas, the most common chromosome involved in structural aberrations was chromosome 1. Breakpoints clustered within chromosome 1p32–p36 (Bomme et al., 1994). These data suggest that chromosome 1p loss is an early event in colorectal tumorigenesis. At least three separate regions of LOH have been consistently documented with chromosome 1p (1p22–1p31, 1p34–1p35 and 1p36). In a variety of histologically diverse human tumors, including breast, colon and neuroblastoma (Bomme et al., 1994; Bieche et al., 1994; Kovacs et al., 1988; Bieche et al., 1998; Lo Cunsolo et al., 1999). LOH in familial breast cancer indicated common regions of loss that included 1p36 (32%) and 1p32 (51%) (Millikan et al., 1999).

A recent report investigated LOH in a variety of solid tumors and found high frequency LOH in stomach, colon and rectum, breast, endometrium, ovary, testis, kidney, thyroid and sarcomas (Ragnarsson et al., 1999). In addition, several studies have shown that deletions in the 1p36 and 1p32 region correlated with poor survival in colon and breast cancers (Borg et al, 1992; Ogunbiyi et al, 1997; Tsukamato et al, 1998). Functional studies using microcell fusion have also mapped a tumor suppressor locus in colon cancer to within chromosome 1p36 (Tanaka et al., 1993). Candidate tumor suppressor genes p73 and Rad54 have been mapped to 1p36 and 1p32, respectively. However, expression studies and mutational analyses have failed to suggest their importance in colon and breast cancers (Han et al., 1999; Ichimiya et al, 1999; Rasio et al, 1997). Thus these data suggest that an important tumor suppressor gene or genes resides within chromosome 1p32–1p36 and is involved at high frequency in a number of histologically diverse human cancers.

Despite all of this information, the identity of the gene or genes involved with chromosome 1 LOH remains elusive. Without identification of a specific gene and deduction of the protein for which it codes, it is impossible to begin developing an effective therapy targeting this product. Thus, it is an important goal to isolate the tumor suppressor(s) located in this region and determine its structure and function.

SUMMARY OF THE INVENTION

Thus, in a first aspect of the invention, there is provided an isolated polynucleotide encoding a polypeptide having an amino acid sequence of SEQ ID NO:1 or SEQ ID NO:2. The polynucleotide may have a nucleic acid sequence of SEQ ID NO:3 or a complement thereof. The polynucleotide may further comprise a promoter operable in eukaryotic cells, for example, a promoter is a heterologous to the coding sequence. Such a promoter could be hsp68, SV40, CMV, MKC, $GAL4_{UAS}$, HSV or β-actin. Alternatively, the promoter can be a tissue specific promoter or an inducible promoter.

In another aspect of the invention, there is provided a nucleic acid of 15 to about 5000 base pairs comprising from about 15 contiguous base pairs of SEQ ID NO:3, or the complement thereof. The nucleic acid may contain 20, 25, 30, 40, 50, 150, 250, 500, 1000, 1500, 2500 or 3500 contiguous base pairs of SEQ ID NO:3, or the complement thereof Also provided is a peptide comprising about 10, 15, 20, 25, 30, 35, 40, 45, or 50 contiguous amino acids of SEQ ID NO: 1 or SEQ ID NO:2, and an expression cassette comprising a polynucleotide encoding a polypeptide having the sequence of SEQ ID NO:1 or SEQ ID NO:2, wherein the polynucleotide is under the control of a promoter operable in eukaryotic cells The expression cassette may be contained in a viral vector, such as a retroviral vector, an adenoviral vector, and adeno-associated viral vector, a vaccinia viral vector, or a herpesviral vector. The expression cassette may further comprise a polyadenylation signal and/or a second polynucleotide encoding a second polypeptide, optionally under the control of a second promoter.

In yet another embodiment, there is provided a method for suppressing growth of a cancer cell comprising contacting the cells with an expression cassette comprising a polynucleotide encoding a polypeptide having the sequence of SEQ ID NO: 1 or SEQ ID NO:2, wherein the polynucleotide is under the control of a promoter operable in eukaryotic cells.

In still yet another embodiment, there is provided a cell comprising an expression cassette comprising a polynucleotide encoding a polypeptide having the sequence of SEQ ID NO: 1 or SEQ ID NO:2, wherein the polynucleotide is under the control of a promoter operable in eukaryotic cells.

In still yet a further embodiment, there is provided a monoclonal antibody that binds immunologically to a polypeptide having the sequence of SEQ ID NO: 1 or SEQ ID NO:2, or an immunologic fragment thereof. The antibody may further comprise a detectable label, for example, a fluorescent label, a chemiluminescent label, a radiolabel or an enzyme. Also provided is the corresponding hybridoma cell, and equivalent polyclonal antisera.

In an additional aspect, there is provided a method of diagnosing a cancer comprising the steps of (i) obtaining a tissue sample from a subject; and (ii) assessing the expression of a CAR-1 tumor suppressor in cells of the sample. The cancer may be selected from the group consisting of brain, lung, liver, spleen, kidney, lymph node, small intestine, pancreas, blood cells, colon, stomach, breast, endometrium, prostate, testicle, ovary, skin, head and neck, esophagus, bone marrow and blood cancer, and specifically is colon cancer, kidney cancer or breast cancer. The cancer may be a carcinoma or a neuroblastoma. The sample may be a tissue or fluid sample. Assessing may comprise assaying for a CAR-1-encoding nucleic acid from the sample, and optionally amplifying the nucleic acid. Alternatively, assessing comprises contacting the sample with an antibody that binds immunologically to a CAR-1 polypeptide, for example, in an ELISA.

The method may involves evaluating the level of CAR-1 expression, for example, comparing the expression of CAR-1 with the expression of CAR-1 in non-cancer samples. The method may involve assessing involves evaluating the structure of the CAR-1 gene or transcript. The evaluating may comprise an assay selected from the group consisting of sequencing, wild-type oligonucleotide hybridization, mutant oligonucleotide hybridization, SSCP, PCR and RNase protection. In particular, the evaluating is wild-type or mutant oligonucleotide hybridization and the oligonucleotide is configured in an array on a chip or wafer.

In still yet a further embodiment, there is provided a method for altering the phenotype of a tumor cell comprising the step of administering to a cell a tumor suppressor designated CAR-1 under conditions permitting the uptake of the tumor suppressor by the tumor cell. The tumor cell may be derived from a tissue selected from the group consisting of brain, lung, liver, spleen, kidney, lymph node, small intestine, blood cells, pancreas, colon, stomach, breast, endometrium, prostate, testicle, ovary, skin, head and neck, esophagus, bone marrow and blood tissue. The phenotype may be selected from the group consisting of apoptosis, angiogenesis, proliferation, migration, contact inhibition, soft agar growth and cell cycling. The tumor suppressor may be encapsulated in a liposome.

In still another aspect of the invention, there is provided a method for altering the phenotype of a tumor cell comprising the step of contacting the cell with a nucleic acid (i) encoding a tumor suppressor designated CAR-1 and (ii) a promoter active in the tumor cell, wherein the promoter is operably linked to the region encoding the tumor suppressor, under conditions permitting the uptake of the nucleic acid by the tumor cell. The nucleic acid may be encapsulated in a liposome, or in a viral particle as part of a retrovirus, adenovirus, adeno-associated virus, vaccinia virus and herpesvirus.

In another embodiment, there is provided a method for treating subject with cancer comprising the step of administering to the subject a tumor suppressor designated CAR-1. The tumor cell may be derived from a tissue selected from the group consisting of brain, lung, liver, spleen, kidney, lymph node, small intestine, blood cells, pancreas, colon, stomach, breast, endometrium, prostate, testicle, ovary, skin, head and neck, esophagus, bone marrow and blood tissue. The subject may be a human. The method may comprising the step of administering to the subject a nucleic acid (i) encoding a tumor suppressor designated CAR-1 and (ii) a promoter active in eukaryotic cells, wherein the promoter is operably linked to the region encoding the tumor suppressor.

Also provided is a non-human transgenic eukaryote lacking a functional CAR-1 gene. The eukaryote may be a mammal. Another embodiment is a non-human transgenic eukaryote that over expresses CAR-1 as compared to a similar non-transgenic eukaryote.

In yet another aspect of the invention, there is provided a method of screening a candidate substance for anti-tumor activity comprising the steps of (i) providing a cell lacking functional CAR-1 polypeptide; (ii) contacting the cell with the candidate substance; and (iii) determining the effect of the candidate substance on the cell. The cell may be a tumor cell, for example, one that has a mutation in the coding region of CAR-1. The tumor cell may have aberrant methylation patterns in the coding region of CAR-1, or be a deletion mutant, an insertion mutant, a frameshift mutant, a nonsense mutant, a missense mutant or splice mutant. The determining may comprise comparing one or more characteristics of the cell in the presence of the candidate substance with characteristics of a cell in the absence of the candidate substance. The characteristic may be CAR-1 expression, phosphatase activity, proliferation, metastasis, contact inhibition, soft agar growth, cell cycle regulation, tumor formation, tumor progression and tissue invasion. The candidate substance is a chemotherapeutic, genetic or radiotherapeutic agent. The candidate substance also may be selected from a small molecule library. The cell may be contacted in vitro or in vivo.

In a further embodiment, there is provided an anti-tumor composition made according to the method comprising the steps of (i) providing a cell lacking functional CAR-1 polypeptide; (ii) contacting the cell with the candidate substance; (iii) determining the effect of the candidate substance on the cell; (iv) identifying a candidate inhibitor substance; and (v) making the composition.

In still yet another embodiment, there is provided an isolated and purified nucleic acid that hybridizes, under high stringency conditions, to a DNA segment comprising about 15 to 3826 bases of SEQ ID NO:3, for example, where the nucleic hybridizes to a DNA segment comprising about 17, 20 or 25 to 3826 bases of SEQ ID NO:3.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

SEQUENCE SUMMARY

Figure 1:
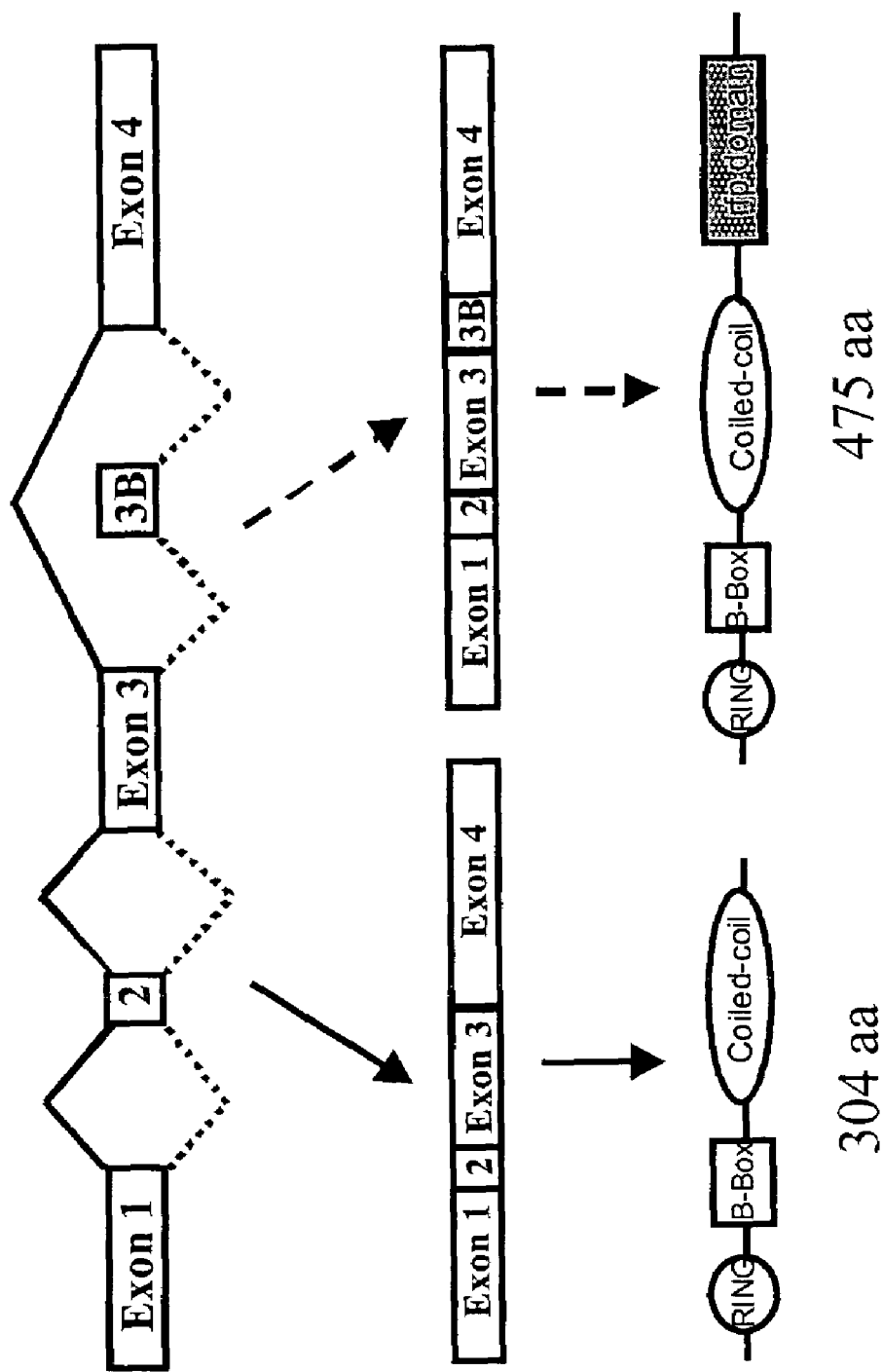
FIG. 1. Schematic of predicted CAR-1 protein structure. The RBCC domains (tripartite motif) are depicted by open ovals/boxes. The rfp domain is depicted by a shaded box. Exon 3B, when spliced out of the CAR-1 transcript, results in a stop codon prior to the rfp domain, which then results in a 304 aa protein in which the rfp domain is out of frame. However, if the exon is included, then a resulting 475 aa protein is made, with the rfp domain in frame.

SEQ ID NO:1=CAR-1 amino acid with alternatively spliced exon; SEQ ID NO:2=CAR-1 amino acid without alternatively spliced exon; SEQ ID NO:3=CAR-1 cDNA; SEQ ID NO:4=BAC clone 392H05 (Accession No. AF161326); SEQ ID NO:5=BAC clone 392H05 (Accession No. AF161326) continued from 3' end of SEQ ID NO:4; SEQ ID NO:6=BAC clone RP11-150F21 (Accession No. AC022262); SEQ ID NO:7=BAC clone RP11-150F21 (Accession No. AC022262) continued from 3' end of SEQ ID NO:6; SEQ ID NO:8=BAC clone RP11-131M11 (Accession No. AC026053); SEQ ID NO:9=CAR-1 5' portion (369 bp) of cDNA fragment SEQ ID NO:4.

DETAILED DESCRIPTION OF THE PREFERRED EMBODIMENTS

I. The Present Invention

The present invention stems from the inventors' identification of a tumor suppressor gene located in the 1p31 to 1p36 region of human chromosome 1. This region is implicated in tumorigenesis by the loss of heterozygosity and by deletions/rearrangement/under expression in cancer cell lines. This discovery facilitates a wide range of endeavors including diagnosis, therapy, and drug screening. Nucleic acids, proteins, antibodies and transgenic cells and animals also are disclosed.

II. The CAR-1 Tumor Suppressor

According to the present invention, there has been identified a tumor suppressor, encoded by a gene in the 1p32 locus, and designated here as CAR-1. This molecule is capable of suppressing tumor phenotypes in various cancers. The term tumor suppressor is well-known to those of skill in the art. Examples of other tumors suppressors are p53, Rb and p16, to name a few. While these molecules are structurally distinct, they form a group of functionally-related molecules, of which CAR-1 is a member. The uses in which these other tumor suppressors now are being exploited are equally applicable here.

In addition to the entire CAR-1 molecule, the present invention also relates to fragments of the polypeptide that may or may not retain the tumor suppressing (or other) activity. Fragments, including the N-terminus of the molecule may be generated by genetic engineering of translation stop sites within the coding region (discussed below). Alternatively, treatment of the CAR-1 molecule with proteolytic enzymes, known as proteases, can produces a variety of N-terminal, C-terminal and internal fragments. Examples of fragments may include contiguous residues of the CAR-1 sequence given in SEQ ID NO:1 and SEQ ID NO:2, of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Features of the Polypeptide

The gene for CAR-1 encodes a either a 475 amino acid polypeptide (SEQ ID NO:1) or a 304 amino acid polypeptide (SEQ ID NO:2), depending on splicing. When the present application refers to the function of CAR-1 or "wild-type" activity, it is meant that the molecule in question has the ability to inhibit the transformation of a cell from a normally regulated state of proliferation to a malignant state, i.e., one associated with any sort of abnormal growth regulation, or to inhibit the transformation of a cell from an abnormal state to a highly malignant state, e.g., to prevent metastasis or invasive tumor growth. Other phenotypes that may be considered to be regulated by the normal CAR-1 gene product are angiogenesis, adhesion, migration, cell-to-cell signaling, cell growth, cell proliferation, density-dependent growth, anchorage-dependent growth and others. Determination of which molecules possess this activity may be achieved using assays familiar to those of skill in the art. For example, transfer of genes encoding CAR-1, or variants thereof, into cells that do not have a functional CAR-1 product, and hence exhibit impaired growth control, will identify, by virtue of growth suppression, those molecules having CAR-1 function.

B. Variants of CAR-1

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3), proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine*−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of CAR-1, but with altered and even improved characteristics.

C. Domain Switching

Domain switching involves the generation of chimeric molecules using different but, in this case, related polypeptides. By comparing the CAR-1 sequences, both with mutants and allelic variants, one can make predictions as to the functionally significant regions of these molecules. It is possible, then, to switch related domains of these molecules in an effort to determine the criticality of these regions to CAR-1 function. These molecules may have additional value in that these "chimeras" can be distinguished from natural molecules, while possibly providing the same function.

Based on the sequence identity, at the amino acid level, of the mouse, dog and human sequences, it may be inferred that even small changes in the primary sequence of the molecule will affect function. Further analysis of mutations and their predicted effect on secondary structure will add to this understanding.

D. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

E. Purification of Proteins

It will be desirable to purify CAR-1 or variants thereof Protein purification techniques are well known to those of skill in the art. These techniques involve, at one level,, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even BPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al, 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fuctose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

F. Synthetic Peptides

The present invention also describes smaller CAR-1-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression, G. Antigen Compositions The present invention also provides for the use of CAR-1 proteins or peptides as antigens for the immunization of animals relating to the production of antibodies. It is envisioned that either CAR-1, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

III. Nucleic Acids

The present invention also provides, in another embodiment, genes encoding CAR-1. A genes for the human CAR-1 molecule have been identified. The present invention is not limited in scope to these genes, however, as one of ordinary skill in the could, using these nucleic acids, readily identify related homologs in various other species (e.g., mouse, rat, rabbit, dog, monkey, gibbon, chimp, ape, baboon, cow, pig, horse, sheep, cat and other species).

In addition, it should be clear that the present invention is not limited to the specific nucleic acids disclosed herein. As discussed below, a "CAR-1 gene" may contain a variety of different bases and yet still produce a corresponding polypeptide that is functionally indistinguishable, and in some cases structurally, from the human and mouse genes disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of CAR-1.

A. Nucleic Acids Encoding CAR-1

Nucleic acids according to the present invention may encode an entire CAR-1 gene, a domain of CAR-1 that expresses a tumor suppressing, or any other fragment of the CAR-1 sequences set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given CAR-1 from a given species may be represented by natural variants that have slightly different nucleic acid sequences but, nonetheless, encode the same protein (see Table 1).

As used in this application, the term "a nucleic acid encoding a CAR-1" refers to a nucleic acid molecule that has been isolated free of total cellular nucleic acid. In preferred embodiments, the invention concerns a nucleic acid sequence essentially as set forth in SEQ ID NO:3, a cDNA. At each point the full cDNA is mentioned, one may also insert SEQ ID NO:9, a 5' portion of the cDNA. The term "as set forth in SEQ ID NO:3" means that the nucleic acid sequence substantially corresponds to a portion of SEQ ID NO:3. The term "functionally equivalent codon" is used herein to refer to codons that encode the same amino acid, such as the six codons for arginine or serine (Table 1), and also refers to codons that encode biologically equivalent amino acids, as discussed in the following pages.

TABLE 1

| Amino Acids   |     |   | Codons                  |
|---------------|-----|---|-------------------------|
| Alanine       | Ala | A | GCA GCC GCG GCU         |
| Cysteine      | Cys | C | UGC UGU                 |
| Aspartic acid | Asp | D | GAC GAU                 |
| Glutamic acid | Glu | E | GAA GAG                 |
| Phenylalanine | Phe | F | UUC UUU                 |
| Glycine       | Gly | G | GGA GGC GGG GGU         |
| Histidine     | His | H | CAC CAU                 |
| Isoleucine    | Ile | I | AUA AUC AUU             |
| Lysine        | Lys | K | AAA AAG                 |
| Leucine       | Leu | L | UUA UUG CUA CUC CUG CUU |
| Methionine    | Met | M | AUG                     |
| Asparagine    | Asn | N | AAC AAU                 |
| Proline       | Pro | P | CCA CCC CCG CCU         |
| Glutamine     | Gln | Q | CAA CAG                 |
| Arginine      | Arg | R | AGA AGG CGA CGC CGG CGU |
| Serine        | Ser | S | AGC AGU UCA UCC UCG UCU |
| Threonine     | Thr | T | ACA ACC ACG ACU         |
| Valine        | Val | V | GUA GUC GUG GUU         |
| Tryptophan    | Trp | W | UGG                     |
| Tyrosine      | Tyr | Y | UAC UAU                 |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:3. Sequences that are essentially the same as those set forth in SEQ ID NO:3 also may be functionally defined as sequences that are capable of hybridizing to a nucleic acid segment containing the complement of SEQ ID NO:3 under standard conditions.

The DNA segments of the present invention include those encoding biologically functional equivalent CAR-1 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

The present invention also encompasses genomic sequences corresponding to the CAR-1 gene. These are included in three BAC clones, the sequences of which are provided as SEQ ID NOS:4–8. The relevant demarcation of exons and introns are provided in the following table.

TABLE 2

Genomic Sequence as ordered from RP11-150F21 (No. AC022262)

The known portion of Exon 1 begins AGGC at nucleotide 24164
The ATG initiation codon is located at nucleotides 24766-8
Exon 1 ends GCAG at nucleotide 25173
Exon 2 begins AGGG at nucleotide 40642
Exon 2 ends CAAG at nucleotide 40737
Exon 3 begins TCTT at nucleotide 46263
Exon 3 ends AGCG at nucleotide 46519
Exon 3B begins GCTC at nucleotide 47839
Exon 3B ends CCAG at nucleotide 47954
Exon 4 begins TGCC at nucleotide 58377
The stop codon TGA (for the truncated protein, excluding exon 3B) is located at nucleotides 58528-30
The stop codon TAG (for the full-length protein, including exon 3B) is located at nucleotides 58925-7
Exon 4 ends TGTC at nucleotide 60701

Genomic Sequence as ordered from RP11-131M11 (No. AC026053)

Nucleotide 1 is located within in Exon 1
The ATG initiation codon is located at nucleotides 187
Exon 1 ends GCAG at nucleotide 588
Exon 2 begins AGGG at nucleotide 8084
Exon 2 ends CAAG at nucleotide 8179
Exon 3 begins TCTT at nucleotide 13428
Exon 3 ends AGCG at nucleotide 13684
Exon 3B begins GCTC at nucleotide 15057
Exon 3B ends CCAG at nucleotide 15172
Exon 4 begins TGCC at nucleotide 23423
The stop codon TGA (for the truncated protein, excluding exon 3B) is located at nucleotides 23574-6
The stop codon TAG (for the full-length protein, including exon 3B) is located at nucleotides 23970-2
Exon 4 ends TGTC at nucleotide 25746

Genomic Sequence as ordered from BAC 392H05 (No. AF161326)

The known portion of our Exon 1 begins AGGC at nucleotide 34306
The ATG initiation codon is located at nucleotides 34914-6
Exon 1 ends GCAG at nucleotide 35321
Exon 2 begins AGGG at nucleotide 50774
Exon 2 ends CAAG at nucleotide 50869
Exon 3 begins TCTT at nucleotide 58182
Exon 3 ends AGCG at nucleotide 58438
Exon 3B begins GCTC at nucleotide 59758
Exon 3B ends CCAG at nucleotide 59873
Exon 4 begins TGCC at nucleotide 71702
The stop codon TGA (for the truncated protein, excluding exon 3B) is located at nucleotides 71853-5
The stop codon TAG (for the full-length protein, including exon 3B) is located at nucleotide 72250-2
Exon 4 ends TGTC at nucleotide 74026

B. Oligonucleotide Probes and Primers

Naturally, the present invention also encompasses DNA segments that are complementary, or essentially complementary, to the sequence set forth in SEQ ID NO:3 or SEQ ID NOS:4–8. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:3 or SEQ ID NOS:4–8 under relatively stringent conditions such as those described herein. Such sequences may encode the entire CAR-1 protein or functional or non-functional fragments thereof Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. Formamide and SDS also may be used to alter the hybridization conditions.

One method of using probes and primers of the present invention is in the search for genes related to CAR-1 or, more particularly, homologs of CAR-1 from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double-stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

In some cases, mutant tumor suppressors may not be non-functional. Rather, they may have aberrant functions that cannot be overcome by replacement gene therapy, even where the "wild-type" molecule is expressed in amounts in excess of the mutant polypeptide. Antisense treatments are one way of addressing this situation. Antisense technology also may be used to "knock-out" function of CAR-1 in the development of cell lines or transgenic mice for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Another approach for addressing the "dominant negative" mutant tumor suppressor is through the use of ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et at, 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al, 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al, 1991; Sarver et al, 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

Within certain embodiments expression vectors are employed to express the CAR-1 polypeptide product, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

(i) Regulatory Elements

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked,"

"under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Tables 3 lists several elements/promoters that may be employed, in the context of the present invention, to regulate the expression of a gene. This list is not intended to be exhaustive of all the possible elements involved in the promotion of expression but, merely, to be exemplary thereof Table 4 provides examples of inducible elements, which are regions of a nucleic acid sequence that can be activated in response to a specific stimulus.

TABLE 3

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |

TABLE 3-continued

Promoter and/or Enhancer

| Promoter/Enhancer | References |
| --- | --- |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 4

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

(ii) IRES

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

(iii) Multi-Purpose Cloning Sites

Vectors can include a multiple cloning site (MCS), which is a nucleic acid region that contains multiple restriction enzyme sites, any of which can be used in conjunction with standard recombinant technology to digest the vector. See Carbonelli et al., 1999, Levenson et al., 1998, and Cocea, 1997, incorporated herein by reference. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

(iv) Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

(v) Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

(vi) Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

(vii) Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

(viii) Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

(ix) Viral Vectors

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670,488). The various viral vectors described below, present specific advantages and disadvantages, depending on the particular gene-therapeutic application.

Adenoviral Vectors: In particular embodiments, an adenoviral expression vector is contemplated for the delivery of expression constructs. "Adenovirus expression vector" is meant to include those constructs containing adenovirus sequences sufficient to (a) support packaging of the construct and (b) to ultimately express a tissue or cell-specific construct that has been cloned therein.

Adenoviruses comprise linear, double-stranded DNA, with a genome ranging from 30 to 35 kb in size (Reddy et al., 1998; Morrison et al., 1997; Chillon et al., 1999). An adenovirus expression vector according to the present invention comprises a genetically engineered form of the adenovirus. Advantages of adenoviral gene transfer include the ability to infect a wide variety of cell types, including non-dividing cells, a mid-sized genome, ease of manipulation, high infectivity and the ability to be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a ψ sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100–200 bp in length), are cis elements, and function as origins of replication and are necessary for viral DNA replication. The ψ sequence is required for the packaging of the adenoviral genome.

A common approach for generating an adenoviruses for use as a gene transfer vector is the deletion of the E1 gene (E1$^-$), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1$^-$, replication-deficient virus is then proliferated in a "helper" cell line that provides the E1 polypeptides in trans (e.g., the human embryonic kidney cell line 293). Thus, in the present invention it may be convenient to introduce the transforming construct at the position from which the E1-coding sequences have been removed. However, the position of insertion of the construct within the adenovirus sequences is not critical to the invention. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. Nos. 5,670,488; 5,932,210, each specifically incorporated herein by reference).

Although adenovirus based vectors offer several unique advantages over other vector systems, they often are limited by vector immunogenicity, size constraints for insertion of recombinant genes and low levels of replication. The preparation of a recombinant adenovirus vector deleted of all open reading frames, comprising a full length dystrophin gene and the terminal repeats required for replication (Haecker et al., 1997) offers some potentially promising advantages to the above mentioned adenoviral shortcomings. The vector was grown to high titer with a helper virus in 293 cells and was capable of efficiently transducing dystrophin in mdx mice, in myotubes in vitro and muscle fibers in vivo. Helper-dependent viral vectors are discussed below.

A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient. Armentano et al., describe the preparation of a replication-defective adenovirus vector, claimed to eliminate the potential for the inadvertent generation of a replication-competent adenovirus (U.S. Pat. No. 5,824,544, specifically incorporated herein by reference). The replication-defective adenovirus method comprises a deleted E1 region and a relocated protein IX gene, wherein the vector expresses a heterologous, mammalian gene.

Other than the requirement that the adenovirus vector be replication defective, or at least conditionally defective, the nature of the adenovirus vector is not believed to be crucial to the successful practice of the invention. The adenovirus may be of any of the 42 different known serotypes and/or subgroups A–F. Adenovirus type 5 of subgroup C is the preferred starting material in order to obtain the conditional replication-defective adenovirus vector for use in the present invention. This is because adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Adenovirus growth and manipulation is known to those of skill in the art, and exhibits broad host range in vitro and in vivo (U.S. Pat. Nos. 5,670,488; 5,932,210; 5,824,54). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Smith, 1998; Hermens and Verhaagen, 1998), coronary diseases (Feldman et al., 1996), muscular diseases (Petrof, 1998), gastrointestinal diseases (Wu, 1998) and various cancers such as colorectal (Fujiwara and Tanaka, 1998; Dorai et al., 1999), pancreatic, bladder (Irie et al., 1999), head and neck (Blackwell et al., 1999), breast (Stewart et al., 1999), lung (Batra et al., 1999) and ovarian (Vanderkwaak et al., 1999).

Retroviral Vectors: In certain embodiments of the invention, the use of retroviruses for gene delivery are contemplated. Retroviruses are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

The retroviral genome and the proviral DNA have three genes: gag, pol, and env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

A recombinant retrovirus of the present invention may be genetically modified in such a way that some of the structural, infectious genes of the native virus have been removed and replaced instead with a nucleic acid sequence to be delivered to a target cell (U.S. Pat. Nos. 5,858,744; 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present invention are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

The growth and maintenance of retroviruses is known in the art (U.S. Pat. Nos. 5,955,331; 5,888,502, each specifically incorporated herein by reference) Nolan et al. describe the production of stable high titre, helper-free retrovirus comprising a heterologous gene (U.S. Pat. No. 5,830,725, specifically incorporated herein by reference). Methods for constructing packaging cell lines useful for the generation of helper-free recombinant retroviruses with amphoteric or ecotrophic host ranges, as well as methods of using the recombinant retroviruses to introduce a gene of interest into eukaryotic cells in vivo and in vitro are contemplated in the present invention (U.S. Pat. No. 5,955,331).

Currently, the majority of all clinical trials for vector-mediated gene delivery use murine leukemia virus (MLV)-based retroviral vector gene delivery (Robbins et al., 1998; Miller et al., 1993). Disadvantages of retroviral gene delivery includes a requirement for ongoing cell division for stable infection and a coding capacity that prevents the delivery of large genes. However, recent development of vectors such as lentivirus (e.g., HIV), simian immunodeficiency virus (SIV) and equine infectious-anemia virus (EIAV), which can infect certain non-dividing cells, potentially allow the in vivo use of retroviral vectors for gene therapy applications (Amado and Chen, 1999; Kimatcheva et al., 1999; White et al., 1999; Case et al., 1999). For example, HIV-based vectors have been used to infect non-dividing cells such as neurons (Miyatake et al., 1999), islets (Leibowitz et al., 1999) and muscle cells (Johnston et al., 1999). The therapeutic delivery of genes via retroviruses are currently being assessed for the treatment of various disorders such as inflammatory disease (Moldawer et al., 1999), AIDS (Amado et al, 1999; Engel and Kohn, 1999), cancer (Clay et al., 1999), cerebrovascular disease (Weihl et al., 1999) and hemophilia (Kay, 1998).

Herpesviral Vectors: Herpes simplex virus (HSV) type I and type II contain a double-stranded, linear DNA genome of approximately 150 kb, encoding 70–80 genes. Wild type HSV are able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Garrido et al., 1999; Lachmann and Efstathiou, 1999), liver (Miytake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernable phases or kinetic classes. These phases of genes are referred to as the Immediate Early (IE) or alpha genes, Early (E) or beta genes and Late (L) or gamma genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

For use in therapeutic gene delivery, HSV must be rendered replication-defective. Protocols for generating replication-defective HSV helper virus-free cell lines have been described (U.S. Pat. Nos. 5,879,934; 5,851,826, each specifically incorporated herein by reference in its entirety). One IE protein, Infected Cell Polypeptide 4 (ICP4), also known as alpha 4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22 and ICP47 (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevented early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B cell malignancies (Suzuki et al., 1998), ovarian cancer (Wang et al., 1998) and Duchenne muscular dystrophy (Huard et al., 1997).

Adeno-Associated Viral Vectors: Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80–85% of the human population has been exposed to AAV. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. The internal non-repeated portion of the genome includes two large open reading frames, known as the AAV replication (rep) and capsid (cap) genes. The rep and cap genes code for viral proteins that allow the virus to replicate and package the viral genome into a virion. A family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

The use of helper virus, however, presents a number of problems. First, the use of adenovirus in a rAAV production system causes the host cells to produce both rAAV and infectious adenovirus. The contaminating infectious adenovirus can be inactivated by heat treatment (56° C. for 1 hour). Heat treatment, however, results in approximately a 50% drop in the titer of functional rAAV virions. Second, varying amounts of adenovirus proteins are present in these preparations. For example, approximately 50% or greater of the total protein obtained in such rAAV virion preparations is free adenovirus fiber protein. If not completely removed, these adenovirus proteins have the potential of eliciting an immune response from the patient. Third, AAV vector production methods which employ a helper virus require the use and manipulation of large amounts of high titer infectious helper virus, which presents a number of health and safety concerns, particularly in regard to the use of a herpesvirus. Fourth, concomitant production of helper virus particles in rAAV virion producing cells diverts large amounts of host cellular resources away from rAAV virion production, potentially resulting in lower rAAV virion yields.

Lentiviral Vectors: Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif; vpr, vpu and nef are deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art, see Naldini et al., (1996); Zufferey et al., (1997); U.S. Pat. Nos. 6,013,516;and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene, such as the STAT-1α gene in this invention, into that packaging cell yields a producer cell which releases infectious viral particles carrying the foreign gene of interest. The env preferably is an amphotropic envelope protein which allows transduction of cells of human and other species.

One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

The heterologous or foreign nucleic acid sequence, such as the STAT-1α encoding polynucleotide sequence herein, is linked operably to a regulatory nucleic acid sequence. Preferably, the heterologous sequence is linked to a promoter, resulting in a chimeric gene. The heterologous nucleic acid sequence may also be under control of either the viral LTR promoter-enhancer signals or of an internal promoter, and retained signals within the retroviral LTR can still bring about efficient expression of the transgene. Marker genes may be utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate, etc., and cell surface markers.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

Lentiviral transfer vectors Naldini et al. (1996), have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector showed no decrease in the average level of transgene expression and no sign of tissue pathology or immune reaction (Blomer et al., 1997). Thus, in the present invention, one may graft or transplant cells infected with the recombinant lentivirus ex vivo, or infect cells in vivo.

Other Viral Vectors: The development and utility of viral vectors for gene delivery is constantly improving and evolving. Other viral vectors such as poxvirus; e.g., vaccinia virus (Gnant et al., 1999; Gnant et al., 1999), alpha virus; e.g., sindbis virus, Semliki forest virus (Lundstrom, 1999), reovirus (Coffey et al., 1998) and influenza A virus (Neumann et al., 1999) are contemplated for use in the present invention and may be selected according to the requisite properties of the target system.

In certain embodiments, vaccinia viral vectors are contemplated for use in the present invention. Vaccinia virus is a particularly useful eukaryotic viral vector system for expressing heterologous genes. For example, when recombinant vaccinia virus is properly engineered, the proteins are synthesized, processed and transported to the plasma membrane. Vaccinia viruses as gene delivery vectors have recently been demonstrated to transfer genes to human tumor cells, e.g., EMAP-II (Gnant et al., 1999), inner ear (Derby et al., 1999), glioma cells, e.g., p53 (Timiryasova et al., 1999) and various mammalian cells, e.g., P-450 (U.S. Pat. No. 5,506,138). The preparation, growth and manipulation of vaccinia viruses are described in U.S. Pat. Nos. 5,849,304 and 5,506,138 (each specifically incorporated herein by reference).

In other embodiments, sindbis viral vectors are contemplated for use in gene delivery. Sindbis virus is a species of the alphavirus genus (Garoff and Li, 1998) which includes such important pathogens as Venezuelan, Western and Eastern equine encephalitis viruses (Sawai et al., 1999; Mastrangelo et al., 1999). In vitro, sindbis virus infects a variety of avian, mammalian, reptilian, and amphibian cells. The genome of sindbis virus consists of a single molecule of single-stranded RNA, 11,703 nucleotides in length. The genomic RNA is infectious, is capped at the 5' terminus and polyadenylated at the 3' terminus, and serves as mRNA. Translation of a vaccinia virus 26S mRNA produces a polyprotein that is cleaved co- and post-translationally by a combination of viral and presumably host-encoded proteases to give the three virus structural proteins, a capsid protein (C) and the two envelope glycoproteins (E1 and PE2, precursors of the virion E2).

Three features of sindbis virus suggest that it would be a useful vector for the expression of heterologous genes. First, its wide host range, both in nature and in the laboratory. Second, gene expression occurs in the cytoplasm of the host cell and is rapid and efficient. Third, temperature-sensitive mutations in RNA synthesis are available that may be used to modulate the expression of heterologous coding sequences by simply shifting cultures to the non-permissive temperature at various time after infection. The growth and maintenance of sindbis virus is known in the art (U.S. Pat. No. 5,217,879, specifically incorporated herein by reference).

Chimeric Viral Vectors: Chimeric or hybrid viral vectors are being developed for use in therapeutic gene delivery and are contemplated for use in the present invention. Chimeric poxviral/retroviral vectors (Holzer et al., 1999), adenoviral/retroviral vectors (Feng et al., 1997; Bilbao et al., 1997; Caplen et al., 1999) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate herein by reference).

The adenovirus/AAV chimeric virus uses adenovirus nucleic acid sequences as a shuttle to deliver a recombinant AAV/transgene genome to a target cell. The adenovirus nucleic acid sequences employed in the hybrid vector can range from a minimum sequence amount, which requires the use of a helper virus to produce the hybrid virus particle, to only selected deletions of adenovirus genes, which deleted gene products can be supplied in the hybrid viral production process by a selected packaging cell. At a minimum, the adenovirus nucleic acid sequences employed in the pAdA shuttle vector are adenovirus genomic sequences from which all viral genes are deleted and which contain only those adenovirus sequences required for packaging adenoviral genomic DNA into a preformed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The adenovirus sequences may be modified to contain desired deletions, substitutions, or mutations, provided that the desired function is not eliminated.

The AAV sequences useful in the above chimeric vector are the viral sequences from which the rep and cap polypeptide encoding sequences are deleted. More specifically, the AAV sequences employed are the cis-acting 5' and 3' inverted terminal repeat (ITR) sequences. These chimeras are characterized by high titer transgene delivery to a host cell and the ability to stably integrate the transgene into the host cell chromosome (U.S. Pat. No. 5,871,983, specifically incorporate herein by reference). In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1 a/E1 b genes of the adenovirus. Alternatively, the AAV sequences may be inserted at an E3 deletion, E2a deletion, and so on. If only the adenovirus 5' ITR/packaging sequences and 3' ITR sequences are used in the hybrid virus, the AAV sequences are inserted between them.

The transgene sequence of the vector and recombinant virus can be a gene, a nucleic acid sequence or reverse transcript thereof, heterologous to the adenovirus sequence, which encodes a protein, polypeptide or peptide fragment of interest. The transgene is operatively linked to regulatory components in a manner which permits transgene transcription. The composition of the transgene sequence will depend upon the use to which the resulting hybrid vector will be put. For example, one type of transgene sequence includes a therapeutic gene which expresses a desired gene product in a host cell. These therapeutic genes or nucleic acid sequences typically encode products for administration and expression in a patient in vivo or ex vivo to replace or correct an inherited or non-inherited genetic defect or treat an epigenetic disorder or disease.

(x) Non-Viral Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

Injection: In certain embodiments, a nucleic acid may be delivered to an organelle, a cell, a tissue or an organism via one or more injections (i.e., a needle injection), such as, for example, either subcutaneously, intradermally, intramuscularly, intervenously or intraperitoneally. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus oocytes* (Harland and Weintraub, 1985).

Electroporation: In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al, 1992), wheat (Zhou et al., 1993), tomato (Hou and Lin, 1996), soybean (Christou et al., 1987) and tobacco (Lee et al, 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al, 1994) and tomato (Tsukada, 1989).

Calcium Phosphate: In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

DEAE-Dextran: In another embodiment, a nucleic acid is delivered into a cell using DEAE-dextran followed by polyethylene glycol. In this manner, reporter plasmids were introduced into mouse myeloma and erythroleukemia cells (Gopal, 1985).

Sonication Loading: Additional embodiments of the present invention include the introduction of a nucleic acid by direct sonic loading. LTK-fibroblasts have been transfected with the thymidine kinase gene by sonication loading (Fechheimer et al., 1987).

Liposome-Mediated Transfection: In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al, 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

Receptor Mediated Transfection: Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al, 1987). It is contemplated that the tissue-specific transforming constructs of the present invention can be specifically delivered into a target cell in a similar manner.

Microprojectile Bombardment: Microprojectile bombardment techniques can be used to introduce a nucleic acid into at least one, organelle, cell, tissue or organism (U.S. Pat. Nos. 5,550,318; 5,538,880; 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991 ); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et al., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

F. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

G. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would, further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

H. Cell Propagation

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth). Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations. Antibodies are and their uses are discussed further, below.

III. Generating Antibodies Reactive With CAR-1

In another aspect, the present invention contemplates an antibody that is immunoreactive with a CAR-1 molecule of the present invention, or any portion thereof An antibody can be a polyclonal or a monoclonal antibody. In a preferred embodiment, an antibody is a monoclonal antibody. Means for preparing and characterizing antibodies are well known in the art (see, e.g., Howell and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to CAR-1-related antigen epitopes. Additionally, it is proposed that monoclonal antibodies specific to the particular CAR-1 of different species may be utilized in other useful applications In general, both polyclonal and monoclonal antibodies against CAR-1 may be used in a variety of embodiments. For example, they may be employed in antibody cloning protocols to obtain cDNAs or genes encoding other CAR-1. They may also be used in inhibition studies to analyze the effects of CAR-1 related peptides in cells or animals. Anti-CAR-1 antibodies will also be useful in immunolocalization studies to analyze the distribution of CAR-1 during various cellular events, for example, to determine the cellular or tissue-specific distribution of CAR-1 polypeptides under different points in the cell cycle. A particularly useful application of such antibodies is in purifying native or recombinant CAR-1, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimido-bencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified CAR-1 protein, polypeptide or peptide or cell expressing high levels of CAR-1. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

IV. Diagnosing Cancers Involving CAR-1

CAR-1 and the corresponding gene may be employed as a diagnostic or prognostic indicator of cancer. More specifically, point mutations, deletions, insertions or regulatory pertubations relating to CAR-1 may cause cancer or promote cancer development, cause or promoter tumor progression at a primary site, and/or cause or promote metastasis. Other phenomena associated with malignancy that may be affected by CAR-1 expression include angiogenesis and tissue invasion.

A. Genetic Diagnosis

One embodiment of the instant invention comprises a method for detecting variation in the expression of CAR-1. This may comprises determining that level of CAR-1 or determining specific alterations in the expressed product. Obviously, this sort of assay has importance in the diagnosis of related cancers. Such cancer may involve cancers of the brain (glioblastomas, medulloblastoma, astrocytoma, oligodendroglioma, ependymomas), lung, liver, spleen, kidney, pancreas, small intestine, blood cells, lymph node, colon, breast, endometrium, stomach, prostate, testicle, ovary, skin, head and neck, esophagus, bone marrow, blood or other tissue. In particular, the present invention relates to the diagnosis of gliomas.

The biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have CAR-1-related pathologies. In this way, it is possible to correlate the amount or kind of CAR-1 detected with various clinical states.

Various types of defects have been identified by the present inventors. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of CAR-1 produced, both by altering the transcription of the gene or in destabilizing or otherwise altering the processing of either the transcript (mRNA) or protein.

A cell takes a genetic step toward oncogenic transformation when one allele of a tumor suppressor gene is inactivated due to inheritance of a germline lesion or acquisition of a somatic mutation. The inactivation of the other allele of the gene usually involves a somatic micromutation or chromosomal allelic deletion that results in loss of heterozygosity (LOH). Alternatively, both copies of a tumor suppressor gene may be lost by homozygous deletion.

It is contemplated that other mutations in the CAR-1 gene may be identified in accordance with the present invention. A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemilluminescent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al, 1989; Gingeras et al, PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double-stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single-stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, M. A., *In: PCR™ PROTOCOLS: A GUIDE TO METHODS AND APPLICATIONS,* Academic Press, N.Y., 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the CAR-1 gene that may then be analyzed by direct sequencing.

(vi) Kit Components

All the essential materials and reagents required for detecting and sequencing CAR-1 and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

(vii) Design and Theoretical Considerations for Relative Quantitative RT-PCR™

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

(viii) Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

B. Immunodiagnosis

Antibodies of the present invention can be used in characterizing the CAR-1 content of healthy and diseased tissues, through techniques such as ELISAs and Western blotting. This may provide a screen for the presence or absence of malignancy or as a predictor of future cancer.

The use of antibodies of the present invention, in an ELISA assay is contemplated. For example, anti-CAR-1 antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for CAR-1 that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

V. Methods of Therapy

The present invention also involves, in another embodiment, the treatment of cancer. The types of cancer that may be treated, according to the present invention, is limited only by the involvement of CAR-1. By involvement, it is not even a requirement that CAR-1 be mutated or abnormal—the overexpression of this tumor suppressor may actually overcome other lesions within the cell. Thus, it is contemplated that a wide variety of tumors may be treated using CAR-1 therapy, including cancers of the brain, lung, liver, spleen, kidney, lymph node, pancreas, small intestine, blood cells, colon, stomach, breast, endometrium, prostate, testicle, ovary, skin, head and neck, esophagus, bone marrow, blood or other tissue. In particular, carcinomas and neuroblastomas are contemplated for treatment.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

A. Genetic Based Therapies

One of the therapeutic embodiments contemplated by the present inventors is the intervention, at the molecular level, in the events involved in the tumorigenesis of some cancers. Specifically, the present inventors intend to provide, to a cancer cell, an expression construct capable of providing CAR-1 to that cell. Because the sequence homology between the human, mouse and dog genes, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock.

Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way CAR-1 may be utilized according to the present invention.

B. Immunotherapies

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

According to the present invention, it is unlikely that CAR-1 could serve as a target for an immune effector given that (i) it is unlikely to be expressed on the surface of the cell and (ii) that the presence, not absence, of CAR-1 is associated with the normal state. However, it is possible that particular mutant forms of CAR-1 may be targeted by immunotherapy, either using antibodies, antibody conjugates or immune effector cells.

A more likely scenario is that immunotherapy could be used as part of a combined therapy, in conjunction with CAR-1-targeted gene therapy. The general approach for combined therapy is discussed below. Generally, the tumor cell must bear some marker that is amenable to targeting, i.e., is not present on the majority of other cells. Many tumor marker exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

C. Protein Therapy

Another therapy approach is the provision, to a subject, of CAR-1 polypeptide, active fragments, synthetic peptides, mimetics or other analogs thereof The protein may be produced by recombinant expression means or, if small enough, generated by an automated peptide synthesizer. Formulations would be selected based on the route of administration and purpose including, but not limited to, liposomal formulations and classic pharmaceutical preparations.

D. Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al, 1992). In the context of the present invention, it is contemplated that CAR-1 replacement therapy could be used similarly in conjunction with chemo- or radiotherapeutic intervention. It also may prove effective to combine CAR-1 gene therapy with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a CAR-1 expression construct and at least one other agent. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either CAR-1 or the other agent will be desired. Various combinations may be employed, where CAR-1 is "A" and the other agent is "B", as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a CAR-1 expression construct is particularly preferred as this compound.

In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a CAR-1 expression construct, as described above.

Agents that directly cross-link nucleic acids, specifically DNA, are envisaged to facilitate DNA damage leading to a synergistic, antineoplastic combination with CAR-1. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of CAR-1 expression constructs to patients with CAR-1-linked cancers will be a very efficient method for delivering a therapeutically effective gene to counteract the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining CAR-1-targeted therapies with chemo- and radiotherapies, it also is contemplated that combination with other gene therapies will be advantageous. For example, targeting of CAR-1 and p53 or p16 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf erb, src, fms, jun, trk, ret, gsp, hst, bcl and abl.

It also should be pointed out that any of the foregoing therapies may prove useful by themselves in treating a CAR-1. In this regard, reference to chemotherapeutics and non-CAR-1 gene therapy in combination should also be read as a contemplation that these approaches may be employed separately.

E. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or admininstration local or regional to a tumor, for example, in the local or regional vasculature or lymphatic system.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VI. Screening for Modulators of CAR-1 Function

The present invention also contemplates the use of CAR-1 and active fragments, and nucleic acids coding therefor, in the screening of compounds for activity in either stimulating CAR-1 activity, overcoming the lack of CAR-1 or blocking the effect of a mutant CAR-1 molecule. These assays may make use of a variety of different formats and may depend on the kind of "activity" for which the screen is being conducted. Contemplated functional "read-outs" include binding to a compound, inhibition of binding to a substrate, ligand, receptor or other binding partner by a compound, inhibition or stimulation of cell-to-cell signaling, growth, metastasis, cell division, cell migration, soft agar colony formation, contact inhibition, invasiveness, angiogenesis, apoptosis, tumor progression or other malignant phenotype.

A. In Vitro Assays

In one embodiment, the invention is to be applied for the screening of compounds that bind to the CAR-1 molecule or fragment thereof The polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of CAR-1 to a natural or artificial substrate or binding partner. Competitive binding assays can be performed in which one of the agents (CAR-1, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small peptide test compounds are synthesized on a solid substrate, such as plastic pins or some other surface. The peptide test compounds are reacted with CAR-1 and washed. Bound polypeptide is detected by various methods.

Purified CAR-1 can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the CAR-1 active region to a solid phase.

Various cell lines containing wild-type or natural or engineered mutations in CAR-1 can be used to study various functional attributes of CAR-1 and how a candidate compound affects these attributes. Methods for engineering mutations are described elsewhere in this document, as are naturally-occurring mutations in CAR-1 that lead to, contribute to and/or otherwise cause malignancy. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of CAR-1, or related pathways, may be explored. This may involve assays such as those for protein expression, enzyme function, substrate utilization, phosphorylation states of various molecules including CAR-1, cAMP levels, mRNA expression (including differential display of whole cell or polyA RNA) and others.

B. In Vivo Assays

The present invention also encompasses the use of various animal models. Here, the identity seen between human and mouse CAR-1 provides an excellent opportunity to examine the function of CAR-1 in a whole animal system where it is normally expressed. By developing or isolating mutant cells lines that fail to express normal CAR-1, one can generate cancer models in mice that will be highly predictive of cancers in humans and other mammals. These models may employ the orthotopic or systemic administration of tumor cells to mimic primary and/or metastatic cancers. Alternatively, one may induce cancers in animals by providing agents known to be responsible for certain events associated with malignant transformation and/or tumor progression. Finally, transgenic animals (discussed below) that lack a wild-type CAR-1 may be utilized as models for cancer development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

C. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for CAR-1 or a fragment thereof. This could be accomplished by x-ray crystallograph, computer modeling or by a combination of both approaches. An alternative approach, "alanine scan," involves the random replacement of residues throughout molecule with alanine, and the resulting affect on function determined.

It also is possible to isolate a CAR-1-specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved CAR-1 activity or which act as stimulators, inhibitors, agonists, antagonists or CAR-1 or molecules affected by CAR-1 function. By virtue of the availability of cloned CAR-1 sequences, sufficient amounts of CAR-1 can be produced to perform crystallographic studies. In addition, knowledge of the polypeptide sequences permits computer employed predictions of structure-function relationships.

VII. Transgenics

In one embodiment of the invention, transgenic animals are produced which contain a functional transgene encoding a functional CAR-1 polypeptide or variants thereof Transgenic animals expressing CAR-1 transgenes, recombinant cell lines derived from such animals and transgenic embryos may be useful in methods for screening for and identifying agents that induce or repress function of CAR-1. Transgenic animals of the present invention also can be used as models for studying indications such as cancers.

In one embodiment of the invention, a CAR-1 transgene is introduced into a non-human host to produce a transgenic animal expressing a human or murine CAR-1 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous CAR-1 by homologous recombination between the transgene and the endogenous gene; or the endogenous gene may be eliminated by deletion as in the preparation of "knock-out" animals. Typically, a CAR-1 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress CAR-1 or express a mutant form of the polypeptide. Alternatively, the absence of one or both alleles of a CAR-1 gene in "knock-out" mice permits the study of the effects that a reduction in or loss of CAR-1 protein has on a cell in vivo. Knock-out mice also provide a model for the development of CAR-1-related cancers.

As noted above, transgenic animals and cell lines derived from such animals may find use in certain testing experiments. In this regard, transgenic animals and cell lines capable of expressing wild-type or mutant CAR-1 may be exposed to test substances. These test substances can be screened for the ability to enhance wild-type CAR-1 expression and or function or impair the expression or function of mutant CAR-1.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Functional Analysis of Chromosomes in Cancer

In earlier studies, the inventors defined a novel genetic locus, Nonpapillary Renal Carcinoma-1 (NRC-1), that mediates tumor suppression and rapid cell death of different histologic types of RCC (Renal Cell Carcinoma) in vivo (Sanchez et al., 1994). In addition, the inventors constructed defined fragment-containing microcell hybrids that are either suppressed or unsuppressed for tumorigenicity in vivo and which narrow the region containing NRC-1 to 1–2 Mb within 3p12 (Lott et al., 1998). It is probable that at least one gene within the NRC-1 locus functions as tumor suppressor gene and that disruption of this gene is involved in the development of sporadic renal cell carcinoma, and potentially, other histologically diverse cancers.

In order to identify the genes responsible for the tumor suppression phenotype, the inventors employed a subtractive hybridization screening strategy. Using Clontech's PCR-Select cDNA Subtraction Kit, they subtracted the hybrid containing the minimal region of chromosome 3p that exhibits the tumor suppression phenotype against the hybrid containing the smaller piece of chromosome 3p which is nonsuppressed. The screening strategy should allow identification of rare as well as abundant messages that are absolutely differentially expressed or are enriched in the suppressing hybrid. Additionally, this screening strategy allows identification of genes which are expressed from the chromosome 3 locus, as well as other genes downstream in the tumor suppression pathway. From this screen, 900 clones containing partial cDNA inserts of sizes ranging from 150–1100 bp were obtained. One clone, CAR-1, did not map back to chromosome 3p12, but rather mapped to the short arm of chromosome 1. This gene is, therefore, a putative downstream target of the tumor suppressor activity contributed by the suppressing region of chromosome 3p12.

Example 2

Preliminary Data Supporting CAR-1 as a Tumor Suppressor Gene

Specifically, CAR-1 maps to chromosome 1p31-1p36. Interestingly, one of five RCC cell lines recently established in our laboratory not only has a deletion in 3p12, but also has a (Sanchez et al., 1994; Bomme et al., 1994) chromosomal translocation with the breakpoint at 1p. Fluorescent in situ hybridization (FISH) mapping using the CAR-1 cDNA as a probe revealed CAR-1 signal on the intact chromosome 1 only. Mouse hybrid cells lines containing human chromosomes 1, 3, 4, and 8 were subjected to PCR with primers specific to a 438 bp fragment of exon 3 of CAR-1. Only the cell line containing human chromosome 1 provided template sufficient to amplify the fragment, additionally confirming that CAR-1 maps to chromosome 1. The 1p31-36 region of chromosome 1 has also shown LOH in other types of cancer such as neuroblastoma and cancers of the breast and colon (Bomme et al., 1994; Biech et al., 1993; Kovacs et al., 1988;

Da Vinci et al., 1996). With this evidence further supporting CAR-1's potential role in the initiation and/or progression of RCC, and possibly other cancers, the inventors then sought to obtain a full-length cDNA clone.

The original 700 bp cDNA obtained from the subtraction was used to screen a retinoic acid induced NT2 neuroepithelial cDNA library. Sequence analysis of the 3.3 kb phagemid insert, although still not full length cDNA, suggested that CAR-1 is a novel gene of the RBCC RING-finger subfamily (FIG. 1). In order to obtain the full-length cDNA sequence, 5' RACE was performed on cDNA from adult normal kidney using the Marathon™ cDNA amplification kit from Clontech™ according to the manufacturer's specifications. RACE products were gel purified, cloned into the TA vector from Invitrogen™ and sequenced by automated process. The translated amino acid sequence predicts that CAR-1 contains all three RBCC domains (also known as a tripartite sequence motif): a N-terminal RING finger Zn binding motif followed by B-box Zn binding motif, and a helical coiled coil domain (Saurin et al., 1996). A C-terminal (rfp) domain is also predicted. In previous work by the inventors, this tumor suppressor had been designated as 7b5. The suppressor is now denoted as Cancer Associated Ring-1, in keeping with its membership in the RING finger protein family.

Three known RBCC subfamily members become oncogenic when chromosomal translocations result in fusion proteins. The PML gene becomes fused with retinoic acid receptor alpha (RARA) in acute promyelocytic leukemia (Pandolfi, 1996), the RET oncogene is Rfp (RET finger protein) fused to a tyrosine kinase domain (Isomura et al., 1992), and TIF1 becomes oncogenic when fused to the B-Raf proto-oncogene (Le Dourain et al., 1995). Additional gene products that contain one or more of the RBCC domains are also associated with tumorigenesis. The BRCA1 gene product contains a N-terminal RING finger domain (Miki et al., 1994) and is a tumor suppressor gene believed to account for approximately 40 to 50% of all familial cases of breast cancer (Szabo & King, 1995). Among the roles of BRCA1 is its interaction with BARD1 (BRCA1 associated RING domain protein), which also contains an N-terminal RING motif (Wu et al., 1994). BARD1/BRCA1 interaction is interrupted by missense mutations within the RING domain of BRCA1 indicating that the RING finger is responsible for protein-protein interactions and that these interactions may be involved in the mediation tumor suppression by BRCA1 (Wu et al., 1994).

Furthermore, the fact that disease-associated missense mutations have been identified within the RING finger (Couch & Weber, 1996) underscores the importance of the domain function for normal activity of the gene. Another related gene is the 11A1.3A gene, whose gene product lacks the RING finger but contains the B Box and coiled coil domains, and is a an established marker used for the diagnosis and monitoring of epithelial ovarian cancer. Other RBCC family members have been shown to be important for development and signal transduction. Significantly, both BRCA1 and TIF1 are phosphoproteins that become localized to the nucleus and are putative transcription factors (Pandolfi, 1996; Le Dourain et al., 1995). In short, CAR-1 shares interesting structural motifs with an important class of genes, many of which play roles in oncogenesis.

Figure 2:
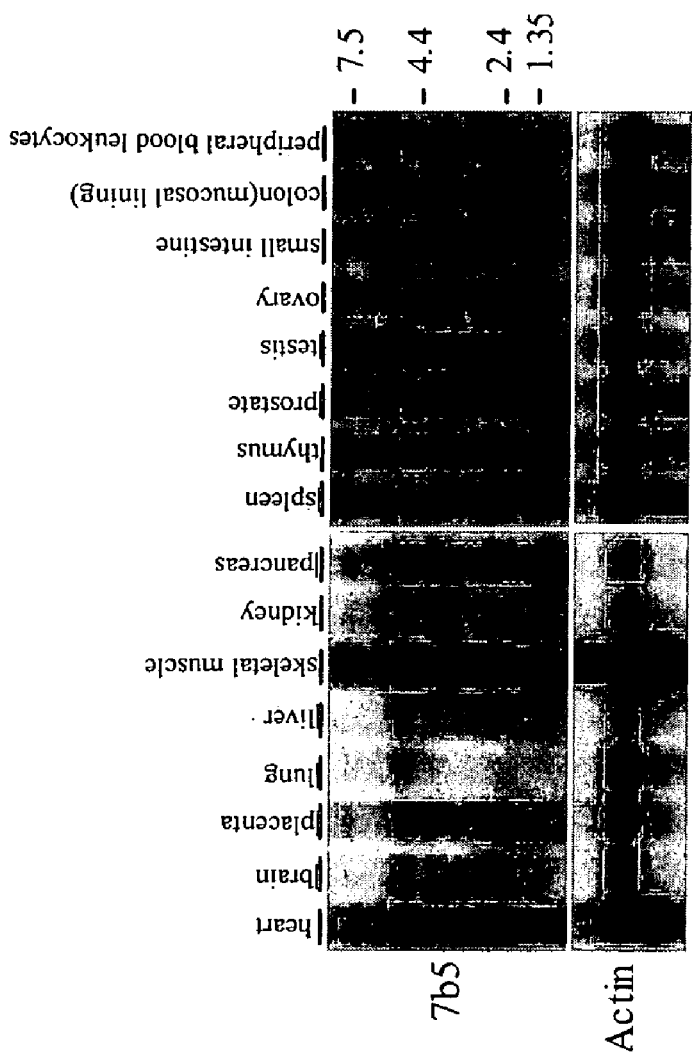
FIG. 2. Northern Blot showing the 4.4 kb CAR-1 transcript in all tissues. A multiple tissue northern blot (Clontech) was hybridized with a radiolabeled CAR-1 partial cDNA. One primary transcript of approximately 4.4 kb is present in all tissues. Other smaller transcripts are visible in skeletal muscle, placenta, brain, and heart. An additional larger transcript is also seen in peripheral blood leukocytes and skeletal muscle. These results indicate that the 4.4 kb CAR-1 RNA is ubiquitously expressed, and that other CAR-1 transcripts, perhaps RNAs derived from alternative splicing, are expressed in a developmental/tissue-specific manner.
Figure 3:
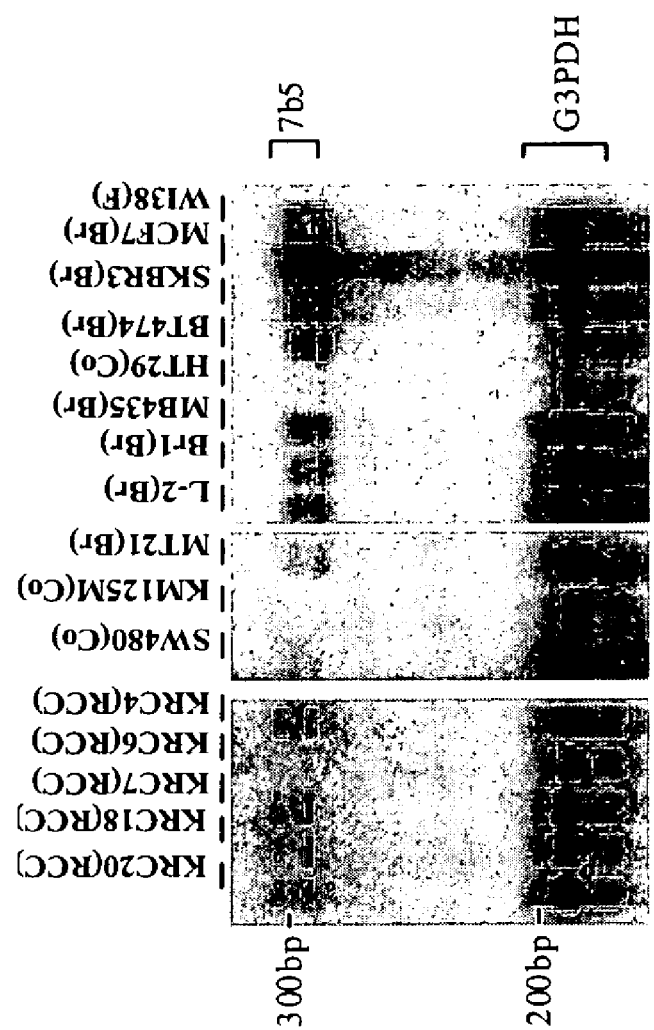
FIG. 3. RNAase protection assay (RPA) showing CAR-1 RNA levels in Renal Cell Carcinoma (RCC), breast cancer (Br), colon cancer (Co), and fibroblast (F) cell lines. Down regulation and/or loss of expression is seen in KRC6, SW480, KM125M, MT21, and HT29 as compared to the WI38 fibroblast control. MCF7, on the other hand, shows an increased level of CAR-1 expression. RPAs were performed on total RNAs from cell lines. A 385 nt CAR-1 radiolabledRNA and a 220 nt G3PDH control RNA were used as probes and were expected to yield a 305 nt and a 195 nt protected fragment, respectively. Doublet bands seen here are not derived from undigested full-length probe and have not been further characterized.
Figure 4:
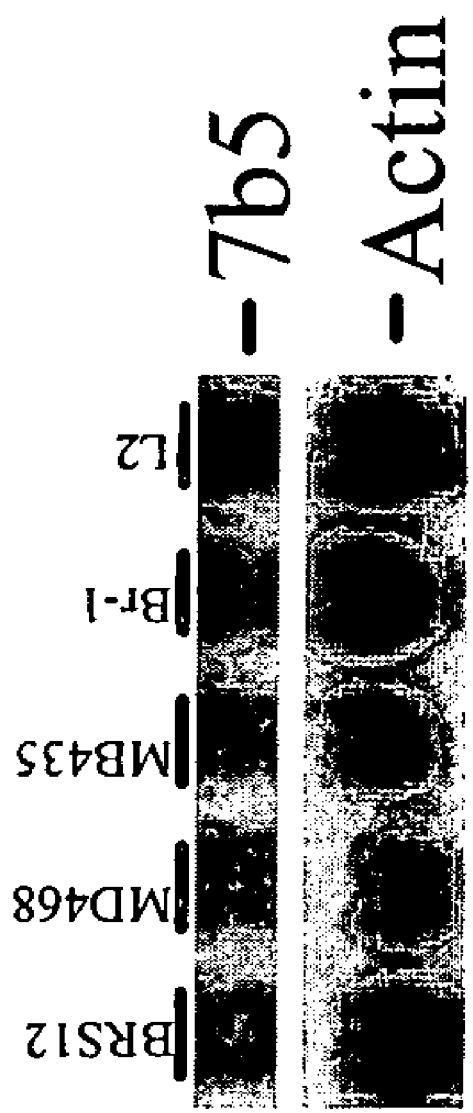
FIG. 4. Northern blot showing down regulation and/or loss expression of CAR-1 in breast cancer cell lines BRS12 and MD468, but not in MB435, Br-1, or L2. The northern blot was performed using total RNA from cell lines and was hybridized as in FIG. 2.
Figure 5:
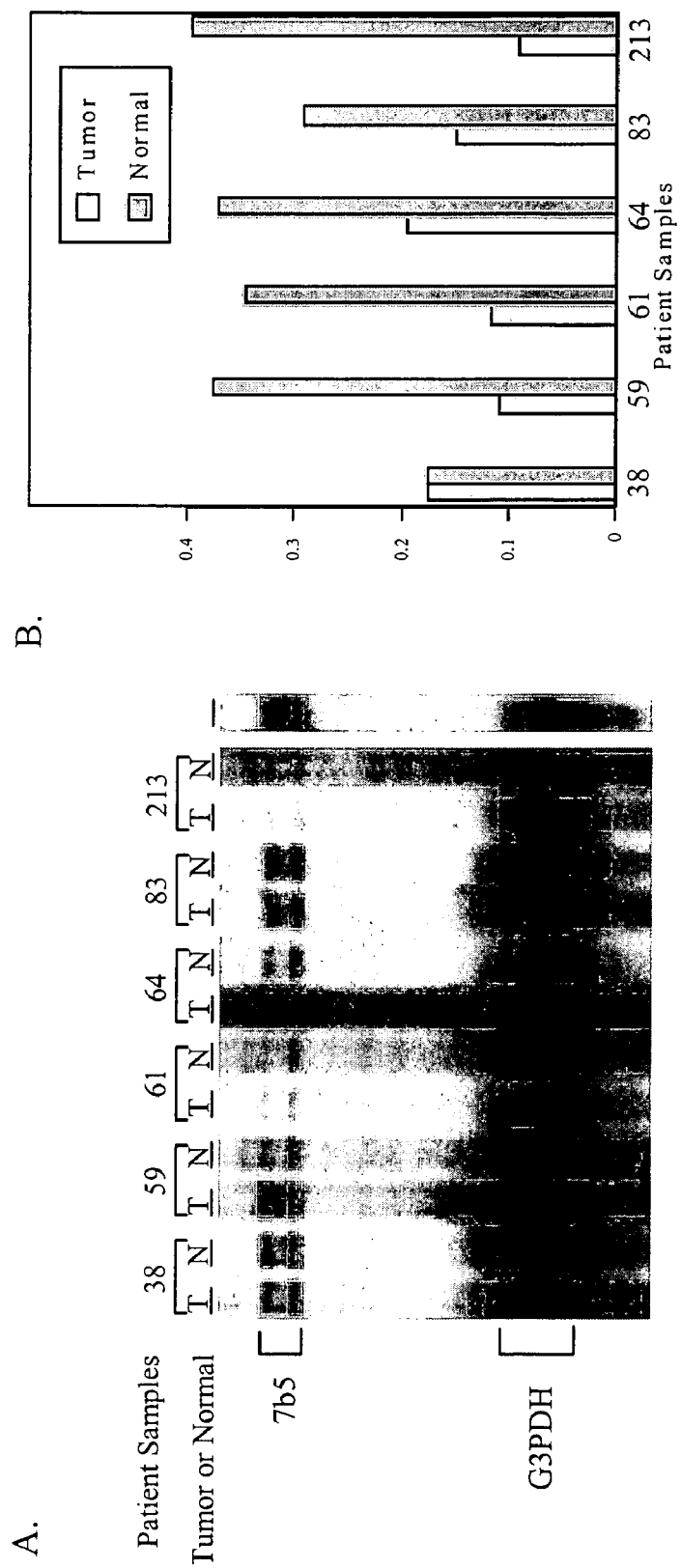
FIG. 5A–5B. CAR-1 transcript is present at lower levels in colon tumor samples (T) than in adjacent normal control colon tissue (N) from the same patient. FIG. A. RNAase protection assay was performed using total RNA from matched tumor/normal samples obtained from Marsha Frazier's laboratory. Assay was performed as in FIG. 3. FIG. B. CAR-1 expression levels were normalized against the control RNA using ImageQuant software. Patient sample 38 showed relatively equal amount of CAR-1 transcript in both the tumor and normal sample. All other samples show less CAR-1 transcript in the tumor sample than in the matched normal control. For patient samples, there was 3.4-fold less CAR-1 in 59T than in normal 59N, 2.9-fold less in 61T than in 61N, 1.9-fold less in 64T than 64N, 1.9-fold less 83T than in 83N, and 4.4-fold less in 213T than in 213N. These preliminary experiments were not performed on microdissected tumor samples; therefore, CAR-1 expression in tumor samples may be resulting from contamination of the tumor with normal adjacent tissue.

Preliminary expression studies further support CAR-1's putative role as a tumor suppressor gene. A multiple tissue Northern blot containing poly A+RNA from human tissues (Clontech) shows a primary CAR-1 transcript of approximately 4.4 kb in all tissues (FIG. 2). This expression pattern is much like other tumor suppressor genes that are thought to play a global role of tumor suppression. Both p53 and BRCA1 are examples of genes exhibiting this general expression pattern. Furthermore, if CAR-1 truly has tumor suppressor activity, one would additionally expect the expression to be disrupted in cancer. Thus, the inventors looked for loss of CAR-1 expression in RCC cell lines because it is the cancer-type on which the original subtraction was performed, and in breast and colon cancer cell lines since LOH of a tumor suppressor at chromosomal location at 1p31–36 has previously been indicated in these cancers. Expression of CAR-1 transcript was examined by Northern blot analysis and/or by RNAse protection assays (RPA). One of the five RCC cell lines examined shows loss of expression (LOE) of the CAR-1 transcript as shown in the RPA in FIG. 3. This cell line, KRC 6, is the one previously mentioned to contain the (Sanchez et al., 1994; Bomme et al., 1994) translocation and to only have one copy of CAR-1 on the normal chromosome 1. It appears that expression of CAR-1 from that chromosome has been disrupted. Significantly, three of the seven breast lines (FIGS. 3 & 4) and three of the three colon lines (FIG. 3) have also exhibited a decrease in, or a loss of expression of CAR-1. Finally, upon comparing 6 pairs of matched tumor/normal samples from colon, five tumor samples show a lower level of CAR-1 expression upon comparison to the adjacent normal tissue (FIG. 5). This expression data is consistent with this gene having tumor suppressive activity.

Example 3

Generation of Anti-Peptide Antibodies Against CAR-1

Figure 6:
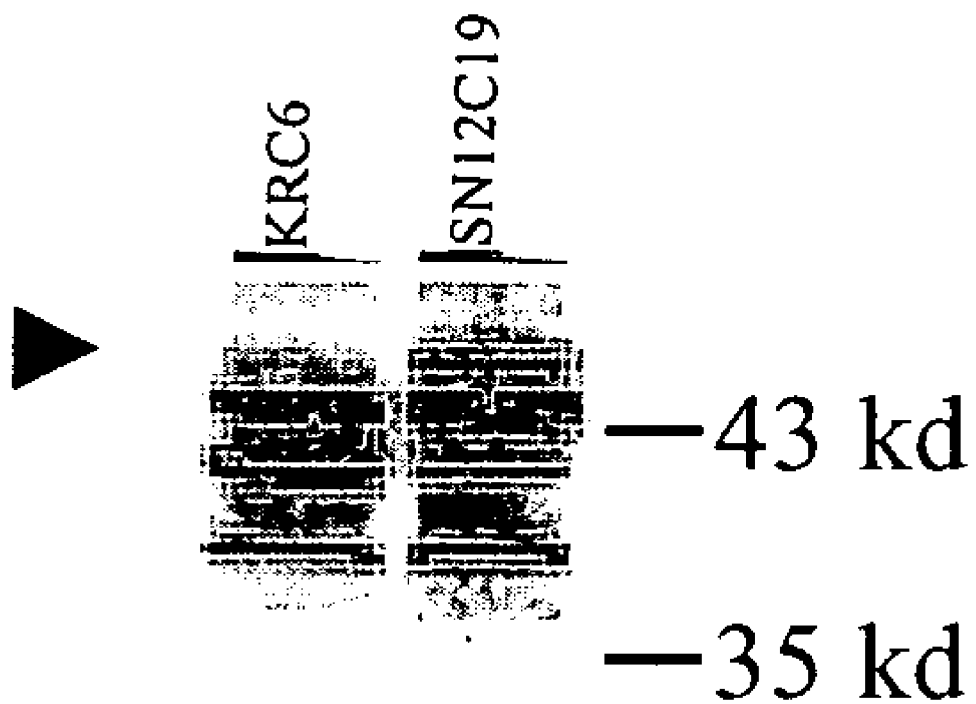
FIG. 6. Western blot analysis of the CAR-1 protein using the C-terminal anti-CAR-1 antibody. This antibody detects a band of appropriate size (indicated by the arrow) that is greatly diminished in expression in the cell line KRC-6, which contains the translocation chromosome and which shows loss of expression of CAR-1 mRNA.

Anti-peptide antibodies were generated to the amino terminal and carboxyl terminal regions of the CAR-1 protein. Laser gene sequence analysis software was utilized to identify non-conserved regions of CAR-1 that also scored highly for antigenicity. Peptide synthesis was performed by Bethyl Laboratories. Peptides were purified by high performance liquid chromatography (HPLC) and their composition verified by amino acid analysis. Polyclonal antibody production was performed by Bethyl Laboratories. Rabbits were immunized with CAR-1 peptides conjugated to bovine serum albumin. Anti-CAR-1 antibodies were affinity-purified using C-terminal or N-terminal CAR-1 peptide linked to activated thiol-Sepharose beads. Multiple bands were detected on Western blots using affinity-purified C-terminal anti-CAR-1 antibody. This antibody detects a band of the appropriate size (about 54 kd) that is either absent or greatly diminished in expression in the cell line KRC-6 containing the translocation chromosome and showing loss of expression of CAR-1 mRNA (FIG. 6).

REFERENCES

The following references, to the extent that they provide exemplary procedural or other details supplementary to those set forth herein, are specifically incorporated herein by reference.

"Manipulating the mouse embryo," *A Laboratory Manual*, 2d Ed., Hogan, Beddington, Costantimi and Long (Eds.), Cold Spring Harbor Laboratory Press, 1994.

Almendro et al, "Cloning of the human platelet endothelial cell adhesion molecule-1 promoter and its tissue-specific expression. Structural and functional characterization," *J Immunol.* 157(12):5411–5421, 1996.

Amado R G, Chen I S, "Lentiviral vectors—the promise of gene therapy within reach?", *Science*, July 30;285(5428): 674–6,1999.

Angel, Bauman, Stein, Dellus, Rahmsdorf, and Herrlich, "12-0-tetradecanoyl-phorbol-13-acetate Induction of the Human Collagenase Gene is Mediated by an Inducible Enhancer Element Located in the 5' Flanking Region," *Mol. Cell. Biol.*, 7:2256, 1987a.

Angel, Imagawa, Chiu, Stein, Imbra, Rahmsdorf, Jonat, Herrlich, and Karin, "Phorbol Ester-Inducible Genes Contain a Common cis Element Recognized by a TPA-Modulated Trans-acting Factor," *Cell*, 49:729, 1987b Atchison and Perry, "Tandem Kappa Immunoglobulin Promoters are Equally Active in the Presence of the Kappa Enhancer: Implications for Model of Enhancer Function," *Cell*, 46:253, 1986.

Ausubel, Brent, Kingston, Moore, Seidman, Smith, Struhl, eds., *Current Protocols in Molecular Biology* (Wiley, N.Y.), 1994.

Banerji, Olson, and Schaffner, "A Lymphocyte-Specific Cellular Enhancer is Located Downstream of the Joining Region in Immunoglobulin Heavy-Chain Genes," *Cell*, 35:729, 1983.

Barany G, Merrifield R B, A chromatographic method for the quantitative analysis of the deprotection of dithiasuccinoyl (Dts) amino acids, Anal Biochem May 1979;95 (1):160–70.

Bates, "Genetic transformation of plants by protoplast electroporation," *Mol Biotechnol*, 2(2):135–145, 1994.

Batra R K, Guttfridge D C, Brenner D A, Dubinett S M, Baldwin A S, Boucher R C, "IkappaBalpha gene transfer is cytotoxic to squamous-cell lung cancer cells and sensitizes them to tumor necrosis factor-alpha-mediated cell death", *Am J Respir Cell Mol Biol August*;21(2):238–45, 1999.

Battraw and Hall, "Stable transformation of sorghum-bicolor protoplasts with chimeric neomycin phosphotransferase II and beta glucuronidase genes," *Theor. App. Genet.*, 82(2):161–168, 1991.

Berkhout, Silverman, and Jeang, "Tat Trans-activates the Human Immunodeficiency Virus Through a Nascent RNA Target," *Cell*, 59:273, 1989.

Bett A J, Prevec L, Graham F L, "Packaging capacity and stability of human adenovirus type 5 vectors", *J Virol*, Oct.;67(10):5911–21, 1993.

Bhattacharjee; An; Gupta, *J. Plant Bioch. and Biotech.* 6, (2):69–73. 1997.

Bieche, Champeme, Matfias, Cropp, Callahan, Ledereau, "Two distinct regions involved in 1p deletion in human primary breast cancer," *Cancer Research*, 1993. 53, 1994.

Bieche, Khodja, Lidereau, "Deletion mapping in breast tumor cell lines point to two distinct tumor-suppressor genes in the 1p32-ter region, one of deleted regions (1p36.2) being located within the consensus region of LOH in neuroblastoma," *Oncology Reports*, 5:167–272, 1998.

Bilbao G, Zhang H, Contreras J L, Zhou T, Feng M, Saito I, Mountz J D, Curiel D T. Construction of a recombinant adenovirus vector encoding Fas ligand with a CRE/Loxp inducible system Transplant Proc 1999 February–March; 31(1–2):792–3.

Blackwell J L, Miller C R, Douglas J T, Li H, Peters G E, Carroll W R, Peters G E, Strong T V, Curiel D T, "Retargeting to EGFR enhances adenovirus infection efficiency of squamous cell carcinoma", *Arch Otolaryngol Head Neck Surg August*;125(8): 856-63, 1999.

Blanar, Baldwin, Flavell, and Sharp, "A Gamma-Interferon-Induced Factor That Binds the Interferon Response Sequence of the MHC Class I Gene, H-2Kb," *EMBO J*, 8:1139, 1989.

Blomer U, Naldini L, Kafri T, Trono D, Verma I M, Gage F H, "Highly efficient and sustained gene transfer in adult neurons with a lentivirus vector", *J Virol September*;71 (9):6641–9, 1997.

Bodine and Ley, "An Enhancer Element Lies 3' to the Human A Gamma Globin Gene," *EMBO J.*, 6:2997, 1987.

Bomme, Bardi, Pandis, Fenger, Kronborg, Heim, "Clonal karyotypic abnormalities in colorectal adenomas: clues to the early genetic events in the adenoma-carcinoma sequence," *Genes, Chromosomes and Cancer*, 10: 190–196, 1994.

Borg, Zhang, Olsson, and E. Wenngren. Chromosome 1 alterations in breast cancer: allelic loss on 1p and 1q is related to lymphogenic metastases and poor prognosis. *Genes, Chromosomes, and Cancer*, 5:311–320, 1992.

Boshart, Weber, Jahn, Dorsch-Hasler, Fleckenstein, and Schaffner, "A Very Strong Enhancer is Located Upstream of an Immediate Early Gene of Human Cytomegalovirus," *Cell*, 41:521, 1985.

Bosze, Thiesen, and Charnay, "A Transcriptional Enhancer with Specificity for Erythroid Cells is Located in the Long Terminal Repeat of the Friend Murine Leukemia Virus," *EMBO J.*, 5:1615, 1986.

Bower et al, *The Plant Journal*, 2:409–416. 1992.

Braddock, Chambers, Wilson, Esnouf, Adams, Kingsman, and Kingsman, "HIV-I Tat Activates Presynthesized RNA In the Nucleus," *Cell*, 58:269, 1989.

Buising and Benbow, "Molecular analysis of transgenic plants generated by microprojectile bombardment: effect of petunia transformation booster sequence," *Mol. Gen. Genet.*, 243:71–81, 1994.

Bulla and Siddiqui, "The Hepatitis B Virus Enhancer Modulates Transcription of the Hepatitis B Virus Surface-Antigen Gene From an Internal Location," *J Virol.*, 62:1437, 1986.

Campbell and Villarreal, "Functional Analysis of the Individual Enhancer Core Sequences of Polyoma Virus: Cell-Specific Uncoupling of DNA Replication From Transcription," *Mol. Cell. Biol.*, 8:1993, 1988.

Campere and Tilghman, "Postnatal Repression of the .alpha.-fetoprotein Gene is Enhancer Independent," *Genes and Dev.*, 3:537, 1989.

Campo, Spandidos, Lang, and Wilkie, "Transcriptional Control Signals in the Genome of Bovine Papilloma Virus Type 1," *Nature*, 303:77, 1983.

Capaldi et al., *Biochem. Biophys. Res. Comm.*, 76:425, 1977.

Caplen N J, Higginbotham J N, Scheel J R, Vahanian N, Yoshida Y, Hamada H, Blaese R M, Ramsey W J. "Adeno-retroviral chimeric viruses as in vivo transducing agents," *Gene Ther* March; 6(3):454–9 1999.

Carbonelli et al. "A plasmid vector for isolation of strong promoters in *Escherichia coli*," *FEMS Microbiol Lett.* 177(1):75–82, 1999.

Casas et al., "Transgenic sorghum plants via microprojectile bombardment," *Proc. Natl. Acad. Sci. USA*, 90(23):11212–11216, 1993.

Case S S, Price M A, Jordan C T, Yu X J, Wang L, Bauer G, Haas D L, Xu D, Stripecke R, Naldini L, Kohn D B, Crooks G M, "Stable transduction of quiescent CD34(+) CD38(−) human hematopoietic cells by HIV-1-based lentiviral vectors", *Proc Natl Acad Sci USA* March 16; 96(6):2988–93, 1999.

Celander and Haseltine, "Glucocorticoid Regulation of Murine Leukemia Virus Transcription Elements is Specified by Determinants Within the Viral Enhancer Region," *J. Virology*, 61:269, 1987.

Celander, Hsu, and Haseltine, "Regulatory Elements Within the Murine Leukemia Virus Enhancer Regions Mediate Glucocorticoid Responsiveness," *J. Virology*, 62:1314, 1988.

Chandler et al., "RNA splicing specificity determined by the coordinated action of RNA recognition motifs in SR proteins," *Proc Natl Acad Sci USA.* 94(8):3596–3601, 1997.

Chang, Erwin, and Lee, "Glucose-regulated Protein (GRP94 and GRP78) Genes Share Common Regulatory Domains and are Coordinately Regulated by Common Trans-acting Factors," *Mol. Cell. Biol.*, 9:2153, 1989.

Chen and Okayama, "High-efficiency transformation of mammalian cells by plasmid DNA," *Mol. Cell. Biol.* 7:2745–2752, 1987.

Chillon M, Bosch A, Zabner J, Law L, Armentano D, Welsh M J, Davidson B L, "Group D adenoviruses infect primary central nervous system cells more efficiently than those from group C", *J Virol* March; 73(3):2537–40, 1999.

Choi, Chen, Kriegler, and Roninson, "An Altered Pattern of Cross-Resistance in Multi-Drug-Resistant Human Cells Results From Spontaneous Mutations in the Mdr-1 (P-glycoprotein) Gene," *Cell*, 53:519, 1988.

Christou et al., *Proc. Nat'l Acad Sci. USA,* 84(12):3962–3966, 1987.

Clay T M, Custer M C, Spiess P J, Nishimura M I, "Potential use of T cell receptor genes to modify hematopoietic stem cells for the gene therapy of cancer", *Pathol Oncol Res;*5(1):3–15, 1999.

Cocea, "Duplication of a region in the multiple cloning site of a plasmid vector to enhance cloning-mediated addition of restriction sites to a DNA fragment," *Biotechniques*, 23:814–816, 1997.

Coffey M C, Strong J E, Forsyth P A, Lee P W, "Reovirus therapy of tumors with activated Ras pathway", *Science*, November 13;282(5392): 1332–4, 1999.

Cohen, Walter, and Levinson, "A Repetitive Sequence Element 3' of the Human c-Ha-ras1 Gene Has Enhancer Activity," *J. Cell. Physiol.*, 5:75, 1987.

Cook et al., "In vitro splicing of the ribosomal RNA precursor of Tetrahymena: involvement of a guanosine nucleotide in the excision of the intervening sequence," *Cell*, 27:487–496, 1981.

Costa, Lai, Grayson, and Darnell, "The Cell-Specific Enhancer of the Mouse Transthyretin (Prealbumin) Gene Binds a Common Factor at One Site and a Liver-Specific Factor(s) at Two Other Sites," *Mol. Cell. Biol.*, 8:81, 1988.

Couch and Weber, "Mutations and polymorphisms in the familial early-onset breast cancer (BRCA1) gene: Breast Cancer Information Care," *Human Mutation*, 8:8–18, 1996.

Cripe, Haugen, Turk, Tabatabai, Schmid, Durst, Gissmann, Roman, and Turek, "Transcriptional Regulation of the Human Papilloma Virus-16 E6-E7 Promoter by a Keratinocyte-Dependent Enhancer, and by Viral E2 Trans-Activator and Repressor Gene Products: Implications for Cervical Carcinogenesis," *EMBO J.*, 6:3745, 1987.

Culotta and Hamer, "Fine Mapping of a Mouse Metallothionein Gene Metal-Response Element," *Mol. Cell. Biol.*, 9:1376, 1989.

Da Vinci, Infusini, Peveri, Risio, Rossini, Giaretti, "Deletions at chromosome 1p by fluorescence in situ hybridization are an early event in human colorectal tumorigenesis," *Gastroenterology*, 111: 102–107, 1996.

Dandolo, Blangy, and Kamen, "Regulation of Polyma Virus Transcription in Murine Embryonal Carcinoma Cells," *J. Virology*, 47:55, 1983.

De Villiers, Schaffner, Tyndall, Lupton, and Kamen, "Polyoma Virus DNA Replication Requires an Enhancer," *Nature*, 312:242, 1984.

DeLuca N A, McCarthy A M, Schaffer P A. "Isolation and characterization of deletion mutants of herpes simplex virus type 1 in the gene encoding immediate-early regulatory protein ICP4" *J. Virol.* November; 56(2):558–70, 1985.

Derby M L, Sena-Esteves M, Breakefield X O, Corey D P, "Gene transfer into the mammalian inner ear using HSV-1 and vaccinia virus vectors", *Hear Res* August; 134(1–2): 1–8, 1999.

Deschamps, Meijlink, and Verma, "Identification of a Transcriptional Enhancer Element Upstream From the Proto-Oncogene Fos," *Science*, 230:1174, 1985.

D'Halluin et al., "Transgenic maize plants by tissue electroporation," *Plant Cell*, 4(12):1495–1505, 1992.

Dorai T, Perlman H, Walsh K, Shabsigh A, Goluboff E T, Olsson C A, Buttyan R "A recombinant defective adenoviral agent expressing anti-bcl-2 ribozyme promotes apoptosis of bcl-2-expressing human prostate cancer cells", *Int J Cancer* September 9; 82(6):846–52, 1999.

Edbrooke, Burt, Cheshire, and Woo, "Identification of cis-Acting Sequences Responsible for Phorbol Ester Induction of Human Serum Amyloid A Gene Expression Via a Nuclear-Factor-.kappa.B-like Transcription Factor," *Mol. Cell. Biol.*, 9:1908, 1989.

Edlund, Walker, Barr, and Rutter, "Cell-Specific Expression of the Rat Insulin Gene: Evidence for Role of Two Distinct 5' Flanking Elements," *Science*, 230:912, 1985.

Engel B C, Kohn D B. Related Articles Stem cell directed gene therapy. Front Biosci. May 1, 1999;4:e26–33.

EPO Application No. 0273085

Fechheimer, Boylan, Parker, Sisken, Patel and Zimmer, "Transfection of mammalian cells with plasmid DNA by scrape loading and sonication loading," *Proc Nat'l. Acad Sci. USA* 84:8463–8467, 1987

Feldman L J, Tahlil O, Steg P G, "Adenovirus-mediated arterial gene therapy for restenosis: problems and perspectives", Semin Interv Cardiol Sep.;1(3):203–8, 1996.

Feng and Holland, "HIV-I Tat Trans-Activation Requires the Loop Sequence Within Tar," *Nature*, 334:6178, 1988.

Feng S, Quickel R R, Hollister-Lock J, McLeod M, Bonner-Weir S, Mulligan R C, Weir G C, "Prolonged xenograft survival of islets infected with small doses of adenovirus expressing CTLA4Ig", *Transplantation* Jun. 27;67(12): 1607–13, 1999.

Firak and Subramanian, "Minimal Transcription Enhancer of Simian Virus 40 is a 74-Base-Pair Sequence that Has Interacting Domains," *Mol. Cell. Biol*, 6:3667, 1986.

Fisher K J, Choi H, Burda J, Chen S J, Wilson J M, "Recombinant adenovirus deleted of all viral genes for gene therapy of cystic fibrosis", *Virology* March 1; 217 (1):11–22 1996.

Foder et al., "Light-directed, spatially addressable parallel chemical synthesis," *Science*, 251:767–773, 1991.

Foecking and Hofstetter, "Powerful and Versatile Enhancer-Promoter Unit for Mammalian Expression Vectors," *Gene*, 45:101, 1986.

Forster and Symons, "Self-cleavage of plus and minus RNAs of a virusoid and a structural model for the active sites," *Cell*, 49:211–220, 1987.

Fraley, Fornari, Kaplan, "Entrapment of a bacterial plasmid in phospholipid vesicles:potential for gene transfer," *Proc Nat'l. Acad. Sci. USA* 76:3348–3352, 1979

Freifelder, Physical Biochemistry, Second Edition, pages 238–246

Frohman, In: *PCR PROTOCOLS. A GUIDE TO METHODS AND APPLICATIONS*, Academic Press, N.Y., 1990.

Fujita, Shibuya, Hotta, Yamanishi, and Taniguchi, "Interferon-β gene regulation: Tandemly repeated sequences of a synthetic 6-bp oligomer function as a virus-inducible enhancer," *Cell*, 49:357, 1987.

Fujiwara T, Tanaka N, "Molecular surgery for human colorectal cancer with tumor suppressor p53 gene transfer", *Nippon Geka Gakkai Zasshi* July; 99(7):463–8, 1998.

Garoff H, Li K J, "Recent advances in gene expression using alphavirus vectors", *Curr Opin Biotechnol* Oct.;9(5): 464–9, 1998.

Garrido J J, Carnicero E, Lim F, Schimmang T., "Differential effects on the survival of neuronal and non-neuronal cells after infection by herpes simplex virus type 1 mutants", *J Neurovirol.* June; 5(3):280–8, 1999.

GB Application No. 2 202 328

Gefter et al., *Somatic Cell Genet.* 3:231–236, 1977.

Gerlach et al., "Construction of a plant disease resistance gene from the satellite RNA of tobacco rinspot virus," *Nature (London)*, 328:802–805, 1987.

Ghosh and Bachhawat, "Targeting of liposomes to hepatocytes," In: *Liver Diseases, Targeted Diagnosis and Therapy Using Specific Receptors and Ligands*, Wu and Wu (Eds.), Marcel Dekker, N.Y., pp 87–104, 1991.

Gilles, Morris, Oi, and Tonegawa, "A Tissue-Specific Transcription Enhancer Element is Located in the Major Intron of a Rearranged Immunoglobulin Heavy-Chain Gene," Cell, 33:717, 1983.

Gloss, Bernard, Seedorf, and Klock, "The Upstream Regulatory Region of the Human Papilloma Virus-16 Contains an E2 Protein-Independent Enhancer Which is Specific for Cervical Carcinoma Cells and Regulated by Glucocorticoid Hormones," *EMBO J.*, 6:3735, 1987.

Gnant M F, Noll L A, Irvine K R, Puhlmann M, Terrill R E, Alexander H R Jr, Bartlett D L, "Tumor-specific gene delivery using recombinant vaccinia virus in a rabbit model of liver metastases", *J Natl Cancer Inst* October 20; 91(20): 1744–50, 1999.

Gnant M F, Puhlmann M, Alexander H R Jr, Bartlett D L, "Systemic administration of a recombinant vaccinia virus expressing the cytosine deaminase gene and subsequent treatment with 5-fluorocytosine leads to tumor-specific gene expression and prolongation of survival in mice", *Cancer Res* July 15; 59(14):3396–403, 1999.

Gnant M F, Puhlmann M, Bartlett D L, Alexander H R Jr, "Regional versus systemic delivery of recombinant vaccinia virus as suicide gene therapy for murine liver metastases", *Ann Surg*, September; 230(3):352–60; discussion 360–1, 1999.

Godbout, Ingram, and Tilghman, "Fine-Structure Mapping of the Three Mouse Alpha-Fetoprotein Gene Enhancers," *Mol. Cell. Biol.*, 8:1169, 1988.

Goding, In: *Monoclonal Antibodies: Principles and Practice*, 2d ed., Orlando, Fla., Academic Press, pp. 60–61, 65–66, 71–74, 1986.

Goodbourn and Maniatis, "Overlapping positive and negative regulatory domains of the human β-Interferon gene," *Proc Natl. Acad. Sci. USA*, 85:1447, 1988.

Goodbourn, Burstein, and Maniatis, "The human β-Interferon gene enhancer is under negative control," *Cell*, 45:601, 1986.

Gopal, "Gene transfer method for transient gene expression, stable transformation, and cotransformation of suspension cell cultures," *Mol. Cell. Biol.*, 5:1188–1190, 1985.

Graham and Van Der Eb, "A new technique for the assay of infectivity of human adenovirus 5 DNA," *Virology* 52:456–467, 1973

Graham F L, Prevec L, "Methods for construction of adenovirus vectors", *Mol Biotechnol* June; 3(3):207–20, 1995.

Greene, Bohnlein, and Ballard, "HIV-1, and normal T-cell growth: Transcriptional strategies and surprises," *Immunology Today*, 10:272, 1989

Grosschedl and Baltimore, "Cell-Type Specificity of Immunoglobulin Gene Expression is Regulated by at Least Three DNA Sequence Elements," *Cell*, 41:885, 1985.

Haecker S E, Stedman H H, Balice-Gordon R J, Smith D B, Greelish J P, Mitchell M A, Wells A, Sweeney H L, Wilson J M, "In vivo expression of full-length human dystrophin from adenoviral vectors deleted of all viral genes", *Hum Gene Ther* October 1; 7(15):1907–14, 1996.

Hagio et al., "Stable transformation of sorghum cell cultures after bombardment with DNA coated microprojectiles," *Plant Cell Rep.*, 10(5):260–264, 1991.

Han, Semba, Abe, Makino, Furukawa, Fukushige, Takahashi, Sakurada, Sato, Matsuno, Nimura, Nakagawara, Horii, "Infrequent somatic mutations of the p73 gene in various human cancers," *Euro. J. Surgical Oncology*, 25:194–198, 1999.

Harland and Weintraub, "Translation of mRNA injected into *Xenopus oocytes* is specifically inhibited by antisense RNA," *J Cell Biol.* 101: 1094–1099, 1985.

Harlow and Lane, In: *Antibodies: A laboratory Manual*, Cold Spring Harbor Laboratories, Cold Spring Harbor, N.Y., 1988.

Haslinger and Karin, "Upstream Promoter Element of the Human Metallothionein-II Gene Can Act Like an Enhancer Element," *Proc Natl. Acad. Sci. U.S.A.*, 82:8572, 1985.

Hauber and Cullen, "Mutational Analysis of the Trans-Activation-Responsive Region of the Human Immunodeficiency Virus Type I Long Terminal Repeat," *J. Virology*, 62:673, 1988.

He et al., *Plant Cell Reports*, 14 (2–3): 192–196, 1994.

Hen, Borrelli, Fromental, Sassone-Corsi, and Chambon, "A Mutated Polyoma Virus Enhancer Which is Active in Undifferentiated Embryonal Carcinoma Cells is not Repressed by Adenovirus-2 E1A Products," *Nature*, 321: 249, 1986.

Hensgens et al., "Transient and stable expression of gusA fusions with rice genes in rice, barley and perennial ryegrass," *Plant Mol. Biol.*, 22(6):1101–1127, 1993.

Hermens W T, Verhaagen J, Viral vectors, tools for gene transfer in the nervous system, Prog Neurobiol July 1998; 55(4):399–432.

Herr and Clarke, "The SV40 Enhancer is Composed of Multiple Functional Elements That Can Compensate for One Another," *Cell*, 45:461, 1986.

Hirochika, Browker, and Chow, "Enhancers and Trans-Acting E2 Transcriptional Factors of Papilloma Viruses," *J. Virol.*, 61: 2599, 1987.

Hirsch, Gaugler, Deagostini-Bauzin, Bally-Cuif, and Gordis, "Identification of Positive and Negative Regulatory Elements Governing Cell-Type-Specific Expression of the Neural-Cell-Adhesion-Molecule Gene," *Mol. Cell. Biol.*, 10:1959, 1990.

Holbrook, Gulino, and Ruscetti, "cis-Acting Transcriptional Regulatory Sequences in the Gibbon Ape Leukemia Virus (GALV) Long Terminal Repeat," *Virology*, 157:211, 1987.

Holzer G W, Mayrhofer J A, Gritschenberger W, Dorner F, Falkner F G, Poxviral/retroviral chimeric vectors allow cytoplasmic production of transducing defective retroviral particles, Virology January 5, 1999; 253(1):107–14.

Horlick and Benfield, "The Upstream Muscle-Specific Enhancer of the Rat Muscle Creatine Kinase Gene is Composed of Multiple Elements," *Mol. Cell. Biol.*, 9:2396, 1989.

Hou and Lin, *Plant Physiology*, 111: 166, 1996.

Howard B D, Kalthoff H, Fong T C., "Ablation of tumor cells in vivo by direct injection of HSV-thymidine kinase retroviral vector and ganciclovir therapy", *Ann NY Acad Sci.*, June 30;880:352–65, 1999.

Huang, Ostrowski, Berard, and Hagar, "Glucocorticoid Regulation of the Ha-MuSV p21 Gene Conferred by Sequences From Mouse Mammary Tumor Virus," *Cell*, 27:245, 1981.

Huard J, Krisky D, Oligino T, Marconi P, Day C S, Watkins S C, Glorioso J C, "Gene transfer to muscle using herpes simplex virus-based vectors", *Neuromuscul Disord* July; 7(5):299–313, 1997.

Hug, Costas, Staeheli, Aebi, and Weissmann, "Organization of the Murine Mx Gene and Characterization of its Interferon- and Virus-Inducible Promoter," *Mol. Cell. Biol.*, 8:3065, 1988.

Hwang, Lim, and Chae, "Characterization of the S-Phase-Specific Transcription Regulatory Elements in a DNA-Replication-Independent Testis-Specific H2B (TH2B) Histone Gene," *Mol. Cell. Biol.*, 10: 585, 1990.

Ichimiya, Nimura, Kageyama, Takada, Sunahara, Shishikura, Nakamura, Sakiyama, Seki, Ohira, Kaneko, McKeon, Caput, Nakagawara, "A. p73 at chromosome 1p36.3 is lost in advanced stage neuroblastoma but its mutation is infrequent," *Oncogene*, 18:1061–1066, 1999.

Imagawa, Chiu, and Karin, "Transcription Factor AP-2 Mediates Induction by Two Different Signal-Transduction Pathways: Protein Kinase C and cAMP," *Cell*, 51:251, 1987.

Imai S, Nishikawa J, Takada K, "Cell-to-cell contact as an efficient mode of Epstein-Barr virus infection of diverse human epithelial cells", *J Virol* May; 72(5):4371–8, 1998.

Imbra and Karin, "Phorbol Ester Induces the Transcriptional Stimulatory Activity of the SV40 Enhancer," *Nature*, 323:555, 1986.

Imler, Lemaire, Wasvlyk, and Waslyk, "Negative Regulation Contributes to Tissue Specificity of the Immunoglobulin Heavy-Chain Enhancer," *Mol. Cell. Biol*, 7:2558, 1987.

Imperiale and Nevins, "Adenovirus 5 E2 Transcription Unit: an E1A-Inducible Promoter with an Essential Element that Functions Independently of Position or Orientation," *Mol. Cell. Biol.*, 4:875, 1984.

Innis et al., "DNA sequencing with Thermus aquaticus DNA polymerase and direct sequencing of polymerase chain reaction-amplified DNA," *Proc Natl Acad Sci USA.* 85(24):9436–9440, 1988.

Irie A, Anderegg B, Kashani-Sabet M, Ohkawa T, Suzuki T, Halks-Miller M, Curiel D T, Scanlon K J, "Therapeutic efficacy of an adenovirus-mediated anti-H-ras ribozyme in experimental bladder cancer", *Antisense Nucleic Acid Drug Dev.*, August; 9(4):341–9, 1999.

Isomura, Tamiya-Koizumi, Suzuki, Yoshida, Taniguchi, Matsuyama, Ishigaki, Sakuma, Takahashi," "RFP is a DNA binding protein associated with the nuclear matrix," *Nucleic Acids Res.*, 20:5305–5310, 1992.

Jakobovits, Smith, Jakobovits, and Capon, "A Discrete Element 3' of Human Immunodeficiency Virus 1 (HIV-1) and HIV-2 mRNA Initiation Sites Mediates Transcriptional Activation by an HIV Trans-Activator," *Mol. Cell. Biol.*, 8:2555, 1988.

Jameel and Siddiqui, "The Human Hepatitis B Virus Enhancer Requires Transacting Cellular Factor(s) for Activity," *Mol. Cell. Biol.*, 6:710, 1986.

Jaynes, Johnson, Buskin, Gartside, and Hauschka, "The Muscle Creatine Kinase Gene is Regulated by Multiple Upstream Elements, Including a Muscle-Specific Enhancer," *Mol. Cell. Biol.*, 8:62, 1988.

Johnson et al., Peptide Turn Mimetics" IN: *Biotechnology And Pharmacy*, Pezzuto et al., eds., Chapman and Hall, New York, 1993.

Johnson, Wold, and Hauschka, "Muscle Creatine Kinase Sequence Elements Regulating Skeletal and Cardiac Muscle Expression in Transgenic Mice," *Mol. Cell. Biol.*, 9:3393, 1989.

Johnston J C, Gasmi M, Lim L E, El der J H, Yee J K, Jolly D J, Campbell K P, Davidson B L, Sauter S L, "Minimum requirements for efficient transduction of dividing and nondividing cells by feline immunodeficiency virus vectors", *J Virol* June; 73(6):4991–5000, 1999.

Joyce, "RNA evolution and the origins of life," *Nature*, 338:217–244, 1989.

Kadesch and Berg, "Effects of the Position of the Simian Virus 40 Enhancer on Expression of Multiple Transcription Units in a Single Plasmid," *Mol. Cell. Biol.*, 6:2593, 1986.

Kaneda et al., "Increased expression of DNA cointroduced with nuclear protein in adult rat liver," *Science*, 243: 375–378, 1989.

Karin, Haslinger, Heguy, Dietlin, and Cooke, "Metal-Responsive Elements Act as Positive Modulators of Human Metallothionein-IIA Enhancer Activity," *Mol. Cell. Biol.*, 7:606, 1987.

Katinka, Vasseur, Montreau, Yaniv, and Blangy, "Polyoma DNA Sequences Involved in the Control of Viral Gene Expression in Murine Embryonal Carcinoma Cells," *Nature*, 290:720, 1981.

Katinka, Yaniv, Vasseur, and Blangy, "Expression of Polyoma Early Functions in Mouse Embryonal Carcinoma Cells Depends on Sequence Rearrangements in the Beginning of the Late Region," *Cell*, 20:393, 1980.

Kato et al., "Expression of hepatitis B virus surface antigen in adult rat liver. Co-introduction of DNA and nuclear protein by a simplified liposome method," *J Biol Chem.*, 266(6):3361–3364, 1991.

Kaufman P L, Jia W W, Tan J, Chen Z, Gabelt B T, Booth V, Tufaro F, Cynader M., "A perspective of gene therapy in the glaucomas", *Surv Ophthalmol.* June; 43 Suppl 1:S91-7, 1999.

Kawamoto, Makino, Niw, Sugiyama, Kimura, Anemura, Nakata, and Kakunaga, "Identification of the human β-Actin enhancer and its binding factor," *Mol. Cell. Biol.*, 8:267, 1988.

Kay M A.Hepatic gene therapy for haemophilia B. *Haemophilia*. July 1998; 4(4):389–92.

Kiledjian, Su, and Kadesch, "Identification and Characterization of Two Functional Domains Within the Murine Heavy-Chain Enhancer," *Mol. Cell. Biol.*, 8:145, 1988.

Kim and Cech, "Three dimensional model of the active site of the self-splicing rRNA precursor of Tetrahymena," *Proc. Natl. Acad. Sci. USA*, 84:8788–8792, 1987.

Klamut, Gangopadyhay, Worton, and Ray, "Molecular and Functional Analysis of the Muscle-Specific Promoter Region of the Duchenne Muscular Dystrophy Gene," *Mol. Cell. Biol.*, 10:193, 1990.

Klein et al., "High-velocity microprojectiles for delivering nucleic acids into living cells," *Nature*, 327:70–73, 1987.

Klimatcheva E, Rosenblatt JD, Planelles V, "Lentiviral vectors and gene therapy", *Front Biosci* June 1; 4:D481–96, 1999.

Knittel et al., *Plant Cell Reports*, 14(2–3):81–86, 1994.

Koch, Benoist, and Mathis, "Anatomy of a new B-Cell-specific enhancer," *Mol. Cell. Biol.*, 9:303, 1989.

Kohler and Milstein, *Eur. J. Immunol.*, 6:511–519, 1976.

Kohler and Milstein, *Nature*, 256:495–497, 1975.

Kohut M L, Davis J M, Jackson D A, Jani P, Ghaffar A, Mayer E P, Essig D A., "Exercise effects on IFN-beta expression and viral replication in lung macrophages after HSV-1 infection". *Am J Physiol.* December; 275(6 Pt 1):L1089–94, 1998.

Kooby D A, Carew J F, Halterman M W, Mack J E, Bertino J R, Blumgart L H, Federoff H J, Fong Y., "Oncolytic viral therapy for human colorectal cancer and liver metastases using a multi-mutated herpes simplex virus type-1 (G207)," *FAS EB J.* August; 13(11):1325–34, 1999.

Kovacs, Erlandsson, Boldog, Ingvarsson, Muller-Brechlin, Klein, Sumegi, "Consistent chromosome 3 deletion and loss of heterozygosity in renal cell carcinoma," *Proc. Nat'l Acad. Sci. USA*, 85:1571–1575, 1988.

Kraus et al., "Alternative promoter usage and tissue specific expression of the mouse somatostatin receptor 2 gene," *FEBS Lett.*, 428(3):165–170, 1998.

Kriegler and Botchan, In: *Eukaryotic Viral Vectors*, Y. Gluzman, ed., Cold Spring Harbor: Cold Spring Harbor Laboratory, N.Y., 1982.

Kriegler et al, In: *Cancer Cells 2/Oncogenes and Viral Genes*, Van de Woude et al. eds, Cold Spring Harbor, Cold Spring Harbor Laboratory, 1984b.

Kriegler et al, In: *Gene Expression*, D. Hamer and M. Rosenberg, eds., New York: Alan R. Liss, 1983.

Kriegler, Perez, Defay, Albert and Liu, "A Novel Form of TNF/Cachectin Is a Cell-Surface Cytotoxix Transmembrane Protein: Ramifications for the Complex Physiology of TNF," *Cell*, 53:45, 1988.

Kriegler, Perez, Hardy and Botchan, "Transformation Mediated by the SV40 T Antigens: Separation of the Overlapping SV40 Early Genes with a Retroviral Vector," *Cell*, 38:483, 1984a.

Krisky D M, Marconi P C, Oligino T J, Rouse R J, Fink D J, Cohen J B, Watkins S C, Glorioso J C, "Development of herpes simplex virus replication-defective multigene vectors for combination gene therapy applications", *Gene Ther*, November; 5(11):1517–30, 1998.

Krisky D M, Wolfe D, Goins WF, Marconi P C, Ramakrishnan R Mata M, Rouse R J, Fink D J, Glorioso J C, "Deletion of multiple immediate-early genes from herpes simplex virus reduces cytotoxicity and permits long-term gene expression in neurons", *Gene Ther.* December; 5(12):1593–603, 1998 .

Kuhl, De La Fuenta, Chaturvedi, Parinool, Ryals, Meyer, and Weissman, "Reversible Silencing of Enhancers by Sequences Derived From the Human IFN-alpha Promoter," *Cell*, 50:1057, 1987.

Kunz, Zimmerman, Heisig, and Heinrich, "Identification of the Promoter Sequences Involved in the Interleukin-6-Dependent Expression of the Rat Alpha-2-Macroglobulin Gene," *Nucl. Acids Res.*, 17:1121, 1989.

Kwoh et al., "Transcription-based amplification system and detection of amplified human immunodeficiency virus type I with a bead-based sandwich hybridization format, *Proc Natl Acad Sci USA.* 86(4):1173–1177, 1989.

Kyte and Doolittle, "A simple method for displaying the hydropathic character of a protein," *J. Mol. Biol.*, 157(1): 105–132, 1982.

Lachmann R H, Efstathiou S., "Use of herpes simplex virus type 1 for transgene expression within the nervous system," *Clin Sci (Colch).* June; 96(6):533–41, 1999.

Lareyre et al., "A 5-kilobase pair promoter fragment of the murine epididymal retinoic acid-binding protein gene drives the tissue-specific, cell-specific, and androgen-regulated expression of a foreign gene in the epididymis of transgenic mice," *J Biol Chem.*, 274(12):8282–8290, 1999.

Larsen, Harney, and Moore, "Repression Medaites Cell-Type-Specific Expression of the Rat Growth Hormone Gene," *Proc Natl. Acad Sci. USA*., 83:8283, 1986.

Laspia, Rice, and Mathews, "HIV-1 Tat Protein Increases Transcriptional Initiation and Stabilizes Elongation," *Cell*, 59:283, 1989.

Latimer, Berger, and Baumann, "Highly Conserved Upstream Regions of the .alpha.sub.1-Antitrypsin Gene in Two Mouse Species Govern Liver-Specific Expression by Different Mechanisms," *Mol. Cell. Biol.*, 10: 760, 1990.

Lazzeri, "Stable transformation of barley via direct DNA uptake. E1 Electroporation- and PEG-mediated protoplast transformation," *Methods Mol. Biol.*, 49:95-106, 1995.

Le Douarin, Zechel, Garnier, Lutz, Tora, Pierrat, Heery, Gronemeyer, Chambon, Losson, "The N-terminal part of TIF1, a putative mediator of the ligand-dependent activation function (AF-2) of nuclear receptors, is fused to B-raf in the oncogenic protein T18," *EMBO J.*, 14:2020–2033, 1995.

Lee et al., "Activation of beta3-adrenoceptors by exogenous dopamine to lower glucose uptake into rat adipocytes," *J. Auton Nerv Syst.* 74(2–3):86–90, 1997.

Lee W H, Shew J Y, Hong F D, Sery T W, Donoso L A, Young L J, Bookstein R Lee E Y. The retinoblastoma susceptibility gene encodes a nuclear phosphoprotein associated with DNA binding activity Nature. October 1987 15–21; 329(6140):642–5.

Lee et al. *Korean J. Genet.*, 11(2):65–72, 1989.

Lee, Mulligan, Berg, and Ringold, "Glucocorticoids Regulate Expression of Dihydrofolate Reductase cDNA in Mouse Mammary Tumor Virus Chimaeric Plasmids," *Nature*, 294:228, 1981.

Leibowitz G, Beattie G M, Kafri T, Cirulli V, Lopez A D, Hayek A, Levine F, "Gene transfer to human pancreatic endocrine cells using viral vectors", *Diabetes* Apr.;48(4): 745–53, 1999.

Lesch K P, "Gene transfer to the brain: emerging therapeutic strategy in psychiatry?"*Biol Psychiatry*, February 1; 45(3):247–53, 1999.

Levenson et al., "Internal ribosomal entry site-containing retroviral vectors with green fluorescent protein and drug resistance markers," *Human Gene Therapy*, 9:1233–1236, 1998.

Lin, Cross, Halden, Dragos, Toledano, and Leonard, "Delineation of an enhancerlike positive regulatory element in the interleukin-2 receptor α-chain gene," *Mol. Cell. Biol.*, 10:850, 1990.

Lo Cunsolo, Iolascon, Cavazzana, Cusano, Strigini, Mazzocco, Giordani, Massimo, De Barnardi, Conte, Tonini, "Neuroblastoma on two siblings supports the role of 1p36 deletion in tumor development," *Cancer Genetics and Cytogenetics*, 126–130, 1999.

Lott, Lovell, Naylor, Killary, "Physical and functional mapping of a tumor suppressor locus for renal cell carcinoma within chromosome 3p12," *Cancer Research*, 58: 3533–3537, 1998.

Lundstrom K, "Alphaviruses as tools in neurobiology and gene therapy", *J Recept Signal Transduct Res* January–July; 19(1–4):673–86, 1999.

Luria, Gross, Horowitz, and Givol, "Promoter enhancer elements in the rearranged alpha-chain gene of the human T-cell receptor," *EMBO J.*, 6:3307, 1987.

Lusky and Botchan, "Transient Replication of Bovine Papilloma Virus Type 1 Plasmids: cis and trans Requirements," *Proc Natl. Acad. Sci. U.S.A.*, 83:3609, 1986.

Macejak and Sarnow, "Internal initiation of translation mediated by the 5' leader of a cellular mRNA," *Nature*, 353:90–94, 1991.

Marienfeld U, Haack A, Thalheimer P, Schneider-Rasp S, Brackmann H H, Poller W, "Autoreplication' of the vector genome in recombinant adenoviral vectors with different E1 region deletions and transgenes", *Gene Ther*, June; 6(6):1101–13, 1999.

Mastrangelo M J, Maguire H C Jr, Eisenlohr L C, Laughlin C E, Monken C E, McCue P A, Kovatich A J, Lattime E C, "Intratumoral recombinant GM-CSF-encoding virus as gene therapy in patients with cutaneous melanoma", *Cancer Gene Ther* September–October; 6(5):409–22 1999.

McCabe and Martinell, *Bio-Technology*, 11(5):596–598, 1993.

McNeall, Sanchez, Gray, Chesterman, and Sleigh, "Hyperinducible Gene Expression From a Metallotionein Promoter Containing Additional Metal-Responsive Elements," *Gene*, 76:81, 1989.

Merrifield B, "Solid phase synthesis", *Science*, April 18; 232(4748):341–7 1986.

Michel and Westhof, "Modeling of the three-dimensional architecture of group I catalytic introns based on comparative sequence analysis," *J. Mol. Biol.*, 216:585–610, 1990.

Miki, Swensen, Shattuck-Eidens, Futreal, Harshman, Tavtigian, Liu, Cochran, Bennett, Ding, "A strong candidate for the breast and ovarian-cancer susceptibility gene," *Science*, 266:66–71, 1994.

Miksicek, Heber, Schmid, Danesch, Posseckert, Beato, and Schutz, "Glucocorticoid Responsiveness of the Transcriptional Enhancer of Moloney Murine Sarcoma Virus," *Cell*, 46:203, 1986.

Miller A D, Miller D G, Garcia J V, Lynch C M. "Use of retroviral vectors for gene transfer and expression," *Methods Enzymol;*217:581–99 1993.

Millikan, Ingles, Diep, Xue, Zhou, Florentine, Sparkes, Haaile, "Linkage analysis and loss of heterozygosity for chromosome 1p in familial breast cancer," *Genes, Chromosomes, and Cancer*, 25:354–361, 1999.

Miyatake S I, Tani S, Feigenbaum F, Sundaresan P, Toda H, Narumi O, Kikuchi H, Hashimoto N, Hangai M, Martuza R L, Rabkin S D. Hepatoma-specific antitumor activity of an albumin enhancer/promoter regulated herpes simplex virus in vivo. Gene Ther. 1999 April; 6(4): 564–72.

Moldawer L L, Edwards P D, Josephs M, Minter R M, Copeland E M 3rd, MacKay S L, Application of gene therapy to acute inflammatory diseases, *Shock* 1999 August ; 12(2):83–101.

Moreau, Hen, Wasylyk, Everett, Gaub, and Chambon, "The SV40 Base-Repair Repeat Has a Striking Effect on Gene Expression Both in SV40 and Other Chimeric Recombinants," *Nucl. Acids Res.*, 9:6047, 1981.

Moriuchi S, Oligino T, Krisky D, Marconi P, Fink D, Cohen J, Glorioso J C, "Enhanced tumor cell killing in the presence of ganciclovir by herpes simplex virus type 1 vector-directed coexpression of human tumor necrosis factor-alpha and herpes simplex virus thymidine kinase", *Cancer Res*, December 15; 58(24):5731–7, 1998.

Morrison M D, Onions D E, Nicolson L, "Complete DNA sequence of canine adenovirus type 1", *J Gen Virol*, April; 78 (Pt 4):873–8, 1997.

Musesing, Smith, and Capon, "Regulation of mRNA Accumulation by a Human Immunodeficiency Virus Trans-Activator Protein," *Cell*, 48:691, 1987.

Naldini L, Blomer U, Gage F H, Trono D, Verma I M, "Efficient transfer, integration, and sustained long-term expression of the transgene in adult rat brains injected with a lentiviral vector", *Proc Natl Acad Sci USA* October 15; 93(21):11382–8, 1996.

Neumann G, Kawaoka Y, "Genetic engineering of influenza and other negative-strand RNA viruses containing segmented genomes", *Adv Virus Res*, 53:265–300, 1999.

Ng, Gunning, Liu, Leavitt, and Kedes, "Regulation of the human β-Actin promoter by upstream and intron domains," *Nuc. Acids Res.*, 17:601, 1989.

Nicolau and Sene, "Liposome-mediated DNA transfer in eukaryotic cells: dependence of the transfer efficiency upon the type of liposomes used and the host cell cycle stage," *Biochim. Biophys. Acta* 721:185–190, 1982.

Nicolau et al. "Liposomes as carriers for in vivo gene transfer and expression," *Methods Enzymol.*, 149:157-176, 1987

Nomoto et al., "Cloning and characterization of the alternative promoter regions of the human LIMK2 gene responsible for alternative transcripts with tissue-specific expression," *Gene*, 236(2):259–271, 1999.

Ogunbiyi, Goodfellow, Gagliardi, Swanson, Birnbaum, Fleshman, Kodner, Moley, "Prognostic value of chromosome 1p allelic loss in colon cancer," *Gastroenterology*, 113:761–766, 1997.

Omitz, Hammer, Davison, Brinster, and Palmiter, "Promoter and Enhancer Elements From the Rat Elastase I Gene Function Independently of Each Other and of Heterologous Enhancers," Mol. Cell. Biol. 7:3466, 1987.

Ondek, Sheppard, and Herr, "Discrete Elements Within the SV40 Enhancer Region Display Different Cell-Specific Enhancer Activities," *EMBO J.*, 6:1017, 1987.

Palmiter, Chen, and Brinster, "Differential Regulation of Metallothionein-Thymidine Kinase Fusion Genes in Transgenic Mice and Their Offspring," *Cell*, 29:701, 1982.

Pandolfi, "P M L, PLZF, and NPM genes in the molecular pathogenesis of acute promyelocytic leukemia, *Haematologica*, 81:472–482, 1996.

PCT Application No. PCT/US87/00880
PCT Application No. PCT/US89/01025
PCT Application No. WO 94/09699
PCT Application No. WO 95/06128
PCT Application WO 88/10315
PCT Application WO 89/06700
PCT Application WO 90/07641
PCT Patent Application No. WO 9217598

Pech, Rao, Robbins, and Aaronson, "Functional Identification of Regulatory Elements Within the Promoter Region of Platelet-Derived Growth Factor 2," *Mol. Cell. Biol.*, 9:396, 1989.

Pelletier and Sonenberg, "Internal initiation of translation of eukaryotic mRNA directed by a sequence derived from poliovirus RNA," *Nature,* 334:320–325, 1988.

Perales et al., "Gene transfer in vivo: sustained expression and regulation of genes introduced into the liver by receptor-targeted uptake," *Proc. Natl. Acad. Sci. USA,* 91:4086–4090, 1994.

Perez-Stable and Constantini, "Roles of Fetal .gamma.-globin Promoter Elements and the Adult .beta.-globin 3' Enhancer in the Stage-Specific Expression of Globin Genes," *Mol. Cell. Biol.,* 10:1116, 1990.

Petrof B J, "Respiratory muscles as a target for adenovirus-mediated gene therapy", *Eur Respir J* February; 11(2): 492–7, 1998.

Picard and Schaffner, "A lymphocyte-specific enhancer in the mouse immunoglobulin kappa gene," *Nature,* 307:83, 1984.

Pignon J M, Vinatier I, Fanen P, Jonveaux P, Tournilhac O, Imbert M, Rochant H, Goossens M., "Exhaustive analysis of the P53 gene coding sequence by denaturing gradient gel electrophoresis: application to the detection of point mutations in acute leukemias," *Hum Mutat;* 3(2):126–32, 1994.

Pinkert, Ornitz, Brinster, and Palmiter, "An Albumin Enhancer Located 10 kb Upstream Functions Along With its Promoter to Direct Efficient, Liver-Specific Expression in Transgenic Mice," *Genes and Dev.,* 1:268, 1987.

Ponta, Kennedy, Skroch, Hynes, and Groner, "Hormonal Response Region in the Mouse Mammary Tumor Virus Long Terminal Repeat Can Be Dissociated From the Proviral Promoter and Has Enhancer Properties," *Proc. Natl. Acad. Sci. U.S.A.,* 82:1020, 1985.

Porton, Zaller, Lieberson, and Eckhardt, "Immunoglobulin Heavy-Chain Enhancer is Required to Maintain Transfected .gamma.2A Gene Expression in a pre-B-cell Line," *Mol. Cell. Biol.,* 10:1076, 1990.

Potrykus et al., *Mol. Gen. Genet.,* 199:183–188, 1985.

Potter et al., "Enhancer-dependent expression of human k immunoglobulin genes introduced into mouse pre-B lymphocytes by electroporation," *Proc Nat'l Acad. Sci. USA,* 81:7161–7165, 1984.

Queen and Baltimore, "Immunoglobulin Gene Transcription is Activated by Downstream Sequence Elements," *Cell,* 35:741, 1983.

Quinn, Farina, Gardner, Krutzsch, and Levens, "Multiple Components are Required for Sequence Recognition of the API Site in the Gibbon Ape Leukemia Virus Enhancer," *Mol. Cell. Biol.,* 9:4713, 1989.

Rabinovitch A, Suarez-Pinzon W, Strynadka K, Ju. Q, Edelstein D, Brownlee M, Korbutt G S, Rajotte RV, "Transfection of human pancreatic islets with an anti-apoptotic gene (bcl-2) protects beta-cells from cytokine-induced destruction", *Diabetes.* June; 48(6):1223–9, 1999.

Ragnarsson, Eiriksdottir, Johsnnsdottir, Jonasson, Egilsson, Ingvarsson, "Loss of heterozygosity at chromosome 1p in different solid human tumors: association with survival," *British Journal of Cancer,* 79:1468–1474, 1999.

Rasio, Murakumo, Robbins, Roth, Silver, Negrini, Schmidt, Burczak, Fishel, Croce, "Characterization of the human homologue of RAD54: a gene located on chromosome 1p32 at a region of high loss of heterozygousity in breast tumors," *Cancer Research,* 57:2378–2383, 1997.

Reddy P S, Idamakanti N, Zakhartchouk A N, Baxi M K, Lee J B, Pyne C, Babiuk L A, Tikoo S K, "Nucleotide sequence, genome organization, and transcription map of bovine adenovirus type 3", *J Virol,* February; 72(2): 1394–402, 1998.

Redondo, Hata, Brocklehurst, and Krangel, "A T-cell-specific transcriptional enhancer within the human T-cell receptor Δ Locus," *Science,* 247:1225, 1990.

Reinhold-Hurek and Shub, "Self-splicing introns in tRNA genes of widely divergent bacteria," *Nature,* 357:173–176, 1992.

Reisman and Rotter, "Induced Expression From the Moloney Murine Leukemia Virus Long Terminal Repeat During Differentiation of Human Myeloid Cells is Mediated Through its Transcriptional Enhancer," *Mol. Cell. Biol.,* 9:3571, 1989.

Resendez Jr., Wooden, and Lee, "Identification of Highly Conserved Regulatory Domains and Protein-Binding Sites in the Promoters of the Rat and Human Genes Encoding the Stress-Inducible 78-kilodalton Glucose-Regulated Protein," *Mol. Cell. Biol.,* 8:4579, 1988.

Rhodes et al., "Transformation of maize by electroporation of embryos," *Methods Mol. Biol.,* 55:121–131, 1995.

Ripe, Lorenzen, Brenner, and Breindl, "Regulatory Elements in the 5' Flanking Region and the First Intron Contribute to Transcriptional Control of the Mouse alpha-1-type Collagen Gene," *Mol. Cell. Biol.,* 9:2224, 1989.

Rippe et al., "DNA-mediated gene transfer into adult rat hepatocytes in primary culture," *Mol. Cell Biol.,* 10:689–695, 1990.

Ritala et al., "Fertile transgenic barley to particle bombardment of immature embryos," *Plant Mol. Biol,* 24(2): 317–325, 1994.

Rittling, Coutinho, Amarm, and Kolbe, "AP-1/jun-binding Sites Mediate Serum Inducibility of the Human Vimentin Promoter," *Nuc. Acids Res.,* 17:1619, 1989.

Robbins P B, Skelton D C, Yu X J, Halene S, Leonard E H, Kohn D B, "Consistent, persistent expression from modified retroviral vectors in murine hematopoietic stem cells," *Proc Natl Acad Sci USA* Aug. 18;95(17):10182–7 1998.

Robbins P D, Ghivizzani S C, "Viral vectors for gene therapy", *Pharmacol Ther* 1998 October; 80(1):35.–47.

Robbins P D, Tahara H, Ghivizzani S C, "Viral vectors for gene therapy", *Trends Biotechnol* 1998 January; 16(1): 35–40.

Rosen, Sodroski, and Haseltine, "The Location of cis-acting Regulatory Sequences in the Human T-Cell Lymphotropic Virus Type III (HTLV-111/L AV) Long Terminal Repeat," *Cell,* 41:813, 1988.

Sakai, Helms, Carlstedt-Duke, Gustafsson, Rottman, and Yamamoto, "Hormone-Mediated Repression: A Negative Glucocorticoid-Response Element From the Bovine Prolactin Gene," *Genes and Dev.,* 2:1144, 1988.

Sambrook et al., *In: Molecular Cloning: A Laboratory Manual,* Vol. 1, Cold Spring Harbor Laboratory Press, Cold Spring Harbor, N.Y., Ch. 7,7.19–17.29, 1989.

Sanchez, El-Naggar, Pathak, Killary, "A tumor suppressor locus within 3p14-p12 mediates rapid cell death of renal cell carcinom in vivo.," *Proc. Nat'l Acad. Sci.,* 91:3383–3387, 1994.

Sarver et al., "Ribozymes as potential anti-HIV-1 therapeutic agents," *Science,* 247:1222–1225, 1990.

Satake, Furukawa, and Ito, "Biological Activities of Oligonucleotides Spanning the F9 Point Mutation Within the Enhancer Region of Polyoma Virus DNA," *J. Virology,* 62:970, 1988.

Saurin, Borden, Boddy, Freemont, "Does this have a familiar RING?" *TIBS,* 21:208–214, 1996.

Sawai K, Ikeda H, Ishizu A, Meruelo D, "Reducing cytotoxicity induced by Sindbis viral vectors", *Mol Genet Metab,* May;67(1):36–42, 1999.

Scanlon et al., "Ribozyme-mediated cleavages of c-fos mRNA reduce gene expression of DNA synthesis enzymes and metallothionein," *Proc Natl Acad Sci USA,* 88:10591–10595, 1991.

Schaffner, Schirm, Muller-Baden, Wever, and Schaffner, "Redundancy of Information in Enhancers as a Principle of Mammalian Transcription Control," *J. Mol. Biol.,* 201:81, 1988.

Searle, Stuart, and Palmiter, "Building a Metal-Responsive Promoter With Synthetic Regulatory Elements," *Mol. Cell. Biol.,* 5:1480, 1985.

Sharp and Marciniak, "HIV Tar: an RNA Enhancer?," *Cell,* 59:229, 1989.

Shaul and Ben-Levy, "Multiple Nuclear Proteins in Liver Cells are Bound to Hepatitis B Virus Enhancer Element and its Upstream Sequences," *EMBO J.,* 6:1913, 1987.

Sherman, Basta, Moore, Brown, and Ting, "Class II box consensus sequences in the HLA-DR α Gene: Transcriptional function and interaction with nuclear proteins," *Mol. Cell. Biol.,* 9:50, 1989.

Singsit et al., "Expression of a Bacillus thuringiensis cryIA (c) gene in transgenic peanut plants and its efficacy against lesser cornstalk borer," *Transgenic Res.,* 6:169–76, 1997.

Sleigh and Lockett, "SV40 Enhancer Activation During Retinoic-Acid-Induced Differentiation of F9 Embryonal Carcinoma Cells," *J EMBO,* 4:3831, 1985.

Smith G M, "Adenovirus-mediated gene transfer to treat neurologic disease", *Arch Neurol* August; 55(8):1061–4, 1998.

Spandau and Lee, "Trans-Activation of Viral Enhancers by the Hepatitis B Virus X Protein," *J. Virology,* 62:427, 1988.

Stephens and Hentschel, "The Bovine Papilloma Virus Genome and its Uses as a Eukaryotic Vector," *Biochem. J.,* 248:1, 1987.

Stewart A K, Lassam N J, Quirt I C, Bailey D J, Rotstein L E, Krajden M, Dessureault S, Gallinger S, Cappe D, Wan Y, Addison C L, Moen R C, Gauldie J, Graham F L, "Adenovector-mediated gene delivery of interleukin-2 in metastatic breast cancer and melanoma: results of a phase 1 clinical trial", *Gene Ther,* March; 6(3):350–63, 1999.

Stewart and Young, "Solid Phase Peptide Synthesis", 2d. ed., Pierce Chemical Co.,1984.

Stuart, Searle, and Palmiter, "Identification of Multiple Metal Regulatory Elements in Mouse Metallothionein-I Promoter by Assaying Synthetic Sequences," *Nature,* 317:828, 1985.

Sullivan and Peterlin, "Transcriptional Enhancers in the HLA-DQ Subregion," *Mol. Cell. Biol.,* 7:3315, 1987.

Suzuki T, Piche A, Kasono K, Xiang J, Gomez-Navarro J, Moriuchi S, Krisky D M, Oligino T, Glorioso J C, Curiel T J, Curiel D T, "Efficient gene delivery into epstein-barr virus (EBV)-transformed human B cells mediated by replication-defective herpes simplex virus-1 (HSV-1): A gene therapy model for EBV-related B cell malignancy", *Biochem Biophys Res Commun,* Nov. 27;252(3):686–90, 1998.

Swartzendruber and Lehman, "Neoplastic Differentiation: Interaction of Simian Virus 40 and Polyoma Virus with Murine Teratocarcinoma Cells," *J. Cell. Physiology,* 85:179, 1975.

Szabo. and King, "Inherited breast and ovarian cancer," *Human Molecular Genetics,* 4:1811–1817, 1995.

Takebe, Seiki, Fujisawa, Hoy, Yokota, Arai, Yoshida, and Arai, "SR.alpha. Promoter: An Efficient and Versatile Mammalian cDNA Expression System Composed of the Simian Virus 40 Early Promoter and the R-U5 Segment of Human T-Cell Leukemia Virus Type 1 Long Terminal Repeat," *Mol. Cell. Biol.,* 8:466, 1988.

Tam et al., *J. Am. Chem. Soc.,* 105:6442, 1983.

Tanaka, Yanoshita, Konishi, Oshimura, Maeda, Mori, Miyaki, "Suppresson of tumorigenicity in human colon carcinoma cells by introduction of normal chromosome 1p36 region," *Oncogene,* 8:2253–2258, 1993.

Tavernier, Gheysen, Duerinck, Can Der Heyden, and Fiers, "Deletion Mapping of the Inducible Promoter of Human IFN-beta Gene," *Nature,* 301:634, 1983.

Thiesen, Bosze, Henry, and Charnay, "A DNA Element Responsible for the Different Tissue Specificities of Friend and Moloney Retroviral Enhancers," *J. Virology,* 62:614, 1988.

Timiryasova T M, Chen B, Haghighat P, Fodor I, "Vaccinia virus-mediated expression of wild-type p53 suppresses glioma cell growth and induces apoptosis", *Int J Oncol* May;14(5):845–54, 1999.

Timiryasova T M, Li J, Chen B, Chong D, Langridge W H, Gridley D S, Fodor I, "Antitumor effect of vaccinia virus in glioma model", *Oncol Res;*11(3):133–44, 1999.

Tomes et al., "Transgenic tobacco plants and their progeny derived by microprojectile bombardment of tobacco leaves," *Plant Mol. Biol.,* 14:261–8, 1990.

Torbet et al., "Transformation of oat using mature embryo-derived tissue cultures," *Crop Science,* 38:226–231, 1998.

Torbet et al., "Use of paromomycin as a selective agent for oat transformation," *Plant Cell Reports,* 14:635–640, 1995.

Tronche, Rollier, Bach, Weiss, and Yaniv, "The Rat Albumin Promoter: Cooperation with Upstream Elements is Required When Binding of APF/HNF 1 to the Proximal Element is Partially Impaired by Mutation or Bacterial Methylation," *Mol. Cell. Biol.,* 9:4759, 1989.

Tronche, Rollier, Herbomel, Bach, Cereghini, Weiss, and Yaniv, "Anatomy of the Rat Albumin Promoter," *Mol. Biol. Med.,* 7:173, 1990.

Trudel and Constantini, "A 3' Enhancer Contributes to the Stage-Specific Expression of the Human Beta-Globin Gene," *Genes and Dev.,* 6:954, 1987.

Tsukada et al., *Plant Cell Physiol.,* 30(4)599–604, 1989.

Tsukamato, Ito, Yoshimoto, Kasumi, Akiyama, Sakamoto, Nakamura, Emi, "Allelic loss on chromosome 1p is associated with progression and lymph node metastasis of primary breast carcinoma," *Cancer,* 82:317–322, 1998.

Tsumaki et al., "Modular arrangement of cartilage- and neural tissue-specific cis-elements in the mouse alpha2 (XI) collagen promoter," *J Biol Chem.* 273(36):22861–22864, 1998.

Tur-Kaspa, Teicher, Levine, Skoultchi and Shafritz, "Use of. electroporation to introduce biologically active foreign genes into primary rat hepatocytes," *Mol. Cell Biol.,* 6:716–718, 1986.

Tyndall, La Mantia, Thacker, Favaloro, and Kamen, "A Region of the Polyoma Virus Genome Between the Replication Origin and Late Protein-Coding Sequences is Required in cis for Both Early Gene Expression and Viral DNA Replication," *Nuc. Acids. Res.,* 9:6231, 1981.

U.S. Pat. No. 4,196,265
U.S. Pat. No. 4,554,101
U.S. Pat. No. 4,683,195
U.S. Pat. No. 4,683,202
U.S. Pat. No. 4,683,202

U.S. Pat. No. 4,684,611
U.S. Pat. No. 4,800,159
U.S. Pat. No. 4,873,191
U.S. Pat. No. 4,879,236
U.S. Pat. No. 4,883,750
U.S. Pat. No. 4,952,500
U.S. Pat. No. 5,217,879
U.S. Pat. No. 5,279,721
U.S. Pat. No. 5,302,523
U.S. Pat. No. 5,322,783
U.S. Pat. No. 5,354,855
U.S. Pat. No. 5,384,253
U.S. Pat. No. 5,506,138
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610
U.S. Pat. No. 5,670,488
U.S. Pat. No. 5,702,932
U.S. Pat. No. 5,736,524
U.S. Pat. No. 5,739,018
U.S. Pat. No. 5,780,448
U.S. Pat. No. 5,789,215
U.S. Pat. No. 5,824,544
U.S. Pat. No. 5,830,725
U.S. Pat. No. 5,849,304
U.S. Pat. No. 5,851,826
U.S. Pat. No. 5,858,744
U.S. Pat. No. 5,871,982
U.S. Pat. No. 5,871,983
U.S. Pat. No. 5,871,986
U.S. Pat. No. 5,879,934
U.S. Pat. No. 5,888,502
U.S. Pat. No. 5,925,565
U.S. Pat. No. 5,928,906
U.S. Pat. No. 5,932,210
U.S. Pat. No. 5,935,819
U.S. Pat. No. 5,945,100
U.S. Pat. No. 5,955,331
U.S. Pat. No. 5,981,274
U.S. Pat. No. 5,994,136
U.S. Pat. No. 5,994,624
U.S. Pat. No. 6,013,515
Van Eck et al, *Plant Cell Reports,* 14(5):299–304, 1995.
Vanderkwaak T J, Wang M, Gomez-Navarro J, Rancourt C, Dmitriev I, Krasnykh V, Barnes M, Siegal G P, Alvarez R, Curiel D T, "An advanced generation of adenoviral vectors selectively enhances gene transfer for ovarian cancer gene therapy approaches", *Gynecol Oncol*, August; 74(2): 227–34, 1999.
Vannice and Levinson, "Properties of the Human Hepatitis B Virus Enhancer: Position Effects and Cell-Type Non-specificity," *J. Virology,* 62:1305, 1988.
Vasseur, Kress, Montreau, and Blangy, "Isolation and Characterization of Polyoma Virus Mutants Able to Develop in Multipotential Murine Embryonal Carcinoma Cells," *Proc Natl. Acad. Sci. U.S.A., 77:1068, 1980.
Vogelstein B. "Cancer. A deadly inheritance," *Nature.* 348 (6303) 681–682, 1990.
Wagner et al., *Science,* 260:1510–1513, 1990.
Walker et al., "Strand displacement amplification—an isothermal, in vitro DNA amplification technique," *Nucleic Acids Res.* 20(7): 1691–1696, 1992.
Wang and Calame, "SV40 Enhancer-Binding Factors are Required at the Establishment but not the Maintenance Step of Enhancer-Dependent Transcriptional Activation," *Cell,* 47:241, 1986.
Wang M, Rancourt C, Navarro J G, Krisky D, Marconi P, Oligino T, Alvarez R D, Siegal G P, Glorioso J C, Curiel D T, "High-efficacy thymidine kinase gene transfer to ovarian cancer cell lines mediated by herpes simplex virus type 1 vector", *Gynecol Oncol* November; 71(2):278–87, 1998.
Weber, De Villiers, and Schaffner, "An SV40 Enhancer Trap Incorporates Exogenous Enhancers or Generates Enhancers From its Own Sequences," *Cell,* 36:983, 1984.
Weihl C, Macdonald R L, Stoodley M, Luders J, Lin G., "Gene therapy for cerebrovascular disease," *Neurosurgery,* February;44(2):239–52; discussion 253, 1999.
Weinberg et al., "Positive and negative controls on cell growth," *Biochemistry,* 28:8263–8269, 1989.
Weinberger, Jat, and Sharp, "Localization of a Repressive Sequence Contributing to B-cell Specificity in the Immunoglobulin Heavy-Chain Enhancer," Mol. Cell. Biol., 8:988, 1984.
White S M, Renda M, Nam N Y, Klimatcheva E, Zhu Y, Fisk J, Halterman M, Rimel B J, Federoff H, Pandya S, Rosenblatt J D, Planelles V, "Lentivirus vectors using human and simian immunodeficiency virus elements", *J Virol,* April; 73(4):2832–40, 1999.
Wilson J M, "When bad gene transfer is good", *J Clin Invest,* December 1; 98(11):2435, 1996.
Winoto and Baltimore, $\alpha$-$\beta$-lineage-specific expression of the $\alpha$ T-cell receptor gene by nearby silencers," *Cell,* 59:649, 1989.
Wong et al., "Appearance of $\beta$-lactamase activity in animal cells upon liposome mediated gene transfer," *Gene,* 10:87–94, 1980.
Wu and Wallace, "The ligation amplification reaction (LAR)—amplification of specific DNA sequences using sequential rounds of template-dependent ligation," *Genomics,* 4:560–569, 1989.
Wu and Wu, "Receptor-mediated in vitro gene transfections by a soluble DNA carrier system," *J. Biol. Chem.,* 262: 4429–4432, 1987.
Wu et al., "Promoter-dependent tissue-specific expressive nature of imprinting gene, insulin-like growth factor II, in human tissues," *Biochem Biophys Res Commun.* 233(1): 221–226, 1997.
Wu G Y, "Recent advances in gene therapy of GI and liver diseases", *Chung Hua Min Kuo Hsiao Erh Ko I Hsueh Hui Tsa Chih,* September–October; 39(5):297–300, 1998.
Yamada M, Oligino T, Mata M, Goss J R, Glorioso J C, Fink D J, "Herpes simplex virus vector-mediated expression of Bcl-2 prevents 6-hydroxydopamine-induced degeneration of neurons in the substantia nigra in vivo", *Proc Natl Acad Sci USA* March 30; 96(7):4078–83, 1999.
Yang, Burkholder, Roberts, Martinell and McCabe, "In vivo and in vitro gene transfer to mammalian somatic cells by particle bombardment," *Proc Nat'l Acad Sci. USA,* 87:9568–9572, 1990.
Yeung S, Bockhold K, Tufaro F. Efficient infection of mature skeletal muscle with herpes simplex virus vectors by using dextran sulfate as a co-receptor. *Gene Ther.,* September; 6(9): 1536–44, 1999.
Yoon S S, Carroll N M, Chiocca E A, Tanabe K K, "Influence of p53 on herpes simplex virus type 1 vectors for cancer gene therapy", *J Gastrointest Surg.* January–February; 3(1):34–48, 1999.

Yutzey, Kline, and Konieczny, "An Internal Regulatory Element Controls Troponin I Gene Expression," *Mol. Cell. Biol.*, 9:1397, 1989.

Zhao-Emonet J C, Boyer O, Cohen J L, Klatzmann D., "Deletional and mutational analyses of the human CD4 gene promoter: characterization of a minimal tissue-specific promoter", *Biochim Biophys Acta*, November 8; 1442(2–3): 109–19, 1998.

Zheng B J, Graham F L, Prevec L, "Transcription units of E1a, E1b and pIX regions of bovine adenovirus type 3", *J Gen Virol* July; 80 ( Pt 7):1735–42, 1999.

Zhou, Broxmyer, Cooper, Harrington, and Srivastava "Adeno-associated virus 2 mediated gene transfer in murine hematopoietic cells, Exp. Hematol (N.Y.), 21:928–933, 1993.

What is claimed is:

1. A method for suppressing growth of a cancer cell comprising directly contacting said cell with an expression cassette comprising a polynucleotide encoding a polypeptide having the sequence of SEQ ID NO:1 or SEQ ID NO:2, wherein said polynucleotide is under the control of a promoter operable in eukaryotic cells.

2. The method of claim 1, wherein said promoter is heterologous to the polynucleotide sequence.

3. The method of claim 2, wherein said promoter is selected from the group consisting of hsp68, SV40, CMV, MKC, GAL4$_{UAS}$, HSV and β-actin.

4. The method of claim 2, wherein said promoter is a tissue specific promoter.

5. The method of claim 2, wherein said promoter is an inducible promoter.

6. The method of claim 2, wherein said expression cassette is contained in a viral vector.

7. The method of claim 6, wherein said viral vector is selected from the group consisting of a retroviral vector, an adenoviral vector, and adeno-associated viral vector, a vaccinia viral vector, and a herpesviral vector.

8. The method of claim 1, wherein said expression cassette further comprises a polyadenylation signal.

9. The method of claim 1, wherein said expression cassette comprises a second polynucleotide encoding a second polypeptide.

10. A method for altering the phenotype of a tumor cell comprising the step of directly contacting the cell with a nucleic acid comprising (i) a region encoding a tumor suppressor designated CAR-1 having the sequence of SEQ ID NO:1 or SEQ ID NO :2 and (ii) a promoter active in said tumor cell, wherein said promoter is operably linked to the region encoding said tumor suppressor, under conditions permitting the uptake of said nucleic acid by said tumor cell.

11. The method of claim 10, wherein said tumor cell is derived from a tissue selected from the group consisting of brain, lung, liver, spleen, kidney, lymph node, small intestine, blood cells, pancreas, colon, stomach, breast, endometrium, prostate, testicle, ovary, skin, head and neck, esophagus, bone marrow and blood tissue.

12. The method of claim 11, wherein the phenotype is selected from the group consisting of apoptosis, angiogenesis, proliferation, migration, contact inhibition, soft agar growth or cell cycling.

13. The method of claim 11, wherein said nucleic acid is encapsulated in a liposome.

14. The method of claim 11, wherein said nucleic acid is a viral vector selected from the group consisting of retrovirus, adenovirus, adeno-associated virus, vaccinia virus and herpesvirus.

15. The method of claim 14, wherein said nucleic acid is encapsulated in a viral particle.

16. A method for treating a subject with cancer comprising the step of directly administering to a cancer cell in said subject a nucleic acid comprising (i) a region encoding a tumor suppressor designated CAR-1 having the sequence of SEQ ID NO:1 or SEQ ID NO:2 and (ii) a promoter active in eukaryotic cells, wherein said promoter is operably linked to the region encoding said tumor suppressor.

17. The method of claim 16, wherein said cancer cell is derived from a tissue selected from the group consisting of brain, lung, liver, spleen, kidney, lymph node, small intestine, blood cells, pancreas, colon, stomach, breast, endometrium, prostate, testicle, ovary, skin, head and neck, esophagus, bone marrow and blood tissue.

18. The method of claim 16, wherein the subject is a human.

* * * * *

SEQUENCE LISTING

```
<160> NUMBER OF SEQ ID NOS: 9

<210> SEQ ID NO 1
<211> LENGTH: 475
<212> TYPE: PRT
<213> ORGANISM: Human

<400> SEQUENCE: 1

Met Ala Cys Ser Leu Lys Asp Glu Leu Leu Cys Ser Ile Cys Leu Ser
  1               5                  10                  15

Ile Tyr Gln Asp Pro Val Ser Leu Gly Cys Glu His Tyr Phe Cys Arg
             20                  25                  30

Arg Cys Ile Thr Glu His Trp Val Arg Gln Ala Gln Gly Ala Arg
         35                  40                  45

Asp Cys Pro Glu Cys Arg Arg Thr Phe Ala Glu Pro Ala Leu Ala Pro
     50                  55                  60

Ser Leu Lys Leu Ala Asn Ile Val Glu Arg Tyr Ser Ser Phe Pro Leu
 65                  70                  75                  80

Asp Ala Ile Leu Asn Ala Arg Arg Ala Ala Arg Pro Cys Gln Ala His
                 85                  90                  95

Asp Lys Val Lys Leu Phe Cys Leu Thr Asp Arg Ala Leu Leu Cys Phe
                100                 105                 110

Phe Cys Asp Glu Pro Ala Leu His Glu Gln His Gln Val Thr Gly Ile
            115                 120                 125

Asp Asp Ala Phe Asp Glu Leu Gln Arg Glu Leu Lys Asp Gln Leu Gln
    130                 135                 140

Ala Leu Gln Asp Ser Glu Arg Glu His Thr Glu Ala Leu Gln Leu Leu
145                 150                 155                 160

Lys Arg Gln Leu Ala Glu Thr Lys Ser Ser Thr Lys Ser Leu Arg Thr
                165                 170                 175

Thr Ile Gly Glu Ala Phe Glu Arg Leu His Arg Leu Leu Arg Glu Arg
            180                 185                 190

Gln Lys Ala Met Leu Glu Glu Leu Glu Ala Asp Thr Ala Arg Thr Leu
        195                 200                 205

Thr Asp Ile Glu Gln Lys Val Gln Arg Tyr Ser Gln Gln Leu Arg Lys
    210                 215                 220

Val Gln Glu Gly Ala Gln Ile Leu Gln Glu Arg Leu Ala Glu Thr Asp
225                 230                 235                 240

Arg His Thr Phe Leu Ala Gly Val Ala Ser Leu Ser Glu Arg Leu Lys
                245                 250                 255

Gly Lys Ile His Glu Thr Asn Leu Thr Tyr Glu Asp Phe Pro Thr Ser
            260                 265                 270

Lys Tyr Thr Gly Pro Leu Gln Tyr Thr Ile Trp Lys Ser Leu Phe Gln
        275                 280                 285

Asp Ile His Pro Val Pro Ala Ala Leu Thr Leu Asp Pro Gly Thr Ala
    290                 295                 300
```

-continued

His Gln Arg Leu Ile Leu Ser Asp Asp Cys Thr Ile Val Ala Tyr Gly
305                 310                 315                 320

Asn Leu His Pro Gln Pro Leu Gln Asp Ser Pro Lys Arg Phe Asp Val
                325                 330                 335

Glu Val Ser Val Leu Gly Ser Glu Ala Phe Ser Ser Gly Val His Tyr
            340                 345                 350

Trp Glu Val Val Ala Glu Lys Thr Gln Trp Val Ile Gly Leu Ala
        355                 360                 365

His Glu Ala Ala Ser Arg Lys Gly Ser Ile Gln Ile Gln Pro Ser Arg
    370                 375                 380

Gly Phe Tyr Cys Ile Val Met His Asp Gly Asn Gln Tyr Ser Ala Cys
385                 390                 395                 400

Thr Glu Pro Trp Thr Arg Leu Asn Val Arg Asp Lys Leu Asp Lys Val
                405                 410                 415

Gly Val Phe Leu Asp Tyr Asp Gln Gly Leu Leu Ile Phe Tyr Asn Ala
            420                 425                 430

Asp Asp Met Ser Trp Leu Tyr Thr Phe Arg Glu Lys Phe Pro Gly Lys
        435                 440                 445

Leu Cys Ser Tyr Phe Ser Pro Gly Gln Ser His Ala Asn Gly Lys Asn
    450                 455                 460

Val Gln Pro Leu Arg Ile Asn Thr Val Arg Ile
465                 470                 475

<210> SEQ ID NO 2
<211> LENGTH: 304
<212> TYPE: PRT
<213> ORGANISM: Human

<400> SEQUENCE: 2

Met Ala Cys Ser Leu Lys Asp Glu Leu Leu Cys Ser Ile Cys Leu Ser
1               5                   10                  15

Ile Tyr Gln Asp Pro Val Ser Leu Gly Cys Glu His Tyr Phe Cys Arg
                20                  25                  30

Arg Cys Ile Thr Glu His Trp Val Arg Gln Glu Ala Gln Gly Ala Arg
            35                  40                  45

Asp Cys Pro Glu Cys Arg Arg Thr Phe Ala Glu Pro Ala Leu Ala Pro
    50                  55                  60

Ser Leu Lys Leu Ala Asn Ile Val Glu Arg Tyr Ser Ser Phe Pro Leu
65                  70                  75                  80

Asp Ala Ile Leu Asn Ala Arg Arg Ala Ala Arg Pro Cys Gln Ala His
                85                  90                  95

Asp Lys Val Lys Leu Phe Cys Leu Thr Asp Arg Ala Leu Leu Cys Phe
            100                 105                 110

Phe Cys Asp Glu Pro Ala Leu His Glu Gln His Gln Val Thr Gly Ile
    115                 120                 125

Asp Asp Ala Phe Asp Glu Leu Gln Arg Glu Leu Lys Asp Gln Leu Gln
130                 135                 140

Ala Leu Gln Asp Ser Glu Arg Glu His Thr Glu Ala Leu Gln Leu Leu
145                 150                 155                 160

Lys Arg Gln Leu Ala Glu Thr Lys Ser Ser Thr Lys Ser Leu Arg Thr
                165                 170                 175

Thr Ile Gly Glu Ala Phe Glu Arg Leu His Arg Leu Arg Glu Arg
            180                 185                 190

Gln Lys Ala Met Leu Glu Glu Leu Glu Ala Asp Thr Ala Arg Thr Leu

```
                195                 200                 205
Thr Asp Ile Glu Gln Lys Val Gln Arg Tyr Ser Gln Gln Leu Arg Lys
    210                 215                 220

Val Gln Glu Gly Ala Gln Ile Leu Gln Glu Arg Leu Ala Glu Thr Asp
225                 230                 235                 240

Arg His Thr Phe Leu Ala Gly Val Ala Ser Leu Ser Glu Arg Ala Ser
            245                 250                 255

Arg Pro Asn Pro Gly Pro Gly His Ser Pro Pro Ala Pro Asp Pro Val
            260                 265                 270

Gly Arg Leu His His Cys Gly Leu Arg Gln Leu Ala Pro Thr Ala Thr
            275                 280                 285

Ala Gly Leu Ala Lys Ala Leu Arg Cys Gly Gly Val Gly Ala Gly Phe
290                 295                 300

<210> SEQ ID NO 3
<211> LENGTH: 3826
<212> TYPE: DNA
<213> ORGANISM: Human

<400> SEQUENCE: 3
aggctgcgct ggaccgaagc ggtggctgct aagctcgcgg gggtaagggg tcgcgctggg      60
ccagggtttg gggccgggat ccggcagctg agcgggccgg caccctcct cttctctgcc     120
ggtcacagcc aatgtacggc tcggcctggc tgccccctcc cccaggattc cccatcccca     180
gcttctcgcc ctccccgcac cgcccccacc ccgggatttc gaccccctta agggctccac     240
cccgctccgg gatcccttc tcccagctcc tatcccttag gactgccccg cccctagaa      300
cctccccgtc aggatctccg tccctcagcc gctcacagcc tcctcccagc gcccatcgcc     360
ttgagctgcc cactacctct agactgccct cccgggctgg cgtcccacgg agtctcagcc     420
gcgcacccct cctcgcgtt accctccttc cggacagcac cccctccctt ctccggtagc     480
tcctaccct gcctgtgcgg gcctcgtccc cgcgcccagc cctcggtgct gcctccgaca     540
gcgccgcgct ctctcagccg ccccccctgcc cctcgggccc cctctctgc tgcccctggc     600
gccatggcgt gcagcctcaa ggacgagctg ctgtgctcca tctgcctgag catctaccag     660
gacccggtga gctgggctg cgagcactac ttctgccgcc gctgcatcac ggagcactgg     720
gtgcggcagg aggcgcaggg cgcccgcgac tgccccgagt gccggcgcac gttcgccgag     780
cccgcgctgg cgcccagcct caagctggcc aacatcgtgg agcgctacag ctccttcccg     840
ctggacgcca tcctcaacgc gcgccgcgcc gcgcgaccct gccaggcgca cgacaaggtc     900
aagctcttct gcctcacgga ccgcgcgctt ctctgcttct tctgcgacga gcctgcactg     960
cacgagcagc atcaggtcac cggcatcgac gacgccttcg acgagctgca gagggagctg    1020
aaggaccaac ttcaggccct tcaagacagc gagcgggaac acaccgaagc gctgcagctg    1080
ctcaagcgac aactggcgga gaccaagtct tccaccaaga gcctgcggac cactatcggc    1140
gaggccttcg agcggctgca ccggctgctg cgtgaacgcc agaaggccat gctagaggag    1200
ctggaggcgg acacgggccg cacgctgacc gacatcgagc agaaagtcca gcgctacagc    1260
cagcagctgc gcaaggtcca ggagggagcc cagatcctgc aggagcggct ggctgaaacc    1320
gaccggcaca ccttcctggc tggggtggcc tcactgtccg agcggctcaa gggaaaaatc    1380
catgagacca acctcacata tgaagacttc cgacctcca agtacacagg ccccctgcag    1440
tacaccatct ggaagtccct gttccaggac atccacccag tgccagccgc cctaaccctg    1500
gacccgggca gcccacca gcgcctgatc ctgtcggacg actgcaccat tgtggcttac    1560
```

-continued

```
ggcaacttgc acccacagcc actgcaggac tcgccaaagc gcttcgatgt ggaggtgtcg    1620
gtgctgggtt ctgaagcctt cagtagtggc gtccactact gggaggtggt ggtggcggag    1680
aagacccagt gggtgatcgg gctggcacac gaagccgcaa gccgcaaggg cagcatccag    1740
atccagccca gccgcggctt ctactgcatc gtgatgcacg atggcaacca gtacagcgcc    1800
tgcacggagc cctggacgcg gcttaacgtc cgggacaagc ttgacaaggt gggtgtcttc    1860
ctggactatg accaaggctt gctcatcttc tacaatgctg atgacatgtc ctggctctac    1920
accttccgcg agaagttccc tgcaagctc tgctcttact tcagccctgg ccagagccac    1980
gccaatggca agaacgttca gccgctgcgg atcaacaccg tccgcatcta gtccaggcag    2040
aaggagacca caacctcctg ggaccactgc cacctgcaag agccctgccc aggaagatag    2100
aagacctgga ctccagccca ccgtggccac tggagacctc aggccagttg tttaccctcc    2160
agcctccagt ctgtaaaatg gaggttgcat tccctacttc ctaaactctc ttccagcatc    2220
gatgttctgt agctctgacc ttgatagggga tacagctttg atccaaggat gtgacatggc    2280
ttctcctcag ggcaacccct gcccaaccct catccccatc ttctcagggg caggggacta    2340
ccttccagtg tctccctcca gcccagccct gacctcagga agtgtcagag catggccagt    2400
agttggcagc ccgaaagaca cacagcaccc tcttatgtcc catggcctaa gacttaccccc    2460
tgaccaagct agtgatgggc catttaccct tgaccccagt ccacagtggt cacaggtagt    2520
acctggtcct agggttgcct gagagccaac ctctcctgcc accccacac caagaactat    2580
atggttccta cttctcccac tgatctgctg gtcagtgatg atgctgtggc ctgtggaagg    2640
cacctggtag ttgagtccac acattatagt catgtgccac caccttcctg cccacaggcc    2700
gagggacagg gtgagggtat acccaaagct gatgcagagc ccattagcct aaaagcaact    2760
gcaggacaag cctccctgga tgatcgaggt ccccagtagc tctgaacaag agtccagcca    2820
accctcttca gccaggcctc tgtgacctgc tagggtgcag gaggcttcca gaagcagttg    2880
ttgtaattag gacccaagca ctgggagggg ctgttggcta gaccccttgt cagacttggc    2940
atctatctca gttaggatcc tgctgcagaa aacaagagcc acttgtagct ggtttaatta    3000
gacaaggatt tactacctgg cccctggtgg cttgcaaaat tgttggaaga gctggagaag    3060
cagactctgc tgaatttcca ggaactccca gcgccagatt catcatgtct gttgtgacca    3120
ggaaagctgc ccccatctgc aggaagccac tatgccagaa agctgctgac tgcagaacta    3180
ggctccctct gccacggtcc gtgccagcca atagatgtcc tgaggcctgc ccctctccca    3240
cttcactcag ttcccaaatc taaatttta caagagattc tgtttggggg aacttaagtc    3300
agatccagaa ccttggctgc aagggagtct gggaaatgtc atttccctag aaggaagtta    3360
gggtgggtgg agcaagcccc acctgcgttt ttctgccaca gcatccaatc gtgaagaact    3420
cgggagaggg tggagtccac atctagggtt gtcctgcccc ttggctctat ccctgcccag    3480
aggtgggaac tggaggagtg ggctgcaaga ctgagcctaa atgtctcccc ggccttgact    3540
tttctttcta gtcctgggc ctagattctg cacttgggt ctctgacaca acacaccatc    3600
ccaaagtagc cggaagagct aaacacaggg ggttcttaaa atggctgccc ccgccacccg    3660
ggcctcccctt gggcaaaagg aattgtcagc cctaccccaa cccttcaact accagaatct    3720
gggccacccc agcagtattt ttatttaaaa tgttgcccat tttatgagtt atgatcaatt    3780
tgtattaaat taaagttaca gatgtcaaaa aaaaaaaaaa aaaaaa           3826
```

<210> SEQ ID NO 4

```
<211> LENGTH: 49744
<212> TYPE: DNA
<213> ORGANISM: Human

<400> SEQUENCE: 4
gttgcccagg ctggagtgca gtggtgcaat atcagttcag tgcaacttcc acttcccagg      60
ttcaagggat ttttttggga ggcttcagct tcccaaatac ctggaaaaca ggcgcccgcc     120
accatgcctg gaaagatggg tagagatggg gtttcaccgt gttaaccagg atggtgtgga     180
cctcctgacc tcatgatctg cctacctctg cctcccaaag tgttgggatt ccaggcgtga     240
gccaccgcgc ccagctggtt ttattatttt tttattgttt tatttgaata agtattactg     300
tggcccaagt acatccaaga atgtaatagc ttaatgcttt cactactatt gtgagtgaaa     360
acttttccct gtgttttga gctgagatgc tggcttgcat tctaaaattc attgatttcc     420
tttagtaacc acacccaccc ccttaagatt ttccaaggtg ggcaaatacg ttatctgcag     480
tgtaatattt tatttcttca tcttctatgt attatgcttt tttgtttctt tttttctgat     540
agctattgct agcatttctc atcatatata aaatgggaat gatgacagaa aggttcagac     600
ttggaatcag aagacatggg tttgagacct ggctctgcca tagaccagct gagtaacctt     660
aggcaaagca aggtaattaa tctctctgag ccttatttct ctagtttctc catttggaaa     720
atgacagggc tgaacttcag tgtatctcaa tgaagtcaga gttggatcat tatttaaaat     780
agtctctctt cattgtgggg ttttgttttg tctgtagttt taataaagaa tagatgctac     840
gggctacttc atggtatgtt gacatgtatt gggaaaatta aacttgaact gtagatctat     900
attttccatg ttatgaagcc agtgattgac ttctctcctg ttgtctgcac ctttcatttt     960
agagataata tgactgtgaa tttggttagc taagatttca tgtcaggttt ttgcctatat    1020
attcacaagt gagattttgg ccatagggtt ttttttttctt tttatctcat ttttgtcttt    1080
taaaatattt ttgtacgaat tattgattta ttcttttctt ttttttttg agatggagtc    1140
ctgctctgtc acccaggctg gagtgcagtg gtgcgatctc agctcactga aacctccgtc    1200
cgggttcaaa tgattcgcct gtgtcagcct cctgagtagc tgagattaca ggcgcctgcc    1260
accatgcctg gctaattttt ttgtattttt agtaaagaca gggctttacc atgttggcca    1320
gactggatga ttttttttc tttcttttt ttttttttt tgagacaggg tcacacactc    1380
gtcacccagg ctggagtgca gtggcgcaat ctcggctcac cgcaacctcc acctcccggg    1440
ttcaagtgat tctcctgcct cagccttccg agtagctggg attacaggca tgtgccacga    1500
tgcccggcta attttgtatt tttaatagag atggggtttc tccatgttgg tcaggctggt    1560
ctcaaactcc cgacctcagg tgatccaccc gcctcggcct cccaaagtgc tgggattacg    1620
ggcataagcc actgcaccca gccatatata tatatatttt ttttgagac agagtcttgc    1680
tctgttgccc agggtggagt gcagtggcgt gatctcagtt cactgcaacc tctgctccca    1740
gttcaagcga ttttcctgcc tcagcctcct gagcagctgg gattacaggt gcctaccacc    1800
atgcccggct aattttttgt ttcttagta gagacagggt ttaccatgt tggccaggct    1860
ggtcttgaac tcctgacctc atgattcacc tgccttggcc tcccaaagtg ctgggactac    1920
aggcatgagc caccacaccc gactggcaat gcattcttta aaaaaaaaa agactcaaca    1980
gtaacatatg gtcctacttt taaggcttca agaagtgtat aagatgaaag agaacagtgc    2040
ttcgacccca cctcatcagg cccttttat agctgagaca gctccttcct gtccagacac    2100
atgtctcgct gtgagacgag atttgcattt acaggaatag cttctaatc tgcatattgg    2160
tctccatccc ttggaaacgt tctccatcct cacctctgca ggtcccgggt accatctctc    2220
```

-continued

```
cccatcttct gccactctct aaatggtagc attcttctga attcctaggc ctccctgtct    2280
tgtaaaccct ccttcttctc agaagaaggg ttatctcctc ccatggcttt aaataccatc    2340
aatatgccac tgcttcccac attttaatct ccagctcaga cctatatatc cagttgacta    2400
agagctacaa acttgcacat ccaactaccc gcttgagatt cctactggga tttcacagac    2460
atctcaagtt taacttgttc agaactgaac tcttgatttc caaccccccaa acttctttca   2520 ctaaaatggg agtgccacta gcccgagtgt tgagggtaaa aaagttggga ttattcttga    2580 attttttggtt tccttttcct tccacatgca gttccacctg caaattgttg ggtgtggttc   2640
caaaatacat tttggtttca gtgaattctt cctctgtggc caccctaatg caagccacca    2700
ttgcctcctg cttgagctac tgcagtagcc attaactggt tttccacccc catactacta    2760
cctgcttacc acccattttc cacgctgcag acagaatgat cttttaaaat cccaaagatt    2820
atgcccctcc tctgcttaac accatctgtg gcttcccatt gctctcagaa taaaacctag    2880
actccttacc acaacgagca aggctcctgc catcttccca ggcacctctg ccctcactcc    2940
tgtccctgtt ttcagctcca cttacctgct ccagtcccat tcctctcctt tctgttttttg  3000 taacacctaa gttgtttctg ctctcagggc ctttgcattc gctcgcccag aatgctcttc    3060
cactcacccc tgaagacagc tgctgtattc tctttcttat gtctcagctc agatgtcacc    3120 tgtcaggga ggccttttcct gactgccctc tctaaagtag gctcacctcc cctagtcaga    3180
taattttgat accctgctta ttttcttcac aacccatcgt aatctgttaa ttatcttgtt    3240
tttgtttact tgcctatagt ctgtcttctc cattagcagg taggctctat gagggcagcc    3300
acgttgtcca gttagtttcc tctgagttcc cagcaccaga cacagtgcct ggcatatagt    3360
aggtgctcac taaatatctg ttgaatgaat tgtgaatgga tgaatcaatc attcaataaa    3420
ctgtgagacc cttgagggtc tcacatctgt tcatatctgt ttccctagta cggaacttgg    3480
catacagtag gttcagtata tgttggaatt aaatagatct ttttttttttt ttttgagatg   3540 gagtctcact ctgtcaccca ggctggagtg cagtgctaca gtcttggctc actgcaacct    3600
ctgcctcccg ggttcaagtg attttgctgc ctcagcttcc cgagtagctg ggattacagg    3660
cgcccgtcac tatgcctggc taatttctgt attttttagta gagacggcat ttcaccatgt   3720
tggtcaggtt ggtcttgaac tcctgacctc aagtgatctg cccgcctcgg cctcccaaag    3780
tgctttgatt acaggcatga gccactgtac ccggccattg tttctttcat ttctatgtct    3840
ttgacaagga taaaccattt tgttttttgtt tattgtttta tttatttttga tgtcaatgtc   3900 ttttttatatc ctctgttcac ttaatttggg aggtcttgaa gttttttctt gcacatagaa    3960
atgagcttgc atatgcatgt gtgcatgtat ttaatatgat gtttgataca aatatttttt    4020
cactctattg gtttattgtt ttagttttgt aattctttgt tattctttca tagaagtttt    4080
gacacactat tttgttttaa ctaagtttgc tgtaattaat aggaaggaaa tctgttactt    4140
tcttttgtgc tctgctgtta tagattatct ttattacata tatatatata tagtcttata    4200
gaaatagaat gtttattaga aaaatttaa cacaaatagt aaaataaaat gattcactaa     4260
tcccaccatt cagagatgac tattgttaaa tgtactttga tttctacttt ttttgggttt    4320
aatggctatt ttatttttgtt ttatttttatt taacacaagg tcacattctg tcaccctggc   4380
cagagtgcag tggcacagtc atgctcactg tagcctccac ctccgaggct caagccatcc    4440
ttcccactcc agcttctgaa tagctcggac tacaggcaca tgccactatg cctggctaat    4500
ttttgtattt tttgcagaga tggggttttg ccatgttgcc caggctggtc ttgagctcct    4560
```

-continued

```
tgttttgttc aagcaatcct cccaccttga gattacagac atgagccacc acgcctgacc    4620
tgataatttt ttttaaaagg ttgtctagtc ttgctaagaa taagcaagac gtttcgttta    4680
ctaatgtcat gatttaacca gttttagctg ctctgatatt aaaaggtgtt tttgttaata    4740
tacttctaaa atattggaaa taatcagagc tgggtgggga gagagaacta agcccaaaat    4800
ctctaattta caatgctgta acattttgaa agaccaatct tgtttttgat ttctactttt    4860
taaaaaagtg tcatagtgca ctttgttttt cactttaaag ttttatatat tgtgagcata    4920
tggttttctt taaatactga cgtgttaggt ggacttttaa atatagaaac attttaaatg    4980
ttcattgagt gctctaaaat aatacatatt tagtgtgtgt attagtttgt tctcacactg    5040
ccaaaaagga atacccaaga atgggtaatt taaaaggaa agaggtttaa ttgacacagt     5100
tctgcatgga tagggaggcc tcaggaaacc tacattcatg gcagaagggg aagcaggcac    5160
atcttacatg gctgcaggag ggagaggtgt gaaggggaa cttccaaaca cttttaaaac     5220
catcagctct catgagaact ccctcactat cataagaata gcatgggcga aactgcccgc    5280
catgatccaa tcacctccca acaggcccct ccctcaatat ttggggatta caattcaaga    5340
tgagatttgg gtggggacac aaagccaaac catatcagtg tgtaaagatg caattcaaca    5400
aatgtgtatg agcacttcac aaatgcaaga tacgatttgg tatagggtgg aatcaagagg    5460
aggcaagtat catgggagtt ttataagaat cttggcaggc aaaattcagg acagttaccc    5520
cagtccatga agagagattc tccttttatt gccaagatgg ggctttctta cttgctgttc    5580
cattttattc tagtttgtta tgctttcaaa agtgtgaatc tgtctggaat gtattgcaat    5640
agcacttacc aagtgtgtcc ctagactaag aagacagaag actcaaataa ataaaattat    5700
aaatgaaaga ggagacatta caggatacca cagaaattca aaggatcata agagaccact    5760
actagcatga ataactatac accaagaaat tggataacct aggcaaaatg gataaattcc    5820
tagcacaaata ttacctacaa agactcaatc atgaagaaac agaaaatctg aatagaccaa   5880
tagtgagtta ggagattgaa tcagtaatca aaaacctccc aacaaagaaa agcccaggac    5940
cttatggctt tactggtgaa ttttaccaaa catgtaaaaa agaattaata ccaatccttc    6000
tgaaatgctt ccacaaaact gaagcagagg gaacacttcc aaactcattt tacaaaacca    6060
caattacctt aacaccaaag ccaaatacac cataagaaaa gaaaattaca ggccatgttc    6120
acagatatgc aaaaatcctc aacaaaatac tagcaatcca aattaaatag cacattaaaa    6180
ggatcataca ccatgatcct tttaaagtgg aatttatccc tgggatgcaa agaaatttta    6240
acatgtctga atttataaat gtgatgtact ataatattac cacaatgaag gataaaaatc    6300
atatgatcat ctcagtagat ggagaacaag catttgacaa aattcagcat cctttcatga    6360
taaaaacttt caacaaatta ggtatggaag gaatgtacct caacatgata agggccatat    6420
atgacaagct cacagctaat gttatactca acaaggatcc taaggtcagg agcaagacta    6480
agatgctcac tctcaccact tctatttagt gtggtactag aagtcctagc cagagcaatt    6540
agagaagagg aagaaataaa agtcatccaa atgggaaagg gagatgtaaa attgtctctg    6600
tttgcagatg acattatctt atatatagaa aactctaagg cttggcgtgg tggctcatgc    6660
ctgtaatcct agcactttgg gaggccaagg ctggtggatc acttaaggtc aggagttcaa    6720
gaccaccctg gccaatgtgg tgaaaccctg tctactagaa atacaaaatt atccaggcgt    6780
aaagatgtgt gcctgtaatc ctagctactt aggaggctga ggcatgagaa ttgcttgaac    6840
ctggaggca gaggttgtag tgagccgaga tcatgccact gcactctagc ctgggcaaca    6900
gagtgagact ccatctcaca cacacacaca aaggccggcg cagtggctca tgcctgtaac    6960
```

-continued

```
cccagcactt tgggaggccg aggcaggcag atcacttaag gtcaggagtt cgagaccagc    7020
ctggacaata tggtgaagcc ctgtctctac taaaaatgca gaaattagct gggcacggtg    7080
atgggtgctt gtaatcccag ctactcagga ggctgaggca caagaatcat ttgagcctgg    7140
gaggtggagg ctgcagtgaa ctgagatggc gccactgcac tccagcctgg cgacagagcc    7200
agactccatc tcaaaaacaa aacaaaacaa acaaacaaaa aaactttaaa gacttcacca    7260
aaaaactatt agacttaata agttcagaaa attagaagat acaaagttaa catacaatgt    7320
ttctatatgc taactatctg aaaaagaaat caagaaaact atcccattta taattgcatc    7380
aaaaaattac ttaggaaatt taaggaggta agagatgtgt acgctgaaaa ctagaaaaca    7440
ttgatgaagg agataaaaaa ggacataaat aaatggaaag atacccatg tttgtgaatt     7500 ggaagaatta atactgttaa aatgtccata ctacccaaag cgatccatag attcaatgca    7560
gtccctatca aaattccaat gatcttttcc ccagaagtat aaaaaaatcc taagatttgt    7620
ataaaaccac aaaacatcct aaatagccaa agtatcttgg gcaaaagaa gaaagctgga     7680 ggcatcacat tatctgattt caaaatatat actagaaagc tataaagtaa gcaaaactgc    7740
atggtactgg cataaaaacg aacatataga ccagtggaat agaatagaga gcccagaaat    7800
aaatccctgc atttacggtc aattgatttt caacaaacgt accaagggac ccacaatggg    7860
gaaaggacag tctttttcca taaattggtg gttgggaaaa cctatatctt ccacatatta    7920
gaagaataaa attggatggt atttcacacc atatacaaaa tggattaaag actttcagat    7980
tgactttttt gttttttttt ttgggggatcc tttagattca ctttctgccc cacagttttg    8040
aaaggcagac ccagttcagg aaactttttt tttttatttt actttaagtt ttagggtaca    8100
tgtgcaacaa cgtgcaggtt ttttacatat gtatacatgt gccctgttgg tgtggtgcac    8160
cccttaactc atcatttaca ttaggtatat tttttaatgt aatccttccc ccgtccccca    8220
accccaaaac aggcctgggt gtgtggtgtt ccccaacctg tgtccaagtg ctgtcattgt    8280
tcaattccca cctatgagtg agaacatgca gtatttggtt ttttgttctt gtgatagttt    8340
ggtcagaatg atggtttcca gtttcatcca tgtccctaca aaggacagga actcatcctt    8400
ttttatggct gcatagtatt ccatggtgta tatgtgccac attttcttaa tccagtctat    8460
cattgatgga catttgggtt ggttccaagt ctttgctatt gtgaacagtg ccacaataaa    8520
catacgtgtg catgcatctt tatagcagca tgatttataa tcctttgggt atatacccag    8580
taatgggatc caaccaggaa actttgagga ggtcagagag acgcaagttg tcaactctgt    8640
tcaccccagc tcagagggag atggtggctc tctgggtggg agtcatcttt cacctaggaa    8700
acccacctgc ccaagccatc tcattccagc tgtaaaggga acaaggggga ggcaagagga    8760
caggggttcc actcatccct ttgctccatt ttaaaccttc ttcctggcac ctttaggtaa    8820
acagctaagc ctgtgtaaat tcaaccagta aaatgatctg attgtcagtc ctctgctgaa    8880
agcccttcag ttgatttccg gtgcgatgcc aaaaaaagct aaattgcctg agaccctgc     8940 ccacctctcc cacctcattt catgccactc ttttctcaca tttcagtttc tcacatttac    9000
tgacttcttt cttgcctcca agtcttcgcc tttgctgttc ccttagctac tccagcattg    9060
gctcattctc atcttaaagg cctcggcttg aatgttgcca tctcaagaag gccttttcca    9120
gacatcctgt tcaaagtagc ccccaccaac ttatgtggtc atattttaca gggatgaggc    9180
tctaaagacc atatttaagg caagaatcat atggtcaaaa ttatcattga aaatccctta    9240
gaaagctatc atattggaat cttgttcatc acacgccctt tcctttcctt tcctttcctt    9300
```

-continued

```
tcctgtaaca tgccagacac acttacaacc ccaaatctct gcatagatct ctctccctca    9360
tcccttcagg tctttgctca aatgtaatgt tctcagtgag aacttcctga ctacccactt    9420
caggctggga gtgacggctc attcttgtaa tcccagcact ttgggaggct gaggcaggag    9480
gatcacttga gcccaggaat ttgaggccag cctgggcaac atattgagat gccatctcta    9540
aatcaaacaa acaaaaaaac tgtaacattt ccattcctgc cccagcattc tataatcccc    9600
ttcagagcct tactttttcc tccatagatc actgtctaac atattataca tttcacttag    9660
aattaagttc tgagggcaaa aatttgttta ttttgttcac tgctgggtcc acagtgccta    9720
aaatactgtc cttcatgtaa atgttcaaga aattactgaa tgaaggaatg aatctttcag    9780
gcctcagctt gggtgtctct ctcctttctc ttactttcta ttccttcatt aggggttcca    9840
tctccgggct ttcatgcatc ctgtatttgt ccctattaaa gaactactga tcacaatgta    9900
ctgtagtttt cctctctaaa tacttgtctt cctgcgtatc taatcctatt gattccataa    9960
agacaggag tgtttctcct actttctagt gtgatctgga acctaagact gtgcttacca   10020
cagagtagac acttagtgtc ttttgaataa actagtttgg gtggtggtgg tgcggtaccc   10080
ctgaatggga gtgggggatg tggctccttg tcagctcctg aataggtcta gatcctgcac   10140
taggaagacc attgactggc atgagctggg ggcctttaaa ataacctcag aatagcacct   10200
gggaacaagc cagctccata cactagtgag ccccaggcag ggaggcacgt aggaccccc    10260
caatagcgct ttctgttttt ccactcagtt aggtgacctt ggggtaggat cgccaaataa   10320
aatacaggac atccagataa atttgaattc agaaaaacaa tgagtaattt tttagcatac   10380
gtgtctcatt gcaatatttg ggatagtctt atactaaagc attactcgtc gtttacctga   10440
aattcaactt caactgggca tcctgcattt tatttgctaa atatggtaac cctactctgg   10500
caagtccctg tacgctgcat gtccctctct gggtttcgct ttctccatct gtggaatggg   10560
cacagttctg tgagacttgc ctcagggatt cctcaggctg agcaaatacc ctcatggatc   10620
gtccctttgt cctggtgagt cgtatgggaa gcgcgcttgt ctgaggagtt tttcgctgtg   10680
taaatatgag aagctccttc ctccaaaagc ctccgttttc tcatctgagc atatgagact   10740
ctcagaagtg gaaacgattg cctggcggaa ccatgactgc tcagtttcca gccaccggaa   10800
cccccagctc acggccccca tcccttgaag ccacggtttt ccgtagcgt aaagtcactt    10860
ccgtattcga gagccttcta ggcttcgagc cacgcgatgt cgcgccctct ggcggctggg   10920
aggagggacc gactttacca aacggtgaga aggaacaggg aagtccattg gttgaaagac   10980
ggagaggcgc agctcagttt tccaacctca accaatgtta aaccgaacct tcgccgaggg   11040
cggggctctc acgggaaagg ggtcaacccg ggactgaggc ggcgtgggaa gcgggcgacc   11100
ttatctctgc tcagctggaa aaaggcccag ggtaacaccg gaagtgggct tatttgcgca   11160
tcagctactt tcgcttctac ttaaaaacgg aggatctggg taaaagaacc gaaaggctgt   11220
acgaacctaa gacttgtctc cgatgtcctt ctcaaccatc aatttcatat gcagggaaa    11280
acacctgctg ggttcacgca gaatataaag gtctttgaaa taattcttga tctctaggcc   11340
aaggagtttt acattttaaa ataatcaagc gtgcctactg cttgccaggc cctgctctcg   11400
ccttcactcg cattattcaa ttaatcgaca caggcctgtg cagtgcgtct taatgacaag   11460
gactcctacc ctccactgcc tgtgttggaa tcctggttct gccagttatt agctgtgtat   11520
cctggcctaa gttactctct gccacagttt ctgactctgt aaaataggat aatagtatct   11580
accttatacc attattctaa agataaataa atttaacata tttaggttgg gcacggtagc   11640
tcacacctgt aatcccagca ctttgggagg ccgaaggtgg aaggattgtt tgagcccagg   11700
```

```
agttcaagac cagcccgggt aaaatagtga aactccccac ctctccaaaa aaaaaaaaaa   11760
aaaaaaatca gccaggcgtg gtggcaagca cctgcggtcc cagctactct ggaggctgag   11820
gtgggaggaa gattgcttga ccctgggagg tcaaggcttc attgagccgt gagtggggca   11880
ctgcactcca gtttgggcaa caaattgaga cctcgtctcc aaaaaaacaa aaaatttaac   11940
gtatttaaag cactcagaac agcacctgac acatggtaac cacagtaacc aggtaagtta   12000
ttttcattta caaattgaga atgaggctt acgtatgaag taacttgtct agaacagata    12060
gcaactagtg gaggcagatt gggaaagtct ctgcctaatc tgaatctcaa tcactatacc   12120
tgccccaccc tcttcctgtg tctacaggga gcctgttatg atcctaattg cctttaaagc   12180
atcagatgta tttatttggt agcatcctat tacaaagtgg ctgctctctg ggcattttg    12240 taatttaat gaagttggtg aggtcctata acttgtctct cagaccaggg gcaaggcttc    12300
tgggaaaagt cagaatggat ggcttcaaga tccacctcct actaaatcct acttatggaa   12360
aaatcagtag aaatgaactt ctgaacatgt ttcatttgag atcttttcag atatccaagt   12420
ggagataatt gtgatttggt gtggtaagtg ctgtgttagt ggaaagcaca gggcaccaag   12480
ggaggtctga ttagggatag ataaagctgc cggccaggat taggacaggc gtggcaaaag   12540
cagcaggtct tggtgaatga gtaggagttg gccaggtaga aaagtctggg gaagttgagg   12600
ggagcattcc agaccagggc actggcgtgt acaagggaat ggtattttga tgattcagag   12660 cccttttctgg gaaccggagt ataggatgga aggtaagaat ggaatggaga ttggggggcat  12720 attacgaaga agtgatctaa gaagacactt cttatcaact aagacagacc ctaagattaa   12780
agaaaccaaa gttaaagtta cttatgggtt gggggttcat catatccctc ctaactctga   12840
tttacaaccc aagaccacta caactttgat tggacagagg accggcctta caaacattct   12900
tttttgataa gcaactgcag accttaagcc agtttcacca gctgataaag gcggtacaca   12960
gactgtcttt gggtcctgtg gttcatcttt tgatataaag agtcaaattc tacctcattt   13020
taatgctaaa attttgcccc aaagtgagca tgggatgagt gttacatata tgtttacgca   13080
ttgtgcatgc actcagctcc cctcataaat atatatagtc ttcccccaca atctgctaaa   13140
tatgtatgac tcttttgtgt aaatatggac cttgtgaggc ataaaaccca acctgctcct   13200
tcccttctcg aagagaaaac acatttggtc cacactggag attctcttcc tggtttgcaa   13260
actaatatca ccgataaagc tctcctttc tactatttac ccattctggt gatcttttgg     13320
acaataaagg gtgatgttcc gaagtatcag caagtcatca gaatttctga gcggggggaga  13380 gaggaggtca gctttgcaca ttatttattt atttattttg agacggagtt ttgcttttgt   13440
tggtcaggct ggagtgcagt ggggtcatct tggctcactg cagcctctgc ctcccgggtt   13500
caagcgattc tcctgcctca gcctcccgag tagttgggat tacaggcatg agccaccatg   13560
cctggctaat tttgtatttt tagtagagat ggggttttcac catgttggtc aggctagtct   13620
caaactcctg acctcacgtg atccacctgc cttggcctcc caaagtgctg ggattacagg   13680
tatgaaccac tgcacctggc cgtagctttg cactttagat ggtgcactag gaggcaagga   13740
agaggatgcg gtaggcagtc tctgagttgt ccttaatgat ttcacatccc agtattcaca   13800
ccctggtgtg atttcctccc gttgagtatg atggaattt attgattcca ttctaatgaa    13860
taaaatatgt tagaagtgac gggttgtcat ttctgagatt cgattacaaa aactccctgt   13920
ggcttctgtt ttgggcacct tctccttgctc tcttgctcac ttgctcttag gaacacagc    13980 agccatcttg tgaactgccc tgtgggtagg tctatgtgtc aaagaacaga tgactaatca   14040
```

-continued

```
acggctagca aggacttgag gacttctaac agctgtgagt gagcttgaaa gtagatcctc    14100
ccccaggcaa gccttagaat gactgcagcc ccagccaaca cctgattgca gccatgtgag    14160
aggccctaag ccagaggacc cagttaagcc atacccaggt tcttgaccct cagaaaggga    14220
gataagtaat attcgtggtt ttaagtttta cctaatttta aggtaatttg ttaggcagca    14280
atagataact aatacagagg gattagaagc aaagacagaa gtagagaaat taggagaggg    14340
tggtggttgt aggccatctc tctaataatg agaacctgaa ttgtgcagtg gctgtgcagg    14400
tgaagagcag aagatgaatt tgagatatgt ttggaaaaag aacagaagac atttggcaat    14460
ggagttggat gtgggaagga gggataaggc agaggagaga gcaatgccag tgtttggtaa    14520
tgtgagggat ggtatttgct agagctgcca gcatgcaggt cactgggdat gagttttaaa    14580
agtggctcct tgagatttct ggcaacaaca agatagatca acaaagcaga ctcaaggttg    14640
gtcaaagaaa acagccactg tgagctgggg aagaaataat gcagaaaaat agaatcaagg    14700
aagagctgga gggaattctc tttcctgagt ttgatttact tgtcaaagtg tatggtatac    14760
cattctcctc ttcatctagc cattctctcc acaaatgttt actaagtgct ttctctgtgc    14820
taggcactgg ggacaaacaa gtaaacacac aagtccctgc cttcatactg ttcataactt    14880
ggttgcagag aaacagtaag attgaggcta ggactttta gccactcctg cagggctctg    14940
agggtctaaa tctgtgctgt ctgttatgtt agccaccggc ttcctgtggc tatgagacac    15000
ttgaaatgtg gccagtccca attgaatgtg ttataagtgt aaaatacacc ctagatttca    15060
aagatgtagt tcaaaagaaa agattgtaaa cgatttcaat aattttttaaa tattgaatat    15120 tgattttagt attatcattg gataacattt tgtatgttta aagaaataa aataaataat    15180 taaaatatat taaattaatt tcacacattt cttttttaaat tagtgaaatt aatttaaata    15240 atagattta cttattttgg ctattagaaa atttaacagc caaaatatgg ctattaggaa    15300
atttaaaatt atctattaaa tatacctcac attatattta tgttggacct cactgactaa    15360
atctgtattc cctaccaact ttatctctct cagtgacttt aattttagtt aatgaaaggt    15420
ttgttttttt ttcattgaaa gtaacagaaa ccttgagggg aaatgaaaat taaatgttag    15480
gggaattgat tgcaagggcc ttctgaatca aggcatggtt gattgagcag tctgggcaag    15540
gagcaggctc gagggccctt cgcagcaaag cttcacaggc attaatgtga ccggctccca    15600
tttttgaatt tgacctccca cattccaatt tctgagaaga cagactctga tcagctcagt    15660
ttaaatcagg gtgtatctac tctggatcca gctgctacgg ctatgggaag aacgcactgt    15720
gagctgccta ctgctttttt cccacccta ccctccagcc actatgttcc ctaaaaggca    15780
gcgtgagctc tccagtctct aggggtcagc aaaccttttc tgtcaagggc cagatagtca    15840
atacttcttt tgctttgtaa ttcttagtgt ttcttttgca actacttcat tctgccctgc    15900
agagcaaaag ctgccagaga caatacataa gtgattggac atggctgtgt tcagtgaaa    15960 cttcatttcc aaaaccaaga ggtgggccat agtttgtcaa cccctaaact gtactttctg    16020
ttccctctgc ctggactatc ctttcactcc ttccttccag caagtgccta gtcatccttc    16080
tggtctcagt tcagatgcca cttcttggag gctcccccta accttcctct cctgactggt    16140
tagttgctcc ttctttatgc tcccacagac ccctgtatcc catacatgca cttctcatac    16200
tctgttgtca ttgttctttt ctaaccactg gcttactaat tctgggtctc atttgttata    16260
aactcaccac ctggcactcc tggcacatgg cacgcacttg agtgtcattg gatgagtgga    16320
agaaaccatg aaccttgtgg ttgacacata gtcagactag atgtcctgag atcttgggta    16380
gtgatgagaa ttctgggctt ttaaaattag cggcatgaga ggcacctcct gtaactccaa    16440
```

```
tacttcagaa aagcatgggg gaatgtttta agatgggaga agtggaaaat tttaagggct    16500
gcaagccctg gataatgtga taagccacac ctcagctggg gtgaaaccag gagtgcactc    16560
cttggaggag gctttgtgct ccttggtaag gttccctgcg gaggccccat caggcccagt    16620
gggtcaggag agagacactg tggggtcgag ggcagccttg gcccatagtc acttacagtt    16680
acagttacag ggcagcagaa tggaccttcc ttgacccaag ggcttggtga gtaacattca    16740
acagatcctg gacaagggca acggaggctg tgaggccaaa gacagtgctc atggcctttg    16800
cgaggcttta tccagctaag cacattgtcc ctgtcgcctc aagagaggaa ggagagtttc    16860
tcttttta at gtcactctta aatgtcacac ctttgggcaa tacagatctg atagggcctt    16920
tcctgggtgt tttgcacaat aagaccaaga gtaaaagagc agtggatctt ccctgtcatc    16980
gtggaccttg aatggcttac ctgggcccct catggggatg gtggggtggg gcaggtgacc    17040
tggaccacc ggcggcacgt tttccattta tacagctgat gaccagcaga gtggatgagg    17100
agagcagggc cgggatggtg atcactgcag cttgcaagcc acccatgcct ggccaagggg    17160
atggggcatc agggcactgc agcttgtaag ccacccacgt ctggccaaag agatggggtg    17220
ttagggcaag ggcagtggaa tgctccccca gggcaggctg tggttttggc cctcagcagc    17280
cttgcccac acaacactgg gctcccacga cacggaggag gcatggtgca gagaaaaagc    17340
aggctgagag gcaaagattg agtgaccttg ggcaagtggc caattgttct tcccctagtg    17400
tttggcactt agaaggtgct gggtacttgc ttgtggaccc aaaggagag atgtgatcct     17460
aataccacca gatgctttac atgccttatt ttactcaacc tggcgagctg cctctgctgt    17520
taccacttac cagctggtga agctgtgatg ccaaggctgg cttctctgag gctaaaacgt    17580
ttataagggg cagaggcagg atttgaaccc agatccgcat gttgccaggc cttcatgcta    17640
tccatgtgct tccccacaag catgctctga acacttaccg tgggccaggc atgtggccca    17700
gccccgtaag acaccacctg gcacgtggca gtccctcaat aaattttagc tgtcattagg    17760
cattactgtt atttcgactc atttgatcct cacagcaacc cagcaagggt aggtattttt    17820
gttcctattt tccagatggg aaatctgagg ctatcgtggt gaagtgtctg gcctaaggtc    17880
cacagctggt taagtggcag ggccaagaat taagtgcagg tggactcttt tcccatgtta    17940
gctaaggcgc ttaggtagca gaggaatcca ataatactgc ctctgtttat ttagttgaag    18000
aatgggaagg agtcattgga aaaggagtaa atggagggcc tttaaaggac tatcctatgg    18060
aaaggagggg gtcagaaaac agagctagga ccaccagaga cacaagggga cccatggaaa    18120
gaaagacctc ctattccggt agtaggatgg gctgctgcac agatagtgag ctccctggca    18180
ccagacatgt ttacgcaggg aagctgtggc atggagagact gcaggaattt tctcttggtg    18240
ctaggagtac atgcgggtct ttgggttttt ggcccacagc agctgccagc ttgctgcgcc    18300
tgccctcttt gggactcttg agaaataggg gagcgaggat gagttgtcag ctctgaaaca    18360
gtcctgtgct cccaggagaa atccctggct cctcatttct tccgtcttct acttcctttt    18420
ccatcccacc cctggcctca gcctcaccag ccttgctgct ttcccgctgg gttccctccc    18480
tgcctccagc tgtgtttcac tccacataaa tatgaccacc ctccttccct gattaaaacc    18540
attcatggat ctgggcgccg tggctcatgc ctataatccc agcactttgg gagccgatgt    18600
gggtggatca cctgagtcag gagttttaag accagcctgg ccaacatggt gaaacccccgt   18660
ctctactaaa aatacaaaaa aaatttagcc gggcatggtg gcacgtgcct gtaatcccag    18720
ctatttggga ggctgagaca ggagaatcac ttgaaccttg aagcgaggtt gcagtgagct    18780
```

```
gagatggcgc cactgcactc ctgcctgggt gacagagcaa gactctgtca aaaacaaaca    18840
aacaaacaaa caaccaaac aaaaacaacc caggtccgca tgctgccagg ccttcacgct     18900
attcatgtgc ttccccacaa gcaagctctg aacacttacc atgagccaga catgtggccc    18960
accccagtaa gagaccacct ggcacgtggc agtccctcaa taaattctag ctgtcgttag    19020
gcattactat tatttcgact catttcattc tcacagcaac ccagcaaggc ttctctgttg    19080
ccctcaggat ggcccacagc ccattgcttt gcccttggtc tcacattgga tcctcagcca    19140
cacagcctca ttgccagcct cctgtccctc aaacatgctg ttcctccttc ctggacaact    19200
ttgcccagca cttactcagc atgcaggtct cagcttcagc agaacctcct ccaggaggaa    19260
cctcttctct tgagttcctg agagcctctc ttgttctcct gagtcctcaa cctatgtgct    19320
atctttgcct ggtcaccatc agctctttga tatagacctg ggatgcggct gttgttgcct    19380
atctcagtgc ctagcaagct gtaggaattg ttgggtaagc gattgaatga gggagtgagg    19440
gagtgaagag cacagtgagg ggtccccagg cccagccctc cctccccacc ctgccggtaa    19500
tgtatttctt tctttgggaa ttgcccaaag ccaatacttg tctggaatga gctggggaag    19560
gtgaacccaa ggcatctatt gttgctgatg agaaattggc ttcaggcaaa acatcattca    19620
tttgtggatg tttcatttct gatggctttt cagattttt tatttttatt gttttcagt    19680 ctcttcaata tgtctagaaa tgaaatttt tattctactc agaactcaat gtgccttttc    19740
attccagagg ctcatttttc tttgcttgta aaaaatcctt catcattatt cttagaatg     19800 gtgcttcttc tcccctattt cctccttgta aaactactaa tctagtataa attttggaac    19860 ttctcattt ctcctctatg atttttatct ttcatatttt ccattactct ataatactga    19920
gcactctcta tgtgccaaaa actataaact catttaatcc tcatagcaac accatgaggt    19980
aggtacatta tagtatatta taacattata acattatagt atatctccat tttatagatg    20040
agaaaattga tacacaaaag gcttaaaaac atacctgaat ctctattgct attaatagta    20100
agtatcagag atttaatacc aggtgtgcgg cttcagaccc catgtatttt tttttttttt    20160
ttttttttga gacagggtca cacactcgtg acccaggctg gagtgcagtg gtgcaatctc    20220
tttgcagcct cgacttccca agctcaggtg attctcccac ctcagcctcc caagtagctg    20280
gaactacaga tatgtgccac catgcccggc taatttttg tatttttagt agagatgggg    20340
ttttgccatt tgcccaggc tggtctccaa ctcctgggct taagcaatcc accagcctca    20400
gcctcccaaa ttgctgggat tacgggtgtg agccaccttg cccagcccac tgcactaata    20460
ttccatacta ttataatttc atctctttgt gctgctttct gtgctgcctt ctgggtaatt    20520
tcttcagatc aatttgagtg tactaattct ctctctccat ctgtgtctaa tctactcttt    20580
aaaacatcta ttgcattttt aatagttcat ttttgctatt tctatttgct tctttttca    20640 taagctcttc ttcttgcctt atgtcttcga ttcctaattt tatctcattt aaacatactt    20700
acattaaaat ttctcaggtt gttctataat cctaattttt ggcgtatgca ccactaagat    20760
ctcccttcaa gaaagaactt gctcttcagc cacacaagtg cagttggctg actacctcaa    20820
gctgttagta ccgttactgc cttcaagata tgcctccgtt ttttagttaa ggctatgctt    20880
ttcttcggca gtccctaagc aataacttta tgaacatggc aggtgtacta tagtcttgct    20940
atttctgctc aacaagggac tttctctaac aggcggtatt tgttctataa tccccctttg    21000
tgttagccaa gactttatca catttgcgtc ccatctaagg ctctctgccc aatcttgatt    21060
ctccccattt tgtcttttac aggcattacc cctcaataaa cccctgcac tcctaatccc     21120 gtctctgcat ttactttctg gaggacccaa ctaaaacagc atgtgaatta tccaggttat    21180
```

-continued

```
ttcatcttct gactttcttt cctagcaatc cttttcctct catactttgt aatgtttttt    21240
accatgagat tatcttcagt gggagttgtt ttctatagaa gtcctgtgtg ccctgcattg    21300
tggaggagaa tcacaggtag tttcacaaga agatccatta gtttaaccag ttccaagaca    21360
aactttatgt caatttctta gctagggttc ccccaaacat cactgccacc atcagacagt    21420
taatgcaaac atgtgaactt aattctcaca cccatactaa tgcagattgt gattacaatt    21480
gcttccaggt gactctttcc tagctctttt ctagctccac ctgagctttt gagctcagct    21540
atatatttt taatgtactt tttatatttt acctagcatt tctatttatt tagcgtaaga    21600
gataaaagga acttcttttc tttctacagt accccatagt caatgaaagt aaaccctgga    21660
acctgcatat atatgcgtat atatatatat atgtgtgtgt gtgtgtgtgt gtgtgtgtgg    21720
aaagagagac atatatatgt gtatatattt ctatataatt tatgttcttg gtcatactat    21780
ctattttta acttttatt ttggaataat tatacattca taggaagctg cagaagactg    21840
ccgaatacac ttcactcagt tcccttcatt cagggaatgt actcaggaat ctgcatttta    21900
gcaggtaatc agaggactca gatgtaggtg caggttgttg caaatgctat cagttcccca    21960
tccatatccc ttggacctt cctaccaact gttagcaacc actcttaacc aatgactctc    22020
agcattggta tataaatacc ctggttccct taccttcat atgcgttatt tttgagtcat    22080
gttttgcacc atttcccaga gtctccctgc taaattaacc gttaataaac cactgtggta    22140
gcactcttat tgtctgcctt cctttcttt atcaattccc acttctctac ccaaatagtc    22200
actttccaaa taagctaatt taactcaaat ctttgtgtgg cggtctgtat ctggtcttct    22260
aagctcagat cagaagtggt cttagatccc aaggatggaa tctaggattg taaaatttgt    22320
cggccaatgg taataagatt ccattattga tggtctttaa tatattgtag aggcctagga    22380
tgaattgggg gacaagatac agatacaagg ggatacaacc atttatgaag tctctctaac    22440
atctgagaga tgtggaggca atggtagtta aagaactggt ggagtttgtt ggttgttgtt    22500
aagtaccatt gaagtgctaa aggaggaaaa tgatagggtc aaattagtca attaccagcc    22560
caggggatgg tatgaaacct agaaagccac tatgacagca ttttaaaatc ccctaatttc    22620
ctacagctgg agggcagata ggtttgaaaa ccacatccag aacctaatga tgaaagtagt    22680
agaagtgtcc cactcccgtt tgctagagga taataggctt cctcctcttg cctgaaaact    22740
atgcagaggc ctccctaag gcagatgcct tgcaagatga tacttgccct cttcaagatc    22800
tgcttctaca ttctcttgcg tcttctaggt caatcactag ggttaaatct catcactcaa    22860
ccattgagga ggtactatct ctgcttaaag aaacaggatt ttggccaggc ttatgcctgt    22920
aatcccagca ctttgggagg ctgaggcagg tgaatcacct gaggtcagga gttcaggacc    22980
agcctggcca atatggtgaa accccatctt ttctaaaaat acaaaaatta gccaggtgtg    23040
gtggtgcaca cctgtagtcc cagctacttg ggaggctgag acaggagaat cacttgaacc    23100
tgggaggcag tggttgcagt gaaccaagat cgtgccattg cctgcctggg ggacacagcg    23160
agactccatc tcaaaaaaca aaacaaaaa caaaacaaa aaaaggatg tttactaaaa    23220
gaactgcagg acctgcctaa tagataccaa taaaaagctg gaagatgtgc ctgctttggg    23280
aagggaagga acataggaag aagggaaatg gaacataggg atggagaaga gaagagttgt    23340
tgataaggag gaagtctcct gagcttctgc acttaccatc ctggcaagaa cacttgggagc    23400
tgggatggtt cagaggacaa aaggatcagt gtccaatcag gaggtagaaa ctacaccact    23460
aatttaaata gagatctaat gtagtgtatt cttaagtagg tataaaatta ttaagtaggt    23520
```

```
aactgcaaag gtaaaaagag aatgctaagt tgtcacaaag atagcaatga caaaagcaga    23580
taccatgccc acggctggtg aaacaaaata agaagtggaa ttatcaaaat ttagaagctt    23640
acaagagaag ttccaagaaa ccaaaaactca gatctctgag gaggaacacc aaagtgttgg    23700
aaactggtgc taggaagtgt tgggaaactg caaactggat tcagctgctg ctaaggaaag    23760
atgctgctga tgccaggggtg aagaagcgtt gctagggtga tgctcacagg aacaggaagc   23820
tgacaggaag tcaataggaa gaagcaagtc cctccttcct gatgctgcga catcaattcc    23880
ctcctgccct cctcattggc aggcataaca gggagcaact ggcaatgctg gaatgtgaat    23940
ttctgaaccc cagccccagc actacacaag ttgatacaga agggtggttg tggcgctaag    24000
aggtgacagc ttaactactg acaagagtta caataaacaa tgtagaaatg tgtgaactga    24060
cataactgga gaaaggagtc aaaagttcag aggagaaatg tattgcctaa aaccaaaga    24120 ccaccagctt agtagcttag tatgtttcca gtacaccttc actggagcaa taaagaatga    24180
gctcctgaag gggcactgac atcattgagc aactcagtgg tggctgcccc ttctatattg    24240
tgttgtagct gctagggaac tggagttcct actgtttctt aatggtgaca ataggattcc    24300
agaacagcag aggccaggta gcagcactta accatcagac acatagtgta tggaattacc    24360
ataatgggca gcaaagtcag aaactcaacc aaggggccct tacccacaga gatttgtggg    24420
attgctaata gaccatgaag ttcctaaggg cgagatcagt gggtgactag caagggtatt    24480
gctgcccaat ataataaaaa cagatcaaga gcatgtaatg tgaagactga ggtgagccat    24540
cacagtggaa aatcactatc cctcacccat ttttcatgct taagctagtc ctcagaccca    24600
gtaccacagt aactgtacac aggagaacaa aaatatccag atatttctat agttggggaa    24660
ttcagagtcc ggactgacac tgattccagg ggatccaaat tgccactata gccctcctgt    24720
taaagtaagg agatatggag gcaagatgat aaatggagtc tttgccaaag cccattttac    24780
agtgagtcca gtgggtcttc acaccctcct gtgactattt tccccatccc tgaatactta    24840
attgggatta gtaaactcag caggcagtaa aaacctcaca tcggtttctt aatctgtaaa    24900
gaaactggtg agggtcaccc aaagcagagg tgacaacagt atgtgtatat atatatatgt    24960
gtatgtgtgt gtgtatatat atatatatat atatatatac atatatatgt gtatatatat    25020
atacgtatat atatatatat atatatgc tggaaagtga attttgaac cccagcccca       25080 gcactacaca agttgataca gaagtgtggt tgcggcgtta agaggcaaca gcttaacaac    25140
tgacaagagt tacaataaac gatgtagaat atatatatat gggggatcaa ctgattatat    25200
agccagagtt tcccattgta agttgtgtac tgtcagatcc acccaactgt atagtcgagt    25260
atgtgcaaca gttatcccat tgaagggtgg acctggaacg ttgtcatgaa ataggcctga    25320
gcaggaccat aggtcacaaa taaactacag aagcaggccc agaatcccct gttgtgatcc    25380
ctgcattgga acctctcccc tcagctcaca cttaggaaat catgagagat tcctgatgac    25440
caggtgacag aggaggaaaa agcttaggcc tggtttatgg acaggttggc acaataggtt    25500
agtggaaaac aaaaatgcac tcttactgca ctacagtccc actcaagggc tcctgaagaa    25560
cagccatgtg gagaattttt tgcaggggca gaactttagg cggtgcattg agtcatcaac    25620
ttggtgcaga aagagtcgtg gcctgaggtc aggaatccca ggcagtagtg aacagttcag    25680
ctgattgctc agggactcgt gaagagcaag actgcaaaat tgcagttaag gaggtctggg    25740
gaagaagcat gtggattgat ctttgagaga agacacaaaa atatgtgggt ctctgtctca    25800
tttcattgtc taccagaggg tgtccatcgc aaagaaggtg ctgaacaatc agttagatag    25860
gatgattcat ccagtggaaa tgagcttatc tctctcctta gctgccccag agcatgcaca    25920
```

```
acagacccat aactgagaag ccatggtaag agggatggaa gccacgcatg gcccaacagc    25980
atgggcttcc tctggccgag gctgacctag gtattactac taagtgtcca atctgtcaaa    26040
gcacaggcag ggctgagctc ttgacatggt accaccccte aaggagggca cccagccaca    26100
tggtgccagt tgattacact ggacccaacc accctggagg tgctgtgact cttctatgac    26160
ttcatgggac tgatacagat ttgccttctc tgtccacaat gtcatgatca gcagcactct    26220
ctcagagttc ccagggtgtg cagtttatca tcaaagcatt cccccataac atggccatgg    26280
agaaagtgag cacatgacca tgttattcac tggtcctgct atttaccata ccaaccaggg    26340
ctgcatcctg agaaaatgct ggaataacca cttgaaggca tagctaattc atcagcttga    26400
agatagggtt gagaacctgt ccttacatgt ttgtttgttt gtttgtttgt tttgagatga    26460
agtctcattc tgttgcccag gctggagtgc agtggcacaa tctcttactt caacctctgc    26520
ctcctgggtt caaggcattc tcttgcctca gcctcccgag tagctgggat tacaggcaac    26580
cgccaccacc cccggctaat ttttgtattt ttagtagaga cggggtttca ccatgttggt    26640
caggctggtc tcaaactcct gacttcgtga tctgcccgtc tcggcctccc aaagtgctgg    26700
gattacaggc gtgagccatc acccctgcc tcccttacat gtatttctat acttgagaca    26760
atagctattg taagggtgct acatcccaa cagtcagaat acataggtct ggaagccaag    26820
aaatgagtgg cctctctcac ctttattccc aatgacccac ttggcaaatt tatgctttct    26880
attgccaaag ctttaggctc tgttgaacca gagatcctag ttctcagagg gtagggagag    26940
atcacttcta ccagaggaca taattgtggt tttactaaac ctaaaattat atctgcctct    27000
ggtaattttg ggatcctcat gacagcagac cagcaagcta agaaaggaga ttctgaacag    27060
gcaggagtaa gtgacccctg ctggaccagg tgagggcat ctaaaagggg tagtaaagtc    27120
ggaagctgag catcagttac actttaggac caactacagc agtggggtct ggaaattgtc    27180
cctcctctta tctgttatcc tttctacctc ttcctcttcc ttcttctcct ctcttcttgt    27240
aacaaatcgt gactttccac cacccaaaga agcagtgaca gaacatgaaa cttaatatga    27300
atgcaagttt atctgagcag gtgcaagggt gaactgtgac acatactgtc aatgccctgc    27360
cattgtccct caaacctgtc aatgtattcc caagacttcc aactgccagc atccacatgg    27420
tagctaaggg atcattttcc cagaactaca gagagctgac tgtacacatc acagttcaca    27480
agtgccaaag aattaaacac caccagggag cagcctcaac actcaaacat ggtgtataaa    27540 tacccccagct ccctcaccct ttgggtggga tgcttctgag gcatcgatca ttctgaggtt    27600
ttgtaccatt tcccagagtt tccctgcagg ataaatcttc agttccccctt tgtgataata    27660 gtgcacccctt atggggctgc cttcccttcc ctgtatcacc ttcccacttc cctattagtg    27720
ttacttatgc tccccaaata aactatttc actttagtcc ttatcttaag gtcagttctt    27780
ggaagaaccc atgctaagac acatgtggct caaggactat gcattgagaa gccctaattt    27840
agagagtgaa ctcatttcta ttttttaaaa atatctttct ccctctctcc cctgactccc    27900 cttctccttta ccccctacacc cgagtttgtg tgtgcacaca tgtgcacaca tatatagaat    27960
atatgaaaaa gatctgagga tatgatccaa gtattaacaa tagttctttc tgaatggtgg    28020
cttcttagtt ttcctctctt ttgttttttct acagcagcaa ctgtgtctcc gaaagtattt    28080
ttaattggca attaggaaat gatgagtgga gtggtgggg agcagagcca ggctgcagtg    28140
ggctgatgct ggcccaagag gatgcacagg ccacagtggg ctgatgctgg cacaggagga    28200
tgtgcaggct gcagtgggct ggtgctggcc caggaggatg tgcaggctgc agtgggctgg    28260
```

-continued

```
tcctggccca ggaggatgtg caggctgcag agggctggcc ctggcccagg aggatgtgca   28320
ggctgcagag ggctggtcct ggcccaggag gatgtgcagg ctgcagtggg ctgctgctgg   28380
cccaggagga tgcgcaggct gcaatgggct gatggtgacg caggaggatg tacagacaat   28440
tctctcaaag tgctgggcta gagacaggca agaaatgagg tggtagctca aggtgggca    28500
actgtagaga gtatcatttg aataggaagt tgagcctgtt tctaggctga ggaaaagcag   28560
ccaatgacaa ggaaggagac aaaaatacag agtcaaaagt gggctcattg aaggagtcag   28620
ttcccagaag aggcctgagt ggattcaagg ggcctaggg gaggaatcca ttctcaacag    28680
aaggtgagct tcatcctctg ggaccaggga aaggggtga agatgaataa tgttagaaat    28740
gcatttattt cagtcatttt tttgttctac tctctgcttc atttcacaga gtacttgagg   28800
tgtttctata gataagttga taggttggag ggactggaag ttgggacatc cccacggagg   28860
gggctccact tcccccatgg agcaggaggc aaggtccccc actgagagga agcaggggtg   28920
tctctgtggg gttacaggag ccaggcaaag gtttggaata gggaggaggc actgagcgac   28980
agagcccagc ttgcccattt ataaagtctg ctaggtggag ctgaccgctc agctgtggcc   29040
cagccagcct gcacaatgtg gagtcatctc cagctgcttg ggcccaggc aagaatcaca    29100
ggaggaggag cctgtgccgc ttacttgtcc tggttttaaa taagtcactt ccccactccc   29160
agccacagtt tcctcatctg ccaatgggga gaaacaagtc aaatctggag atttgatcct   29220
attgtgagga tcaaatcaaa taacacacat gaagcaccta gcacagtgcg tggcactcgg   29280
aagttgctca atgttccttc ttctgctcct ctgccttcaa gtgggcttga gcaaatgtaa   29340
cctggatagg aagggacgtg gatgttgtat cttgtattgg tggatgctgt tacatgcaac   29400
aattttaaat acagccgact ctcattactt tctgtagccc ttaaaaaagc tatggcatca   29460
ggctcctgtg agtctctggc cacatttta gcaaccagtc aacatacaac attgttttat    29520
ttatttattt atttagacat ggagtttcgc tctattgccc aggctgcagt gcagtggtgc   29580
aatctcagct cactgcaacc tccacttcct gggttcaggt gattctcgtg cctcaacctc   29640
acaagtagct ggaattacaa gcacccgcca ccacgcccag ctaattttg ttttttagta    29700
gagatggggg tttcaccatg ttggccaggc tggtctcaaa ctcctgaccg caggtgatcc   29760
tcctgcctta gcctcccaaa atgctgggat tacaggagtg agccactgga cccagccaca   29820
actttgtttt atgtgtgttt ctgcttagag acccttattg aatatataaa ttgttgattc   29880
actagcactg aactcacagc caacactact gtaactcatg tctgaacaaa gcttatcaag   29940
cacacgtatt ttctccttaa ggcacatcac agccttcttg tgcttgagaa caccagagag   30000
cacttcagca caatgcttgg ggccatttta aatagcaaaa tcaccaacaa aaaggcacaa   30060
aaaatgagaa cggttcgcaa caaataagtc acaaaaagaa tacttgttta cactatgaca   30120
gctgagacaa gaaggcaggg tgtccctttg ttccacttca gctgggaaca tatgtgtggg   30180
taagtcaaga ttttcaccac tgtacataag tatgtccaca aataatagca attgtgcctc   30240
aagtattgat ttgaaggtta caaataaatt ttagaagtag gtgattttgc aaatatggaa   30300
tccataaata atgaggatca attttcttta tttttctga ttacaaaaat atatataata    30360
aacagagcta tctaatgtaa aagttaaagt ccccccataat cccagcccac aaatgaacac   30420
aattagaata tagttctata gaattttgt tatgcaaata atgcctgtga ttgtgtctaa    30480
gtctgtgggt gtctatgtgt cagtgtattt gggtctttct tttctttttc tcactcaaca   30540
atagctcttg gatagctttc cagaaaaaaa aaattcctga tgttaatttc tggagtatga   30600
atggaagcag atggcataca ctgcagtcag gatctctaag tcttagttca gaccactcaa   30660
```

```
ccacatcaga tgtggagaga gcaatgactt gccaaatgta aagataatca acagttttag    30720
tgttctgcat cttaatggag atggaataag gtcaagagaa gaactgctca gaggataaaa    30780
ggactgaaca ctgggaagta aagtgaaaga gaagagactg ggtcgggcac ggtggctcac    30840
acctataatc ccagcactct gggaggccaa ggcaggcaga tcacttgagg tcaggagttt    30900
gagaccagcc tggccaacat ggtgaaaccc cctctctact aaaaatacaa aaattagctt    30960
ggcgtggtgg cgggcacctg taatcccagc tactcgggag gctgaagcac aagaattgct    31020
tgaggctggg aggtggaggt tgcagtgagc caagattgca ccacttcact ccagcctggg    31080
caacagagca agactccatt tcaaaagaaa aaaaaagag tctgtgactt tcagccagag    31140
aaaaccacat tctgtgtcct ttggaggaga ttagacctac atattaagac tatttactga    31200
aaggatttag acaatagagt aaaatagtac cagagccttt tctaaaaaca gctgcaaaat    31260
tggctgggcg cagtggctca tgcctgtatt cccagcactt tgggaggcag aggcggttgg    31320
atgacctgag gtcaggagtt tgagaccagc ctgaccaata tggtgaaacc ctgtctttac    31380
taaaaataca aaaattagcc aggcatggtg gtatgcgcct gtagtcccag ctactaggga    31440
ggctgagata ggagaatcac ttggacctgg gaggcagagg ttgcagtgag ccaagatcat    31500
gccactgtgc tccagccagg gtgacagagc gagactccat ctcaaataaa taaataataa    31560
aaacagctgc aaaatagtat ggagaaagct gggctgctgc aacaaaagac ccaaaataca    31620
atggctttta gaaaataagt ttacttctca ctctgtagtc catgtcaggg tggctgtact    31680
tcatgcagtc attcaggaac ccaggatcct cccatatctt tgctccatca gcccttttga    31740
agcattattg aagctgtgtc cctggtacat ctatgttcca actcaagaga agagaaaatg    31800
gagcatggga gagcaaaagc ttcatgcctt aaggtctatt tctatttatg ttctattaga    31860
aagattttag tcaccaagtc tcactcggct gcaagaacag ctgggatgta tgatctctag    31920
tggaccagcc attcctccga ctgctactct actacataga agaacaggag gatgaagttt    31980
agtggacagc tagcaatttc catcacatct cctttatttg agccttggta tcttcctcta    32040
taaaacgggg ataataatat aaactagtta aggctgcttt gggactgaaa tccaataata    32100
tatgtgagaa tgcttagcaa gccctactgt gcctgataag aatttctcat tgattttgcc    32160
ctctagactg ccagctcctt gggagcaagg agcatagttt attccacctc ctcacaaaga    32220
cctgcttgga gtcagcatca gtaaatacat gttgaataat gaagtcactg tttcatccat    32280
catcaagcct tttttttttt ttcatttcat ttcaaatgct tcaataattt agactctgcc    32340
ctgttcactt tccccacccc ctcattaggg gtgcacgtca gtatatcagt tgggattctc    32400
tgggttgcaa agtgacaatg cactactgtt aaactggctt atgcaataag atggaccatc    32460
tcacatatcc tgaagtccag actctgcatc agaataaaag cttcttttcc ctaggactct    32520
cttggccttg ccctcccttc tgtatttgct gcatcctcag actgggagca agatggctgt    32580
tgcaattcca agcattgcca ccaaacatat cccagcaaag ggggcagact gttttgcaaa    32640
gtaaagagac catttcctga aaccccctct ctgccatagg cttcccccttt agttttttcag    32700 ggtggacctg cccaaaccgt cactggcaag aggaatgaga ccaccataat ggacttggac    32760
caaacaagac tcactccatg agaccaccat aatggacttg gaccaaacaa gactcactcc    32820
tggaaatggg ctggggtcag ccttccttgg gtcacttggg aagggggcc acctgaccaa    32880 aatcagggct ctgcccataa gaaaatgttg agaaactgct gttgcatgag caaccaaatt    32940 attttttctcg caatgatgga gattctgggc cagatgaggg tgtgatggag aaagtgttaa    33000
```

```
ccatagagaa ctaaactgag agcttttcta taaactgtac ctcaataaag tttaacacca    33060
atgaagatat ttttggagga ggcagaaact ggtagccacc ctctatggct catttccctc    33120 accccgtat ccaaccatca ccaaatgtca ccgtgtctgt acttgcaata ccctagtctt     33180
ctctccttac ccactgctga ggccccagtt cgggtctcac ctcctgcagg cacgatgaca    33240
acagcacctt aggggtgccc agtctttcct tcctcctgca acccagggcg ttgatgcggt    33300
tattcagcta cacaccttta ctgtgtgctg agtgctgtgc atccgcagac acattggaaa    33360
agctccctgt tttcttcacc ttgcagatgg tataatgatt atctccaaga cttcctgaaa    33420
cccaatcgga ccaggtcatt cccttgcctg aaagccccat gccttcaaga aattctttac    33480
catgacccac aatgccctcc agcccaccca ggctcctttt ccaccccacc cccaacagta    33540
cagaattact agcacttcct tcactgcgcc ctccccttc acgcctctat gcttttgcac     33600
aggctgtctc ctctgcctag aaatccctta tccctctcc atctggcaca caagacaagt     33660
tctcctatta ctttttctcc ctctctcctg ctccacccct caccgcctta cacacacaca    33720
cacacacaca cacacacaca aatacagcac tccagaattg tttgccaatg gaggcagcct    33780
ccggggccag atgttagcca gggctttcca aacttctccc caagcactcc ttaagaaagt    33840
gaagaggaaa tgggacccca gggcttagga gtgtgagggc cttgaactcg ctctaagcaa    33900
gcagggcatt tcaagagttt tatctttata ttttatgcag aagttgtatt ccaaatatat    33960
tcttgttcgt tttaatacaa aatatgattt tttctacatc ttcaaatcga tgatccagaa    34020
agatgctcct tgtttatttg ttgtgctctc aaattagctg ctccgcctcg ccgcggggac    34080
cctaagcgag acctggatgc agttccaagt acacaccccg aaggaacagc tgggcttcgc    34140
ttccctggga gctggaggat ggtgggggtg gggcggggtc aaccggctgg tggcccccc    34200 cctccccgc ccgctgcggg ggcggatttg cttgggtccc gcccacgggg gcggggaggc    34260
acccgcggcc accggcagct cggattcggc tggttccggg ttgagaggct gcgctggacc    34320
gaaccggtgg ctgctaacct cgcggggta aggggtcccg ctgggccagg tttggggccg    34380
ggatcccgca gctgaacggg ccggcacccc tcctcttctc tgccggtcac aaccaatgta    34440
ctgctcggcc tggctgcccc ctcccccagg attcccatc cccaggttct tgcccttccc     34500
ggaccgcccc cacctgggga tttcgaccct cttaagggtt ccaccccggt ccggattcc     34560 cttttcccag cttctattcc ttaggactgc ccggcccct aagacctccc cagttaggat     34620
ctccgtctcc tcagccgctc atacgcttct ttccagcgcc attcgccttt gagctgcccc    34680 ctacctttt tattgccttc ccgggctggc tttccactga ttttcagccg cgcacccttt    34740
cctcgcgtta ccttctttcc ggacagcacc ccttcccttc tccggtaggt cctaccccag    34800
cctgtgcggg cctcgtcccc gcgccagcc ctcggtgctg cctccgacag cgccgcggct     34860
ctattagccg cccccctgcc cctcgggccc ccttatatgc tgcccctggc gccatggcgt    34920
gcagcttcaa ggacgagctg ctgtgctcca tctgcctgag catttaccag gacccggtga    34980
gcctgggctg cgagcactac ttctgccgcc gctgcatcac ggagcactgg gtgcggcagg    35040
aggcgcaggg cgcccgcgac tgcccgagt gccggcgcac gtttgccgag cccgcgctgg     35100
cgcccagcct caagctggcc aacattgtgg agcgctacag ctccttcccg ctggacgcca    35160
tcctcaacgc gcgccgcgcc gcgcgaccct gccaggcgca cgacaaggtc aagctttttt    35220
gcctcacgga ccgcgcgctt ctctgcttct tttgcgacga gcctgcactg cacgagcagc    35280
atcaggtcac cggcattgac gacgccttcg acgagctgca ggtgcgctac ccggcctgcc    35340
tggggaaggg gcggggccgg gctggatgtg gggccgggcg ggggtggg tcaggctgg      35400
```

-continued

```
accgcgggcc aggcccagtc agaatggtcc tggggcgggg ccgccagcag ggtcagggcc    35460
ctatcaggag taacgcgggg cagggagggg cggggccgcc gcatggcggg gccgtggggg    35520
cggggccttg ggcagtccgg accctgaggg atctgagaca gacctggagt accggctggt    35580
ccgcggttag ggagaagtcg gggatgcgga tgggatggcg gaaacaagtg agatcagaac    35640
tggaccagat actgggctgg ggcagggttg tggacaaacc ggaatcagag ttgggcaaag    35700
gcagggccac tgtcagactg agggcgaggt cgcgaggatg ggtctgtatt aaaccgggta    35760
gctgagctct ggcaggctgg gggttctgtg ggggcggaga ctggatcaga tgtgcatcag    35820
gactaagagg agtacggggg ctagaatgtg ctggacaggt gagggtgaaa cctaatagag    35880
tggtataagt tagggtgcca aagtgctgag agggcaggtt tgagtaccga gggttaggcc    35940
aaggtgtatg aggggttaag actgagatca ggtccagata ctctacaaca agtttagatt    36000
taagccagag tagaggccag gttgagtggg gccaggactt aaaggtaaag atttggagaa    36060
taaggcccag atgtaaggtg attcaagaag ggaggggcta gacctctagg agtctctaga    36120
ggtttttgat gacctccttg gctctgtccc ccacatcagg acttttgaag aataagtgaa    36180
acggtacatg cagagtgacc tgagcatagt tggcatagaa ctctaatcgg tctcccttaa    36240
gacttcctgt cttcactgac aaactcctac tcaaatttta aggccttgct caaatatcct    36300
ttccgtgaag ccttctccaa gttccactgg tcaaacaaac aaacaaacaa acaaaaacat    36360
tagaactgca tttccccaaa tgctctctat taataagtgt gggaaatata gtatatttt    36420 tatacccacc cccttggaga attttcagtg tgcatttgca tattaaaagc ttagagaaat    36480
tttgttgcaa ataaatctat tttactgtgt ttaataaaat ggttcccaag cttacttggg    36540
cctggaatcc tttttttcaag ctaaatcact taaatccagc agccccatgt acctggcttt    36600
gggatactag tcgagcacgt agttctccaa ggccagagac agaatcttat ttttcctatt    36660
tatgccccca aagcctggtg caaggcctgg cccacagtac acaccaataa aggccaaatg    36720
aatgaacgaa agaatgacca accctggcct aagctggacc acactgtgga gcgtttggaa    36780
gcagaaggtt tttggctcaa acattttatg aaaatggagt gggctaactt gggaggtaat    36840
gagctttctg gcctcgagat actcaaacag aaactaaata attactttcc cctgtattgt    36900
aggggtcccc aaccccctcca cacaatagtt tttgagtagg cctgcaccca gcagatgccc    36960
atgggcctca ggagaaatgg cccatgttca ccatcgctcc ttccctgtcc cttttatctc    37020
aaaactacaa ctgactccct tccagtctag ctgtctgagg atgaaggccc catcagaggg    37080
tgagcaaggg cctgggcctt tgggagcctg cacaagggtt ggcctccac ccccagagcc    37140 atcgtgctag gcgctgctgc tgtccatctc cccgtctatg gagtcacata agcaggaaga    37200
gtttgagggg actctgtctg aaaccatctg tccaacctct tcatcatgta ggaatggaaa    37260
gtgaggcctg gagaagttat gtgacttgcc caaggccaca attccagaca gtgagagagc    37320
cagggctata gggcacagcc tgacccagat ccctcttctc tgatctctcc cctccttgtc    37380
tgaccttcta gcctctgctt cagagccttg gttctcctgt ctgcaaacca ggaaatccaa    37440
attactgtat gttgggcttc tgtactctat cccatgacct gggggacaca ggagaaattg    37500
aacatgtatt acctacaaat attattgaaa tgcttcatta ttgggtgaaa agtaaaacag    37560
gactgccact tgcttactct ctagtgcact gtcgtggggt tggacatact tgggttccaa    37620
acctgctgtg ggcactgtgt gcaccttggt gagtcacttc atgtaaacgc tgatgctctg    37680
tctgtacaat ggggtcagga tgcttccttc ctaccaggac ttttgtgaag ctgacctggg    37740
```

```
attaacctgc tatttgaggt tcaaaggcac acagtacggg ctggaataac atacagccca    37800
ccttttctct ttctgcctgt gagagctcat gtgcccagct gagtgaatgc ccagactctc    37860
ctctctggcc cgagaaggag gccttgcttt agtgtgtcct ttgggcttgg caatttggtg    37920
gcagagaaat ctgcctccca tctagagagg atgtgctgct gggtgagatt caaggcaccc    37980
tccaccccac ctgcctctcc ctccatatgg ggaaggcaag gcttattagc tatttatgca    38040
gcagaaataa ggctgaaccc ccctctctt cccttttct cccagcagct gatggagctg      38100
gggcccttct gcagaattac agactcagag ccatgcagat gatctggtgc cacatccact    38160
tgacagatgg ggaaacagga gagggagagg gaggaaggga acttgcctaa ggcctcgaag    38220
ccagaggaag ctgggcctat actcagctgg agtctcccaa caccctacct agcagttggg    38280
gtgcagcttt tacatttatt ataaatcctt gaggcatcag agcagagaaa ttaagagccc    38340
tgctttgtac ccaggtaatc tcaatcctgg ctctaccatt tactgtgtga ctttgggaag    38400
attatttacc atctctgagc cttgggtcct tcatggacag catggaagta attatattag    38460
gattaaacaa gatgatgttt ataaaaactt agtactgcac ttggcaccta acagcactca    38520
ataaatgaca gctatagtag gttacatcgt actcggcatt attgacattt ggggctagat    38580
aaccgttgtg cagggccatc ttgtgtgtta taggaagtct ggtagcattc ctggcctcta    38640
cccattagat gccagtagca aactccaccc accccgcaag ttgtgacaat caaaaccatc    38700
tccaagcatt gacaaatgtc tcctagagtc aaaatcacct ctagttgaga aacctgacct    38760
agaaaagtcc cactgaactt taaaacttca ggtcaaatat cacctcctct gtgaagcctt    38820
ccctgaccta ctaagcacaa ttgctttgta ctccagatta catcacaggg gtcagatcct    38880
gacatgctgt gtgtccttgg tcacgtcact ttgcttctct aaggctcctt ctctaaggtt    38940
catctataac aagaggatat gatgttcctg ggaaggatgt tgtaagggtt agggatcctt    39000
tatcagaagt gcctagtact gtgcctggca tagtaggcac cccaaaacta ttttttaaatg   39060 tcttttattct gattataaaa ttaacataag aagcagagct gtataatgta aaagttaaag   39120 tcccccccata ataataccccc atgaaacatg gcaggagtta ctatacagtt ctaaggattt   39180
ttatgtaacc tgtgggtgtg catgtgcatg tgtgtgcatg cgtacatgca tgtgtgtgtg    39240
catgtgtgtg catgtgtgca tgcatgtgtg tgcatgtgtg tgtgtgtgca tgtgtgtgtg    39300
tgcatgtgta tgtgtgttgg tgttttcctc cccacctcca ctgctgagta cctggaccac    39360
tgagcaaagt ggagggaagg agcccatttc caaagagttc agggcttctc agccaatatt    39420
catcgagccc agtctgaatg cctgggactg cactaagggc ttttcttgca ttacctcatt    39480
taattttcat agcaccctgt gggatgggta ttgttatcta tttcttctac tgatgaagaa    39540
acagactcag aggaattaag tgactcattt ggtcacccag ctggtaaatg gcagggccag    39600
gattggaagc cagtctgact aggccacata tcgtccctga gctacctctg agggctgggt    39660
aattgtctcc cagccaccct gcctgtcctg tattgacagg gctaggccat ctgtgccagc    39720
tgacgccccg agggcaggtg gttgggacgt catcttggtc agagcagacg tggcatccgg    39780
ctctctggcc atctcaggtt cctaacccc agagaggga tccgattcag tttcagccgc      39840
cccctccagg cctcatgtga ccattggagc ccttcccaag gcttccttca tgccagagaa    39900
gacagcagtg gatcagcctt ggacgcaagc cctggtaggc agggtatggt gatccagtga    39960
caccaaggca gccacccaag gagggagggg ggtgggggct aggttcaaat ctcggctctg    40020 gttttttttcc aggagagggg gtgacaccct cttacccaat ttgagaaatg gaagtaagaa   40080
ctagccctcc tgctttctgt ataaagagag agaaagagtt gctaaatatc caaagaaatg    40140
```

```
agagattcag aggcactttta ttttgtagca tggacaggaa ggcagctggg ttgtctgtgt   40200
tgtggggaag tggctctgct gttacttttc caaggagagg gcaggatttc tatgccaaca   40260
gcagcctctg tgagggcaaa gctggctgtg ggtcaaactc agagctggcc gctggcatct   40320
ccacatccct cttcacaggt gtctgggcag ccaggatacc tttgctgagc acgggccaca   40380
gtgtagaagc ttagggccaa cattggggac cccaatatgt ttattttata gaaagaaaaa   40440
agacctggta gggactaaca atgatgaaac aatgactcta taaaattata gcccaagttt   40500
tggaggcaca aagtaagtta tggggcactt actgtgtgcc aggtgctgtg ttataggcat   40560
ttgattctca caaggatttt ttcgttccct actccctgag tgggactgag atcagtacca   40620
tctcacagat gaagaaaatg aggctgagag attcagtaac cttcccaaga tcacactgca   40680
agtaggaaga aaagctgaga ttcaaagtgg tctttctgac tcagaattca ccctccttcc   40740
caacacgcca actgtcccag ggagcaccaa atggggagga acctgagaaa ccatctggtt   40800
gacacgctcc ccattttgca gatggggaaa ctgccttgcc cagggttaga ccagagctca   40860
gctctcccga ctcagtccag tgttgttttc ccagtaccat ttaccttcct gacctccatc   40920
tctgcttgaa cactcagagg gatgaggcag atttggaggt gagttctgtc ttggattcag   40980
ggattccttt aataatttct gggctgggcg cagtggccca cgcctgtaat cccagcactt   41040
caggaggcca aggcaggcgg atcacctgag tttgagatca gcctggccaa cattatgaaa   41100
cccccatctc tactaaaaat acaaaaaaaa aaaaattag ctgggcattt gtggcacaca   41160
cctataatcc cagctactcg ggaggctgag gcacgagaat cgcttgaacc gggaggcaga   41220
ggttgcagtg agctgagatt gttccactac tctccagcct gggtgacaga gtgagactcc   41280
atcttaaaaa aaatacatat acatatacat atacatatac atacatatat acatatacat   41340
ataaatacat gtgtgtgtgc atatatatgt atatgtgtgt atatatatat atatacacac   41400
atatatgtat gtgtgtgtgt gtatatatat atatatacac acacacataa tttctttagc   41460
cagtatctgt gccatggcta cagagggcca gccctgtgtt gggcccagga aaaaactaca   41520
caagacctgg ccctgtgtgg tcccgaaaga taggcccata aactggtagg ttgctgtaac   41580
tgaggcttgc tctgttgagc tgaatcctaa aagatacgct gagtacttca ggccagggag   41640
caaaaagaaa gatgttatgg acagagggaa caaaaacatg cacagcctgg tgcaaattgt   41700
tccacggact gggttcaagg ctttgacagg cagtcatgct ctccttctct ctctctcccc   41760
cagcctacct ctcatttaat tctaacagta accctatgag atggatctca ttgccccatt   41820
ttataaatgg agaaactgag gctcagaaac tgtgcctagc tgggcacagt agctcacacc   41880
tgtaactcca ttactttgag aggtcaaggc aagaggattg cttgagccca gaagttcgag   41940
accagtgtgg gcaacatggc aaaaccctat ctctataaaa aatgcaaaaa aattagctgg   42000
gcatggtttc atgcacctgt attcccagct atttgggagg ctgaggtggg aggatcactt   42060
gagcccagga ggttgaaact gcagtgagct gtgatggtgc cactgcactc cagccagcct   42120
gggcaacaaa gtgagaccct gtctcaaaaa accaaaaagg aaaaacagaa actgtgccta   42180
agggcctgga agggagaag ggagaagaag ggggaagaag aaaggggga aaagaatata   42240
aatgtattta ctacctctga attgtacacc taaaaatggt aaagatgata aggtatatat   42300
gtatatttta cctcaataaa attttttta aaaagaggct aagcacagtg gcttatgctt   42360
ctaatcccag ctcttgggag gccaaggtgg gaggatcatt tgaggccaga agctaggagt   42420
tcgagaccat cctgggcaac acagagagac cccatctcta caataaattt ttaaaaatta   42480
```

```
tccaggcatg atgcatgcct gtagtgtgag gtacttggga ggctgaggca ggaggattac    42540
ttgagcccca ggagtttgag gctatagtga gctatgattg caccactgca cttcagccta    42600
ggtgatagag tgagcccttg tctctaaaaa aatttttttt aattagggaa aaaaaaaaaa    42660
agaaagaaac tgtgcttaag gtcagaaaac cactaagtgt ccctgaagct gaaacttgaa    42720
ctcaggttat ctgagtgtga ccagggacag gcatggaggt gagcacacat gtgttcaggt    42780
ggttcgttgt ggctagaggg gagggtgtgg caggaggagg taagaatgga aaagcaaggc    42840
ttgaccagct caggaagggc tttgaatgct tgaatgtgca catacatgca cacacacaca    42900
tacacacata cacatgcatg cgcacacaag ctcacacaca cacatgcacg cacccattga    42960
gcttgatcct tacttaacat gctaggaagc cagaaacaaa tgtgagcagg caagtgcagc    43020
ccggccaggt ctgcattatg gaccaagcac tgtggggcag tgtgccaggg agctggtgg     43080 gagaccctag aagcagggac tggccagatg ttgccagaga ttgtgtggct cagaagtgca    43140
cagggagggt tggggctcaa agatataaaa taattccagt ctgttgggag gaccaggagc    43200
atccagttct aggtatagat gaaggattgg ggttggggga ggaaagggag aggcaagttc    43260
aagtttgtca cggtcaggtt tctggcatcc ttgggtcaga gagggaaaga gagagcagta    43320
cccagacatg gagaagagga gaggcttgag cacctattgt gtgcagcgcc atgctgggcc    43380
gtgtcatagg tgccatctca cttagccctt catcacaaca ctgtgaaagc ttgcggaggt    43440
gagccctgag cgaaagtcat gctgtcagga tttgaacaca ggcttttctg atgaaaagtc    43500
cctgaagcca gagctgagat ggcttttcca c agctgctttg tccctggac cagagggagg   43560 gatggcctca cagcaggaga tatctggcct tgggaacatt tgagccctgc ctctctgtgc    43620
cccccaactc ctctgttgcc ccagtcctgg cttcttcata ccaataaaga gcccccagag    43680
cctcaaagct ggcatatttg cataactgtg tgctcagggc tgcgcagaat ccacagcccc    43740 acccttgag gtgtgtcctc cccactcact tcatcctgcc ctgccaccc ccgctccgat      43800 ggggccctgt ggaatccaac tctcccaggc tgacattcaa ggcctcctcc agtgcccacc    43860
cctaccctag ctagccccag gtggcctttc caggttgtga ctccacccac ctgtcacatg    43920
cctggctgca gccatcccca accaccccga cttcctgcac acgtgagggt gggcccttac    43980
ccaacctgtt ctccccacct gcaatgccct ggcccatcct ggagacttga aggaaccctg    44040
gccatccatc ttcctttgtc cttccatcag aaacaaactc cttccttgaa gctcccccg     44100 ttctgagtcc caactttaca tatagttact atgatgataa tgacaactaa gattgattga    44160
gctcaccctg tacgtcatgt caggtcatga attaagtcat ttcattccca gagcaagcct    44220
atggagcagg tgctgttagg ccttacttaa tagatttgag gtccggtgcc atggctgatg    44280
cctgtaatca cagcactttg ggaggccaag gtaggcagat cacttgaggt caggagttca    44340
agaccagcct gaccaacatg gtgaaacccc atctctacta aaaatacaaa aattagccag    44400
gcgtggtgtc gggcgcctat aatcccagct actcaggagg ctgaggcagg agtatcactt    44460
gaacctggga ggcagaggtt gtagtgagcc aaaatcgcac cactacaccc cagactgggt    44520
tacagagcga gattctgtct caaaaaaata aaaaataaaa ataagacctt actttacaga    44580
tttggaaacc aaggtggagg gagggtgctg tgagcacagc caggtgttgt cagctgttct    44640
ggatcctagc aggccctcca tgtttatcct gttcttcttt gtattttacc tattcaagtt    44700
tcttcctcat cgactaactg caaattttc aaggaccatg tataggccca ccctggagc     44760 ggccagcaca aagcctgaca ctcattgggt actcagaaat ttttgctgca ttgatttgca    44820
tgggaggtag ggaggccaag agattttgaa catggatttt cggagccact gagagcctcc    44880
```

```
cctctgcctc ttactagctg tgtgaactta ggcaagctgc ctaacctcac tgagcctcaa    44940
tttccccctc tgtgagatgg acgcaataaa gacactacta accttgtgga ttgttgtgag    45000
aattaggtga caagatgcct gtgaaattca aacccaaacc acatccgcct ccagcccctc    45060
tggtcctggg tctctgccgt taccagtgtc cttcctcagg gttaagctgt atcacttgag    45120
agtttatcag gctccagttt cctgtgtgac ctctctgctg gagtaaaatt tctagtttgt    45180
tctcctgtgt caagctgtgt ggccgtgggc cagtcagtcc cttcccttgg gcctgtgttt    45240
cctgtcctgg caatccaagg ggttggacca gatggtccct gcagtctctt cctgctctgg    45300
ccatctgaga agggaaggag gggccacctg acacagtga gggatgaaga cacaaagaag    45360
cgactaggga gccgcatacg ggacacagtg accgctctgt ctcccgagca cccagggtgt    45420
gccaggctct gtgccctgtg aggctgaaca cttcttacca ttgtctcact ttatcctccc    45480
aaccctagga gatatgatta tccccatttt tcagacaagg cactggggca cagagaggtt    45540
aggtgacatc ctagggtcac acagcccaat gggtggtaga gccagtcttc taaccaagga    45600
aggagacacg ttgagcggg aggggtgaca cagctcaggc agccttctaa gtcctacctt    45660
ctggactcta gggtttggtt ttcctaattt agctgtttct ttgggctctg cacctagccc    45720
atccaaggaa ctctgcctgc tgggggcctt ctctcccctc ccacccttc gaggtgaact    45780
ctgactcacc ctaccctcat ccttgggcag ggacatcctg aaaactcacc gaggccaggg    45840
gtgtgtggcc gtgtcctagg tactgaaatt gtgaaaatct ccctttcca cagtccttgc    45900
cctcaaaagc ccataatcta gtgggggaga ttttgttgt tgttgttta aagatggggt    45960
ctcgctctgt cacccaggct ggaatgtaca atctagtagg ggagatttt ttttttttaa    46020
agagactggg ctgtgtcacc caggctggag tgcagtggca cgatcttggc tcactgcaac    46080
ctcctgggtt aaagcgattc ttgctcctca gcctcccaag tagctggaat tacaggcatc    46140
caccaccatg cccggctaat ttttgtattt ttagtagaga cggggttttg ccatgttggc    46200
caggctggtt ttgaacttct gaccttaggt gatccaaagg tctcagcctc agcctcccaa    46260
agggttggga ttcaggtgt gagccactgt gcccggccta gtaggggaga ttgacaggta    46320
accttgcaat taaaatgcag tgtgtgccat caggggtacaa gtgtgggaca ctgtgcatgc    46380
agagtttgag acatgtactc ccaggggagg tgacatttga tctgggtctt gagagatgtg    46440
taaaggcctg gagagccctg cgagctgctc agtgtgtctg cagcagtact gtccactaga    46500
actctctggt agaacgggca gttctgtgtc tgcactgtct gatacagcag cccaggtggc    46560
tggcaagcac ttgaaatgtg gccagtgcaa ccgaggagct gaattttcca ttttatttca    46620
ttttaattaa ttgcaatta aatagccacg tgtgtcgtat tgaacagcac acgtctggac    46680
caagagctag gactggagaa gaaaaggttg gggccagcag tagagccttg aatgtcaccc    46740
taaggctttg tgcctttctt cccagacaat gtggaaatct gcagactggc acaatgggga    46800
gagtgagagg gggaagcatt tatacatctg ccctttagaa caatcactgc agctgctgtg    46860
cagggcactt ggagcagcag gagagctaga ggcaggagg agcctgggc cacagcccag    46920
aaaagaagtg ataaaaaccg aaccagaggc agcacgcata gagaggagag aacaaattcc    46980
agagcaaacc tagtgactgg attggttttgg aggcggtagg aatcaaggat gactctcact    47040
ccgaggtttc tggctgggat ggagttaggg gaggggtgcc cttcactgag atggggaata    47100
tggggagagg agcaagttg ggatctccta acacgatcgc agcattcccc atgatgtaag    47160
tgtctgtgtc cctgactgtc accccaacac atgcacacct catggcatca cgtttaggac    47220
```

```
tcacacctca tctctcccca tccttgacac agcaccatgt ggggcccaag gtctcaacac    47280
atgtttgtgg aatgggcaaa tgagtgttct gattctcccg gatccaggag gaaggagcaa    47340
gcccgctgtc cttattccct gactgcaaaa tcaggagga aatgtccagg tttctcaagt     47400
gccctgagca atgtgaggaa ggcagactcc aaggcagttt ctcagaaatc ctgaagagct    47460
gcctgggtgg ctgggttttt tgtggaccca tgggggccac caggggggaga attgtagcac   47520
ttggcccatc tcctcaacat ctgcctctca gccacactgt gtcccaggct ggatagccca    47580
aggctgtcag aggcacctga ggagcggtct ttttactctc ttaggcaaac aagattcctc    47640
tgctccgagg actgtatccg ctcaagctgc acacgaatgt taggaatgac tttcagctgt    47700
tagtaacaga gccctggctg aagtagctgc agtcagatgg ggtgcgtttc tctctcatgt    47760
aagacaagtc tctaggaaag gactccaggt gggtgtgctg cggcaggttg cactggctcc    47820
tgagagctga ttgtgtgcat ctcatcccaa tgccaagtcc aagtactact tcacactgat    47880
agcttgaaat ccacttgagt gggaacattt acaccatgga aattggcact gttgggggatt   47940
taaaaaaaaa aagttttttt cagacagcca gcttcctagc atgtcactga gtaaaccgat    48000
ggtgtggcag ccccacagtc atcagggact cgggctcctt cttccttcta ctcttctggt    48060
ttcagcttgt gactttggtc tttacagttg cctcatggcc tgagatggct gccagagttc    48120
caacaattgc atcagcatgg gctctcaaaa caagcagctt gtattttgt attttacccc      48180
cattttcatg gcggggtcct cctcatcctt ctgctgtcac ctcctcagag aagccttccc    48240
tggccaccct acctaaagtc ccctccatct cacactggtt tattttcttt gcaggacaca    48300
ccatattggt aacctcgctc ctttattatt ttccttgttt gttgtctgtt ttccccacca    48360
gactagtccc tatgatcagg gacggtgtct gtcttgtcct tcgccataat cccagtgcct    48420
caacagtgcc tggtacataa tagttgccca agaaatgttt tttaaatgaa taattgatag    48480
taatcaaaga taattttgtt tcctgcattc ttccatcagc atgtcatcat gaatattttc    48540
ccatgttgct gcctagtctg taaaattaat tgaactagac atttaccaag gccctccctg    48600
gtctgacaag ctgaatgagt gggagggagg tggatgtgaa caggtaagtc agccttcctg    48660
gcactgctca cagcccagac tgacttgggg aattcagagg ccatttccag gaacttcatt    48720
cacgcagcaa gcgtcattga gtcccatctc agtgccaggc tgttgctggg tgtgaggtat    48780
atggagaggg agcagtagga gccacccctgg aggacttgtg ggccaatacg gggacgaaga   48840
agagacagac aggagaacaa ctggcgataa tacaatgggg tagattccca atgcctgcag    48900
acagctggac cctgtgctag ggagcactca cctccacaac ccatttatca cttgacaaat    48960
aatcactgag tccctgggca taaggcaggg aacaagccag acaagattcc tactactctc     49020
atgaaactca cattctagtg aggagataag caataaacac acagtcaaat atattcagac    49080
agcagaaggc gcaaggaaga ccgtgaatcc agatgtgtga cagggtatga ggaggtgcca    49140
ctgtgcgtgg ggcggtcagg caagactctt caaggaggtg gcatctgagt taaattaatg    49200
gtacaaagga gtcaccgtga gaaactttga gagtggaggc caccagccag agggaatagc    49260
cagggcatag tctgaagatt ggaacgagct caagatggtg gaggcacagg aagaaggcca    49320
ctggctggat gggagtgatg ggggagggtg ttggagacag aggtgggatc agagggtgcc    49380
ccaaactcag caatcaagat gaatagtatt taatgccata tttcttaaat caaaattaat    49440
gcaaaaaacc cacgatgaac aaaattcaac atttcaaaca aggccaggat cactaacaat    49500
gttttgttga gccacactgg aacctgagac aaaggaaaaa tcagtgaggc tgattgtgtt    49560
ttttatttaaa attttgatat cttgtgtgtt gtggatttgt tgttattcat cgcaggagtc    49620
```

-continued

| | |
|---|---|
| atcatggtag aaaacgtgtc acctggcatc aagatcatgg tctccacaac caggctgtcc | 49680 |
| gggttccaat tccttcttta ccattatatg tttatctgta tgctatgggg ccagtttctt | 49740 |
| gacc | 49744 |

<210> SEQ ID NO 5
<211> LENGTH: 30625
<212> TYPE: DNA
<213> ORGANISM: Human
<220> FEATURE:
<221> NAME/KEY: modified_base
<222> LOCATION: (4754)..(30625)
<223> OTHER INFORMATION: n = A or C or G or T/U

<400> SEQUENCE: 5

| | |
|---|---|
| tctctgtatc tttttctcca tcagaagatg gagataataa ttgtgcctcc cttagggtta | 60 |
| ctgagaggcc caaatgattt aatataagca aagagctaag aactgtgccc agcccactgt | 120 |
| agccctcgga gaatgttggc agctagtctg tagcattgga ctggtacagc tttggttcct | 180 |
| tagagcagtg gtccccaacc ttttagcac caggggaccag cttcatggaa gacaattttt | 240 |
| ccacaaaccg caggggggtgg gggtggggtg atggtttcag gatgattcaa gcacattaca | 300 |
| tttattgtgc actttatttc tattattatt tcattgtaat atataatgga gtatttacac | 360 |
| aactcaacat gatgtaggat cagtgggagc cctgagcttg ttttcgca gctagacagt | 420 |
| cccatctggg ggtgacgaaa gacagtgagt gatcatcagg cattagattc tcataaggag | 480 |
| caggcaacct agatccctcc catgtgcagt tcacactcct gtgagaatct aatgccacca | 540 |
| ctgatccaac aggaggtgga gtcaggtggt aatgccagcg atgaggagcg gctgcaaata | 600 |
| cagatggttt gccctcccc accactgttc atctcctgct gtgcgtccag gttcctaaca | 660 |
| agctatggac caatacccac ctgtggcctg ggggttggag acccctgcct taattctaag | 720 |
| cggggatcca gggccaagtg tggggagcca gagagtgtgt atgtggaagt cgattgtcac | 780 |
| agaagcctct aggtgtggcca agaggagga ggttgttgca agatgcagg tgaaagatac | 840 |
| ggacgggttc tggaggtgtt taggagacag actctacagg acttgctggt ggttgaactg | 900 |
| tgacgggagg caagtgttgg aggttgggga caaagaccag gctaaccccc agcgcctggc | 960 |
| agtggtcagg gctgaatgcc tgggccaggc atggcccctg cccccatccc ggccctgtgt | 1020 |
| gtgtttcaga gggagctgaa ggaccaactt caggcccttc aagacagcga gcgggaacac | 1080 |
| accgaagcgc tgcagctgct caagcgacaa ctggcggaaa ccaaggtgag cctggccggg | 1140 |
| gcgcggaagt ggggccggca aatatgatgg cagggcttcg aggggcgggg ccagctgggg | 1200 |
| aagaagggcg gggcctcggg tgtgcggtgg aaacctggct tcaaggagcc aaacctggat | 1260 |
| tgagaagggc aggtggggga agagggtagg gcatccgtga agttcaatgg ggcggcaccc | 1320 |
| accccatcat gactggcggc aaggatgtgg gctggtccct cggttaagga cggggccatt | 1380 |
| tctcccttcc cactttgggt ggaagttgag gcgggtcccg ggaccctccg gaaaccccct | 1440 |
| gcctcctgaa gggctgggga atgtgctcag tctctttctc ctctccctt attaaaaccg | 1500 |
| cccaaccctg gtgttgtgac acacacttgt agtcccagtc tcttcagagg ccgaggcaag | 1560 |
| atgatggctt gagcccagga gtttgagacc agcctggcca atataacgag atgccttctc | 1620 |
| tacaaaaaaa aaaaaaaaat tgaatatagc caggcgtagt ggcacatgcc tgtagtccca | 1680 |
| gctactctgg agactgagac agatgggaag attgcctgag cccaggagtt tgaggctgca | 1740 |
| gtaggccatg atcatgccac tgcactccag cctgggtgac agagtgatac cctgtctcta | 1800 |

-continued

```
aaatgaatga atgaatgaat gaatgaataa gcccattgcc taggagtcaa tcctgagcat    1860
gtcccctcga agccctccag aggtggccca gccctggtat catctcccct taagctcagg    1920
ccatgggata cagactctga aaggtagggc caaactctgc agtctctggc taccgtggtt    1980
tgggaaacaa acaaacaaac aaacaaacag acttttccac tgacttgaga aggacatggg    2040
ttctgatccc accactaact cactgtgtga ctttgggtaa attgcatgct ttcctgggtc    2100
cccacccttc ccatctgtcc agtggggact gccaggctca gtccagcact ctgggactgg    2160
aaggtgccgg gtggagtccc cactatacaa agtgactctg tgtcgtgagg cctggggtga    2220
tttcaggctg accccgctct gtcagcagga gctgcggcag agccttagga atgcgctggg    2280
cctctggagg tcatcctggg gcctgaaaac accattggaa acccagatct atgccccagc    2340
ttggccacca acccactgtg gggtctcagg aaaggtcatg acaaacaatt cttcacaaaa    2400
cattccaaag tgcctctggg caggaccctc gggggcaaca gatgataaac agtcacagga    2460
tgctggcctc attgcttctt gcagcctcag tttccccaac tgtctggtga ttctgtacct    2520
cttggatgat gagaagcaaa tggaagcctc tctctgtatg agagcggagt attatgggct    2580
gttccttctc cccagcagca ctctcttctc tccacatccc acccctctt tgttttctc      2640 cagtgacctc ttcctccccc gctttcctgt ccatctgtct gcctctgggg ggtcctgtgg    2700
ggccacatcc ccctcgagtt cccccagccc cacttcctgt ttggactggg gtgtttatac    2760
aagaaatgcc tatggatgct ttggaggtca tatttcacct ggtgcctgac tcggctttcc    2820
tgctgcgcct gcccctccaa tggcctggcc tgagggcctg tctgatctcc ctcctcaggc    2880
cctctgtttt ccttggtcgg cgccctggcg gggtgatgca ttcttggcag ggtgttttc     2940 tgaaagggcc ccagcgcctc caggccctag ggtgttccaa gggatgtggt gggttggggt    3000
gggggctgtt tccccagcca cagagctgaa aggaggggt tggggaaagg gtgaatttgc     3060
cctggaaaga actagaataa atggggtgca ccagttgagc agaacttttc tctgtgctga    3120
gaattgtgtt cctttcatt atcctgccaa cctcacagaa tgtcacctcc acgagagcag     3180
gattccctaa aacctagcac agtgtttggc acacaataag tagttataaa aaagtgatt     3240 gaaaggaaaa aaaatcggc caggcacagt ggctcacgcc tgtaatccta gcactttggg     3300
aggctgaggc gggcggatca cctgaggtca ggagttcaag accagcctgg ccaatatggt    3360
gaaaccccgt ctttactaaa aatacaaaaa ctagctgggc atggtggtgg gtgcctgtaa    3420
tcccagctac tcaagaggct gaggcaggag aattgcttga acccaggagg tggaggttgt    3480
agtgagccaa tatcgagcca ctgcacccca gcctgggcaa caagagtgag actccatctc    3540
aaaaaaataa aaacaacaa aacaaaaac caaaaaaaca ggaaagaaaa aaaatcgtcc       3600
caggtaggaa ctgttgttat ctcaatctta tcagtgaggc aactgaggca cagagaggtt    3660
gagggaccaa cctgaagtcc cacagctaga aaatggcaac ttgggagctt accatccagt    3720
cctgtcagag cccagtgcat agtgcagctg ggatgtctcc tggggtgtcc tgcaagagct    3780
atggctttgt agtcagcaag ccaggtaggt cagtaggact catcgggaat gtacttgggg    3840
ctccaggggt ggctgccact ctgatgttcc actgctggct gccctgtccc tgccttcccc    3900
cctttccctc ccatcctttt ttgtccttga cattgaaa ccccagcctg gaagaagct       3960 ggagcctgca cccagctcta cggagcaatt tcagacaaga cttttccctc cttcaccct     4020 caagcaactc ctgattgcca gccttgtacc aggctctggg atgggcacag ggtgcagag     4080 ccgagggaga tgtcattcct acccagcagg ggcccactta ctagccaggg agacagaaaa    4140
tgtgggacaa tgtattaaga ctgttgacaa aaggctctgg gaacatccaa gtgcctgaaa    4200
```

```
gagaggaaag ttatctctga agaggtcact ttcaagctag gtcttgcagg atgagtagga      4260
gtttgccagt tgaatacagg gtttgggtag ggtcattcta ggcaggtgga gttgcaatgc      4320
agtggcgcta gggaggtaag ctaggggttaa attgagaagg tccttgaatg ccagactaaa     4380
gagttcagca ttttactacg tgtcaaggag ctaaagaagg ttcctaaact caggatcatc      4440
tgtgattcag ttggcacatt agaaggatca ctctgacagt gagtttgctg gcaaagacaa      4500
gagttgactt gtagaccaag tgagttggaa agacctgtgg gaccccagag ggatgtgttg      4560
gggagactgt tggaaaaatg ggtgtggcac tcaggagaca ggcaaggcca tctatatgga      4620
cttgggaacc atccttaaag cagttcaagt tgaaaatggg ggcaggtgtt cagggtgagg      4680
atggaaggcg ctgacctgga tgagccccga ggaacatggg aggcagagag gcagcagtca      4740
catagatggg aggcnnnnnn nnnntcttcc ccccagttgg cttcaggtgg tatatttcta      4800 aggcgggat caaaactaaa ctattttaat tactttctgt gtaagaagta acataatcag       4860
atttctattc tggcagaggg tactctatac attaacattt aaacatctca acgtggcatt      4920
caatagctgt accatctatt cttgatcaaa agtacagaaa aatcaaaaca aaaccccaca      4980
atgaagacag accatttcaa taaggaacca actctaactt tgtgaagata cactggaatg      5040
gcctcacttc aaaaaaagaa gcaacattag taattaaagt tcagcccccct catttttccaa    5100 gctagagaag taagactcag agagattaag taacttgcct aaggttaccc agcaagtaca      5160
tggtagcatt cgccttagtg gccttcacag ttcagcccctg gcctgcacct tccagcaaga    5220
ttctccccca ctcagcagca ggctgcttct gtgctgcatg gattgttgca gtagtcaccc      5280
tctgacaagt ttgccactgg tggactgctg tttctgtgac actgcagcct ctcctcaaag     5340
gtttcaatat cagccttgga gggaggagcc ctcctcctct gtgtttctaa gttcctgcct      5400
tcttcactct ccctcaggac caggggtggt agctgatttt accccttta gtaattgtaa       5460 tgaaccacct ttacagttaa ccattcttta tgttaaaatt tccctgttca aattactagt      5520
gtgacatttg tatcctgata cagtctcttc ctgaaactat gattggacat tatgccttct      5580
gactctatgc accatttcct tagccttttcc tattttatat cttttttgtct ctgtgctaca   5640 tttggatact ttcttcaact ctatcttccc attctctcat tctctcttct gttgtctcta     5700
atatgctgct taccctggcc ataatttcaa ttttcatatt tttcatttct agttctattt      5760
aatccttttt aaaatctgct acaacatatt tttatattca cttattcttt ggtcatattt      5820
tcaatttctt atttcttcaa acattgtaaa agaatgttag cacctgataa ttccaatata     5880
tgaagtaaac gcaggtctga tctgctacct attgcttttg cggttcttcc tcacgatgac      5940
ttgtttcttt gtatgttgtg attttttgact gtgagctcat gtactttgaa accttatcag     6000
tgagaagcct aaactgaaga ttcctcctcc agagagaatt tgtttgcttc tgctaaatga      6060
aattattttg aggcttaagg tttttcaaac catatttaat gtgaatttgg gccataagcc      6120
caaaagaagg ctggcttgtg gttacaaaat ctcaattttt ttctctcttc caatcactac      6180
caagatcaaa acagtgaagt tttcttgctg ccattctctg tagaatgggc tttttttctct    6240 agttgactct tacactaagg atgtacttct tttgggttct cagctctatg taagggcatc      6300
ctattggatt ctccatcttg actaggccct aggaacccac acagatatca aaactgaagg      6360
tcaatgctac catgattcag catacactcc aaaacaaaaa tccagtttca gaattaggtt      6420
gccatttaat acatatttgg ataatcactg ttttgtatgc ttgggacaca ctaataaaca      6480
aaatacacaa aggtccttgt cctcttgggg tttacagttt agcagggggg aggcaaacaa      6540
```

```
gtaaattata tagtatgtta gaaggtaata agcactacag aaaaaaaaaa gaatagaaca    6600
cacaacacct aaggcacaat ccataaaaga aataattgat aaactggact ttattaaaat    6660
taaaaatttc tgcactgcaa aagacaatat tcaccaggcg tggtgactca cacctgtaat    6720
cccagcactt tgggaggtcg aggcaggcag atcacttgag gccaggagtt cgagaccagc    6780
ctggacaaca tggtgaaacc ccgtctctac taaaaataca aaaactagcc aggcttggta    6840
gtgcacacct gtaatcccag ccattcaaga ggctgcggca ggagaatcgc ttgagcctgg    6900
gaggcgaagg ttgcagtgag ccaagatctc accactgcac tccatccagc ctgggtgaca    6960
gagcaagact ctaacttaaa aaaaaaaaaa aagaaaaaga aatgttaag agaagacaag    7020 ccacagactg ggagaaaata gttgcaaaag acacatctga taaggactg ttatccaaaa    7080 tatatgaaga actcttaaaa ctcaaaaatg agaaaacaaa caagtaaaac tctgtttaaa    7140
atggtcaaag gactttaaca gatacttcgc caaagaatat atacagatgg caaataaaca    7200
tatgtcatca gggaaatata aattaaaaca acaaatacca ctgaacactt actcaaatgg    7260
ccaaaattca gaacactggt aacaccaaat gctggtgtgg atgtggagca acaagaactc    7320
ccattcattg ctggtgggaa tgcaaaatgg tacagccgct ttgaaatacc gtttggcaat    7380
tttctacaaa actaaacata ttcttaccat atgatccagc aattgtactc cttagtattt    7440
acccaaagga gttaaaaatt gcttgtcaca caaaaactta cacatagatg tttataatag    7500
ctttattcat aattgccaaa acttggaagc aaccaagatg tccttcagta ggtgaatgga    7560
taaactgctg tatacccaga taatggaata ttattcagtg ctaaaaagaa atgagctatc    7620
aagccatgaa aggaatgaag gaaacttaag tgcatattac taagtgaaag aagtcaatct    7680
gggccacggt ggttcatgcc tgtaatccca gcactttggg aggccaaggt gggcgaatca    7740
cttgagttca ggtgttcaag accagcttgg ccaacatggt gaaaccccat ctctactaaa    7800
aatacaaaaa ttatccgggc atagtggcgg ggtcctgtaa tcccagctac tagggaggct    7860
gaggctggag aatcgcctga acccaggagg tggaggttgc aatgatccga gattgtgcca    7920
tcacactcca gcctgggtga caggagcaaa actccatctc aaaaaactaa taataataaa    7980
agcaaaaaaa ataaagactt cactatgtcc ttgagagaac attttcaccc tgtcccctag    8040
ccctcactcc agctccctca tccctcctac ccccaagcca gaaacctggg cattatcccc    8100
agctcctttc tcttctgtac ccctctagcc aacacagcag ggtcaaagag gctgccctct    8160
agatgtttct caaaccgtgt tcctcaccat tgctgctgct cctctagttc aggcctcatt    8220
ttctcacctg ggccatttca ttagctattt aatggaccac atagaacatg cccatccttt    8280
cctaccacca tgcttttgca tgtgacattt cccccaccac gcgtgccctt tcccacccttt    8340 tcctctctgt gtgtcaaggc tctcgatttc ctcctctcac ccagagatca ccccatctgc    8400 tccccccagcc ataaccctg acgactgtcc cccacagtct tccaccaaga gcctgcggac    8460
cactatcggc gaggccttcg agcggctgca ccggctgctg cgtgaacgcc agaaggccat    8520
gctagaggag ctggaggcgg acacggcccg cacgctgacc gacatcgagc agaaagtcca    8580
gcgctacagc cagcagctgc gcaaggtcca ggagggagcc cagatcctgc aggagcggct    8640
ggctgaaacc gaccggcaca ccttcctggc tggggtggcc tcactgtccg agcggtaagt    8700
gccacccgcc ggggccctcc ccggctgacc atcccctcct caacccatgc tgggcagtgg    8760
gagtggaggc agatgggatc cttagcagag aattctttca ttcaaatttt catcaaacat    8820
ttacgggaca tctgctatgg gtaggagcat gaagccttga gtatgaaggc cagtgaggct    8880
tgaactagag gagcagcagc aatggtgagg aacacagttt gaaaaccatt tagagggcag    8940
```

```
ccactttgac cctgctgtct tggctctagg ggtgcaggag agaaaggatc tgggaataaa    9000
gacttcatat atttacatta ttatatatgt aatatattct gtatacatta tagatagtag    9060
gtagcattta atagtgttta caatcataat ataaatatat tacatattat tttatttatg    9120
ataatgttgg cattacgtgt tactatataa aggctttata ttactgtaac cctctcagtc    9180
cctttgaaag tagttaccac tgtcatcatc atttcatgca tgtagaaact gaggctcccg    9240
ctgggcacgg tggctcacac ctgtaatccc agcactttgg gaggccgagg caggtggatt    9300
acctgagtca ggagttcagg accagcctga ctaacatggt gaaacccgt ctttactaaa     9360
aaaaaataca aaaattagcc gggcgtggtg gcaggcacct gtagtcccag ctattcagga    9420
ggctgaggca ggagaattgc ttgaacccag gaggcagagg ttgcagtgag ctgagatcgc    9480
gccattgcac ttcagcctgg gcaataagag cgaaactctg tctcaaaaaa aaaagaaaa     9540
aaagaaaaa aactgaggct ctgaaaaggt acatcagttg gccaaggccc ccatctggt      9600
aactggtaag ccaggattca agcctaggtc tctgtgaccc caaatcttcc cttagtagta    9660
ataacactta gtcattggtt tgttggtgat caatactgat tgctaagatc atgaatttgg    9720
cattgaccgt gaccgagcac tgtgctgagc atctgtatat gttatgccat gtaattctca    9780
caaaaagcct agaaggctga tgctagcata gcacccattt taaagatgag aagactgagg    9840
gaatggttag agaggccaga agcagcacaa gcaggcactt gaatctgagt cccacagact    9900
tctcactcat gaccacatcc tatgccagct gccctgaagg tggctgcggg gccctggca    9960
ttggggcagg aatccagtcc ctggtgcagc ccctttcct gctctccttc caggctcaag     10020
ggaaaaatcc atgagaccaa cctcacatat gaagacttcc cgacctccaa gtacacaggc    10080
cccctgcagt acaccatctg gaagtccctg ttccaggaca tccacccagg taaggcatgg    10140
gttatcatgg tccagagcta ggtggggcat gtcccagcac agcccagccc cctgtcctaa    10200
acacagcatg gggcagttgg ggtgaatgag cagagtgcct tgctgagcac ctagtgtgtt    10260
ccaggacctg tcctgggcac ctgcacaatc actcagctca gtggaccttc ataacacccc    10320
aggagatggc tgggcgtggt ggctcacacc tgtaatccca gcactttggg aggctgaggt    10380
gggtggatca tgaggtcagg agttcgagac cagcctggtc aacatggtga acccctgtct    10440
ctattaaaaa tacaaaaatt agctgggcat ggcggcgtgc acctgtaatc ccagctactc    10500
gagaggctga ggcaggagaa ttgcttgaac ccaggaggca gaggttgcag tgagctgaga    10560
ctgagccact gcactccagc ctgggcaaca gagcaagact ccatctcgga aaaaaggaa     10620
gaaaaaaaa aaacttgaga taggttccat tagcaaaccc attctccaaa tgaaatgact     10680
gaggcctgga cacttcataa actccttcta tacaacaggg tacataaaag ttcacatcag    10740
gaactgttct aggtgctgga aataccatag taagcaaaac aggcaaaaat ccctgccctc    10800
acgcatctta catcctaggg tgtgagatag aaagtagaca aaagtaaatc agaaaaatac    10860
agagcatatt agatactgac aaaaaataag gaaggggct gggaaaggtg agacaggatg     10920
gagattttag acaggtggtc caggaaccag cccgcactga gaaggaagca ttagagtcaa    10980
gggctgaaga agagtgagcc acgtaggtat ctggaggaag agtgctcctg gcatggggac    11040
agcaagtgca aaggacctga ggcaggagca catctcactc tcaccagtct ccctctgttt    11100
cccaggcagg aagagcaagg aggttaacgt ggctggaggg agatgagtga aaggagggt     11160
caaggtgaaa agactgagaa ggtagcagtg ccagacacc acgagggtct gtaggccatt      11220
gtgagaactt tggattttat gctgagtgag atgagagcca gtggagggct tggagccatg    11280
```

```
aagtgacgtg aactggttta agttttttaa ggatcccttt ggctagtggg ttgaaaataa    11340
accgaagggg gtgaaggatg ggggctggga aatgggttag gaaaccactg cataatccag    11400
gcaagaagtg atatgggcgt caaacagggt ggtgttattt gaaggggggtg gaaagggggtg   11460 gaatttagga catattttgt aaggacagcc aacaggattt gctagcggat tagcaaatcc    11520
aggtgtgaaa gaaagaagac gagggagata gtaattattt cagccaaagt gactaaaagg    11580
atgaagttgt aagcctgtaa ggtttgtgat gccaattagt tatctcagca ctgatgctga    11640
aaaggcagta gggatgacaa gccagcaata caaaaggaag gtcagcacca gcatcattag    11700
catatggaca gcttttaatg agcctggaca agatcaccta ggaagtgggg gcggatagaa    11760
aagacagagg gctgccctaa catcaggagc cccggaacac tcctagaagt cagggacaag    11820
agggggaccc agccaaggag accgagaagg agcagtcaga gggataggag ggcaacccag    11880
gtatgtcctg gaagcctgga ggaagcgttt ccaggagaga gtggctaaca gtgacaaagg    11940
ctgctgagcc aagcatggga gaacccagaa gagactattc tccagattta gcaacaggga    12000
agtcattggt ggccttgatg agagctggtt gggtggagca gtaggggcca aagcctggtt    12060
ggagctggtc caagagaggt ggaggcaatg ctttaaagga gttttcaagc gaaggagaga    12120
gagtgtggca gtgctgtttt ttatgataga agaaatacag catatctgtg agatgattgg    12180
aaagatccag taaggggac agaattaagg atgtaggaga ggaagttgca ggagtgacag    12240
ccttgactgc agcccagcct tgactgcgat ttgctgcatg gctgagagcc agcttctgct    12300
gggagcccag acagttcatt ttcaggagcc cagagaaagt agaataagtg ggcacccaaa    12360
gccagtgggg cagtggtggg cgctaggggg aatctcttct aatggcttaa cctttctcag    12420
taaagcagga agcaagatca tcagcggaga tgggagcaag ggatgagagg tttgcaaata    12480
gagaagaagg tctgaaacag gtttctagta aacttatcag gtgttgggac tgggaaatca    12540
gtgccttccc aaaatcacag atccccccca agggcagatt caaaatgaat ggcagcagag    12600
aaccctgtgt gttcctgagt caggcacgat gtcctttaga ggagagacct ggatagagaa    12660
gtgaattctc cctgagaaat gggaagtgtt attatcctca ttttttcaga ataagtaacg    12720
gaggcacaga gctgttagga acttgtcctt ggtcacgact tggaaatgct acagccagga    12780
cttaaacccc aacgtcgggc cccaaagcct gtgcccttcc ttacctacta agctcactgg    12840
ccattctctg acctcacaca caccaggaag gaggctgggg agaccaaggc tcagggaaac    12900
tcactgactc cctcaggtca cacagggggtc aaagtttctt ccatctggct ggattcattc    12960
ttctgttcca caaacatcaa aagtccctca aggcacgttc aaaaatcagg ggaggccggg    13020
catggtggct catgcctgta attccagcac tttgggaggc caggcaggcg gatcacttga    13080
ggtcaggagt tcgagaccag cctggccaac atggtgaaac cccgtctcta ctaaaaatac    13140
aaaaagaatt agccaggtgt gtgtggcacat gcctgtaatc ccagctactt gggagactga    13200
ggcaggagaa ttgtttgaac ccaggaagca gaggctgcag tgagctgcga ttgtgccact    13260
gcactccaga ctggatgaca gagtgataca tctcaaaaaa aaaaaaaaaa aaacagaaag    13320 aaagattat ataattttta actcaataac cctaagaagt atgtgctgtt tagtaaccct    13380
atgttgcaag ggaggaaacg catagagagg ctaacttgct caaggtcaca cagaaaataa    13440
ggggcacctc tgcactatat acactttccc catcttcaca acaagcctgc aaggtgggaa    13500
ctattatctc attccacagt ggaggaatct gaggcccagc gaagccaagt gatttgccta    13560
aaatcacaca gctggtaagt ggcaaagcct ggactcaaac tcagggctgt gccctggtga    13620
gaaatttgaa atggaaaggc ccaggatcat gttagagcaa accctggggc cccagctctt    13680
```

```
caaacgctga attctaattg ttagagctgt ctgtgtcccc ttgatacagg agcaggcagg   13740
cagaggccct gcctgtacct tggaacccag cctaggatca gcactgagaa aacaaagctc   13800
aagtgtgttg actgaattgg ggattatact cacaactctt ccctaaacag acaagatgct   13860
aagaggctga atgtggtaat ttggatttat ttgtgtttat tttcattctc ttttaggcta   13920
cacacaaatg tgaaaaaaaa aataatagtg tgtaacaatt aaggaattca tacagtttct   13980
ctgaagccag accggagtca tttctaacaa atgtgatgag aaaacaacaa ctatttaaaa   14040
aaacaatact cagctgaaaa ttctcacttt ctccagctgc tgtcttcaga gccacccggg   14100
aggggaataa acaaggctgt tgactacagc tctgttccac attctctgat ggttctcagg   14160
ctttggcctg catcagaatc acctggaggg cttgtgaaaa cacacattgc caggcccttt   14220
tccagagttt ttgattcaat aggtttgggg tggccctgag aataagtaat tcttttttttt   14280 tttttttttt ttttttgagac aaaattttttg ttcttgttgc ccaggttgga gtgcaatggc   14340
gtggtctcgg ttcactgcaa cctctgcctt ccgggttcaa gtgattctcc tgcctcagcc   14400
tcccaagtag atgggattac aggcaccgc caccataccc agctaatttt tgtattttta   14460
gtagagacag ggtttcacca tctcagccag gctggtctcg aactcctgac ctcaggtgac   14520
ccaccagcct cagcctccca agtgctggg attacaggtg tgagccacca cgcccagcca   14580
agaatatata gttctgacaa gttcccaggt gaagctgata ctaccagtcc aggaaccaca   14640
ctttgagagc ccctaaccta aacagacctg aagcacagca ggcaaagaga tcaaagctgt   14700
gtacctttga aagaaggcgt caagtccttg ccccaacccc tctctggcaa ggaggtttgg   14760
tgggccaaaa accaacctgg gctggaaggc tatattattt ttagacaata ggagcacatc   14820
cataaatata cacacttact atgtacccac agagatttac aacaaaaaaa attgttttaa   14880
ataggagtac acaattcacg gggtatatan nnnnnngag tgcagtggcg tgatctcggc   14940
tcactgcaac ctctgcctcc tgggttcagg caatttttcct gcctcggcct cccaaatagc   15000
tgggattaca ggcacacgcc actgcaccca gctaattttt gtattttag tagagacggt   15060 gtttcaccat gttggccagg gtggtcttga actcctgacc tcgtgatccg cccaccttgg   15120
cctcccaaag tgctaggatt acaggcgtga gccaccgcgc ccagcctcaa aaaaaacaaa   15180
tttaattaag aaaaaaaaaa gatctaaaga tggttccata tagctgagca agataatgga   15240
agagagaatg agaagctggc aggcccccaga tcctacaggg ccttgaatgc caggctgagg   15300
tgcctggact gcctctccga gctgtgacaa acatggagca ggtggcagct gaggctagaa   15360
ggctccccag gctccctgct ccagggctgt cctgggtcag tgactgggga gggaatcgga   15420
ccctcggatg cacttttgcc tcccaaaact tagtctcagc ctcccaaagt gctggcatta   15480
caggcgtgag ccaccacacc cggcccatct ttagatctta aatgagccat attctccctc   15540
atctacatgt tttgtattct ccctcatcta cacgtttgca catgccattc ccttcggctg   15600
cagcccctct aaacaatcct tagtctttga tggccaactc ttactctcct tggcatctta   15660
gtttataaaa ccttcctctg agaagccttc ctggatttct caaggcaacc tgggcttaca   15720
tggtctcact gttttgtcat tgtctgtgtg gctgtctcac tcactaaact gtgaactgtg   15780
agggtcaggg gccaggtctg attcactccc agcagctagc acagcaaatg tttgtcgata   15840
aatgcataac aaaatgaatg gatcctagtc tcagttctgt ttctagaata gcgcctcaat   15900
aaaataggtg cttagtaagt atttgctgac tgaagaaact tgctgcacag ccttgaacaa   15960
gtcactgcct cctctgaact tcagtttctt cctctgaaat agggatgcta gtgttcccct   16020
```

```
ctcaactccc tcataaggga gcaaagggat gtggaacttg ccatcacccc agtgcagggt    16080
ttctcaacca cagccccatt gacactggag gctggaccat tccttgttgc agggcccgc    16140 tctgtgctct gcaggatgtt tagtggcatc cctggcctct atccattaga tgccagtagc    16200
cagtagccac cccactcagt tgtaacaacc aaaaatgtct ctggactttg ccagatgtcc    16260 ctggaagca aaattggccc agttgagaac cactgctcta gagaaagctg cctgccagag    16320
aggagctgag ggaggaacag actgtgctcc aacatcctgc ccagagcaga ggcccctggg    16380
gagttcaaaa agcaccagcc tggttggctg ggccccttc tttgtctgtg gggcctgtga    16440
aatcagtctg gctcctctgc caccaccaaa gcccttatg tccagatggg aggggtgccc    16500
ccagggacct agcccatgga ttctagcagc ttcctgcctg cccctcccct ccagctcagg    16560
cttcctattg ggtcacctga gaaccccatc cagcacctgt cactcccctg ctctggcact    16620
tccaccctcc cccacctccc acccctgtat cccaccccca gcctaacatt aggaagctct    16680 cctcaactg tgaccttctt acctacctgg tctaaatccc ccaactccca ggcacaaact    16740
gcctcctcag ccaggccagg cagcccattg tcccaaggac accaggagca gcctgccttg    16800
ctcctgcctt ctccccatcc tgggctgctc tccccgcccc ctgctaatct gaatccagtc    16860
attttgagtc ccggcacatt ccttgcctag ctgtgtgacc cagagcaatg cactcccctc    16920
tcagagcccc agtttcctca tctgtaaaac aaggatagtt gcatttctct cccagggtag    16980
ctatgcagat taaattattt gtttgtaata atgatcctgt aacacttagt aagtacttga    17040
ttcctgtctg tttattgtta ttatcatcat gaatcgacag atggtcccca gtcttttttt    17100
tttttttttt cctttttgaa acggagtttc gctcttgttg cccaggctgg agtgcaatgg    17160
cacaatcttg gctcaccaca acctccgcct cccagattca gcgattctc ctgcctcagc    17220 ctcccaagta gctgggatta caggcatgtg ccaccatgcg ccgctaattt tttgtatttt    17280
tagtagagac agggttttcta catgttggcc aggctgatct cgaactccgg acctcaggtg    17340
atccgcctgc ctcggcctcc caaagtgctg gaattacggg cgtgagccac caagcccagc    17400
ctccccagtc ttgctgaaca ggcttctggg ggccacatgc tgggaagagc atgatgtgaa    17460
aagacctcag ctgaagttcc aactctgctt cctctccaag tggcagcttg agcaagccac    17520
ttacctcaga gttgtctcct ggagcctca gtcctctctt ctgaaaaatg gctaaaacaa    17580
tttgtgcccc tgggtctgtc gtggtgctcc catgagctag tgagtgtgag aatgttttg    17640 cacatgtctg ccctgtacat ctgagggact gaggaacctg gttttttaaa ggcctggcca    17700
gaggaaaacc cttacagcca gcctttcatg ttctgtcagg cctctgcatg ttcaaaccct    17760
ctgttcttga aaacaaagaa acacaatcca ctcactgcca aacacctgtg ctgggctgtg    17820 cccccgggagg gctttctccg ctgcttgggc aaaaagtgat ggctcagtgg tggccaggaa    17880
aaatctcctg ggacctccac agtccatgat ccttcctgaa tgcctttgac ctcaaggtct    17940
cagaaatgct taaatgaatg gacaacacac ctggagacca gacgggctgc ctcagtgtct    18000
ggcttgtttt tataaatctt ggtgtcccgg gacttaaaaa tgagctctga cctgtagaat    18060
agtgagcccc cagggactgc gcttgttttg ctgggcctgt cacctcctgg ggatgaggga    18120
cagatggagg aactgatttc tcagagggg aagggtgtt gccatgcccc ttctaggtcc    18180 cttctctggtt tgaaggttgt tactcctgtt agccctagcc tcggggagg agccccagga    18240 gccaagaccc tgtgttaatg attcgtgcaa ggccttggag gtggcttcag ccagggtgcc    18300 acccctgcc ccagcctcac cccttggggt ataaaagtct cctaagagtc aggccacacc    18360
cccgcctaag agagtggcag gccctgcccc taggccggcc cagtgagtgg caggcccgtgt    18420
```

```
acccatcctg tccctgggc ttcaagcagc acaggtccgc tcgccagggc tggcattcac   18480
tgggtcagga tttcctccaa tctgcaggct tatctttgtc tactggtctc agacccacgg   18540
agagccccct tgtctccctc ctagggtgcc ctcccactca tcagtggcac acaagtggc    18600
tcacattgtc ctacataagc tacaagtctg aagctgagcc cttatacctg cttgagggta   18660
ccccccgccc cgcaccagtc cttctgccct gagcctcggt tgctgcctgt tgctggtctc   18720
aaatcaccca ggcgccttag atatcatgcc taggttcccc cagcactctg aactgctgct   18780
gttcatgcct gggcactgtg catcgctctt ctgcccctcc gctgtcacac ctgagtgtga   18840
tccacatccc actgtcatag ggtggcccca cctatgtctg attaggttcc tcttctcaat   18900
ctagctcttc cccctaccac acactcctcc tacagctccc tcccactccc acctcccgac   18960
cccactgtgg gaattgccca cattccacca ggcaggggcc ccctggttct gacaagctgc   19020
ctgtggccag tcagaccaca gggtgaaaca tccagccacc aactcagtgg ccgtcctctc   19080
ttggttcccc gtcttctatg tccctggaca gaggattgtg tttccattga cccctctatt   19140
cacaaggcta attacttcca tacagccctc taagtccaaa ggacagaaac aaagagggta   19200
aaatgcaaaa ctaaacttac tcctggcaaa gatcatggaa ggaacttgat ataggtcact   19260
ggtccagtgg gtatatgaac agaggcacag ttcagggact ggctgtagct ccctgttggg   19320
gacagtcccc atcattgagg catcttattt ctgcacatca gtgcagccaa cagaggcaac   19380
tgaagtaggg agaatgctcc agccaagcat aaccatgtcc ccacttcgcc agtaaaggaa   19440
agagccagag agctggatgt ccaagacccc aaggaacaga ggcaattcct tcttcccact   19500
tttcctcatc tctgtcttgc tgttgcctgg aaatggtcat tcaggctaag gaaagccaat   19560
cccagttttcc tccttctcct ctggccagtt atcagctccc tcaggagca gagagtaaac   19620
agaggtctta acaagggttc atgaaatttt tagtcagacc tgctaagccg gtgtggccag   19680
cccagagcca ggtgatgcag cccatgccac ctgcccaaca caaacatggc cagtttaatt   19740
tggtgagttt ttccggaaat gtgccacaag ccaggccctg gggtgggctc tggacacaca   19800
agggagagcc ccattagaca gtacacggtc cttgccctct tggtgcaaat ggggaaatag   19860
ggcaaaatgt gatcacagaa gataataccc cacgccagta tcagggcaca aataaagcta   19920
aagaatttca ggccaggtgc agtggctcac acctataatc ccagcactgt gagaggctga   19980
ggcagcagga tcacttgagg ccaggagttc gagaccagcc tggccaacat gcgaaacct    20040
cattttatg aaaaatttaa aaattagctg cgcatagtga tgcatgccta tagtctcagc    20100
tactcaagag gctgaagcag gaggatcact taagcctagg agttggaggc tccaatgagc   20160
tatgatgaca ctactgcact ccagcctggg tggcagagtg agaccctgtc tgtatttttt   20220
tttttaaaa gaatccagca cagtggctca tgcctgtaat cccagaactt tgggaggccg   20280
aggtgggcag atcacttgag gccaggagtt caagaccagc ctggccaaca tgacgaaacc   20340
ctgtctctac taaaaataca aaaattagc caggcgtggt ggcgcgtgcc tataatccca   20400
actactcgag aggctgaagc atgagaatca cttgaacctg ggaggtggaa gttgcactgg   20460
gccaaaatca tcccactgca ttccctcctg ggggataaag caagactctg tctccaataa   20520
ataaataaga aaagaagag gcaaaaggaa tttcagagga cagaacgagc acatctgctg   20580
ggtgaccagg aaggcttccc aaagggtggg ccttttgaat agagcctctg ggggtggttg   20640
caacaagcag aaaggaggag gtggagggaa ccgtgtaagc agaggctttg gacctaagtg   20700
gggtaggggg caaaagtgag aggttggctg ggagaaagga ctggcgctag attgcagacg   20760
```

-continued

```
accttggtta gtcctggctc tgccaatatt tgcaggatga cctaagtttg tcatgtctcc    20820
cctctgggtc tcagtttcct catctgtcaa atggaagagt tggcctagaa ttcatggttt    20880
tcaatctttt cagacccatt gtctactttt cataacaaat catgtgtaat atctcaaaga    20940
taatataacc tttttataat ttcaagtgta acctttcac aatttcaagt gttgtgtgtg    21000
tatatgtaca tagatacata ctctgactat taatatgaag gaaaatagaa ggaaattatt    21060
aataataaaa tattttgtat gtcaacatgt agatgctcac ccacaatcac actagaaaac    21120
ctaacaaagc agccaggtcc tctcgtcata ggtaaaacac catcctgcct caaatgccta    21180
tacaggtagg ttgtctcact cagtggtgtt gcccttaggg atgtattttc caacaaagca    21240
aacagttctt agggaagttc caaacaaaac aaatgcagcc ttcccttcat ttacacagtg    21300
gttgcattct gaaatattca gtatatatta aaactgcaaa aaaatttca tgtttataca    21360 tgaaatggag ttaggttata ctttcttatc cttataaaaa agattttca tccacatgaa    21420 tgtctgctgg gacacgtgaa aatcactggg agtcggggaa ggtgtgggc aaaacttccc    21480 tttgcagaac tgtcctgtcc atttcgtggt ctttagcatc cctggatccc agctgttgtt    21540
aagacaacct gaacacactc accaatttcc ccattccccc taggggcag taccaactgg    21600 atcatctgga acctcccttc cagctctaaa attccccaat tctaggcctc attctggtta    21660
attcaacaaa catttgccag tgcccactat gtgctccgcc ctgggcatca ggcagtgaac    21720
aagcagctgt agcccctgct cccctgcaga caatatctgg aaggacctta accaccaccc    21780
ttccattcta cagaggagga agatgaggcc cacagagggc agacttgtat tcaaggtcac    21840
acagcaggtc agaagcctcc tgcgtaccaa ccaaaactct gccctcagga aggcactgca    21900
tggtgggtcc acacccttct ccccactcat cctctctccc tcctccaacc ccacagtgc    21960 cagccgccct aaccctggac ccgggcacag cccaccagcg cctgatcctg tcggacgact    22020
gcaccattgt ggcttacggc aacttgcacc cacagccact gcaggactcg ccaaagcgct    22080
tcgatgtgga ggtgtcggtg ctgggttctg aacccttcag tactggcgtc cactactggg    22140
aggtggtggt ggcggaaaaa acccagtggg tgatcgggct ggcacacaaa gccgcaagcc    22200
gcaagggcag catccaaatc cagcccagcc gcggcttcta ctgcatcgtg atgcacgatg    22260
gcaaccagta cagcgcctgc acggagccct ggacgcggct taacgtccgg acaagcttg    22320 acaaggtggg tgtcttcctg gactatgacc aaggcttgct catcttctac aatgctgatg    22380
acatgtcctg gctctacacc ttccgcgaga aattccctgg caagctctgc tcttacttta    22440
gccctggcca gagccacgcc aatggcaaga acgtttagcc gctgcggatc aacaccgtcc    22500
gcctttagtt caggcagaag gagaacacaa ctcctgggaa cactgccacc tgcaagagcc    22560
ctgcccagga gatagaaaac ctggactcca gcccaccgtg gccactggag acctcaggcc    22620
acttgtttac cctccagcct ccagtctgta aaatggaggt tgcattccct acttcctaaa    22680
ctctcttcca gcatcgatgt tctgtacctc tgaccttgat agggaaacag ctttgatcca    22740
aggatgtgac atggcttctc ctcagggcaa cccctgccca accctcatcc ccatcttctc    22800 agggcaggg gactaccttc cagtgtctcc ctccagccca gccctgacct caggaagtgt    22860
cagagcatgg ccagtagttg gcagcccgaa agacacacag caccctctta tgtcccatgg    22920
cctaagactt acccctgacc aagctagtga tgggccattt accttgacc ccagtccaca    22980 gtggtcacag gtagtaccctg gtcctagggt tgcctgaaag ccaacctctc ctgccacccc    23040
cacaccaaga aatatatggt tcctacttct cccactgatc tgctggtcag tgatgatgct    23100
gtggcctgtg gaaggcacct ggtaattgaa tccacacatt atagtcatgt gccaccacct    23160
```

-continued

```
tcctgcccac aggccgaggg acagggtgag ggtatacccA aagctgatgc aaagcccatt   23220
agcctaaaag caactgcagg acaagcctcc ctggatgatc gaggtcccca gtagctctga   23280
acaagagtcc agccaaccct cttcagccag gcctctgtga cctgctaggg tgcaggaggc   23340
ttccagaagc agttgttgta attaggaccc aagcactggg gagggctgt tggctaaacc    23400 ccttgtcaga cttggcatct atctcagtta ggatcctgct gcagaaaaca agagccactt   23460
gtagctggtt taattagaca aggatttact acctggcccc tggtggcttg caaaattgtt   23520
ggaagagctg gagaagcaga ctctgctgaa tttccaggaa ctcccagcgc cagattcatc    23580
atgtctgttg tgaccaggaa agctgccccc atctgcagga agccactatg ccagaaagct    23640
gctgactgca gaactaggct ccctctgcca cggtccgtgc cagccaatag atgtcctgag    23700
gcctgcccct ctcccacttc actcagttcc caaatctaaa tttttacaag agattctgtt    23760
tgggggaact taagtcagat ccagaacctt ggctgcaagg gagtctggga aatgtcattt    23820
ccctagaagg aagttagggt gggtggagca agccccacct gcgtttttct gccacagcat   23880
ccaatcgtga aaaactcggg agagggtgga gtccacatct agggttgtcc tgcccccttgg   23940 ctctatccct gcccagaggt gggaactgga ggagtgggct gcaaaactga gcctaaatgt    24000
ctccccggcc ttgacttttc tttctagtcc tggggcctaa attctgcact tggggtctct    24060
gacacaacac accatcccaa agtagccgga aaagctaaac acaggggtt cttaaaatgg     24120 ctgcccccgc cacccgggcc tcccttgggc aaaaggaatt gtcagcccta ccccaaccct    24180
tcaactacca gaatctgggc cacccccagca gtattttat ttaaaatgtt gcccatttta    24240
tgagttatga tcaatttgta ttaaattaaa gttacagatg tcagtagcca gttccattca   24300
ttttgacaaa cacacaggcc cacccagctc tgtcccaggc agtgcacaca catgagcata   24360
gctaatccac aaagcagccc ggctgggtaa atggtattat gctcattta cagaggagga    24420 aaattgaggt tcagagagaa gccaagactt acctgggtc ccatatccca tgctggcaag    24480
tgccacacca caaacctgtc caaaaactta ccagccaggg aaggctgtca gtctttacct    24540
ggaggagagg tggtggtagt cttgggagca ggcagcagg agctcatggg gcagtggcaa    24600
gagcctggtt tcgggaacca cacagacctc agctcaaatc caggctccat cactgtgtga   24660
ctttagaaaa atgaccaccc tctctgggac tcagttttcc cacatggaag atgaggatac   24720
caatttcaca taatttattg gtaagctgta aagtgcagtg cacttaagga ggccctaccc   24780 tatccccca gctgcctccc agagtcagtg cctggagttg tatgggtttc ctgaacctct    24840
gggctggctc tgacccaaga agtctgtctt tctccttatg ggctgtgacg ggtatggaac   24900
cacctagacc aggaccatcc tgaggtccat cccacctctg actgatgagg aagcatcctg   24960
gctgggagtt aggacaggct ctgcatgtgg acacacaggc tgtgcacact taagtggaaa   25020
agactgtcga ctaaagaaga aatatcaagg ttttaaagaa ttaaagttca ctttacttag   25080
aagtcttact gagtactata gacaggccta gagcccagca gcggcccttt agagaggttc   25140
tatcagtcgg gcccaggaca gtattttagc ccactgctta tatacaggtg gtggaggttt    25200
agtacacgca aaatcacatc acacttgctc agaagtaaca ttaaagccac cgggcgcagt   25260
ggctcatgcc tgtaatccca acactttggg aggccaaggc aggcggatca cctgaggttg   25320
ggagttcaaa accgccctga ccaacgtgga gaaacccgt ctctactaaa aaatacaaaa     25380
ttagccgggt gtggtggcac atgcctgtaa tcccagctgc tcgggaggct gaggcaggag   25440
aatctcttga acccgggagg cggaggttgc ggtgagctgg aaatcgcccc attgcactcc   25500
```

```
agcctgggca aagagcgaaa ctccgtctca aaaaaaaaag aagtaacatt aaagcggaat    25560
catatatcaa cgtttgcatg taagagtgtg tctgggctat agattacaga ggcataatca    25620
tgaatgccat cagacactat cttctgtaca ggaaaaggca aggactaggt ttatttatct    25680
tttaaggaac gtagtgactc aggcaagaga catgggggcc atgcccacta ttctgtcttg    25740
tctccaaagt atccctccac agagccgcac atggtcacag agtcagaggc ttgtgaaatt    25800
atgctggcaa acagaaatga gggaagtagc ttcttccatt tgctactgtg tctcccaggc    25860
cactgggtgc tctctgcagt gtgcaaggga gtacagcacc cctgggagcc caggactggt    25920
gttggctttc tgttaagtca ttttcaccct aagccattct tggcctcctc acccacagaa    25980
tgagggaggt taggctgcag gccacaggtg gatcttcatc tacagcctgg agctggggag    26040
agggaaccac cccagtcatt gacttgcctg ggtttctagg aagaggaatc aaaacaagga    26100
tgggaaacgg gctgttggca ggggtgggtg gaaaagtctc tgattgtctg atggagagca    26160
gcccagttca cagggaagtg actggggtga ttctgagaat agagtatccc aagccctccc    26220
ccatcctctc agatccctgt gactgctcta aaaccacgcc ctctcatttt ggctcagtgg    26280
atctgtcttt gctcagcctt ctccctctgg gtcggagca cccctccat ggcgcattcc    26340
accttctccc cactcagcct cagcagcagc tccaagaaat gctggccact tcccaggctt    26400
tactcacagt ttccacgtgt gtggaagtaa ctatagaggc caaatttgca ttatcaactg    26460
gggactcctg gaaatggggg tgtctccaaa agatatattt gatacacctc cagagaattc    26520
ctgaaggaaa gaatctgggg ttgtcaggct gatatcatga accccacatt taacacatta    26580
agtgaagaga ggggacaaag gccaggcttg ggaaggaagg agggatcaac aaagccctta    26640
cccaggacag ataaaaatga tagaatggca gtaaccccat ttggagcccc catttgtagt    26700
cagcaagcaa agtactggtc ctttttacac cttatctaac catcgagaca cgcccctgtg    26760
gttggtatca ttatctcagt gttttgagcag ggaaacgtca cttcccagag acccacagc    26820
cagtactcgg cagagctgga aatcaaaccc ggtccatcca aagctaaagc cagatgtctc    26880
tttactggac ctctctggaa atgcttctca actttgatga tggctccagt gacaggcagc    26940
agccaccagg actgtgatct ccctgggatt taaagtggga ggttaaacca ggctccacgc    27000
cactgcggaa ttgtgcaatt gtaagtcaag tctcaattgt gagccaagct tctcccaggg    27060
tcagaggtgg agttagaaag gccccatgtg accctgagca agtctctctc cttccctggt    27120
cctcagtttc cccatctcta ttggggaagg gttaggtatc tattctagtt gattaattgc    27180
cagggcctga gctctgatgg tccaggattc tgtaagtcta acgttaggtc ccacggcttg    27240
ccctgctcag cacctaataa ggccattagc tctggctcct tctctctggg gtggcagcag    27300
ggacagaaaa caacagagat acattctctt ggcagcacag aactcagctc aagggttctg    27360
gggatggggc cttccctcct gccagggagg ccatctcgag aggctgactg ctcacacctg    27420
gcagcactc tgtctcctcc cctcctgcct gggtcccagc tctgttcacc accccaaagc    27480
acatcaccac aaggtcagtt gcaaaggccc ggtatcacag gcttaaatac agagggctag    27540
gagggaggtg ggaggtggga gaggaaggtg gagtactaac aaaggtgttg aattatcact    27600
gcccatcagg acacggttat ttccccttac tttgggacac caaagattct acacaatctt    27660
cctataatcc tgaaccacaa aagggaggca cagcctccaa aaaaagtag gagagggag    27720
gggggaagta cttttatttt gaaatgtgtt cattttcctt tgttttattt tctatcttga    27780
tgaaaagaat atatttttaa acctaaatac aaaatagtac agttttctat ttttttttaa    27840
gttccaggat acatgtgcag gacgtgcagg tttgttacat aggtaaatgt gtgctatggt    27900
```

-continued

```
ggtttgctgc acctatcaac ctatcagaac agttttctat ctgctttaaa aatttcaaca   27960
gttctatcat atttttatta caaaatgctc cccctccct tgaaattaaa tgaagagggg    28020
gaagggttga cactgtggac cagagaccca gggacttcct accctgatgt catgataagg   28080
gctggggaag ggctttcagg aagctggcat cagaggcaca aagcttcagg tcctggtgag   28140
cttcccaaaa ctgtgagact agatgtgatc gaatctgaat gctggaaggg tctgagtgat   28200
cctccagtct aacctgaagc ccagagaggg ttagtttcta gctccacatc acacagcata   28260
tggtggagct gagatgagta ctcaagtgtc ctggttccca gtcagcacat aggggaggga   28320
gattgactaa ctgagagggc cccagcccag gcaaagaaaa ggaacacagg ccaggctgga   28380
agggacaggg ccagagctta ggagggaggt gctcagagga gaagggtccc acatctaaga   28440
aggtttgcgg gggtacaaga gggcctatca gagttggggg ctgcagctcc tccgagagga   28500
gaaggagggg gcaaagggt gatcaaatca ggaagtcctc cctggggtgt gcatgccagt    28560
cagcatcacg ggccccaaca tggctgatga gagaccctg atctcagccc tgccatttac     28620
atagaagaaa actgagacac agatgcaaag acagcagcct gcagggcaca gtcagggcca   28680
gatccaagtc tcctgactcc cagccatcgg ctctttcat gcaaacttca gtctccctct     28740
tgtggattct ggtgtctcct cctacccct gggaacctgg agcctgagca aaggagaag     28800
gggagagagg agggttccaa caaccccagg caccaggagc tgggtgcctt cctctgttgt   28860
cctctccaag gagaagagag agctggcctg gacctccagg gcagagccac ttcatacctg    28920
cccacacctg gtcctccttt gctggcaaca gagttcagg ctagcaccag ccacagcaag    28980
gacaaagccc agcccaggca gctgctggag ctgcagggag tcccaggtaa gtgaaagcat   29040
tgggactgat ggcccaaggg ggttccctga tttcatggca ctagagaaag ccctgggata   29100
tcaggtggtt tgaatgtttt gaagtctttt tccccagaaa agagctcttg cccctcact    29160
ccctgcaggc tgagcccctg tgcctgcttc tctgcttacc acataccgca ggtcaaaggc    29220
cctccctgac caagctgcca gatttgccaa tcagaagcga ggtcctgggg cccagcagca   29280
ctgttcttgc cactgggaga agggagaagc agatatggga cctgaaaggt caccaaaaaa    29340
agcaaacagg ctggaggttt gtgcctctca ccagggtggg gctgtgagtc gagacctggg   29400
taaaccccag ctccgtctct gactcaccaa tgacccctgga cagctccttc atcgccaccg   29460
taagcatccc tgttcctcat cggctgaaca agagggacag gcaaaggttc tagcctgagg   29520
cagcttcctg gagtttgtcc attggtaccc ctctctcccc tctttcctct tagggacccc   29580
cctctgccac actcctggaa agtccttccc cacttctttc attcctccat caaaatttac     29640
cctccggtgt tcctcaggtt aactggctta ctgtttaaga tgtctccctg tctacaacct   29700
atgcacattt ataataggaa ccactcccgg aagagtagct gatggtggga ttttagaaac   29760
cctgacaagc agcagaggaa agattatggg gaggatagaa agagataggg gacttctcat   29820
gacaccatat ggcagctcta cagcagctgc tggtggctcc tgtctttcca gctgatctgt   29880
cccactcttg cccccatcct cagcaatcag ccctccccac cagcagccca atacaggcta   29940
atggccacgc accacagcct ttctgtttgc aggggcttcc tctgcaggag gaaaacaacc   30000
tatgcatata atgttagaat cagacatgtg gacctttatg atcccacgtg gagaatgata   30060
agcatatttt tggccttaat gaatctgctt ttggagtaat tttcccccta cctaatgccc   30120
tccttttcct tacggttgaa atcttactca tccttcatgt cccactcaag gcagggtgtg   30180
tcagtcatcc aggtccagga gattcactga ccctgggctt tccaagaagg actttgggtc   30240
```

-continued

```
tcccactgcc actaggcatg agcatctcaa gatggggatc ctgtcctatg gttttgcatg      30300
ctgggtgcag agagaatgtc agaaaatgtt ttttggctga aaagtagcta atgtcaagct      30360
gtaattttga aactacccca tctccaagat gggaggaac ttacagacca gagataaccc       30420
ctccctgatg atgctgagcc cccagagcga ccctcactga tcattccccc gacacctaga     30480
ttttgtgcag ggagagccag ggaaaagagg cagaaactag gaaagttatt tgtttgcttt      30540
tttaacaaat tataacataa cttgtgctca ttttaaaaaa tgaaataaaa cacagtagaa      30600
attctcattc tccttnnnnn nnnnn                                            30625
```

<210> SEQ ID NO 6
<211> LENGTH: 45845
<212> TYPE: DNA
<213> ORGANISM: Human
<400> SEQUENCE: 6

```
gaattccata tacaggttta ttccaatccc tatgaaagtt tcaatggcat tcttttacaga       60 aataggaaaa gcaattctaa aatttgtatg gaaccacaaa agaccacaag tagccaaagc      120
aatttagaga aagaaaaaca aagttgaagg catcacatttt cctgattttt aattatatta     180
taaaggtatg gtaatcaaaa cagtatagta ctgacataaa agacagacac atagacaaat     240
ggaacagaat agagagccca gaaataaact cagtcatata tggtcaacta attttttgaca     300 agggtaccaa gaagacataa tggggaaaag acagcctctt caatagatgg tgctgaaaaa     360
ctagatttcc acatgccaaa aaatgtggaa actggactct tatattatac agaaaaaaat     420
caactcaaaa tggacaaagg acctaaatat aagaaccaaa accataaaat ttctaaaaga     480
aaacacagag gaaaagctcc ttgactttgg ccttggtaat aattttctgg atatcacaca     540
aaaagctcag gctataaaag caaaaataaa taaatgggac tacatcaaac caaagagctt     600
cttcacagca ggggaaacag tcagtaaaag gaaaaggcag catacaaaat gggagaaaat     660
gtttgcaaac cgtacatctg atatccaaaa tatataagaa actcaaacaa ttcaatagca     720
agaaacaata gcaagaaaac aaataaccca attaaaaaat gcgcaaagga ctgaaaagac     780
atttcttcaa agaagacatt aaaatggtca atacgtgtat gaaaaggtgt tcaacatcac     840
taatcatcag ggaaatgcga atcaaaacca caaggagata tcacctcaca cctgttaaga     900
tggttattat caaaagatg agagataaca catgttaaga gtgtggagaa aagggaaccc     960
ttgtacactg ttggtgggaa tgtagatcgg tacagccatt gtggaaaaca gcatggaggt    1020
ttccaaagaa attaaaaata gaagtactat atgacccagc aatccttctt gtgggtatat    1080
acaaaaatga aataaaatca tcatctcata gaaacgtctg tactcccatg ttcattgcag    1140
cattattcac aatagccatg atatgaaaac aaactaaaat atccatcgat ggatgaatgg    1200
gtaaagaaac catggtgcac atatatgatg gaatatcatt cagccttaaa aaaggagatc    1260 ctgccatttta ccacaacatg gatgaacttg gaagacatta tgctaaatga aataagccaa    1320
acacagaaag gaaatattg catgatctca cttatatgtg gaatcatcaa aaaaagaaa     1380 agtcagaaag atggagaata aaatggtaga tgggaaggag taaataggga gatgtagatc    1440
caaggataca gtgttgtagc tatgtaggat gaacaaatct ggagatctaa tgtaacacat    1500
aaggactatc actaataata ttgtattata tttgagattt ttgttgaaag aatggatttt    1560
aggtggtatt cccacaaaag gaaaggagta actatttgag atgatggata tgttaatttg    1620
cttgactaca ttaacaactt cgccaaatgt atgtatacca aacatcatat ttaaggtatt    1680
tatatacctt aaatatatac aataaaaatt ttaaataaaa aagtgatctt cactgggctg    1740
```

-continued

```
aggaactcca ctattgttcc tagcacattg agtgttttaa tcaagattga gtgctggctt    1800
ttataaattt tttttctgca tcaattaaga tgattatata gcttttcttt ctcagcctgt    1860
caacatgata aattatagtg attgatttgg gatgcttaaa ccaatcttac attcccgagg    1920
catagtatcc ttttggtcat gatatagcgt ctttttttt ttttttatg gagtctcgct     1980 ctgtcaccca ggctggagtg cagtggcgca atctcggctc actgcaagcc ccgcctcccg    2040
ggttcacgtc attctcctgc ctcagcctcc ccagtagctg ggactacagg cggccgccac    2100
catgcctggc tgatttttt tgtatttta gtagagacag ggtttcacca tgttagccag      2160
gatgatctca atctcctgac cttgtgatcc gcccgccctc gcctcccaaa gtgctgggat    2220
tacaggcgtg agccaccacg cccggcctga tacagtgtct tctttatata ttgttaaatt    2280
caacctgctg gttttatagg atgaattgga aaatattccc tcctcttcaa ttttatggaa    2340
gattttattt agaatttgta ttatttcctt cttatatgtt tggaagaatt cctcagtgaa    2400
gctgtctgga cctggagttt tatttatgga aaggcttta aatacgaatt caatttatgt      2460
aatatttgag ggctattcag gttatttatt tcttcttgag tgaactttgg tagtttttat    2520
cttttgagga atttgtccat ttcatctaag ttatccaact tcttggcaca aggtgctca     2580 tagtactccc ttattatcct tttgatgtat ttagaatctg tggtgatgtc acccttcat     2640 tcttggtatt gaaataattt atattttctt tccctttttt cccaaatcag tctggataga    2700
gatttgtcaa ttttactggt ctgctctatg aaccagcttt tgttgtcatt gatgttctgt    2760
atcgcttttg ttttctattt cattgaattt tgctttcatc tttatcattt atttcttctg    2820 cttacttac atttaatttt ctcttttgt tgtttcttaa ggtgaaagct aaggcccttg     2880
attaatatag agcatttagt gctataactt tccttctatg tactatgtag cagcatccta    2940 caaatttta tatgtgtatt accatttta ttccattcaa atatttta tttgtcttt       3000 gatttcttct ttagcccatg gattgtttag aagtatgtta ttcagtttct aaatacttgc    3060
agattttcca gagatctttc cattattgac ttttaatttt atttcattgt tgtcaggaaa    3120
tatactttat atgacttgag ttcatttaaa tttatcaatc cttgtttcat gccccagaat    3180
atggtctgtc ttagtaaatg ttccgtgtta gctgaaatta atgtgtactt tgctgatgtt    3240
ggatgaagtg ttctataaat gtctattaga tcaagttggc tgacagtatt gttcaactcc    3300
tgtatcttta ctgatctatg cctactcttt ctatcaactt ctaatagaag ggtgttggaa    3360
tctcctacta tcattgtggc tttgtctctt tttccttgca gttcgttcta tcagtttttg    3420
cttcatgcat gtattagttt gctagggctg ccataataca gcactataga caatgtggct    3480
taaacaaaaa aaaattatt tcctcacaga tatggaggcc agaaatccaa gattaagatt    3540
tcagcagggt tgatgtcttc tgaggcctct ctccttgtct tgtagatgac ggtcttctcc    3600
ctgtgtcttc acatcatatt ccctctgtac cttgtctgtg tccaaattct ctcttcttac    3660
aaagacacca gtcatagtag attagggccc accctaattt aacctgatta tctctttaaa    3720
tatcctatct ccaaatatag tcacattgga ggttaggact ttatgatttt ggaaagggta    3780
cacaatttag cccataacaa tgtatttcaa agctcccta ttagttgctt aggacttcta     3840
tgttctcctg attaattgac cccctttct tgtgaaata actcacttta tctctaataa      3900
taacctttac tctgaaatct acttcatttt gattggctat gatgtgatat atattttcc     3960 atccttttac ttttaacctg tttgtatctt atatttaaag tggatgtctt ataagtaaca    4020
tatagctgtg ccttgctttt ttattcagtc tgaaaatcta tactttttaa ttggagtatt    4080
```

```
taaatctttt acattaatgt aattcttgat atggttgagt ttgaattctg gctatctgac    4140
ttctgtttgt cctatttcaa ttttttcttc cattttttct cttttttctgc cttttttgga   4200 ttgagtattt tttcttctct ttctttttta agagacaggg tttcactctg tcacctgggc    4260
tggagtgcag tggcacaatc atagctcatt gtaatgtaac ctctaactcc tgggctcaag    4320
tgatccttcc accttagctt cttgcctaag gtattttgtc acagcagcag gaatagataa    4380
gacaacagcc taccttcaag tgatagtaca ccacctcaca aacagaatat gacccttata    4440
acagtacact tccacttagc ccctcctgga ctttgtgcta ttgttgtcag atattttact    4500 ggttttttg ttttgttttg ttttgtttgt ttgttttgtt ttgttttga gatggagttt      4560 tgctctgttg cccaggctgg agtgcagtgg cgccatctta tctcacggca acgtctgcct    4620
cccaggttca agcaattctc ctgcctcagc ctcccgagta gctgggatta caggcacctg    4680
ctatcacacc tggctaattt ttgtattttt agtagagatg gggtttcccc atgccaggat    4740
ggtctcaaac tcccaacctc aggtgatcca cctgcctcag cctcccaaag tgctgggatt    4800
acaggcgtga gccatcatgc ccggcctaga tattttactt ttacttataa ccccacagta    4860
acaatgcatt gttattgctt ttgctctaaa ttgttgatta tctttaaagg gatttaaata    4920 attttttaaaa ggcattattt tttacccaca taattgccat ttccagtact tttcatttct    4980
ttacatagat ccagatttcc atcttgtatc attttctttc tgcttgaata acttcctta    5040 acatttcttg taagtacagg tctgctggtg ataaattctt tcagtttttg tatttccaag    5100
aaagtattta tttcccttc attttttgaaa tatattttca atgggtgtag aattctagct    5160
tggtagattt ttcctttcag tactttaaag atgttgttcc actatctctt agcttgcatt    5220
gtttataata aaaaaaatct actgtcattc tttgttcctc tgtgtaatgt ttcttcttcc    5280
tttagcggtt tttaagattc tctcatttta acttgttttg agcaatttga ttgtgatgtg    5340
ccttggtgta tttttttcttt atgtttcttg tgtttaggtt tgttgagttt catggttatg    5400
tgagtttata gttttcatca aatttggaaa ttttcagat gtttcttcaa ttttttttctt    5460 ttcttcccctt ctctccttaa gggactccaa atatacatat gttaggctgc tttaaattat    5520
cccatgactc actgatgctc tttttatttg tttttgtctt ttttctttct gtgttttatt    5580
ttggatagct tctattgctg tatcttcaag tttacaaatc tgttcttctg cagtgtcaaa    5640
actgccatta atctcatcca gtatattttt cacttcaaac attgtgattt tcatgtttgg    5700
atgtttgatt tgagtatttt taaaatatct tctattattc tgtttaacat gtttaatctt    5760
tcttctggct ttttgaacat atggaattca gttacaattg gtgttttaaa gtctttgcct    5820
cctaattcta tcatgtgtca cttctgggtc agttttgatt gattgactga ttgacttttc    5880 tcttttaaa ttttttgatac aggatcttgc tctgttgccc aggctggagt atagtggcat    5940
gatcatggtt cacatcagcc tcaacctccc aggctcaagt gatcctccca cctcagcctc    6000
ctaagtagct gaaactagag gcgtgcatca ccatactcag ctaatttttg tattttttgc    6060
agagatgggg ttttgccatg ttgtccaggc tggtctccaa actcctgagc tcaaacaatc    6120
tgcccacctt ggccttacaa agtgctggga ttacaggcat gagccaccat gcccagcttt    6180
gacttttctc ttcttttttta tttttgtttt ttaaatttaa tagagatagc atctcactgt    6240
gttgcccagg ttggtcttga actactgggc tcaaataccc tggtctccca aagtgctagg    6300
atttaggatt tataggcatg agccaccaca cttggccgac ttttctcttc tttatacata    6360
gtatttttct gcactttcac ttgcctggta atttttatt ggatgctaga cattgtaaat    6420
tttacttttt gggggctct ggataatttt tatatgccta taaatattct ttagctttgt    6480
```

```
tcttaatgta gttaagttac tctgagataa tttgatcctt tcaggtctta ctttcaacat    6540
tcttggcaga accccagtag catttagtca agagttaaat tcccttgtta ctgaggcaaa    6600
acccttctga gtgctctaca cagtgcctca agagttatga gattttttcta ctgtggccgg   6660 tgggaagatc actattcctg actatatgtg aactctgaga atgttttttct ctactctttt   6720 tgtaaagttc tttcccaagg cttgggtcat ttcctcacat gcacatgatc agtactcagt    6780
actatgaagt gctctccttt ctgggactct gcccggcaaa ctctagcttc cttggcttcc    6840
ttggcctctc agctctgtct cctcctctca gaaagacctc cagggttagc ctgggttccc    6900
tcccccgtac tgtggcctgg aaactctttc taggcagtaa ggttggaaac tgtttagctc    6960
accttgcttg tttcccagag attgctcccc tttttgccta atgtccaatg ccttgagaac    7020
catcgtttca tatatagtta tgcactgcat aacgactttt gatcaatgat ggacgcatat    7080
gtgacagtgg tcccaaaaga ttacaatgga gctgaaaaat tcctatcccc tagtgatgcc    7140
atagccatct gtattagtca gggttctcca gagagacaga actaatagga tatatgtata    7200
tatatgaaag ggagtttatt agggaggatt ggctcacacg attacaaggc aaagtcccac    7260
aataggctgt ctgcaaactg gggaggagag aagccagtag tggctcagtc tgagtctgac    7320
agcctcaaaa caagggaagc caacagtgca gccttcagtc aatggctgaa ggcccaagat    7380
cccccagcaa gccactggtg caagacccag aatccaaaga ccaaagaacc tggactctga    7440
tgtccaagag caggaggagc agaagaaagc atccagcaca gaagaaagaa ggaagccaga    7500
caactcagca agctaggata tcccaccttc tttcacctgc tttgttctag ctggcagccc    7560
attggatggc acccacccac attgagggtg ggtcttcctc tcccagtccg ccaactcaaa    7620
tgtaaatctc tggcaacata ctcacaggca cacccagaaa cagtactttg ccagccatct    7680
aggcatcctt caatccaatc aaattgacac ctaatattaa ccatcaaaat gtcatagtgc    7740
aatatattac tcacatgttt gtagtgatgc tggtgtaaac ggcctactgc actgccagtc    7800
atataaaagt ctagcacata caattatgta cagtacataa tacttgataa ttataataaa    7860
cagctgttac tggtttatgt atactatgct ataattttta tcattatttt aaagtgtact    7920
ccttctactt attaaaagaa aaaaagtta actgcaaaac aacctctggc aggtccttca    7980
ggaggtattc cagaagaaga cattgttagc ataggacatg acagctccat gcatgttatt    8040 accccctgata accttccagt ggggcgagat gtggacttgg aagacagtga tatcaatgat   8100
cttgaccctg tgtgggccta ggctaatgca tatgtttgtg tctttgtttt ttatttgttt    8160
gtttgcttgt ttgtttgttt ttgagatgga gccttgctct gtcacccagg ctggagtgca    8220
atggagcaat cttggctcac tgcaacctct gtctcccagg ttcaagcaat tctcctgtct    8280
cagcctccta gtagctggga attacaggcg cctgccacca tgcccggcta attttttgtat   8340 ttttagtaga gacagggttt caccatgttg gccaggctgg tctcgaactc ctgacctcaa    8400
gcaatccacc tgactcggcc tcccaaagtg ttgggattac aggtgtggac cactgcaccc    8460
agcctgtgtc tttggtttta acaaagaagt ttaaaaagta aaacctaaga ataataattt    8520
aaaaaataca aaaaggctta tagaataagg atataaagaa aatatttttag tacagctgta   8580 caacgtgtac atgttttaag ctaagtgtta ttacagaaga gcccaaaagt ttttaaaagt    8640
ttaaaaagtt tataaagtaa aaaagttaca gaaagctaag gttaatttat tatcgaagaa    8700
agaaaatttt tttataaatt tagtgtagcc atagtgtaca gtgtttatga agtctacaga    8760
attatgcata atgtcctaca acttcacatt cactcaccac ccactcactg actcaccgag    8820
```

```
agcaacttcc agtcctgcaa gcttcacttg tggtaagtgc cctatagaaa tataccatac   8880
tttaatcttt tatgccatat ttttagtctg cctttctatg tttagatatg tttaaacaca   8940
aatacttacc attgtgttac aattgccaac agtattcaat acagtaactt cctgtacagg   9000
agcctaggag caacaggctc tacatgtagc ccaggtgtgt agtaggctat gacatccagg   9060
tttgtgtaag tatcctctat gatgtttcag taaggacaaa aaacacctaa aggtgcattt   9120
ctcagaatac atcctcatca ttaaataatt atcaataata actgttttgt ccagttttat   9180
ttgttgttcc aggtgaaaag gtaaatctgg ttcttattct tccattttga ttggaagatt   9240
cttcccctct gagctgaatt ttttcttgc taaagtccac ccttcataaa ttctttgagc    9300
aaaagtctga gattagtaaa acctcagtct gtatatatct gaaatgtct ttattttgca    9360
ttcatcctta aatgctggtt aactgaatgt agaatttgtt tttctgatca cttcaaaggt   9420
attagtccac tggcatctat tgttgctgat gagaaattgg cttcaggcag aacatcattc   9480
atttgtggat gtttcatttc tgatggcttt tcagattttt ttatttttat tgtttttcag   9540
tctcttcaat atgtctagaa atgaaatttt ttattctact cagaactcaa tgtgcctttt   9600
cattccagag gctcattttt ctttgcttgt agaaaatcct tcatcattat ttcttagaat   9660
ggtgcttctt ctcccctatt tcctccttgt agaactacta atctagtata aattttggaa   9720
cttctcattt tctcctctat gattttatc tttcatattt tccattactc tataatactg    9780
agcactctct atgtgccaag aactataaac tcatttaatc ctcatagcaa caccatgagg   9840
taggtacatt atagtatatt ataacattat aacattatag tatatctcca ttttatagat   9900
gagaaaattg atacacaaaa ggcttaaaaa catacctgaa tctctattgc tattaatagt   9960
aagtatcaga gatttaatac caggtgtgcg gcttcagacc ccatgtattt ttttttttt   10020
ttttttttg agacagggtc acacactcgt cacccaggct ggagtgcagt ggtgcaatct   10080
ctttgcagcc tcgacttccc aagctcaggt gattctccca cctcagcctc ccaagtagct   10140
ggaactacag atatgtgcca ccatgcccgg ctaattttt gtatttttag tagagatggg   10200
gttttgccat tttgcccagg ctggtctcca actcctgggc ttaagcaatc caccagcctc   10260
agcctcccaa attgctggga ttacgggtgt gagccacctt gcccagccca ctgcactaat   10320
attccatact attataattt catctctttg tgctgctttc tgtgctgcct tctgggtaat   10380
ttcttcagat caatttgagt gtactaattc tctctctcca tctgtgtcta atctactctt   10440
taaaacatct attgcatttt taatagttca tttttgctat ttctatttgc ttctttttc    10500
ataagctctt cttcttgcct tatgtcttcg attcctaatt ttatctcatt taaacatact   10560
tacattaaaa tttctcaggt tgttctataa tcctaatttt tggcgtatgc accactaaga   10620
tctcccttca agaaagaact tgctcttcag ccacacaagt gcagttggct gactacctca   10680
agctgttagt accgttactg ccttcaagat atgcctccgt tttttagtta aggctatgct   10740
cttcttcggc agtccctaag caataacttt atgaacatgg caggtgtact atagtcttgc   10800
tatttctgct caacaaggga cttctctaa caggcggtat tgttctata atccccttt     10860
gtgttagcca agactttatc acatttgcgt cccatctaag gctctctgcc caatcttgat   10920
tctccccatt ttgtctttta caggcattac ccctcaataa accccttgca ctcctaatcc   10980
cgtctctgca tttactttct ggaggaccca actaaaacag catgtgaatt atccaggtta   11040
tttcatcttc tgactttctt tcctagcaat ccttttcctc tcatactttg taatgttttt   11100
taccatgaga ttatcttcag tgggagttgt tttctataga agtcctgtgt gccctgcatt   11160
gtggaggaga atcacaggta gtttcacaag aagatccatt agtttaacca gttccaagac   11220
```

-continued

```
aaactttatg tcaatttctt agctagggtt cccccaaaca tcactgccac catcacacag    11280
ttaatgcaaa catgtgaact taattctcac acccatacta atgcagattg tgattacaat    11340
tgcttccagg tgactctttc ctagctcttt tctagctcca cctgagcttt tgagctcagc    11400
tatatatttt ttaatgtact ttttatattt tacctagcat ttctatttat ttagcgtaag    11460
agataaaagg aacttctttt ctttctacag tacccccatag tcaatgaaag taaaccctgg   11520
aacctgcata tatatgcgta tatatatata tatgtgtgtg tgtgtgtgtg tgtgtgtgtg    11580
gagagagaga catatatatg tgtatatatt tctatataat ttatgttctt ggtcatacta    11640 tctattttttt aacttttttat tttggaataa ttatacattc ataggaagct gcagaagact   11700
gccgaataca cttcactcag ttcccttcat tcagggaatg tactcaggaa tctgcattttt   11760 agcaggtaat cagaggactc agatgtaggt gcaggttgtt gcagatgcta tcagttcccc    11820
atccatatcc cttggacctt tcctaccaac tgttagcaac cactcttaac caatgactct    11880
cagcattggt atataaatac cctggttccc ttacccttca tatgcgttat ttctgagtca    11940
tgttttgcac catttcccag agtctccctg ctaaattaac cgttaataaa ccactgtggt    12000
agcactctta ttgtctgcct tccttttctt tatcaattcc cacttctcta cccaaatagt    12060
cactttccaa ataagctaat ttaactcaaa tctttgtgtg gcggtctgta tctggtcttc    12120
taagctcaga tcagaagtgg tcttagatcc caaggatgga atctaggatt gtaaaatttg    12180
tcggccaatg gtaataagat tccattattg atggtcttta atatattgta gaggcctagg    12240
atgaattggg ggacaagata cagatacaag gggatacaac catttatgaa gtctctctaa    12300
catctgagag atgtggaggc aatggtagtt aaagaactgg tggagtttgt tggttgttgt    12360
taagtaccat tgaagtgcta aaggaggaaa atgataggg caaattagtc aattaccagc    12420 ccagggatg gtatgaaacc tagaaagcca ctatgacagc attttaaaat cccctaattt     12480
cctacagctg gagggcagat aggtctgaaa accacatcca gaacctaatg atgaaagtag    12540
tagaagtgtc ccactcccgt ttgctagagg ataataggct tcctcctctt gcctggaaac    12600
tatgcagagg cctcccctaa ggcagatgcc ttgcaagatg atacttgccc tcttcaagat    12660
ctgcttctac attctcttgc gtcttctagg tcaatcacta gggttaaatc tcatcactca    12720
accattgagg aggtactatc tctgcttaaa gaaacaggat tttggccagg cttatgcctg    12780
taatcccagc actttgggag gctgaggcag gtgaatcacc tgaggtcagg agttcaggac    12840
cagcctggcc aatatggtga accccatct cttctaaaaa tacaaaaatt agccaggtgt    12900
ggtggtgcac acctgtagtc ccagctactt gggaggctga gacaggagaa tcacttgaac    12960
ctgggaggca gtggttgcag tgaaccaaga tcgtgccatt gcctgcctgg gggacacagc    13020
gagactccat ctcaaaaaac aaaaacaaaa acaaaaacaa aaaaaggat gtttactaaa     13080 agaactgcag gacctgccta atagatacca ataaaaagct ggaagatgtg cctgctttgg    13140
gaagggaagg aacataggaa gaagggaaat ggaacatagg gatggagaag agaagagttg    13200
ttgataagga ggaagtctcc tgagcttctg cacttaccat cctggcaaga acacttggag    13260
ctgggatggt tcagaggaca aaaggatcag tgtccaatca ggaggtagaa actacaccac    13320
taatttaaat agagatctaa tgtagtgtat tcttaagtag gtataaaatt attaagtagg    13380
taactgcaaa ggtaaaaaga gaatgctaag ttgtcacaaa gatagcaatg acaaaagcag    13440
ataccatgcc cacggctggt gaaacaaaat aagaagtgga attatcaaaa tttagaagct    13500
tacaagagaa gttccaagaa accaaaaactc agatctctga ggaggaacac caaagtgttg    13560
```

-continued

```
gaaactggtg ctaggaagtg ttgggaaact gcaaactgga ttcagctgct gctaaggaaa    13620
gatgctgctg atgccagggt gaagaagcgt tgctagggtg atgctcacag gaacaggaag    13680
ctgacaggaa gtcaatagga agaagcaagt ccctccttcc tgatgctgcg acatcaattc    13740
cctcctgccc tcctcattgg caggcataac agggagcaac tggcaatgct ggaatgtgaa    13800
tttctgaacc ccagccccag cactacacaa gttgatacag aagggtggtt gtggcgctaa    13860
gaggtgacag cttaactact gacaagagtt acaataaaca atgtagaaat gtgtgaactg    13920
acataactgg agaaaggagt caaaagttca gaggagaaat gtattgccta aaaccaaaag    13980
accaccagct tagtagctta gtatgtttcc agtacacctt cactggagca ataaagaatg    14040
agctcctgaa ggggcactga catcattgag caactcagtg gtggctgccc cttctatatt    14100
gtgttgtagc tgctagggaa ctggagttcc tactgtttct taatggtgac aataggattc    14160
cagaacagca gaggccaggt agcagcactt aaccatcaga cacatagtgt atggaattac    14220
cataatgggc agcaaagtca gaaactcaac caaggggccc ttacccacag agatctgtgg    14280
gattgctaat agaccatgaa gttcctaagg gcgagatcag tgggtgacta gcaagggtat    14340
tgctgcccaa tataataaaa acagatcaag agcatgtaat gtgaagactg aggtgagcca    14400
tcacagtgga aaatcactat ccctcaccca tttttcatgc ttaagctagt cctcagaccc    14460
agtaccacag taactgtaca caggagaaca aaaatatcca gatatttcta tagttgggga    14520
attcagagtc cggactgaca ctgattccag gggatccaaa ttgccactat agccctcctg    14580
ttaaagtaag gagatatgga ggcaagatga taaatggagt cttttgccaaa gcccattttta    14640 cagtgagtcc agtgggtctt cacaccctcc tgtgactatt ttccccatcc ctgaatactt    14700
aattgggatt agtaaactca gcaggcagta gaaacctcac atcggtttct taatctgtaa    14760
agaaactggt gagggtcacc caaagcagag gtgacaacag tatgtgtata tatatatatg    14820
tgtatgtgtg tgtgtatata tatatatata tatatatata tacatatata tgtgtatata    14880
tatatacgta tatatatata tatatatata tgctggaaag tgaatttctg aaccccagcc    14940
ccagcactac acaagttgat acagaagtgt ggttgcggcg ctaagaggca acagcttaac    15000
aactgacaag agttacaata aacgatgtag aatatatata tatgggggat caactgatta    15060
tatagccaga gtttcccatt gtaagttgtg tactgtcaga tccacccaac tgtatagtcg    15120
agtatgtgca acagtaatcc attgaagggt ggacatggaa cgttgtcatg aactaggcct    15180
gagcaggacc agaggtcaca aataaactac agaagcaggc ccagaatccc ctgttgtgat    15240
ccctgcattg gaacctctcc cctcagctca cacttaggaa atcatgagag attcctgatg    15300
accaggtgac agaggaggaa aaagcttagg cctggtttat ggacaggttg gcacaatagg    15360
ttagtggaaa acaaaaatgc actcttactg cactacagtc ccactcaagg gctcctgaag    15420
aacagccatg tggagaattt tttgcagggg cagaacttta ggcggtgcat tgagtcatca    15480
acttggtgca gaaagagtcg tggcctgagg tcaggaatcc caggcagtag tgaacagttc    15540
agctgattgc tcagggactc gtgaagagca agactgcaaa attgcagtta aggaggtctg    15600
gggaagaagc atgtggattg atctttgaga gaagacacaa aaatatgtgg gtctctgtct    15660
catttcattg tctaccagag ggtgtccatc gcagagaagg tgctgaacaa tcagttagat    15720
aggatgattc atccagtgga aatgagctta tctctctcct tagctgcccc agagcatgca    15780
caacagaccc ataactgaga agccatggta agagggatgg aagccacgca tgcccaaca    15840 gcatgggctt cctctggccg aggctgacct aggtattact actaagtgtc caatctgtca    15900
aagcacaggc agggctgagc tcttgacatg gtaccacccc tcaaggaggg cacccagcca    15960
```

```
catggtgcca gttgattaca ctggacccaa ccaccctgga ggtgctgtga ctcttctatg   16020
acttcatggg actgatacag atttgccttc tctgtccaca atgtcatgat cagcagcact   16080
ctctcagagt tcccagggtg tgcagtttat catcaaagca ttcccccata acatggccat   16140
ggagaaagtg agcacatgac catgttattc actggtcctg ctatttacca taccaaccag   16200
ggctgcatcc tgagaaaatg ctggaataac cacttgaagg catagctaag tcatcagctt   16260
gaagataggg ttgagaacct gtccttacat gtttgtttgt ttgtttgttt gttttgagat   16320
gaagtctcat tctgttgccc aggctggagt gcagtggcac aatctcttac ttcaacctct   16380
gcctcctggg ttcaagggat tctcttgcct cagcctcccg agtagctggg attacaggca   16440
accgccacca cccccggcta atttttgtat ttttagtaga cgggggttt caccatgttg   16500 gtcaggctgg tctcaaactc ctgacttcgt gatctgcccg tctcggcctc ccaaagtgct   16560
gggattacag gcgtgagcca tcacaccctg cctcccttac atgtatttct atacttgaga   16620
caatagctat tgtaagggtg ctacatcccc aacagtcaga atacataggt ctggaagcca   16680
agaaatgagt ggcctctctc acctttattc ccaatgaccc acttggcaaa tttatgcttt   16740
ctattgccaa agctttaggc tctgttgaac cagagatcct agttctcaga gggtagggag   16800
agatcacttc taccagagga cataattgtg gttttactaa acctaaaatt atatctgcct   16860
ctggtaattt tgggatcctc atgacagcag accagcaagc taagaaagga gattctgaac   16920
aggcaggagt aagtgacccc tgctggacca ggtgaggggc atctagaaag ggtagtagag   16980
tcggaagctg agcatcagtt acactttagg accaactaca gcagtggggt ctggagattg   17040
tccctcctct tatctgttat ccttctacc tcttcctctt ccttcttctc ctctcttctt   17100
gtaacaaatc gtgactttcc accacccaaa gaagcagtga cagaacatga aacttaatat   17160
gaatgcaagt ttatctgagc aggtgcaagg gtgaactgtg acacatactg tcaatgccct   17220
gccattgtcc ctcaaacctg tcaatgtatt cccaagactt ccaactgcca gcatccacat   17280
ggtagctaag ggatcatttt cccagaacta cagagagctg actgtacaca tcacagttca   17340
caagtgccaa agaattaaac accaccaggg agcagcctca acactcaaac atggtgtata   17400 aatacccag ctccctcacc ctttgggtgg gatgcttctg aggcatcgat cattctgagg   17460
ttttgtacca tttcccagag tttccctgca ggataaatct tcagttcccc tttgtgataa   17520
tagtgcaccc ttatggggct gccttcc ctt ccctgtatca ccttcccact tccctattag   17580
tgttacttat gctccccaaa taaactattt tcactttagt ccttatctta aggtcagttc   17640
ttggaagaac ccatgctaag acacatgtgg ctcaaggact atgcattgag aagccctaat   17700
ttagagagtg aactcatttc tatttttaa aaatatcttt ctccctctct cccctgactc   17760
cccttctcct taccctaca cccgagtttg tgtgtgcaca catgtgcaca catatataga   17820
atatatgaaa aagatctgag gatatgatcc aagtattaac aatagttctt tctgaatggt   17880
ggcttcttag ttttcctctc ttttgttttt ctacagcagc aactgtgtct ccgaaagtat   17940
ttttaattgg caattaggag atgatgagtg gagtggtggg ggagcagagc caggctgcag   18000
tgggctgatg ctggcccaag aggatgcaca ggccacagtg gctgatgct ggcacaggag   18060 gatgtgcagg ctgcagtggg ctggtgctgg cccaggagga tgtgcaggct gcagtgggct   18120
ggtcctggcc caggaggatg tgcaggctgc agagggctgc cctggcccag gaggatgtgc   18180
aggctgcaga gggctggtcc tggcccagga ggatgtgcag gctgcagtgg gctgctgctg   18240
gcccaggagg atgcgcaggc tgcaatgggc tgatggtgac gcaggaggat gtacagacaa   18300
```

```
ttctctcaaa gtgctgggct agagacaggc aagaaatgag gtggtagctc aaggtggggc    18360
aactgtagag agtatcattt gaataggaag ttgagcctgt ttctaggctg aggaaaagca    18420
gccaatgaca aggaaggaga caaaaataca gagtcaaaag tgggctcatt gaaggagtca    18480
gttcccagaa gaggcctgag tggattcaag gggccctagg ggaggaatcc attctcaaca    18540
gaaggtgagc ttcatcctct gggaccaggg aaaggggtg aagatgaata atgttagaaa    18600
tgcatttatt tcagtcattt ttttgttcta ctctctgctt catttcacag agtacttgag    18660
gtgtttctat agataagttg ataggttgga gggactggaa gttgggacat ccccacggag    18720
ggggctccac ttcccccatg gagcaggagg caaggtcccc cactgagagg aagcagggt     18780 gtctctgtgg ggttacagga gccaggcaaa ggtttggaat agggaggagg cactgagcga    18840
cagagcccag cttgcccatt tataaagtct gctaggtgga gctgaccgct cagctgtggc    18900
ccagccagcc tgcacaatgt ggagtcatct ccagctgctt gggccccagg caagaatcac    18960
aggaggagga gcctgtgccg cttacttgtc ctggttttag ataagtcact tccccactcc    19020
cagccacagt ttcctcatct gccaatgggg agaaacaagt caaatctgga gatttgatcc    19080
tattgtgagc atcaaatcaa ataacacaca tgaagcacct agcacagtgc gtggcactcg    19140
gaagttgctc aatgttcctt cttctgctcc tctgccttca agtgggcttg agcaaatgta    19200
acctggatag aagggacgt ggatgttgta tcttgtattg gtggatgctg ttacatgcaa     19260
caattttaaa tacagccgac tctcattact ctctgtagcc cttaaaagag ctatggcatc    19320
aggctcctgt gagtctctgg ccacattttt agcaaccagt caacatacaa cattgttta    19380 tttatttatt tatttagaca tggagtttcg ctctattgcc caggctgcag tgcagtggtg    19440
caatctcagc tcactgcaac ctccacttcc tgggttcagg tgattctcgt gcctcaacct    19500
cacaagtagc tggaattaca agcaccccgc accacgccca gctaatttt gtttttagt      19560 agagatgggg gtttcaccat gttggccagg ctggtctcaa actcctgacc gcaggtgatc    19620
ctcctgcctt agcctcccaa aatgctggga ttacaggagt gagccactgg acccagccac    19680
aactttgttt tatgtgtgtt tctgcttaga gacccttatt taatatataa attgttgatt    19740
cactagcact gaactcacag ccaacactac tgtaactcat gtctgaacaa agcttatcaa    19800
gcacacgtat tttctcctta aggcacatca cagccttctt gtgcttgaga acaccagaga    19860
gcacttcagc acaatgcttg gggccatttt aaatagcaaa atcaccaaca aaaggcaca    19920 aaaaatgaga acggttcgca acaaataagt cacaaaaaga atacttgttt acactatgac    19980
agctgagaca agaaggcagg gtgtcccttt gttcaccttc agctgggaac atatgtgtgg    20040
gtaagtcaag attttcacca ctgtacataa gtatgtccac aaataatagc aattgtgcct    20100
caagtattga tttgaaggtt acaaataaat tttagaagta ggtgattttg caaatatgga    20160
atccataaat aatgaggatc aattttcttt attttttctg attacaaaaa tatatataat    20220
aaacagagct atctaatgta aaagttaaag tcccccataa tcccagccca caaatgaaca    20280
caattagaat atagttctat agaattttg ttatgcaaat aatgcctgtg attgtgtcta      20340
agtctgtggg tgtctatgtg tcagtgtatt tgggtctttc ttttcttttt ctcactcaac    20400
aatagctctt ggatagcttt ccagaaaaaa aaattcctg atgttaattt ctggagtatg      20460
aatgaagcca gatggcatac actgcagtca ggatctctaa gtcttagttc agaccactca    20520
accacatcag atgtggagag agcaatgact tgccaaatgt aaagataatc aacagtttta    20580
gtgttctgca tcttaatgga gatgaataa ggtcaagaga agaactgctc agaggataaa     20640
aggactgaac actgggaagt aaagtgaaag agaagagact gggtcgggca cggtggctca    20700
```

```
cacctataat cccagcactc tgggaggcca aggcaggcag atcacttgag gtcaggagtt    20760
tgagaccagc ctggccaaca tggtgaaacc ccctctctac taaaaataca aaaattagct    20820
tggcgtggtg gcgggcacct gtaatcccag ctactcggga ggctgaagca caagaattgc    20880
ttgaggctgg gaggtggagg ttgcagtgag ccaagattgc accacttcac tccagcctgg    20940
gcaacagagc aagactccat ctcaaaagaa aaaaaaaga gtctgtgact ttcagccaga    21000
gaaaaccaca ttctgtgtcc tttggaggag attagaccta catattaaga ctatctactg    21060
aaaggattta gacaatagag taaaatagta ccagagcctc ttctaaaaac agctgcaaaa    21120
ttggctgggc gcagtggctc atgcctgtat tcccagcact ttgggaggca gaggcggttg    21180
gatgacctga ggtcaggagt ttgagaccag cctgaccaat atggtgaaac cctgtcttta    21240
ctaaaaatac aaaaattagc caggcatggt ggtatgcgcc tgtagtccca gctactaggg    21300
aggctgagat aggagaatca cttggacctg ggaggcagag gttgcagtga gccaagatca    21360
tgccactgtg ctccagccag ggtgacagag cgagactcca tctcaaataa ataaataata    21420
aaaacagctg caaatagta tggagaaagc tgggctgctg caacaaaaga cccaaaatac    21480
aatggctctt agaaaataag tttacttctc actctgtagt ccatgtcagg gtggctgtac    21540
ttcatgcagt cattcaggaa cccaggatcc tcccatatct ttgctccatc agcccttttg    21600
aagcattatt gaagctgtgt ccctggtaca tctatgttcc aactcaagag aagagaaaat    21660
ggagcatggg agagcaaaag cttcatgcct taaggtctat ttctatttat gttctattag    21720
aaagatttta gtcaccaagt ctcactcggc tgcaagaaca gctgggatgt atgatctcta    21780
gtggaccagc cattcctccg actgctactc tactacatag aagaacagga ggatgaagtt    21840
tagtggacag ctagcaattt ccatcacatc tcctttattt gagccttggt atcttcctct    21900
ataaaacggg gataataata taaactagtt aaggctgctt tgggactgaa atccaataat    21960
atatgtgaga atgcttagca agccctactg tgcctgataa gaatttctca ttgattttgc    22020
cctctagact gccagctcct tgggagcaag gagcatagtt tattccacct cctcacaaag    22080
acctgcttgg agtcagcatc agtaaataca tgttgaataa tgaagtcact gtttcatcca    22140
tcatcaagcc ttttttttttt tttcatttca tttcaaatgc ttcaataatt tagactctgc    22200
cctgttcact ttccccaccc cctcattagg ggtgcacgtc agtatatcag ttgggattct    22260
ctgggttgca aagtgacaat gcactactgt taaactggct tatgcaataa gatggaccat    22320
ctcacatatc ctgaagtcca gactctgcat cagaataaaa gcttctcttc cctaggactc    22380
tcttggcctt gccctcccct ctgtatttgc tgcatcctca gactgggagc aagatggctg    22440
ttgcaattcc aagcattgcc accaaacata tcccagcaaa gggggcagac tgttttgcaa    22500
agtaaagaga ccatttcctg aaaacccctc tctgccatag gcttcccctt tagttttttca    22560 ggctggacct gcccaaactg tcactggcaa gaggaatgag accaccataa tggacttgga    22620
ccaaacaaga ctcactccat gagaccacca taatggactt ggaccaaaca agactcactc    22680
ctggaaatgg gctggggtca gccttccttg ggtcacttgg ggaaggggc cacctgacca    22740 aaatcagggc tctgcccata agaaaatgtt gagaaactgc tgttgcatga gcaaccaact    22800
atttttctcg caatgatgga gattctgggc cagatgaggg tgtgatggag aaagtgttaa    22860
ccatagagaa ctaaactgag agctttttca taaactgtac ctcaataaag tttaacacca    22920
atgaagatat ttctggagga ggcagaaact ggtagccacc ctctatggct catttccctc    22980 accccgtat ccaaccatca ccaaatgtca ccgtgtctgt acttgcaata ccctagtctt    23040
```

```
ctctccttac ccactgctga ggccccagtt cgggtctcac ctcctgcagg cacgatgaca    23100 acagcaccctt aggggtgccc agtctttcct tcctcctgca acccagggcg ttgatgcggt    23160
tattcagcta cacacccttta ctgtgtgctg agtgctgtgc atccgcagac acattggaaa    23220
agctccctgt cttcttcacc ttgcagatgg tataatgatt atctccaaga cttcctgaaa    23280
cccaatcgga ccaggtcatt cccttgcctg aaagccccat gccttcaaga aattctttac    23340
catgacccac aatgccctcc agcccaccca ggctccttct ccaccccacc cccaacagta    23400
cagaattact agcacttcct tcactgcgcc ctcccctttc acgcctctat gcttttgcac    23460
aggctgtctc ctctgcctag aaatcccttt tcccctctcc atctggcaca caagacaagt    23520
tctcctatta cttttttctcc ctctctcctg ctccacccct caccgcctta cacacacaca    23580
cacacacaca cacacacaca aatacagcac tccagaattg tttgccaatg gaggcagcct    23640
ccggggccag atgttagcca gggctttcca aacttctccc caagcactcc ttaagaaagt    23700
gaagaggaaa tgggacccca gggcttagga gtgtgagggc cttgaactcg ctctaagcaa    23760
gcagggcatt tcaagagttt tatctttata ttttatgcag aagttgtatt ccaaatatat    23820
tcttgttcgt tttaatacaa aatatgattt tttctacatc ttcaaatcga tgatccagaa    23880
agatgctcct tgtttatttg ttgtgctctc aaattagctg ctccgcctcg ccgcggggac    23940
cctaagcgag acctggatgc agttccaagt acacaccccg aaggaacagc tgggcttcgc    24000
ttccctggga gctggaggat ggtgggggtg gggcgggtc aaccggctgg tggccccgcc     24060
ctcccccgcc cgctgcgggg gcggagttgc ttgggtcccg ccccggggc ggggaggcag     24120 ccgcggccac cggcagctcg gattcggctg gttccgggtt gagaggctgc gctggaccga    24180
agcggtggct gctaagctcg cggggtaag gggtcgcgct gggccaggg ttggggccgg      24240 gatccggcag ctgagcgggc cggcacccct cctcttctct gccggtcaca gccaatgtac    24300
ggctcggcct ggctgccccc tcccccagga ttccccatcc ccagcttctc gccctccccg    24360
caccgccccc accccgggat ttcgaccccc ttaagggctc caccccgctc cgggatcccc    24420
ttctcccagc tcctatccct taggactgcc ccgcccccta gaacctcccc gtcaggatct    24480
ccgtccctca gccgctcaca gcctcctccc agcgcccatc gccttgagct gcccactacc    24540
tctagactgc cctcccggc tggcgtccca cggagtctca gccgcgcacc ccttcctcgc     24600
gttaccctcc ttccggacag cacccccctcc ctttctccggt agctcctacc cctgcctgtg   24660
cgggcctcgt ccccgcgccc agccctcggt gctgcctccg acagcgccgc gctctctcag    24720
ccgcccccct cgccctcggg ccccctctc tgctgccct gggccatggc gtgcagcctc      24780
aaggacgagc tgctgtgctc catctgcctg agcatctacc aggacccggt gagcctgggc    24840
tgcgagcact acttctgccg ccgctgcatc acggagcact gggtgcggca ggaggcgcag    24900 ggcgccgcg actgccccga gtgccggcgc acgttcgccg agcccgcgct ggcgcccagc    24960
ctcaagctgg ccaacatcgt ggagcgctac agctccttcc cgctgacgc catcctcaac    25020 gcgcgccgcg ccgcgcgacc ctgccaggcg cacgacaagg tcaagctctt ctgcctcacg    25080
gaccgcgcgc ttctctgctt cttctgcgac gagcctgcac tgcacgagca gcatcaggtc    25140
accggcatcg acgacgcctt cgacgagctg caggtgcgct accggcctg cctggggaag    25200 gggcggggcc gggctggagg tgggccggg cggggggtgg ggtcagggct ggaccgcggg     25260
ccaggcccag tcagaatggt cctggggcgg ggccgccagc aggtcaggg ccctatcagg     25320 agtaacgcgg ggcagggagg ggcggggccg ccgcatggcg gggccgtggg ggcggggcct    25380
tgggcagtcc ggaccctgag ggatctgaga cagacctgga gtaccggctg gtccgcggtt    25440
```

```
agggagaagt cggggatgcg gatgggatgg cggaaacaag tgagatcaga actggaccag   25500
atactgggct ggggcagggt tgtggacgaa ccggaatcag agttgggcaa aggcagggcc   25560
actgtcagac tgagggcgag gtcgcgagga tgggtctgta ttaaaccggg tagctgagct   25620
ctggcaggct gggggttctg tgggggcgga gactggatca gatgtgcatc aggactaaga   25680
ggagtacggg ggctagaatg tgctggacag gtgagggtga aacctaatag agtggtataa   25740
gttagggtgc caaagtgctg agagggcagg tttgagtacc gagggttagg ccaaggtgta   25800
tgaggggtta agactgagat caggtccaga tactctacaa caagtttaga tttaagccag   25860
agtagaggcc aggttgagtg gggccaggac ttaaaggtaa agatttggag aataaggccc   25920
agatgtaagg tgattcaaga agggagggc tagacctcta ggagtctcta gaggtttttg    25980
atgacctctt tggctctgtc ccccacatca ggacttttga agactaagtg aaacggtaca   26040
tgcagagtga cctgagcata gttggcatag aactctaatc ggtctccctt aagacttcct   26100
gtcttcactg acaaactcct actcaacttt taaggccttg ctcaaatatc ctctccgtga   26160
agccttctcc aagttccact ggtcaaacaa acaaacaaac aaacaaaaac attagaactg   26220
catttcccca aatgctctct attaataagt gtgggaaata tagtatattt tttatacccca  26280 cccccttgga gaattttcag tgtgcatttg catattaaaa gcttagagaa attttgttgc   26340
aaataaatct atttttactgt gtttaataaa atggttccca agcttacttg ggcctggaat  26400 cctttttttca agctaaatca cttaaatcca gcagccccat gtacctggct ttgggatact  26460
agtcgagcac gtagttctcc aaggccagag acagaatctt atttctccta tctatggccc   26520
caaagcctgg tgcaaggcct ggcccacagt acacaccaat aaaggccaaa tgaatgaacg   26580
aaagaatgac caaccctggc ctaagctgga ccacactgtg gagcgtttgg aagcagaagg   26640
tttttggctc aaacatttta tgaaaatgga gtgggctaac ttgggaggta atgagctctc   26700
tggcctcgag atactcaaac agaaactaaa taattacttt cccctgtatt gtagggctc    26760 ccaacccctc cacacactag tctttgagta ggcctgcacc cagcagatgc ccatgggcct   26820
caggagaaat ggcccatgtt caccatcgct ccttccctgt ccctttatc tcaaaactac    26880 aactgactcc cttccagtct agctgtctga ggatgaaggc cccatcagag ggtgagcaag   26940 ggcctgggc tctgggagcc tgcacaaggc ttggccctcc accccagag ccatcgtgct     27000 aggcgctgct gctgtccatc tccccgtcta tggagtcaca taagcaggaa gagtttgagg   27060
ggactctgtc tgaaaccatc tgtccaacct cttcatcatg taggaatgga aagtgaggcc   27120
tggagaagtt atgtgacttg cccaaggcca caattccaga cagtgagaga gccagggcta   27180
tagggcacag cctgacccag atccctcttc tctgatctct ccctccttg tctgaccttc    27240 tagcctctgc ttcagagcct tggttctcct gtctgcaaac caggaaatcc aaattactgt   27300
atgttgggct tctgtactct atcccatgac ctgggggaca caggagaaat tgaacatgta   27360
ttacctacaa atattattga aatgcttcat tattgggtga aaagtaaaac aggactgcca   27420
cttgcttact ctctagtgca ctgtcgtggg gttggacata cttgggttcc aaacctgctg   27480
tgggcactgt gtgcaccttg gtgagtcact tcatgtaaac gctgatgctc tgtctgtaca   27540
atggggtcag gatgcttcct tcctaccagg acttttgtga agctgacctg ggattaacct   27600
gctatttgag gttcaaaggc acacagtacg ggctggaata acatacagcc cacctttcct   27660
ctttctgcct gtgagagctc atgtgccag ctgagtgaat gcccagactc tcctctctgg    27720
cccgagaagg aggccttgct ttagtgtgtc ctctgggctt ggcaatttgg tggcagagaa   27780
```

```
atctgcctcc catctagaga ggatgtgctg ctgggtgaga ttcaaggcac cctccacccc   27840
acctgcctct ccctccatat ggggaaggca aggcttatta gctatttatg cagcagaaat   27900
aaggctgaac ccaccctcac atcccttct ctcccagcag ctgatggagc tggggccctt    27960
ctgcagaatt acagactcag agccatgcag atgatctggt gccacatcca cttgacagat   28020
ggggaaacag gagagggaga gggaggaagg gaacttgcct aaggcctcga agccagagga   28080
agctgggcct atactcagct ggagtctccc aacaccctac ctagcagttg gcgtgcagct   28140
tttacattta ttataaatcc ttgaggcatc agagcagaga aattaagagc cctgctttgt   28200
acccaggtaa tctcaatcct ggctctacca tttactgtgt gactttggga agattattta   28260
ccatctctga gccttgggtc cttcatggac agcatggaag taattatatt aggattaaac   28320
aagatgatgt ttataaaaac ttagtactgc acttggcacc taacagcact caataaatga   28380
cagctatagt aggttacatc gtactcggca ttattgacat tgggctag ataaccgttg     28440
tgcagggcca tcttgtgtgt tataggaagt ctggtagcat tcctggcctc tacccattag   28500
atgccagtag caaactccac ccaccccgca agttgtgaca atcaaaacca tctccaagca   28560
ttgacaaatg tctcctagag tcaaaatcac ctctagttga aaacctgac ctagaaaagt    28620
cccactgaac tttaaaactt caggtcaaat atcacctcct ctgtgaagcc ttccctgacc   28680
tactaagcac aattgctttg tactccagat tacatcacag gggtcagatc ctgacatgct   28740
gtgtgtcctt ggtcacgtca ctttgcttct ctaaggctcc ttctctaagg ttcatctata   28800
acaagaggat atgatgttcc tgggaaggat gttgtaaggg ttagggatcc tttatcagaa   28860
gtgcctagta ctgtgcctgg catagtaggc accccaaaac tatttttaaa tgtctttatt   28920
ctgattataa aattaacata agaagcagag ctgtataatg taaaagttaa agtccccca    28980
taataatacc ccatgaaaca tggcaggagt tactatacag ttctaaggat ttttatgtaa   29040
cctgtgggtg tgcatgtgca tgtgtgtgca tgcgtacatg catgtgtgtg tgcatgtgtg   29100
tgcatgtgtg catgcatgtg tgtgcatgtg tgtgtgtgtg catgtgtgtg tgtgcatgtg   29160
tatgtgtgtt ggtgtcttcc tccccacctc cactgctgag tacctggacc actgagcaaa   29220
gtggagggaa ggagcccatt tccaaagagt tcagggcttc tcagccaata ttcatcgagc   29280
ccagtctgaa tgcctgggac tgcactaagg gcttttcttg cattacctca tttaatcttc   29340
atagcaccct gtgggatggg tattgttatc tatttcttct actgatgaag aaacagactc   29400
agaggaatta agtgactcat ttggtcacgc agctggtaaa tggcagggcc aggattggaa   29460
gccagtctga ctaggccaca tatcgtccct gagctacctc tgagggctgg gtaattgtct   29520
cccagccacc ctgcctgtcc tgtattgaca gggctaggcc atctgtgcca gctgacgccc   29580
cgagggcagg tggttgggac gtcatcttgg tcagagcaga cgtggcatcc ggctctctgg   29640
ccatctcagg ttcctaaccc ccagagaggg gatccgattc agtctcagcc gcccctcca    29700
ggcctcatgt gaccattgga gcccttccca aggcttcctt catgccagag aagacagcag   29760
tggatcagcc ttggacgcaa gccctggtag gcagggtatg gtgatccagt gacaccaagg   29820
cagccaccca aggagggagg gggctggggg ctaggttcaa atctcggctc tggtttcttc   29880
caggagaggg ggtgacaccc tcttacccaa tctgagaaat ggaagtaaga actagccctc   29940
ctgctttctg tataaagaga gagaaagagt tgctaaatat ccaaagaaat gagagattca   30000
gaggcacttt attttgtagc atggacagga aggcagctgg gttgtctgtg ttgtggggaa   30060
gtggctctgc tgttacttt ccaaggagag ggcaggattc ctatgccaac agcagcctct    30120
gtgagggcaa agctggctgt gggtcaaact cagagctggc cgctggcatc tccacatccc   30180
```

```
tcttcacagg tgtctgggca gccaggatac ctttgctgag cacgggccac agtgtagaag    30240
cttagggcca acattgggga ccccaagatg tttattttat agaaagaaaa aagacctggt    30300
agggactaac aatgatgaaa caatgactct ataaaattat agcccaagtt ttggaggcac    30360
aaagtaagtt atgggcact tactgtgtgc caggtgctgt gttataggca tttgattctc    30420
acaaggattt tttcgttccc tactccctga gtgggactga gatcagtacc atctcacaga    30480
tgaagaaaat gaggctgaga gattcagtaa ccttcccaag atcacactgc aagtaggagg    30540
aagagctgag attcaaagtg gtctttctga ctcagaattc ccctccttc ccaacacgcc    30600 aactgtccca gggagcacca atggggagg aacctgagaa accatctggt tgacacgctc    30660
cccattttgc agatgggaa actgccttgc ccagggttag accagagctc agctctcccg    30720
actcagtcca gtgttgtttt cccagtacca tttaccttcc tgacctccat ctctgcttga    30780
acactcagag gatgaggca gatttggagg tgagttctgt cttggattca gggattcctt    30840
taataatttc tgggctgggc gcagtggccc acgcctgtaa tcccagcact tcaggaggcc    30900
aaggcaggcg gatcacctga gtttgagatc agcctggcca acattatgaa accccccatct    30960 ctactaaaaa tacaaaaaaa aaaaaaatta gctgggcatt cgtggcacac acctataatc    31020
ccagctactc gggaggctga ggcacgagaa tcgcttgaac cgggaggcag aggttgcagt    31080
gagctgagat tgttccacta ctctccagcc tgggtgacag agtgagactc catcttaaaa    31140
aaaatacata tacatataca tatacatata catatacata tacatatata tatacatata    31200
catatacata taaatacatg tgtgtgtgca tatatatgta tatgtgtgta tatatatata    31260
tatacacaca tatatgtatg tgtgtgtgtg tatatatata tatatacaca cacacataat    31320
ttctttagcc agtatctgtg ccatggctac agagggccag ccctgtgttg ggcccaggag    31380
agaactacac aagacctggc cctgtgtggt cccgaaagat aggcccataa actggtaggt    31440
tgctgtaact gaggcttgct ctgttgagct gaatcctaaa agatacgctg agtacttcag    31500
gccagggagc agaaagaaag atgttatgga cagagggaac aaaaacatgc acagcctggt    31560
gcagattgtt ccacggactg ggttcaaggc tttgacaggc agtcatgctc tccttctctc    31620
tctctccccc agcctaccct tcatttaatt ctaacagtaa ccctatgaga tggatctcat    31680
tgccccattt tataaatgga gaaactgagg ctcagaaact gtgcctagct gggcacagta    31740
gctcacacct gtaactccag tactttgaga ggtcaaggca agaggattgc ttgagcccag    31800
aagttcgaga ccagtgtggg caacatggca aaccctatc tctataaaaa atgcaaaaaa    31860
attagctggg catggtttca tgcacctgta gtcccagcta tttgggaggc tgaggtggga    31920
ggatcacttg agcccaggag gttgaaactg cagtgagctg tgatggtgcc actgcactcc    31980
agccagcctg ggcaacagag tgagaccctg tctcaaaaaa ccaaaaagga aaacagaaa    32040 ctgtgcctaa gggcctggaa agggagaagg gagaagaagg gggaagaaga aaggggggaa    32100
aagaatataa atgtatttac tacctctgaa ttgtacacct aaaaatggta aagatgataa    32160
ggtatatatg tatattttac ctcaataaaa tttttttaa aaagaggcta agcacagtgg    32220
cttatgcttc taatcccagc tcttgggagg ccaaggtggg aggatcattt gaggccagaa    32280
gctaggagtt cgagaccatc ctgggcaaca cagagagacc ccatctctac aataaattt    32340 taaaaattat ccaggcatga tgcatgcctg tagtgtgagg tacttgggag ctgaggcag    32400 gaggattact tgagccccag gagtttgagg ctatagtgag ctatgattgc accactgcac    32460
ttcagcctag gtgatagagt gagcccttgt ctctaaaaaa atttttttta attagggaaa    32520
```

```
aaaaaaaaaa gaaagaaact gtgcttaagg tcagaaaacc actaagtgtc cctgaagctg    32580
aaacttgaac tcaggttatc tgagtgtgac cagggacagg catggaggtg agcacacatg    32640
tgttcaggtg gttcgttgtg gctagagggg agggtgtggc aggaggaggt aagaatggaa    32700
aagcaaggct tgaccagctc aggaagggct ttgaatgctt gaatgtgcac atacatgcac    32760
acacacacat acacacatac acatgcatgc gcacacaagc tcacacacac acatgcacgc    32820
acccattgag cttgatcctt acttaacatg ctaggaagcc agaaacaaat gtgagcaggc    32880
aagtgcagcc cggccaggtc tgcattatgg accaagcact gtggggcagt gtgccagggg    32940
agctggtggg agaccctaga agcagggact ggccagatgt tgccagagat tgtgtggctc    33000
agaagtgcac agggagggtt ggggctcaaa gatataaaat aattccagtc tgttgggagg    33060
accaggagca tccagttcta ggtatagatg aaggattggg gttgggggag gaaagggaga    33120
ggcaagttca agtttgtcac ggtcaggttt ctggcatcct tgggtcagag agggaaagag    33180
agagcagtac ccagacatgg agaagaggag aggcttgagc acctattgtg tgcagcgcca    33240
tgctgggccg tgtcataggt gccatctcac tttagccttc atcacaacac tgtgaaagct    33300
tgcggaggtg agccctgagc gaaagtcatg ctgtcaggat ttgaacacag gcttttctga    33360
tgaagagtcc ctgaagccag agctgagatg gctttccaca gctgctttgt cccctggacc    33420
agagggaggg atggcctcac agcaggagag atctggcctt gggaacattt gagccctgcc    33480
tctctgtgcc ccccaactcc tctgttgccc cagtcctggc ttcttcatac aataaagag     33540 ccccagagcc tcaaagctgg catatttgca taactgtgtg ctcagggctg cgcagactcc    33600
acagccccac cctctgaggt gtgtcctccc cactcacctc atcctgccct gcccacccc     33660 gctccgatgg ggccctgtgg aatccaactc tcccaggctg acattcaagg cctcctccag    33720
tgcccacccc taccctagct agcccagct ggccttttcca gcttgtgact ccacccacct    33780
gtcacatgcc tggctgcagc catccccaac cacccgact tcctgcacac gtgagggtgg    33840 gccccctaccc aacctgttct ccccacctgc aatgccctgg cccatcctgg agacttgaag    33900
gaaccctggc catccatctt cctttgtcct tccatcagaa acaaactcct tccttgaagc    33960
tccccccgtt ctgagtccca actttacata tagttactat gatgataatg acaactaaga    34020
ttgattgagc tcaccctgta cgtcatgtca ggtcatgaat taagtcattt cattcccaga    34080
gcaagcctat ggagcaggtg ctgttaggcc ttacttaata gatttgaggt ccggtgccat    34140
ggctgatgcc tgtaatcaca gcactttggg aggccaaggt aggcagatca cttgaggtca    34200
ggagttcaag accagcctga ccaacatggt gaaaccccat ctctactaaa aatacaaaaa    34260
ttagccaggc gtggtgtcgg gcgcctataa tcccagctac tcaggaggct gaggcaggag    34320
tatcacttga acctgggagg cagaggttgt agtgagccaa gatcgcacca ctacacccca    34380
gactgggtta cagagcgaga ttctgtctca aaaaataaa aaataaaaat aagaccttac     34440
tttacagatt tggaaaccaa ggtggaggga gggtgctgtg agcacagcca ggtgttgtca    34500
gctgttctgg atcctagcag gccctccatg tttatcctgt tcttctttgt attttaccta    34560
ttcaagtttc ttcctcatcg actaactgca aatttttcaa ggaccatgta taggcccacc    34620
cctggagcgg ccagcacaaa gcctgacact cattgggtac tcagaaattt tgctgcatt     34680 gatttgcatg ggaggtaggg aggccaagag attttgaaca tggattttcg gagccactga    34740
gagcctcccc tctgcctctt actagctgtg tgaacttagg caagctgcct aacctcactg    34800
agcctcaatt tccccctctg tgagatggac gcaataaaga cactactaac cttgtggatt    34860
gttgtgagaa ttaggtgaca agatgcctgt gaaattcaaa cccaaaccac atccgcctcc    34920
```

```
agccctctg gtcctgggtc tctgccgtta ccagtgtcct tcctcagggt taagctgtat    34980
cacttgagag tttatcaggc tccagtttcc tgtgtgacct ctctgctgga gtaaaatttc    35040
tagtttgttc tcctgtgtca agctgtgtgg ccgtgggcca gtcagtccct tcccttgggc    35100
ctgtgtttcc tgtcctggca atccaagggg ttggaccaga tggtccctgc agtctcttcc    35160
tgctctggcc atctgagaag ggaaggaggg gccacctgga cacagtgagg atgaagaca     35220 caaagaagcg actagggagc cgcatacggg acacagtgac cgctctgtct cccgagcacc    35280
cagggtgtgc caggctctgt gccctgtgag gctgaacact tcttaccatt gtctcacttt    35340
atcctcccaa ccctaggaga tatgattatc cccattttc agacaaggca ctggggcaca    35400
gagaggttag gtgacatcct agggtcacac agcccaatgg gtggtagagc cagtcttcta    35460
accaaggaag gagacacgtt ggagcgggag gggtgacaca gctcaggcag ccttctaagt    35520
cctaccttct ggactctagg gtttggtttt cctaagttag ctgtttcttt gggctctgca    35580
cctagcccat ccaaggaact ctgcctgctg ggggccttct ctcccctccc acctttcga     35640 ggtgaactct gactcagcct agcctcatcc ttgggcaggg acatcctgaa gactcagcga    35700
ggccaggggt gtgtggccgt gtcctaggta ctgagattgt gaaaatctcc cctttccaca    35760
gtccttgccc tcaagagccc ataatctagt gggggagatt tttgttgttg ttgttttaaa    35820 gatgggtct cgctctgtca cccaggctgg aatgtacaat ctagtagggg agatttttt      35880 ttttttaaag agactgggct gtgtcaccca ggctggagtg cagtggcacg atcttggctc    35940
actgcaacct cctggttaa agcgattctt gctcctcagc ctcccaagta gctggaatta    36000
caggcatcca ccaccatgcc cggctaattt ttgtattttt agtagagacg gggttttgcc    36060
atgttggcca ggctggtttt gaacttctga ccttaggtga tccaaaggtc tcagcctcag    36120
cctcccaaag ggttgggatt acaggtgtga gccactgtgc ccggcctagt aggggagatt    36180
gacaggtaac cttgcaatta aaatgcagtg tgtgccatca gggtacaagt gtgggacact    36240
gtgcatgcag agtttgagac atgtactccc aggggaggtg acatttgatc tgggtcttga    36300
gagatgtgta aaggcctgga gagccctgcg agctgctcag tgtgtctgca gcagtactgt    36360
ccactagaac tctctggtag aacgggcagt tctgtgtctg cactgtctga tacagcagcc    36420
caggtggctg gcaagcactt gaaatgtggc cagtgcaacc gaggagctga attttccatt    36480
ttatttcatt ttaattaatt gcaatttaaa tagccacgtg tgtcgtattg aacagcacac    36540
gtctggacca agagctagga ctggagaaga aaaggttggg gccagcagta gagccttgaa    36600
tgtcacccta aggctttgtg cctttcttcc cagacaatgt ggaaatctgc agactggcac    36660
aatgggagag tgagagggg gaagcattta tacatctgcc ctttagaaca atcactgcag    36720
ctgctgtgca gggcacttgg agcagcagga gagctagagg cagggaggag cctggggcca    36780
cagcccagaa agaagtgat aaaaaccgaa ccagaggcag cacgcataga gaggagaaa     36840 caaattccag agcaaaccta gtgactggat tggtttggag gcggtaggaa tcaaggatga    36900
ctctcactcc gaggtttctg gctgggatgg agttagggga ggggtgccct tcactgagat    36960
ggggaatatg gggagaggag caagtttggg atctcctaac acgatcgcag cattccccat    37020
gatgtaagtg tctgtgtccc tgactgtcac cccaacacat gcacacctca tggcatcacg    37080
tttaggactc acacctcatc tctccccatc cttgacacag caccatgtgg ggcccaaggt    37140
ctcaacacat gtttgtggaa tgggcaaatg agtgttctga ttctcccgga tccaggagga    37200
aggagcaagc ccgctgtcct tattccctga ctgcaaaatc agggaggaaa tgtccaggtt    37260
```

```
tctcaagtgc cctgagcaat gtgaggaagg cagactccaa ggcagtttct cagaaatcct    37320
gaagagctgc ctgggtggct gggtcttctg tggacccatg ggggccacca gggggagaat    37380
tgtagcactt ggcccatctc ctcaacatct gcctctcagc cacactgtgt cccaggctgg    37440
atagcccaag gctgtcagag gcacctgagg agcggtcttt ctactctctt aggcaaacaa    37500
gattcctctg ctccgaggac tgtatccgct caagctgcac acgaatgtta ggaatgactt    37560
tcagctgtta gtaacagagc cctggctgaa gtagctgcag tcagatgggg tgcgtttctc    37620
tctcatgtaa gacaagtctc taggaaagga ctccaggtgg gtgtgctgcg gcaggttgca    37680
ctggctcctg agagctgatt gtgtgcatct catcccaatg ccaagtccaa ctactacttc    37740
acactgatag cttgaaatcc acttgagtgg gaacatttac accatggaaa ttggcactgt    37800
tggggattta aaaaaaaaaa gttttctca gacagccagc ttcctagcat gtcactgagt     37860
aaaccgatgg tgtggcagcc ccacagtcat cagggactcg ggctccttct tccttctact    37920
cttctggttt cagcttgtga ctttggtctt tacagttgcc tcatggcctg agatggctgc    37980
cagagttcca acaattgcat cagcatgggc tctcaaaaca agcagcttgt atttttctat    38040
cttaccccca ttttcatggc tggctcctcc tcatccttct gctgtcacct cctcagagaa    38100
gccttccctg gccaccctac ctaaagtccc ctccatctca cactgcttta ttttctctgc    38160
aggacacacc atattggtaa cctcgctcct ttattatttt ccttgtttgt tgtctgtctt    38220
ccccaccaga ctagtcccta tgatcaggga ctgtgtctgt cttgtccttc gccataatcc    38280
cagtgcctca acagtcctg gtacataata gttgcccaag aaatgttttt taaatgaata    38340
attgatagta atcaaagata attttgtttc ctgcattctt ccatcagcat gtcatcatga    38400
atattttccc atgttgctgc ctagtctgta aaattaattg aactagacat ttaccaaggc    38460
cctccctggt ctgacaagct gaatgagtgg gagggaggtg gatgtgaaca ggtaagtcag    38520
ccttcctggc actgctcaca gcccagactg acttggggaa ctcagaggcc atttccagga    38580
acttcattca cgcagcaagc gtcattgagt cccatctcag tgccaggctg ttgctgggtg    38640
tgaggtatat ggagagggag cagtaggagc caccctggag gacttgtggg ccaatacggg    38700
gacgaagaag agacagacag gagaacaact ggcgataata caatgggcta gattcccaat    38760
gcctgcagac agctggaccc tgtgctaggg agcactcacc tccacaaccc atttatcact    38820
tgacaaataa tcactgagtc cctgggcata aggcaggaa caagccagac aagattccta     38880
ctactctcat gaaactcaca ttctagtgag gagataagca ataaacacac agtcaaatat    38940
attcagacag cagaaggcgc aaggaagacc gtgaatccaa atgtgtgaca gggtatgagg    39000
aggtgccact gtgcgtgggg cggtcaggca agactcttca aggaggtggc atctgagtta    39060
aattaatggt acaaaggagt caccgtgaga aactctgaga gtggaggcca ccagccagag    39120
ggaatagcca gggcatagtc tgaagattgg aacgagctca agatggtgga ggcacaggaa    39180
gaaggccact ggctggatgg gagtgatggg ggagggtgtt ggagacagag gtgggatcag    39240
agggtgcccc aaactcagca atcaagatga atagtattta atgcaatatt tcttaaatca    39300
aaattaatgc aaaaaaccca cgatgaacaa aattcaacat ttcaaacaag gccaggatca    39360
ctaacaatgc tctgctgagc cacactggaa cctgagacaa aggaaaaatc agtgaggctg    39420
attgtgtttt tatttaaaat tttgatatct tgtgtgttgt ggatttgttg ttattcatcg    39480
caggagtcat catggtagaa aacgtgtcac ctggcatcaa gatcatggtc tccacaacca    39540
ggctgtccgg gttccaattc cttcttacc attatatgtt tatctgtatg ctatgggcc      39600 agtttcttga cctctctgta tcttttttctc catcagaaga tggagataat aattgtgcct    39660
```

```
cccttagggt tactgagagg cccaaatgat ttaatataag caaagagcta agaactgtgc   39720
ccagcccact gtagccctcg gagaatgttg gcagctagtc tgtagcattg gactggtaca   39780
gctttggttc cttagagcag tggtccccaa ccttttttagc accagggacc agcttcatgg   39840
aagacaattt ttccacaaac cgcagggggt gggggtgggg tgatggtttc aggatgattc   39900
aagcacatta catttattgt gcactttatt tctattatta tttcattgta atatataatg   39960
gaataattac acaactcaac atgatgtagg atcagtggga gccctgagct tgttttttccg   40020 cagctagaca gtcccatctg ggggtgacgg aagacagtga gtgatcatca ggcattagat   40080
tctcataagg agcaggcaac ctagatccct cccatgtgca gttcacactc ctgtgagaat   40140
ctaatgccac cactgatcca acaggaggtg gagtcaggtg gtaatgccag cgatgaggag   40200
cggctgcaaa tacagatggt ttgcccctcc ccaccactgt tcatctcctg ctgtgcgtcc   40260
aggttcctaa caagctatgg accaataccc acctgtggcc tgggggttgg agacccctgc   40320
cttaattcta agcgggatc cagggccaag tgtggggagc cagagagtgt gtatgtggaa   40380
gtcgattgtc acagaagcct ctagggtggc caaagaggag gaggttgttg caaagatgca   40440
ggtgaaagat acggacgggt tctggaggtg tttaggagac agactctaca ggacttgctg   40500
gtggttgaac tgtgacggga ggcaagtgtt ggaggttggg gacagagacc aggctaaccc   40560
ccagcgcctg gcagtggtca gggctgaatg cctgggccag gcatggcccc tgcccccatc   40620
ccggccctgt gtgtgtttca gagggagctg aaggaccaac ttcaggccct tcaagacagc   40680
gagcgggaac acaccgaagc gctgcagctg ctcaagcgac aactggcgga gaccaaggtg   40740
agcctggccg gggcgcggag gtggggccgg cagagatgag ggcagggctt cgaggggcgg   40800
ggccagctgg ggaagagggg cggggcctcg ggtgtgcggt ggaaacctgg cttcaaggag   40860
ccaaacctgg agtgagaagg gcagggtggg gaagagggta gggcatccgt gaagttcaat   40920
ggggcggcac ccaccccatc atgactggcg gcaaggatgt gggctggtcc ctcggttaag   40980
gacgggccca tttctcccctt cccactttgg gtggaagttg aggcgggtcc cgggaccctc   41040
cggaaacccc ctgcctcctg aagggctggg gaatgtgctc agtctctttc tcctctcccc   41100
ttattaaaac cgcccaaccc tggtgttgtg acacacactt gtagtcccag tctcttcaga   41160
ggccgaggca agatgatggc ttgagcccag gagtttgaga ccagcctggc caatataacg   41220
agatgccttc tctacaaaaa aaaaaaaaaa attgaatata gccaggcgta gtggcacatg   41280
cctgtagtcc cagctactct ggagactgag acagatggga agattgcctg agcccaggag   41340
tttgaggctg cagtaggcca tgatcatgcc actgcactcc agcctgggtg acagagtgat   41400
accctgtctc taaaatgaat gaatgaatga atgaatgaat aagcccattg cctaggagtc   41460
aatcctgagc atgtcccctc gaagccctcc agaggtggcc cagccctggt atcatctccc   41520
cttaagctca ggccatggga tacagactct gaaaggtagg gccaaactct gcagtctctg   41580
gctaccgtgg tttgggaaac aaacaaacaa acaaacaaac agacttttcc actgacttga   41640
gaaggacatg ggttctgatc ccaccactaa ctcactgtgt gactttgggt aaattgcatg   41700 cttttcctggg tccccagcct tcccatctgt ccagtgggga ctgccaggct cagtccagca   41760
ctctgggact ggaaggtgcc gggtggagtc cccactatac agagtgactc tgtgtcgtga   41820 ggcctgggt gatttcaggc tgaccccgct ctgtcagcag gagctgcggc agagccttag   41880
gaatgcgctg ggcctctgga ggtcatcctg gggcctgaag acaccattgg aaacccagat   41940
ctatgcccca gcttggccac caacccactg tggggtctca ggaaggtcat gacaaacaat   42000
```

```
tcttcacaga acattccaga gtgcctctgg gcaggaccct cggggggcaac agatgataaa   42060
cagtcacagg atgctggcct cattgcttct tgcagcctca gtttcccaa ctgtctggtg    42120
attctgtacc tcttggatga tgagaagcaa atggaagcct ctctctgtat gagagcggag   42180
tattatgggc tgttccttct ccccagcagc actctcttct ctccacatcc cacaccctct   42240
ttgttttct ccactgacct cttcctcccc cgctttcctg tccatctgtc tgcctctggg    42300
gggtcctgtg gggccacatc cccctcgagt tcccccagcc ccacttcctg tctggactgg   42360
ggtgtttata caagaaatgc ctatggatgc tttggaggtc atatttcacc tggtgcctga   42420
ctcggctttc ctgctgcgcc tgcccctcca atggcctggc ctgagggcct gtctgatctc   42480
cctcctcagg ccctctgttt tccttggtcg gcgccctggc ggggtgatgc attcttggca   42540
gggtgttttt ctgaaagggc cccagcgcct ccaggcccta gggtgttcca agggatgtgg   42600
tgggttgggg tgggggctgt ttccccagcc acagagctga aggagggg ttggggaaag    42660
ggtgactctg ccctggaaag aactagaata aatgggtgc accagttgag cagaactttt   42720
ctctgtgctg agaattgtgt tcctcttcat tatcctgcca acctcacaga atgtcacctc   42780
cacgagagca ggattcccta aacctagca cagtgtctgg cacacaataa gtagttataa   42840
aaaaagtgat tgaaaggaaa aaaaaatcgg ccaggcacag tggctcacgc ctgtaatcct   42900
agcactttgg gaggctgagg cgggcggatc acctgaggtc aggagttcaa gaccagcctg   42960
gccaatatgg tgaaacccccg tctctactaa aaatacaaaa actagctggg catggtggtg   43020
ggtgcctgta atcccagcta ctcaagaggc tgaggcagga gaattgcttg aacccaggag   43080
gtggaggttg tagtgagcca atatcgagcc actgcacccc agcctgggca acaagagtga   43140
gactccatct caaaaaaata aaaacaaca aaacaaaaa ccaaaaaaac aggaaagaaa    43200
aaaaatcgtc ccaggtagga actgttgtta tctcaatctt atcagtgagg caactgaggc   43260
acagagaggt tgagggacca acctgaagtc ccacagctag aaaatggcaa cttgggagct   43320
taccatccag tcctgtcaga gcccagtgca tagtgcagct gggatgtctc ctgggtgtc   43380
ctgcaagagc tatggctttg tagtcagcaa gccaggtagg tcagtaggac tcatcgggaa   43440
tgtacttggg gctccagggg tggctgccac tctgatgttc cactgctggc tgccctgtcc   43500
ctgccttccc cccttccct cccatcctct ctcgtccttg agacattgaa accccagcct   43560
ggaaagaagc tggagcctgc acccagctct acggagcaat ctcagacaag actcttccct   43620
ccttcacccc tcaagcaact cctgattgcc agccttgtac caggcgctgg gatgggcaca   43680
ggggtgcaga gccgagggag atgtcattcc tacccagcag gggcccactt actagccagg   43740
gagacagaaa atgtgggaca atgtattaag actgttgaca aaaggctctg gaacatcca   43800
agtgcctgaa agagaggaaa gttatctctg aagaggtcac tttcaagcta ggtcttgcag   43860
gatgagtagg agtttgccag ttgaatacag ggtttgggta gggtcattct aggcaggtgg   43920
agttgcaatg cagtggcgct agggaggtaa gctagggtta aattgagaag gtccttgaat   43980
gccagactaa agagttcagc atttttactac gtgtcaagga gctaaagaag gttcctaaac   44040
tcaggatcat ctgtgattca gttggcactt tagaaggatc actctgacag tgagtttgct   44100
ggcaaagaca agagttgact tgtagaccaa gtgagttgga aagacctgtg ggaccccaga   44160
gggatgtgtt ggggagactg ttggaaaaat gggtgtggca ctcaggagac aggcaaggcc   44220
atctatatgg acttgggaac catccttaaa gcagttcaag ttgaaaatgg ggcaggtgt    44280
tcagggtgag gatggaaggc gctgacctgg atgagcccg aggaacatgg gaggcagaga   44340
ggcagcagtc acagagatgg gaggcaaagc agaactttca actgggagag ggtggcgagt   44400
```

```
                                              -continued gggctaagtg ctgcagagtg gtctaggagg agccagagga gtagctgcgg agtctgggcg    44460
cctgtggagg gcagctccag gtggtgcagg gacgacggac cccatcttcc ccatcagcaa    44520
catgccgctg cagaggcctc caccctcccc gggtgaggag gctcaggaag gccacggcag    44580
cctggccgtg catccccaga ctctcgtccg ccccccttttg tctgcctggc gttctgggtg    44640
ggcatgcgca gcgaggctgg cccaccgcca gcagttcttc ctgcaggcca gcagccgcgc    44700
gtcggggagg gaacaggccc taattgagcc tttgtagagc ctcccacaga gccctgggca    44760
ctgaacacag tggggtttct gactccatga actcccagcc agaatcccac aaagtaaaat    44820
tgcagaggca ggccccacat gctgctgcag cctggccgca cttctatagc ccgtgtcgtc    44880
ctgacgttaa gccttcctc atgcggctcc ctctgcctgt tcccctgacc cccaactgac    44940
atcctgccca tccctcaggc cccggctcag aacccgtctc tcaatgaaga cttccgggaa    45000
acgcttatta gaattgcagt cttcaataac caggctcttt ctctgcgcct tggagtgcgc    45060
acaacaacac ccctcattt catcttcacc acaatcctac aatgcagttt ttgttactcc    45120
tttcacagat aagaaaacta aggttcacag ctcttaggca actgacgttg ccatagctag    45180
agacccagag ctagagtcct tacgcagact gtcaggcacc aaacctgtgc ccttcactac    45240
ttcacccttc ctgagcctca cagtgccctt gggggcagag aaaaccatga aagttcatgc    45300
ttacctccct gatcctgtct ataaacacca gtccttgctc cttagccaga gggtcctaga    45360
ggtaacagga gacagcgagt aaccaccaag gttttctcaa tacgttgcaa tttacaaagc    45420
tctttgatgt ctgtgatctt gtcatctttc cttgagcccc ctgaatgagc cccatgaatg    45480
atttttttaa aataaagact tcagccgggc acgatggctc acgtctgtaa tcccagcact    45540
ttgggaggcc aaggtgggca gatcacctaa cgtcaggtgt ttgagaccag cctggccaac    45600
atggtgaaac cccatctcta ctaaaaatac aaaaattatc cgggcatagt ggcgggctcc    45660
tgtaatccca gctactaggg aggctgaggc tggagaatcg cctgaaccca ggaggtggag    45720
gttgcaatga tccgagatcg tgccatcaca ctccagcctg ggtgacagga gcaaaactcc    45780
atctcaaaaa actaataata ataaaagcaa aaaaaataaa gacttcacta tgtccttgag    45840
agaac                                                                45845

<210> SEQ ID NO 7
<211> LENGTH: 23433
<212> TYPE: DNA
<213> ORGANISM: Human
<220> FEATURE:
<221> NAME/KEY: modified_base
<222> LOCATION: (5071)..(23433)
<223> OTHER INFORMATION: n = A or C or G or T/U

<400> SEQUENCE: 7
atcttcaccc tgtcccctag ccctcactcc agctccctca tccctcctac ccccaagcca      60
gaaacctggg cattatcccc agctcctttc tcttctgtac ccctctagcc aacacagcag     120
ggtcaaagag gctgccctct agatgttttct caaaccgtgt tcctcaccat tgctgctgct     180
cctctagttc aggcctcatt ttctcacctg ggccatttca ttagctattt aatggaccac     240
atagaacatg cccatccttt cctaccacca tgcttttgca tgtgacattt ccccaccac      300 gcgtgccctt tcccaccctt tcctctctgt gtgtcaaggc tctcgatttc ctcctctcac     360
ccagagatca ccccatctgc tcccccagcc ataaccctg acgactgtcc cccacagtct     420
tccaccaaga gcctgcggac cactatcggc gaggccttcg agcggctgca ccggctgctg     480
```

-continued

| | |
|---|---|
| cgtgaacgcc agaaggccat gctagaggag ctggaggcgg acacggcccg cacgctgacc | 540 |
| gacatcgagc agaaagtcca gcgctacagc cagcagctgc gcaaggtcca ggagggagcc | 600 |
| cagatcctgc aggagcggct ggctgaaacc gaccggcaca ccttcctggc tggggtggcc | 660 |
| tcactgtccg agcggtaagt gccacccgcc ggggccctcc ccggctgacc atccctcct | 720 |
| cgacccatgc tgggcagtgg gagtggaggc agatgggatc cttagcagag aattctttca | 780 |
| ttcaaatctt catcaaacat ttacgggaca tctgctatgg gtaggagcat gaagccttga | 840 |
| gtatgaagcc agtgaggctt gaactagagg agcagcagca atggtgagga acacagtttg | 900 |
| aaaaccatct agagggcagc cactttgacc ctgctgtctt ggctctaggg gtgcaggaga | 960 |
| gaaaggatct gggaataaag acttcatata tttacattat tatatatgta atatattctg | 1020 |
| tatacattat agatagtagg tagcatttaa tagtgtttac aatcataata taaatatatt | 1080 |
| acatattatt ttatttatga taatgttggc attacgtgtt actatataaa ggctttatat | 1140 |
| tactgtaacc ctctcagtcc ctttgaaagt agttaccact gtcatcatca tttcatgcat | 1200 |
| gtagaaactg aggctcccgc tgggcacggt ggctcacacc tgtaatccca gcactttggg | 1260 |
| aggccgaggc aggtggatta cctgaggtca ggagttcagg accagcctga ctaacatggt | 1320 |
| gaaacccccgt ctctactaaa aaaaaataca aaaattagcc gggcgtggtg gcaggcacct | 1380 |
| gtagtcccag ctattcagga ggctgaggca ggagaattgc ttgaacccag gaggcagagg | 1440 |
| ttgcagtgag ctgagatcgc gccattgcac ttcagcctgg gcaataagag cgaaactctg | 1500 |
| tctcaaaaaa aaaagaaaa aaagaaaaa aactgaggct ctgaaaagct acatcagttg | 1560 |
| gccaaggccc cccatctggt aactggtaag ccaggattca agcctaggtc tctgtgaccc | 1620 |
| caaatcttcc cttagtagta ataacactta gtcattggtt tgttggtgat caatactgat | 1680 |
| tgctaagatc atgaatttgg cattgaccgt gaccgagcac tgtgctgagc atctgtatat | 1740 |
| gttatgccat gtaattctca caaaaagcct agaaggctga tgctagcata gcacccattt | 1800 |
| taaagatgag aagactgagg gaatggttag agaggccaga agcagcacaa gcaggcactt | 1860 |
| gaatctgagt cccacagact tctcactcat gaccacatcc tatgccagct gccctgaagg | 1920 |
| tggctgcggg gcccctggca ttggggcagg aatccagtcc ctggtgcagc ccctttcct | 1980 |
| gctctccttc caggctcaag ggaaaaatcc atgagaccaa cctcacatat gaagacttcc | 2040 |
| cgacctccaa gtacacaggc cccctgcagt acaccatctg gaagtccctg ttccaggaca | 2100 |
| tccacccagg taaggcatgg gttatcatgg tccagagcta ggtggggcat gtcccagcac | 2160 |
| agcccagccc cctgtcctaa acacagcatg gggcagttgg ggtgaatgag cagagtgcct | 2220 |
| tgctgagcac ctagtgtgtt ccaggacctg tcctgggcac ctgcacaatc actcagctca | 2280 |
| gtggaccttc ataacacccc aggagatggc tgggcgtggt ggctcacacc tgtaatccca | 2340 |
| gcactttggg aggctgaggt gggtggatca tgaggtcagg agttcgagac cagcctggtc | 2400 |
| aacatggtga aaccctgtct ctattaaaaa tacaaaaatt agctgggcat ggtggcgtgc | 2460 |
| acctgtaatc ccagctactc gagaggctga ggcaggagaa ttgcttgaac ccaggaggca | 2520 |
| gaggttgcag tgagctgaga ctgagccact gcactccagc ctgggcaaca gagcaagact | 2580 |
| ccatctcgga aaaaaggaa gaaaaaaaa aaacatgaga taggttccat tagcaaaccc | 2640 |
| attctccaga tgaaatgact gaggcctgga cacttcatag actccttcta tacaacaggg | 2700 |
| tacataagag ttcacatcag gaactgttct aggtgctgga gataccatag taagcaaaac | 2760 |
| aggcaaaaat ccctgccctc acgcatctta catcctaggg tgtgagatag aaagtagaca | 2820 |
| aaagtaaatc agaaaaatac agagcatatt agatactgac aaagaataag gaaggggct | 2880 |

-continued

```
gggaaaggtg agacaggatg gagattttag acaggtggtc caggaaccag cccgcactga    2940
gaaggaagca ttagagtcaa gggctgaaga agagtgagcc acgtaggtat ctggaggaag    3000
agtgctcctg gcatggggac agcaagtgca aaggacctga ggcaggagca catctcactc    3060
tcaccagtct ccctctgttt cccaggcagg aagagcaagg aggttaacgt ggctggaggg    3120
agatgagtga gaaggagggt caaggtgaag agactgagaa ggtagcagtg ccagacacc     3180
acgagggtct gtaggccatt gtgagaactt tggattttat gctgagtgag atgagagcca    3240
gtggagggct tggagccatg aagtgacgtg aactggttta agttttttaa ggatcccttt    3300
ggctagtggg ttgagaatag accgaagggg gtgaaggatg ggggctggga aatgggttag    3360
gagaccactg cataatccag gcaagaggtg atgtgggcgt gaagcagggt ggtggtagtg    3420
gaggggtgg gaagggtgg gatttaggac atattttgta aggacagcca acaggatttg      3480
ctagcggatt agcaaatcca ggtgtgaaag aaagaagacg agggagatag taattatttc    3540
agccaaagtg actaaaagga tgaagttgta agcctgtaag gtttgtgatg ccaattagtt    3600
atctcagcac tgatgctgaa aaggcagtag ggatgacaag ccagcaatac aaaaggaagg    3660
tcagcaccag catcattagc atatggacag ctttttaatga gcctggacaa gatcacctag   3720
gaagtggggg cggatagaaa agacagaggg ctgccctaac atcaggagcc ccggaacact    3780
cctagaagtc agggacaaga gggggaccca gccaaggaga ccgagaagga gcagtcagag    3840
ggataggagg gcaacccagg tatgtcctgg aagcctggag gaagcgtttc caggagagag    3900
tggctaacag tgacaaaggc tgctgagcca agcatgggga aacccagaag agactattct    3960
ccagatttag caacagggaa gtcattggtg gccttgatga gagctggttg ggtggagcag    4020
tagggggccaa agcctggttg gagctggtcc aagagaggtg gaggcaatgc tttaaaggag    4080
ttttcaagcg aaggagagag agtgtggcag tgctgttttt tatgatagaa gaaatacagc    4140
atatctgtga gatgattgga aagatccagt agagggaca gaattaagga tgtaggagag     4200
gaagttgcag gagtgacagc cttgactgca gcccagcctt gactgcgatc tgctgcatgg    4260
ctgagagcca gcttctgctg ggagcccaga cagttcatct tcaggagccc agagaaagta    4320
gaataagtgg gcaccaaagc cagtggggca gtggtgggcg cttgggggat tctcttctga    4380
tggcttcacc tttctcagta aagcaggaag caagatcatc agcggagatg ggagcaaggg    4440
atgagaggtt tgcagataga gaagaaggtc tgaaacaggt ttctagtaga cttatcaggt    4500
gttgggactg ggaaatcagt gccttcccaa aatcacagat ccccccccaag ggcagattca   4560
aactgactgg cagcagagaa ccctgtgtgt tcctgagtca ggcacgatgt cctttagagg    4620
agagacctgg atagagaagt gaattctccc tgagaagtgg gaagtgttat tatcctcatt    4680
ttttcagaat aagtaacgga ggcacagagc tgttaggaac ttgtccttgg tcacgacttg    4740
gaaatgctac agccaggact taaacccccaa cgtcggcccc agagcctgtg cccttcctta   4800
cctactaagc tcactggcca ttctctgacc tcacacacac caggaaggag gctggggaga    4860
ccaaggctca gggagactca ctgactccct caggtcacac aggggtcaga gtttcttcca    4920
tctggctgga ttcattcttc tgttccacaa acatcaaaag tccctcaagg cacgttcaag    4980
agtcagggga ggccgggcat ggtggctcat gcctgttatt ccttcacttt gggaggcaag    5040
gcaggcggat cacttgaggt caggagttcg nnnnnnnnnn nnnnnnnnnn nnnnnnnnnn    5100
nnnnnnnnnn nnnnnnnnnn nnnnnnnnnn nnnnnnnnnn nnnnnnnnnn nnnnnnnnnn    5160
nnnnnnnnnn tggagtctcg ctctgtcgcc caggctggag tgcagtggcg cgatctcggc    5220
```

```
tcactgcaag gtctgcctcc cgggttcacg ccattctccc gcctcagcct cccgagtagc    5280
tgggactgca ggcacctgcc aagacgcctg gctaattttt tgtattttta gtagagacgg    5340
ggtttcaccg tgttagccag gatggtctcg atctcctgac ctcatgttct gcccgtcttg    5400
gcctcccaaa gtgctgggat tacaggcgtg aataccgcg cctggccact tttttttttt    5460
ggatacggag tttcgctctg tcaaccaggc tggagtgcag tggcgtgatc tcggctcact    5520
gcaacctctg cctcctgggt tcaggcgatt ttcctgcctc ggcctcccaa gtagctggga    5580
ttacaggcac acgccactgc acccagctaa ttttttgtatt tttagtagag acggtgtttc    5640
accatgttgg ccagggtggt cttgaactcc tgacctcgtg atccgcccac cttggcctcc    5700
caaagtgcta ggattacagg cgtgagccac cgcgcccagc ctcaaaaaaa acaaatttaa    5760
ttaagaaaaa aaaagatct aaagatggtt ccatatagct gagcaagata atggaagaga    5820
gaatgagaag ctggcaggcc ccagatccta cagggccttg aatgccaggc tgaggtgcct    5880
ggactgcctc tccgagctgt gacagacatg gagcaggtgg cagctgaggc tagaaggctc    5940
cccaggctcc ctgctccagg gctgtcctgg gtcagtgact ggggagggaa tcggagcctc    6000
ggatgcactt tgcctcccca gaacttagtc tcagcctccc aaagtgctgg cattacaggc    6060
gtgagccacc acacccggcc catctttaga tcttaaatga gccatattct ccctcatcta    6120
catgttttgt attctccctc atctacacgt ttgcacatgc cattcccttc ggctgcagcc    6180
ctctacacaa tccttagtct ttgatggcca actcttactc tccttggcat cttagtttat    6240
aaaaccttcc tctgagaagc cttcctggat ttctcaaggc aacctgggct tacatggtct    6300
cactgttttg tcattgtctg tgtggctgtc tcactcacta gactgtgaac tgtgagggtc    6360
aggggccagg tctgattcac tcccagcagc tagcacagca aatgtttgtc gataaatgca    6420
taacaaaatg aatggatcct agtctcagtt ctgtttctag aatagcgcct caataaaata    6480
ggtgcttagt aagtatttgc tgactgaaga aacttgctgc acagccttga acaagtcact    6540
gcctcctctg aacttcagtt tcttcctctg aaataggat gctagtgttc ccttctcaac    6600
tccctcataa gggagcaaag ggatgtggaa cttgccatca ccccagtgca gggtttctca    6660
accacagccc cattgacact ggaggctgga ccattccttg ttgcagggcc ccgctctgtg    6720
ctctgcagga tgtttagtgg catccctggc ctctatccat tagatgccag tagccagtag    6780
ccaccccact cagttgtaac aaccaaaaat gtctctggac tttgccagat gtccctggga    6840
agcaaaattg gcccagttga gaaccactgc tctagagaaa gctgcctgcc agagaggagc    6900
tgagggagga acagactgtg ctccaacatc ctgcccagag cagaggcccc tggggagttc    6960
agagagcagc agcctggttg gctgggcccc tttctttgtc tgtggggcct gtgaagtcag    7020
tctggctcct ctgccagcac caaagccctt tatgtccaga tgggaggggt gccccaggg    7080 acctagccca tggattctag cagcttcctg cctgcccctc ccctccagct caggcttcct    7140
attgggtcac ctgagaaccc catccagcac ctgtcactcc cctgctctgg cacttccacc    7200
ctcccccacc tcccacccct gtatcccacc cccagcctaa cattaggaag ctctcctcca    7260
actgtgacct tcttacctac ctggtctaaa tcccccaact cccaggcaca aactgcctcc    7320
tcagccaggc caggcagccc attgtcccaa ggacaccagg agcagcctgc cttgctcctg    7380
ccttctcccc atcctgggct gctctccccg cccctgcta atctgaatcc agtcattttg    7440
agtcccggca cattccttgc ctagctgtgt gacccagagc aatgcactcc cctctcagag    7500
ccccagtttc ctcatctgta aaacaaggat agttgcattt ctctcccagg gtagctatgc    7560
agattaaatt atttgtttgt aataatgatc ctgtaacact tagtaagtac ttgattcctg    7620
```

-continued

```
tctgtttatt gttattatca tcatgaatcg acagatggtc cccagtcttt ttttttttttt    7680
tttttctttt tgagacggag tttcgctctt gttgcccagg ctggagtgca atggcacaat    7740
cttggctcac cacaacctcc gcctcccaga ttcaagcgat tctcctgcct cagcctccca    7800
agtagctggg attacaggca tgtgccacca tgcgccgcta atttttttgta tttttagtag    7860
agacagggtt tctacatgtt ggccaggctg atctcgaact ccggacctca ggtgatccgc    7920
ctgcctcggc ctcccaaagt gctggaatta cgggcgtgag ccaccaagcc cagcctcccc    7980
agtcttgctg aacaggcttt ctggggccac atgctgggaa gagcatgatg tgaaaagacc    8040
tcagctgaag ttccaactct gcttcctctc caagtggcag cttgagcaag ccacttacct    8100
cagagttgtc tccttggagc ctcagtctcc tcttctgaaa aatggctaga acaatttgtg    8160
cccctgggtc tgtcgtggtg ctcccatgag ctagtgagtg tgagaatgtt tttgcacatg    8220
tctgccctgt acatctgagg gactgaggaa cctggttttt taaaggcctg gccagaggaa    8280
aacgcttaca gccagccttt catgttctgt caggcctctg catgttcgaa gcctctgttc    8340
ttgagaacaa agaaacacaa tccactcact gccaagcagc tgtgctgggc tgtgcccccgg   8400
gagggctttc tccgctgctt gggcagaatg tgattgctca gtggtggcca ggaaacatct    8460
cctgggacct ccacagtcca tgatccttcc tgaatgcctt tgacctcaag gtctcagaga    8520
tgcttaaatg aatggacaac acacctggag accagacggg ctgcctcagt gtctggcttg    8580
tttttataaa tcttggtgtc ccggggactta gaaatgagct ctgacctgta gaatagtgag    8640
cccccaggga ctgcgcttgt tttgctgggc ctgtcacctc ctgggatgaa gggacagatg    8700
gaggaactga cttctcagag ggggaagggg tgttgccatg cccttctag gtcccttct    8760
ggtctgaagg ttgttactcc tgttagccct agcctcgggg agggagcccc aggagccaag    8820
accctgtgtt aatgattcgt gcaaggcctt ggaggtggct tcagccaggg tgccacaccc    8880
tgccccagcc tcaccccttg gggtatagaa gtctcctaag agtcaggcca cccccgcc    8940
taagagagtg gcaggccctg cccctaggcc ggcccagtga gtggcaggcc ctgtacccat    9000
cctgtccctt gggcttcaag cagcacaggt ccgctcgcca gggctggcat tcactgggtc    9060
aggatttcct ccaatctgca ggcttatctt tgtctactgg tctcagaccc acggagagcc    9120
cccttgtctc cctcctaggg tgccctccca ctcatcagtg gcaccacaag tggctcacat    9180
tgtcctacat aagctacaag tctgaagctg agcccttata cctgcttgag ggtaccccccc   9240
gccccgcacc agtccttctg ccctgagcct cggttgctgc ctgttgctgg tctcaaatca    9300
cccaggcgcc ttagatatca tgcctaggtt cccccagcac tctgaactgc tgctgttcat    9360
gcctgggcac tgtgcatcgc tcttctgccc ctccgctgtc acacctgagt gtgatccaca    9420
tcccactgtc atagggggtgg cccacctatg tctgattagg ttcctcttct caatctagct    9480
cttcccccta ccacacactc ctcctacagc tccctcccac tcccacctcc cgaccccact    9540
gtgggaattg cccacattcc accaggcagg ggcccctgg ttctgacaag ctgcctgtgg     9600
ccagtcagac cacagggtga acatccagc caccaactca gtggccgtcc tctcttggtt     9660
ccccgtcttc tatgtccctg acagaggat tgtgtttcca ttgaccctc tattcacaag     9720
gctaattact tccatacagc cctctaagtc caaaggacag aaacaaagag ggtaaaatgc    9780
aaaactaaac ttactcctgg caaagatcat ggaaggaact tgatataggt cactggtcca    9840
gtgggtatat gaacgagggc acagttcagg gactggctgt agctccctgt tggggacagt    9900
cccccatcatt gaggcatctt atttctgcac atcagtgcag ccaacagagg caactgaagt    9960
```

-continued

```
agggagaatg ctccagccaa gcataaccat gtccccactt cgccagtaaa ggaaagagcc    10020
agagagctgg atgtccaaga ccccaaggaa cagaggcaat tccttcttcc cactttcct     10080
catctctgtc ttgctgttgc ctggaaatgg tcattcaggc taaggaaagc caatcccagt    10140
ttcctccttc tcctctggcc agttatcagc tccctcaggg agcagagagt aaacagaggt    10200
cttaacaagg gttcatgaaa ttttagtca gacctgctaa gccggtgtgg ccagcccaga     10260
gccaggtgat gcagcccatg ccacctgccc aacacaaaca tggccagttt aatttggtga    10320
gtctttccgg aaatgtgcca caagccaggc cctgggctgg gctctggaca cacaagggag    10380
agccccatta gacagtacac ggtccttgcc ctcttggtgc aaatggggaa ataggcaaa     10440
atgtgatcac agaagataat accccatgcc agtatcaggg cacaaataaa gctaaagaat    10500
ttcaggccag gtgcagtggc tcacacctat aatcccagca ctgtgagagg ctgaggcagc    10560
aggatcactt gaggccagga gttcgagacc agcctggcca acattgcgaa acctcatctc    10620
tatgaaaaat ttaaaaatta gctgcgcata gtgatgcatg cctatagtct cagctactca    10680
agaggctgaa gcaggaggat cacttaagcc taggagttgg aggctccaat gagctatgat    10740
gacactactg cactccagcc tgggtggcag agtgagaccc tgtctgtatt tttttttt     10800
aaaagaatcc agcacagtgg ctcatgcctg taatcccaga actttgggag gccgaggtgg    10860
gcagatcact tgaggccagg agttcaagac cagcctggcc aacatgacga aaccctgtct    10920
ctactaaaaa tacaaaaaat tagccaggcg tggtggcgcg tgcctataat cccaactact    10980
cgagaggctg aggcatgaga atcacttgaa cctgggaggt ggaggttgca gtgggccaag    11040
atcatgccac tgcattccct cctgggggat aaagcaagac tctgtctcca ataaataaat    11100
aagaaaaaga agaggcaaaa ggaatttcag aggacagaac gagcacatct gctgggtgac    11160
caggaaggct tcccaaaggg tgggccttttt gaatagagcc tctggggtg gttgcaacaa     11220
gcagagagga ggaggtggag ggaaccgtgt aagcagaggc tttggaccta agtgggtag     11280
ggggcagaag tgagaggttg gctgggagaa aggactggcg ctagattgca gacgaccttg    11340
gttagtcctg gctctgccaa tatttgcagg atgacctaag tttgtcatgt ctcccctctg    11400
ggtctcagtt tcctcatctg tcaaatggaa gagttggcct agaattcatg gtttcaatc     11460
ttttcagacc cattgtctac ttttcataac aaatcatgtg taatatctca agataaatat    11520
aaccttttta taatttcaag tgtaaccttt tcacaatttc aagtgttgtg tgtgtatatg    11580
tacatagata catactctga ctattaatat gaaggaaaat agaaggaaat tattaataat    11640
aaaatatttt gtatgtcaac atgtagatgc tcacccacaa tcacactaga aacctaaca    11700
aagcagccag gtcctctcgt cataggtaaa acaccatcct gcctcaaatg cctatacagg    11760
taggttgtct cagtcagtgg tgttgcccctt agggatgtat tttccaacaa agcaaacagt    11820
tcttagggaa gttccaaaca aaacaaatgc agccttccct tcatttacac agtggttgca    11880
ttctgaaata ttcagtatat attaaaactg caaaaaaat ttcatgttta tacatgaaat     11940
ggagttaggt tatagtttct tatccttata aaaagatttt ttcatccaca tgaatgtctg    12000
ctgggacacg tgaaaatcac tgggagtcgg ggaaggtgtg gggcagaact tccctttgca    12060
gaactgtcct gtccatttcg tggtctttag catccctgga tcccagctgt tgttaagaca    12120
acctgaacac actcaccaat ttccccattc cccctagggg gcagtagcaa ctggatcatc    12180
tggaagctcc cttccagctc taaaattccc caattctagg cctcattctg gttaattcaa    12240
caaacatttg ccagtgccca ctatgtgctc cgccctgggc atcaggcagt gaacaagcag    12300
ctgtagcccc tgctcccctg cagacaatat ctggaaggac cttaaccacc cccttccat    12360
```

```
tctacagagg aggaagatga ggcccagaga gggcagactt gtattcaagg tcacacagca   12420
ggtcagaggc ctcctgcgta ccaaccagaa ctctgccctc aggaaggcac tgcatggtgg   12480
gtccacagcc ttctccccac tcatcttctc tccctcctcc aaccccaca gtgccagccg   12540 ccctaaccct ggacccgggc acagcccacc agcgcctgat cctgtcggac gactgcacca   12600
ttgtggctta cggcaacttg cacccacagc cactgcagga ctcgccaaag cgcttcgatg   12660
tggaggtgtc ggtgctgggt tctgaagcct tcagtagtgg cgtccactac tgggaggtgg   12720
tggtggcgga gaagacccag tgggtgatcg gctggcaca cgaagccgca agccgcaagg   12780
gcagcatcca gatccagccc agccgcggct tctactgcat cgtgatgcac gatggcaacc   12840
agtacacgcg ctgcacggag ccctggacgc ggcttaacgt ccgggacaag cttgacaagg   12900
tgggtgtctt cctggactat gaccaaggct tgctcatctt ctacaatgct gatgacatgt   12960
cctggctcta caccttccgc gagaagttcc ctggcaagct ctgctcttac ttcagccctg   13020
gccagagcca cgccaatggc aagaacgttc agccgctgcg gatcaacacc gtccgcatct   13080
agtccaggca gaaggagacc acaacctcct gggaccactg ccacctgcaa gagccctgcc   13140
caggagatag aagacctgga ctccagccca ccgtggccac tggagacctc aggccagttg   13200
tttaccctcc agcctccagt ctgtaaaatg gaggttgcat tccctacttc ctaaactctc   13260
ttccagcatc gatgttctgt agctctgacc ttgataggga tacagctttg atccaaggat   13320
gtgacatggc ttctcctcag ggcaaccct gcccaaccct catccccatc ttctcagggg   13380 cagggggacta ccttccagtg tctccctcca gcccagccct gacctcagga agtgtcagag   13440
catggccagt agttggcagc ccgaaagaca cacagcaccc tcttatgtcc catggcctaa   13500
gacttacccc tgaccaagct agtgatgggc catttaccct tgaccccagt ccacagtggt   13560
cacaggtagt acctggtcct agggttgcct gagagccaac ctctcctgcc acccccacac   13620
caagaactat atggttccta cttctcccac tgatctgctg gtcagtgatg atgctgtggc   13680
ctgtggaagg cacctggtag ttgagtccac acattatagt catgtgccac caccttcctg   13740
cccacaggcc gagggacagg gtgagggtat acccaaagct gatgcagagc ccattagcct   13800
aaaagcaact gcaggacaag cctccctgga tgatcgaggt ccccagtagc tctgaacaag   13860
agtccagcca cccctcttca gccaggcctc tgtgacctgc tagggtgcag gaggcttcca   13920
gaagcagttg ttgtaattag gacccaagca ctgggagggg ctgttggcta gacccctttgt   13980 cagacttggc atctatctca gttaggatcc tgctgcagaa acaagagcc acttgtagct   14040 ggtttaatta gacaaggatt tactacctgg cccctggtgg cttgcaaaat tgttggaaga   14100
gctggagaag cagactctgc tgaatttcca ggaactccca cgccagatt catcatgtct   14160 gttgtgacca ggaaagctgc cccatctgc aggaagccac tatgccagaa agctgctgac   14220
tgcagaacta ggctccctct gccacggtcc gtgccagcca atagatgtcc tgaggcctgc   14280
ccctctccca cttcactcag ttcccaaatc taaatttta caagagattc tgtttgggg   14340 aacttaagtc agatccagaa ccttggctgc aagggagtct gggaaatgtc atttccctag   14400
aaggaagtta gggtgggtgg agcaagcccc acctgcgttt ttctgccaca gcatccaatc   14460
gtgaagaact cggagaggg tggagtccac atctagggtt gtcctgcccc ttggctctat   14520
ccctgcccag aggtgggaac tggaggagtg ggctgcaaga ctgagcctaa atgtctcccc   14580
ggccttgact tttctttcta gtcctggggc ctagattctg cacttgggt ctctgacaca   14640 acacaccatc ccaaagtagc cggaagagct aaacacaggg ggttcttaaa atggctgccc   14700
```

-continued

```
ccgccacccg ggcctccctt gggcaaaagg aattgtcagc cctacccaa cccttcaact    14760 accagaatct gggccacccc agcagtattt ttatttaaaa tgttgcccat tttatgagtt    14820
atgatcaatt tgtattaaat taaagttaca gatgtcagta gccagttcca ttcattttga    14880
caaacacaca ggcccaccca gctctgtccc aggcagtgca cacacatgag catagctaat    14940
ccacaaagca gcccggctgg gtaaatggta ttatgctcat tttacagagg aggaaaattg    15000
aggttcagag agaagccaag acttacctgg ggtcccatat cccatgctgg caagtgccac    15060
accacaaacc tgtccaaaaa cttaccagcc agggaaggct gtcagtcttt acctggagga    15120
gaggtggtgg tagtcttggg agcaggcagc aggcagctca tggggcagtg gcaagagcct    15180
ggtctcggga accacacaga cctcagctca atccaggct ccatcactgt gtgactttag    15240
aaaaatgacc accctctctg ggactcagtt ttcccacatg aagatgagg ataccaattt    15300 cacataattt attggtaagc tgtaaagtgc agtgcactta aggaggccct accctatccc    15360
cccagctgcc tcccagagtc agtgcctgga gctgtatggg tttcctgaac ctctgggctg    15420
gctctgaccc aagaagtctg tctttctcct tatgggctgt gacgggtatg gaaccaccta    15480
gaccaggacc atcctgaggt ccatcccacc tctgactgat gaggaagcat cctggctggg    15540
agttaggaca ggctctgcat gtggacacac aggctgtgca cacttaagtg gaaaagactg    15600
tcgactaaag aagaaatatc aagctttaa agaattaaag ttcactttac ttagaagtct    15660
tactgagtac tatagacagg cctagagccc agcagcggcc ctttagagag gttctatcag    15720
tcgggcccag gacagtattt tagcccactg cttatataca ggtggtggag gtttagtaca    15780
cgcaaaatca catcacactt gctcagaagt aacattaaag ccaccgggcg cagtggctca    15840
tgcctgtaat cccaacactt tgggaggcca aggcaggcgg atcacctgag gttgggagtt    15900
caaaaccgcc ctgaccaacg tggagaaacc ccgtctctac taaaaaatac aaaattagcc    15960
gggtgtggtg gcacatgcct gtaatcccag ctgctcggga ggctgaggca ggagaatctc    16020
ttgaacccgg gaggcggagg ttgcggtgag ctggagatcg cgccattgca ctccagcctg    16080
ggcaaagagc gaaactccgt ctcaaaaaaa aagaagtaa cattaaagcg gaatcatata    16140
tcaacgtttg catgtaagag tgtgtctggg ctatagatta cagaggcata atcatgaatg    16200
ccatcagaca ctatcttctg tacaggaaaa ggcaaggact aggttatttt atctttaag    16260 gaacgtagtg actcaggcaa gagacatggg ggccatgccc actattctgt cttgtctcca    16320
aagtatccct ccacagagcc gcacatggtc acagagtcag aggcttgtga aattatgctg    16380
gcaaacagaa atgagggaag tagcttcttc catttgctac tgtgtctccc aggccactgg    16440
gtgctctctg cagtgtgcaa gggagtacag caccctggg agcccaggac tggtgttggc    16500
tttctgttaa gtcattttca ccctaagcca ttcttggcct cctcacccac agaatgaggg    16560
aggttaggct gcaggccaca ggtggatctt catctacagc ctggagctgg ggagagggaa    16620
ccaccccagt cattgacttg cctgggtttc taggaagagg aatgagaacg aggatgggag    16680
aggggctgtt ggcaggggtg ggtggagagg tctctgattg tctgatggag agcagcccag    16740
ttcacaggga agtgactggg gtgattctga gactagagta tcccaagccc tcccccatcc    16800
tctcagatcc ctgtgactgc tctaaaacca cgccctctca ttttggctca gtggatctgt    16860 cttttgctcag ccttctccct ctgggtcgg agcaccccct ccatgcgcca ttccaccttc    16920
tccccactca gcctcagcag cagctccaag aaatgctggc cacttcccag gctttactca    16980
cagtttccac gtgtgtggaa gtaactatag aggccaaatt tgcattatca actgggact    17040 cctggaaatg ggggtgtctc caagagatat atttgataca cgtccagaga attcctgaag    17100
```

```
gaaagaatct ggggttgtca ggctgatatc atgaacccca catttaacac attaagtgaa    17160 gagagggggac aaaggccagg cttgggaagg aaggagggat caacaaagcc cttacccagg    17220
acagataaaa atgatagaat ggcagtaacc ccatttggag ccccccatttg tagtcagcaa    17280 gcaaagtact ggtccttttt acaccttatc taaccatcga gacacgcccc tgtggttggt    17340
atcattatct cagtgtttga gcagggaaac gtcacttccc agaggaccca cagccagtac    17400
tcggcagagc tggaaatcaa acccggtcca tccaaagcta aagccagatg tctctttact    17460
ggacctctct ggaaatgctt ctcaactttg atgatggctc cagtgacagg cagcagccac    17520
caggactgtg atctccctgg gatttaaagt gggaggttaa accaggctcc acgccactgc    17580
ggaattgtgc aattgtaagt caagtctcaa ttgtgagcca agcttctccc agggtcagag    17640
gtggagttag aaaggcccca tgtgaccctg agcaagtctc tctccttccc tggtcctcag    17700
tttccccatc tctattgggg aagggttagg tatctattct agttgattaa ttgccagggc    17760
ctgagctctg atggtccagg attctgtaag tctaacgtta ggtcccacgg cttgccctgc    17820
tcagcaccta ataaggccat tagctctggc tccttctctc tggggtggca gcagggacag    17880
aaaacaacag agatacattc tcttggcagc acagaactca gctcaagggt tctggggatg    17940
gggccttccc tcctgccagg gaggccatct cgagaggctg actgctcaca cctgggcagc    18000
actctgtctc ctcccctcct gcctgggtcc cagctctgtt caccacccca aagcacatca    18060
ccacaaggtc agttgcaaag gcccggtatc acaggcttaa atacagaggg ctaggaggga    18120
ggtgggaggt gggagaggaa ggtggagtac taacaaaggt gttgaattat cactgcccat    18180
caggacacgg ttatttcccc ttactctggg acaccaaaga ttctacacaa tcttcctata    18240
atcctgaacc acaaaggga ggcacagcct ccaaaaaaaa gtaggagagg ggaggggga    18300 agtacttta ttttgaaatg tgttcatttt tctttgtttt attttctatc ttgatgaaaa    18360
gaatatattt ttaaacctaa atacaaaata gtacagtttt ctatttttttt ttaagttcca    18420 ggatacatgt gcaggacgtg caggtttgtt acataggtaa atgtgtgcta tggtggtttg    18480
ctgcacctat caacctatca gaacagtttt ctatctgctt taaaaatttc aacagttcta    18540
tcatatttct attacaaaat gctccccccct cccttgaaat tagatgaaga gggggaaggg    18600
ttgacactgt ggaccagaga cccagggact tcctaccctg atgtcatgat aagggctggg    18660
gaagggcttt caggaagctg gcatcagagg cacaaagctt caggtcctgg tgagcttccc    18720
aaaactgtga gactagatgt gatcgaatct gaatgctgga agggtctgag tgatcctcca    18780
gtctaacctg aagcccagag agggttagtt tctagctcca catcacacag catatggtgg    18840
agctgagatg agtactcaag tgtcctggtt cccagtcagc acataggga gggagattga    18900 ctaactgaga gggcccagc ccaggcaaag aaaaggaaca caggccaggc tggaagggac    18960
agggccagag cttaggaggg aggtgctcag aggagaaggg tcccacatct aagaaggtct    19020
gcgggggtac aagagggcct atcagagttg ggggctgcag ctcctccgag aggagaagga    19080
gggggcaaaa gggtgatcaa atcaggaagt cctcccctggg gtgtgcatgc cagtcagcat    19140
cacgggcccc aacatggctg atgagagacc cctgatctca gccctgccat ttacatagaa    19200
gaaaactgag acacagatgc aaagacagca gcctgcaggg cacagtcagg gccagatcca    19260
agtctcctga ctccccagcc atcggctctt ttcatgcaaa cttcagtctc cctcttgtgg    19320
attctggtgt ctcctcctac cccctgggaa cctggagcct gagcagaagg agaagggag    19380 agaggagggt tccaacaacc ccaggcacca ggagctgggt gccttcctct gttgtcctct    19440
```

```
ccaaggagaa gagagagctg gcctggacct ccagggcaga gccacttcat acctgcccac    19500
acctggtcct cctttgctgg caacagagtt cagagctagc accagccaca gcaaggacaa    19560
agcccagccc aggcagctgc tggagctgca gggagtccca ggtaagtgaa agcattggga    19620
ctgatggccc aaggggggttc cctgatttca tggcactaga gaaagccctg ggatatcagg    19680
tggtttgaat gttttgaagt cttttttcccc agaaaagagg ctcttgcccc ctcactccct    19740
gcaggctgag ccctgtgcct gcttcctctg cttaccacat accgcaggtg caaaggccct    19800
ccctgaccaa gctgccagat ctgccaatca gaagcgaggt cctggggccc agcagcactg    19860
ttcttgccac tgggagaagg gagaagcaga tatgggacct gaaaggtcac caaaaaaagc    19920
agacaggctg gaggtttgtg cctctcacca gggtggggct gtgagtcgag acctgggtaa    19980
accccagctc cgtctctgac tcaccaatga ccctggacag ctccttcatc gccaccgtaa    20040
gcatccctgt tcctcatcgg ctgaacaaga gggacaggca aaggttctag cctgaggcag    20100
cttcctggag tttgtccatt ggtacccctc tctcccctct ttcctcttag gaccccctc     20160 tgccacactc ctggaaagtc cttccccact tctttcattc tccatcaaa atttaccctc     20220 cggtgttcct caggttaact ggcttactgt ttaagatgtc tccctgtcta caacctatgc    20280
acatttataa taggaaccac tcccggaaga gtagctgatg gtgggatctt agaaaccctg    20340
acaagcagca gaggaaagat tatggggagg atagaaagag ataggggact tctcatgaca    20400
ccatatggca gctctacagc agctgctggt ggctcctgtc tttccagctg atctgtccca    20460 ctcttgccccc catcctcagc actcagccct ccccaccagc agcccaatac aggctaatgg    20520
ccacgcacca cagcctttct gtttgcaggg gcttcctctg caggaggaaa caacctatg     20580 catataatgt tagaatcaga catgtggacc tttatgatcc cacgtggaga atgataagca    20640 tattttggc cttaatgaat ctgcttttgg agtactcttc cccctaccta atgcctcct     20700 tttccttact gttgaaatct tactcatcct tcatgtccca ctcaaggcag gctgtgtcag    20760
tcatccaggt ccaggagatt cactgaccct gggctttcca agaaggactc tgggtctccc    20820
actgccacta ggcatgagca tctcaagatg gggatcctgt cctatggttt tgcatgctgg    20880
gtgcagagag aatgtcagaa aatgttttct ggctgaaaag tagctaatgt caagctgtaa    20940
ttttgaaact accccatctc caagatggga gggaacttac agaccagaga taaccccctcc   21000 ctgatgatgc tgagcccccca gagcgaccct cactgatcat tcccccgaca cctagatttt    21060
gtgcagggag agccagggaa aagaggcaga gactaggaaa gttatttgtt tgcttttta     21120 acaaattata acataacttg tgctcatttt aaaaaatgaa aataaacaca gtagaaattc    21180
tcattctcct tcttcccccag tcccagaagt cagcagctat taacagtcag tgcgagtctt    21240
gcaggcattt ttgcttacac ataaacaaat gtcatttct tttacacaaa tatgatcatc    21300
tttcacatac tgtccatctt tctatgtgtt ctgtggtgta agtagaagcc caaccctttc    21360
ccctgccacc tccctggacc tcgggctcct caggctccta caaatgaaat tattggtcaa    21420
aagattttct catttaaaat gtgttgcttt cctgggtcgt tttatttcct tgtaacatgc    21480
tcattatgga aaatttggaa aatacacaag acacaaagga aaaaaatcat ccatcagcca    21540
ctgtccagag ataactgctg ctagcatttt gaggataagg tttacagtct ttcctttcct    21600 ttctttttt tttttttttt ttgttgttgt tgttgttgag acaggatctc gctctgtcac    21660
ccagactgga atgcagtggc acgatcacag tgcctcagcc tcccaactag ctaggactat    21720
tattgggcgt gctaatttaa aaagaaattt tgcagagaca gggtctcgct atgttgccta    21780
ggctcatctt gaactcctgg tctcaagcaa cctctccact cagcttctta aagtgttggg    21840
```

-continued

| | | | | |
|---|---|---|---|---|
| attacaggca | tgaaccactg | cacctagacc | agcctttttt | ctacgtgagt ctattctacg | 21900 |
| taaatcaaac | cactttgcct | attgttccat | aacctgtttt | tttccactta ataaaagatt | 21960 |
| gttattccat | gttagtctac | agcatcagtt | tagtatgctg | tgtgacctca gggccacctt | 22020 |
| agaagcctac | ttttcctaac | ccccattctg | agtagggaac | ctgccgcagc agatgcccag | 22080 |
| aacgctcttg | ctccagggtg | taacctctgc | ctactggctc | cctttcagga ataaaatgcc | 22140 |
| ctgagaagtc | cctgagcact | tgcctcctcc | acctcccctg | agctgaaatc ccagcacccc | 22200 |
| actgatggtt | atgcagtccc | cctgcaactt | ctccggcgcc | acctaccggt gcagtaagta | 22260 |
| gaagcccacc | cctttcccct | gccacctccc | tggaccctca | gctcctcggc tctgctgcca | 22320 |
| acccaagacc | caaggtgggg | aggatggagg | tgggggcctg | ggtggtcctg actgtgaggc | 22380 |
| aagggaagcc | ctctggactc | aagttgggca | agcgacagtg | cctcttgccc ttgtaccgtg | 22440 |
| gccagctttc | cctcagaatg | atgagactga | ggaagggaca | ggggcaggta ggtatcagag | 22500 |
| gtgggccaag | gagggtgctg | agccacttga | aagttttctg | gttcccaaag caaatacccca | 22560 |
| gcttcccagc | ccaagcccat | actctgccca | aggaatttac | tagccaaata gtgtggttaa | 22620 |
| gtgtgatgtt | gggcaagatc | cccctctgg | ggatctcagt | cttcttacca attatacaag | 22680 |
| gggaaatata | gccaggtggt | ttctaagcca | ccttcccagc | tctgaaactc taaaacccaa | 22740 |
| ctggaatcca | tgttttcaaa | tgctctgttt | tctctcaaag | tccctgtacg cctcatgatt | 22800 |
| agttgaatcc | aattatagac | caggtctggt | ttgaaatatc | attaacataa taattattat | 22860 |
| gggctgtcct | ctcatttaat | cctcacaaca | agcataagag | gagataccat ttttatcctc | 22920 |
| tttttactga | taagaacaca | aggtccagag | agttaagatg | actttctgct tacgtggcag | 22980 |
| agctcacatt | tgaacccagg | gctgtgtgac | tcccaaacct | gtgctcctta ttagcctcca | 23040 |
| gtccccatac | taccctgtga | tgggtgtagg | gatcattctt | cccttgctac agttaaggaa | 23100 |
| actgaggcca | aacagaagag | atgttttcct | cagggtcaca | tagcaagttc atggcacagc | 23160 |
| tgggtgaacc | caggctctgt | gtctcctggc | caaccgtcac | tcccccactc ccaacaagca | 23220 |
| ctggctgatt | ttcttttctt | tttttttttt | tggagactga | gtcttgctct gtcgcccagg | 23280 |
| ctggagtgca | gtgatgtgat | ctcagctcac | tgcaacctct | gcctcctggg ttcaagcaat | 23340 |
| tatcctgtct | cagcctccca | gcagctggg | actacaagca | cgcaccacca cgcccagcta | 23400 |
| atttttgtat | ttttagtaga | gacagggtnn | nnn | | 23433 |

<210> SEQ ID NO 8
<211> LENGTH: 30676
<212> TYPE: DNA
<213> ORGANISM: Human
<220> FEATURE:
<221> NAME/KEY: modified_base
<222> LOCATION: (6671)..(30676)
<223> OTHER INFORMATION: n = A or C or G or T/U

<400> SEQUENCE: 8

| | | | | |
|---|---|---|---|---|
| cagccgcgca | cccttcctc | gcgttaccct | ccttccggac | agcaccccct cccttctccg | 60 |
| gtagctccta | cccctgcctg | tgcgggcctc | gtccccgcgc | ccagccctcg gtgctgcctc | 120 |
| cgacagcgcc | gcgctctctc | agccgccccc | ctgcccctcg | gccccctct ctgctgcccc | 180 |
| tgggccatgg | gtgcagcctc | aaggacgagc | tgctgtgctc | catctgcctg agcatctacc | 240 |
| aggacccggt | gagcctgggc | tgcgagcatt | acttctgccg | ccgctgcatc acggagcact | 300 |
| gggtgcggca | ggaggcgcag | ggcgcgcgac | tgccccgagt | gccggcgcac gttcgccgag | 360 |

-continued

```
cccgcgctgg gcccagcctc aagctggcca acatcgtgga gcgctacagc tccttcccgc    420
tggacgccat cctcaacgcg cgccgccgcg cgaccctgcc aggcgcacga caaggtcaag    480
ctcttctgcc tcacggaccg cgcgcttctc tgcttcttct gcgacgagcc tgcactgcac    540
gagcagcatc aggtcaccgg catcgacgac gccttcgacg agctgcaggt gcgctacccg    600
gcctgcctgg ggaagggcg gggccgggct ggaggtgggg ccggcgggg ggtgggtgca    660 gggctggacc gcgggccagg cccagtcaga atggtcctgg ggcggggccg ccagcaaggt    720
cagggcccta tcaggagtaa cgcggggcag ggaggggcgg gcgcgcgcat ggcggggccg    780 tggggcggg gccttgggca gtccggaccc tgagggatct gagacagacc tggagtaccg    840
gctggtccgc ggttagggag aagtcgggga tgcggatggg atggcggaaa caagtgagat    900
cagaactgga ccagatactg gctgggca gggttgtgga cgaaccggaa tcagagttgg    960
gcaaaggcag ggccactgtc agactgaggg cgaggtcgcg aggatgggtc tgtattaaac    1020
cgggtagctg agctctggca ggctgggggt tctgtggggg cggagaccgg atcagatgtg    1080
catcaggact aagaggagta cgggggctag aatgtgctgg acaggtgagg gtgaaaccta    1140
atagagtggt ataagttagg gtgccaaagt gctgagaggg caggtttgag taccgagggt    1200
taggccaagg tgtatgaggg gttaagactg agatcaggtc cggatactct acaacaagtt    1260
tagatttaag ccagagtaga ggccaggttg agtggggcca ggacttaaag gtaaagatt   1320 ggagaataag gcccagatgt aaggtgattc aagaagggag gggctagacc tctaggagtc    1380
tctagaggtt tttgatgacc tctttggctc tgtcccccac atcaggactt ttgaagacta    1440
agtgaaacgg tacatgcaga gtgacctgag catagttggc atagaactct aatcggtctc    1500
ccttaagact tcctgtcttc actgacaaac tcctactcaa cttttattga gccttgctca    1560
aatatcctct ccgtgaagcc ttctccaagt tccactggtc aaacaaacaa acaaacaaac    1620
aaaaacatta gaactgcatt tccccaaatg ctctctatta ataagtgtgg gaaatatagt    1680
atatttttta tacccacccc cttggagaat tttcagtgtg catttgcata ttaaaagctt    1740
agagaaattt tgttgcaaat aaatctattt tactgtgttt aataaaatgg ttcccaagct    1800
tacttgggcc tggaatcctt ttttcaagct aaatcactta aatccagcag ccccatgtac    1860
ctggctttgg gatactagtc gagcacgtag ttctccaagg ccagagacag aatcttattt    1920
ctcctatcta tggccccaaa gcctggtgca aggcctggcc cacagtacac accaataaag    1980
gccaaatgaa tgaacgaaag aatgaccaac cctggcctaa gctggaccac actgtggagc    2040
gtttggaagc agaaggtttt tggctcaaac attttatgaa aatggagtgg gctaacttgg    2100
gaggtaatga gctctctggc ctcgagatac tcaaacagaa actaaataat tactttcccc    2160
tgtattgtag gggctcccaa cccctccaca cactagtctt tgagtaggcc tgcacccagc    2220
agatgcccat gggcctcagg agaaatggcc catgttcacc atcgctcctt ccctgtccct    2280
tttatctcaa aactacaact gactcccttc cagtctagct gtctgaggat gaaggcccca    2340
tcagagggtg agcaagggcc tgggcctctg ggagcctgca caaggcttgg ccctccaccc    2400
ccagagccat cgttttaggc gctgctgctg tccatctccc cgtctatgga gtcacataag    2460
caggaagagt ttgaggggac tctgtctgaa accatctgtc caacctcttc atcatgtagg    2520 aatgaaagt gaggcctgga gaagttatgt gacttgccca aggccacact tccagacagt    2580
gagagagcca gggctatagg gcacagcctg acccagatcc ctcttctctg atctctcccc    2640
tccttgtctg accttctagc ctctgcttca gagccttggt tctcctgtct gcaaaccagg    2700
aaatccaaat tactgtatgt tgggcttctg tactctatcc catgacctgg gggacacagg    2760
```

```
agaaattgaa catgtattac ctacaaatat tattgaaatg cttcattatt gggtgaaaag    2820
taaaacagga ctgccacttg cttactctct agtgcactgt tgtggggttg gacatacttg    2880
ggttccaaac ctgctgtggg cactgtgtgc accttggtga gtcacttcat gtaaacgctg    2940
atgctctgtc tgtacaatgg ggtcaggatg cttccttcct accaggactt ttgtgaagct    3000
gacctgggat taacctgcta tttgaggttc aaaggcacac agtacgggct ggaataacat    3060
acagcccacc tttctctttt ctgcctgtga gagctcatgt gcccagctga gtgaatgccc    3120
agactctcct ctctggcccg agaaggaggc cttgctttag tgtgtcctct gggcttggca    3180
atttggtggc agagaaatct gcctcccatc tagagaggat gtgctgctgg gtgagattca    3240
aggcaccctc caccccacct gcctctccct ccatatgggg aaggcaaggc ttattagcta    3300
tttatgcagc agaaataagg ctgaacccac cctcacatcc ccttctctcc cagcagctga    3360
tggagctggg gcccttctgc agaattacag actcagagcc atgcagatga tctggtgcca    3420
catccacttg acagatgggg aaacaggaga gggagaggga ggaagggaac ttgcctaagg    3480
cctcgaagcc agaggaagct gggcctatac tcagctggag tctcccaaca ccctacctag    3540
cagttggcgt gcagctttta catttattat aaatccttga ggcatcagag cagagaaatt    3600
aagagccctg ctttgtaccc aggtaatctc aatcctggct ctaccattta ctgtgtgact    3660
ttgggaagat tatttaccat ctctgagcct tgggtccttc atggacagca tggaagtaat    3720
tatattagga ttaaacaaga tgatgtttat aaaaacttag tactgcactt ggcacctaac    3780
agcactcaat aaatgacagc tatagtaggt tacatcgtac tcggcattat tgacatttgg    3840
ggctagataa ctgttgtgca gggccatctt gtgtgttata ggaagtctgg tagcattcct    3900
ggcctctacc cattagatgc cagtagcaaa ctccacccac cccgcaagtt gtgacaatca    3960
aaaccatctc caagcattga caaatgtctc ctagagtcaa aatcacctct agttgagaaa    4020
cctgacctag aaaagtccca ctgaacttta aaacttcagg tcaaatatca cctcctctgt    4080
gaagccttcc ctgacctact aagcacaatt gctttgtact ccagattaca tcacagggggt    4140 cagatcctga catgctgtgt gtccttggtc acgtcacttt gcttctctaa ggctccttct    4200
ctaaggttca tctataacaa gaggatatga tgttcctggg aaggatgttg taagggttag    4260
ggatccttta tcagaagtgc ctagtactgt gcctggcata gtaggcaccc caaaactatt    4320
tttaaatgtc tttattctga ttataaaatt aacataagaa gcagagctgt ataatgtaaa    4380
agttaaagtc cccccataat aatacccccat gaaacatggc aggagttact atacagttct    4440
aaggattttt atgtaacctg tgggtgtgca tgtgcgtgtg tgtgcatgcg tacatgcatg    4500
tgtgtgtgca tgtgtgtgca tttgtgcatg catgtgtgtg tgtgcatgtg tgtgtgtgtg    4560
cgtgtgtgtg tgcatgtgta tgtgtgttgg tgtcttcctc cccacctcca ctgctgagta    4620
cctggaccac tgagcaaagt ggagggaagg agcccatttc caaagagttc agggcttctc    4680
agccaatatt catcgagccc agtctgaatg cctgggactg cactaagggc ttttcttgca    4740
ttacctcatt taatcttcat agcacccctgt gggatgggta ttgttatcta tttcttctac    4800
tgatgaagaa acagactcag aggaattaag tgactcattt ggtcacgcag ctggtaaatg    4860
gcagggccag gattgaagc cagtctgact aggccacata ccgtccctga gctacctctg    4920
agggctgggt aattgtctcc cagccaccct gcctgtcctg tattgacagg gctaggccat    4980
ctgtgccagc tgacgcccg agggcaggtg gttgggacgt catcttggtc agagcagacg    5040
tggcatccgg ctctctggcc gtctcaggtt cctaaccccc agagagggga tccgattcag    5100
```

-continued

```
tctcagccgc cccctccagg cctcatgtga ccattggagc ccttcccaag gcttccttca   5160
tgccagagaa gacagcagtg gatcagcctt ggacgcaagc cctggtaggc agggtatggt   5220
gatccagtga caccaaggca gccacccaag gagggagggg gctgggggct aggttcaaat   5280
ttcggctctg gtttcttcca ggagaggggg tgacaccctc ttacccaatc tgagaaatgg   5340
aagtaagaac tagccctcct gctttctgta taaagagaga gaaagagttg ctaaatatcc   5400
aaagaaatga gagattcaga ggcactttat tttgtagcat ggacaggaag gcagctgggt   5460
tgtctgtgtt gtggggaagt ggctctgctg ttacttttcc aaggagaggg caggatttct   5520
atgccaacag cagcctctgt gagggcaaag ctggctgtgg gtcaaactca gagctggccg   5580
ctggcatctc cacatccctc ttcacaggtg tctgggcagc caggatacct ttgctgagca   5640
cgggccacag tgtagaagct tagggccaac attgggaccc ccaagatgtt tattttatag   5700
aaagaaaaaa gacctggtag ggactaacaa tgatgaaaca atgactctat aaaattatag   5760
cccaagtttt ggaggcacaa agtaagttat ggggcactta ctgtgtgcca ggtgctgtgt   5820
tataggcatt tgattctcac aaggattttt tcgttcccta ctccctgagt gggactgaga   5880
tcagtaccat ctcacagatg aagaaaatga ggctgagaga ttcagtaacc ttcccaagat   5940
cacactgcaa gtaggaggaa gagctgagat tcaaagtggt ctttctgact cagaattcac   6000
cctccttccc aacacgccaa ctgtcccagg gagcaccaaa tggggaggaa cctgagaaac   6060
catctggttg acacgctccc cattttgcag atggggaaac tgccttgccc agggttagac   6120
cagagctcag ctctcccgac tcagtccagt gttgttttcc cagtaccatt taccttcctg   6180
acctccatct ctgcttgaac actcagaggg atgaggcaga tttggaggtg agttctgtct   6240
tggattcagg gattccttta ataatttctg ggctgggcgc agtggcccac gcctgtaatc   6300
ccagcacttc aggaggccaa ggcaggcgga tcacctgagt ttgagatcag cctggccaac   6360
attatgaaac ccccatctct actaaaaata caaaaaaaaa aaaattagc tgggcattcg   6420 tggcacacac ctataatccc agctactcgg gaggctgagg cacgagaatc gcttgaaccg   6480
ggaggcagag gttgcagtga gctgagatta ttccactact ctccagcctg ggtgacagag   6540
tgagactcca tcttaaaaaa aatacatata catatacata aacatataca tatacatata   6600
catatacata catgtgtgtg tgcatatata tgtatatgtg tgtatatata tatatatata   6660
tatatacaca nnnnnnnnnn nnnnnnnnnn nnnnnnnnnn nnnnnnnnnn nnnnnnnnnn   6720
nnnnnnnnnn nnnnnnnnnn nnnnnnnnnn nnnnnnnnnn nnnnnnnnnn nnnnnnnnnn   6780
nnnnnnnaac aaggccagga tcactaacaa tgctctgctg agccacactg gaacctgaga   6840
caaaggaaaa atcagtgagg ctgattgtgt ttttatttaa aattttgata tcttgtgtgt   6900
tgtggatttg ttgttattca tcgcaggagt catcatggta gaaaacgtgt cacctggcat   6960
caagatcatg gtctccacaa ccaggctgtc cgggttccaa ttccttcttt accattatat   7020
gtttatctgt atgctatggg gccagtttct tgacctctct gtatcttttt ctccatcaga   7080
agatggagat aataattgtg cctcccttag ggttactgag aggcccaaat gatttaatat   7140
aagcaaagag ctaagaactg tgcccagccc actgtagccc tcgagaatg ttggcagcta   7200 gtctgtagca ttggactggt acagctttgg ttccttagag cagtggtccc caaccttttt   7260
agcaccaggg accagcttca tggaagacaa ttttccaca aaccgcaggg ggtgggggtg   7320
gggtgatggt ttcaggatga ttcaagcaca ttacatttat tgtgcacttt atttctatta   7380
ttatttcatt gtaatatata atggaataat tacacaactc aacatgatgt aggatcagtg   7440
ggagccctga gcttgttttt ccgcagctag acagtcccat ctgggggtga tggaagacag   7500
```

```
tgagtgatca tcaggcatta gattctcata aggagcaggc aacctagatc cctcccatgt    7560
gcagttcaca ctcctgtgag aatctaatgc caccactgat ccaacaggag gtggagtcag    7620
gtggtaatgc cagcgatgag gagcggctgc aaatacagat ggtttgcccc tccccaccac    7680
tgttcatctc ctgctgtgcg tccaggttcc taacaagcta tggaccaata cccacctgtg    7740 gcctggggt tggagacccc tgccttaatt ctaagcgggg atccaggcc aagtgtgggg    7800 agccagagag tgtgtatgtg gaagtcgatt gtcacagaag cctctagggt ggccaaagag    7860
gaggaggttg ttgcaaagat gcaggtgaaa gatacgacg ggttctgag gtgtttagga    7920 gacagactct acaggacttg ctggtggttg aactgtgacg ggaggcaagt gttggaggtt    7980
ggggacagag accaggctaa cccccagcgc ctggcagtgg tcaggctga atgcctgggc    8040 caggcatgcc cctgccccca tcccggccct gtgtgtgttt cagagggagc tgaaggacca    8100
acttcaggcc cttcaagaca gcgagcgcga acacaccgaa gcgctgcagc tgctcaagcg    8160
acaactggcg gagaccaagg tgagcctgcc cggggcgcgg aggtgttgcc ggcagagatg    8220
agggcagggc ttcgagggcg gggccagctg gggaagaggg cggggcctcg ggtgtgcggt    8280
ggaaacctgg cttcaaggag ccaaacctgg agtgagaagg gcagggtggg gaagagggta    8340
gggcatccgt gaagttcaat ggggcggcac ccaccccatc atgactggcg gcaaggatgt    8400
gggctggtcc ctcggttaag gacggggcca tttctccctt cccactttgg gtggaagttg    8460
aggcggtccc gggacctccg gaaacccct gcctcctgaa gggctgggga atgtgctcag    8520
tctctttctc ctctcccctt attaaaaccg cccaaccctg tgttgtgac acacacttgt    8580 agtcccagtc tcttcagagg ccgaggcaag atgatggctt gagcccagga gtttgagacc    8640
agcctggcca atataacgag atgccttctc tacaaaaaaa aaaaaaaaaa ttgaatatag    8700
ccaggcgtag tggcacatgc ctgtagtccc agctactctg gagactgaga cagatgggaa    8760
gattgcctga gcccaggagt ttgaggctgc agtaggccat gatcatgcca ctgcactcca    8820
gcctgggtga cagagtgata ccctgtctct aaaatgaatg aatgaatgaa tgaatgaata    8880
agcccattgc ctaggagtca atcctgagca tgtcccctcg aagccctcca gaggtggccc    8940
agccctggta tcatctcccc ttaagctcag gccatgggat acagactctg aaaggtaggg    9000
ccaaactctg cagtctctgg ctaccgtggt ttgggaaaca aacaaacaaa caaacaaaca    9060
gacttttcca ctgacttgag aaggacatgg gttctgatcc caccactaac tcactgtgtg    9120
actttgggta aattgcatgc tttcctgggt ccccagcctt cccatctgtc cagtggggac    9180
tgccaggctc agtccagcac tctgggactg gaaggtgccg ggtggagtcc ccactataca    9240
gagtgactct gtgtcgtgag gcctggggtg atttcaggct gaccccgctc tgtcagcagg    9300
agctgcggca gagccttagg aatgcgctgg gcctctggag gtcatcctgg ggcctgaaga    9360
caccattgga aacccagatc tatgcccag cttggccacc aacccactgt ggggtctcag    9420
gaaggtcatg acaaacaatt cttcacagaa cattccagag tgcctctggg caggaccctc    9480 ggggcaaca gatgataaac agtcacagga tgctggcctc attgcttctt gcagcctcag    9540
tttccccaac tgtctggtga ttctgtacct cttggatgat gagaagcaaa tggaagcctc    9600
tctctgtatg agagcggagt attatgggct gttccttctc cccagcagca ctctcttctc    9660
tccacatccc acacctctt tgtttttctc cactgacctc ttcctccccc gctttcctgt    9720
ccatctgtct gcctctgggg ggtcctgtgg ggccacatcc ccctcgagtt ccccagccc    9780 cacttcctgt ctggactggg gtgttatac aagaaatgcc tatggatgct ttggaggtca    9840
```

-continued

```
tatttcacct ggtgcctgac tcggctttcc tgtgcgcctg ccctccaat ggcctgcctg    9900 agggcctgtc tgatctccct cctcaggccc tctgttttcc ttggtcggcg cctggcgggg    9960
tgatgcattc ttggcagggt gttttctga aagggcccca gcacctccag gccctagggt   10020
gttccaaggg atgtggtggg ttggggtggg ggctgtttcc ccagccacag agctgaaagg   10080
agggggttgg ggaaagggtg actctgccct ggaaagaact agaataaatg gggtgcacca   10140
gttgagcaga acttttctct gtgctgagaa ttgtgttcct cttcattatc ctgccaacct   10200
cacagaatgt cacctccacg agagcaggat tccctaaaac ctagcacagt gtctggcaca   10260
caataagtag ttataaaaaa agtgattgaa aggaaaaaaa aatcggccag gcacagtcgt   10320
cacgcctgta atcctagcac tttgggaggc tgaggcgggc ggatcacctg aggtcaggag   10380
ttcaagacca gcctggccaa tatggtgaaa ccccgtctct actaaaaata caaaaactag   10440
ctgggcatgg tggtgggtgc ctgtaatccc agctactcaa gaggctgagg caggagaatt   10500
gcttgaaccc aggaggtgga ggttgtagtg agccaatatc gagccactgc accccagcct   10560
gggcaacaag agtgagactc catctcaaaa aaataaaaaa caacaaaaac aaaaaccaaa   10620
aaaacaggaa agaaaaaaaa tcgtcccagg taggaactgt tgttatctca atcttatcag   10680
tgaggcaact gaggcacaga gaggttgagg gaccaacctg aagtcccaca gctagaaaat   10740
ggcaacttgg gagcttacca tccagtcctg tcagagccca gtgcatagtg cagctgggat   10800
gtctcctggg gtgtcctgca agagctatgg ctttgtagtc agcaagccag gtaggtcagt   10860
aggactcatc gggaatgtac ttggggctcc aggggtggct gtcactctga tgttccactg   10920
ctggctgccc tgtccctgcc ttccccctt tccctcccat cctctctcgt ccttgagaca   10980
ttgaaacccc agcctggaaa gaagctggag cctgcaccca gctctacgga gcaatctcag   11040
acaagactct tccctccttc acccctcaag caactcctga ttgccagcct tgtaccaggc   11100
tctgggatgg gcacagggt gcagagccga gggagatgtc attcctaccc agcaggggcc   11160
cacttactag ccagggagac agaaaatgtg ggacaatgta ttaagactgt tgacaaaagg   11220
ctctgggaac atccaagtgc ctgaaagaga ggaaagttat ctctgaagag gtcactttca   11280
agctaggtct tgcaggatga gtaggagttt gccagttgaa tacaggggttt gggtagggtc   11340 attctaggca ggtggagttg caatgcagtg gcgctaggga ggtaagctag ggttaaattg   11400
agaaggtcct tgaatgccag actaaagagt tcagcatttt actatgtgtc aaggagctaa   11460
agaaggttcc taaactcagg atcatctgtg attcagttgg cactttagaa ggatcactct   11520
gacagtgagt ttgctggcaa agacaagagt tgacttgtag accaagtgag ttggaaagac   11580
ctgtgggacc ccagagggat gtgttgggga gactgttgga aaaatgggtg tggcactcag   11640
gagacaggca aggccatcta tatggacttg ggaaccatcc ttaaagcagt tcaagttgaa   11700
aatgggggca ggtgttcagg gtgaggatgg aaggcgctga cctggatgag ccccgaggaa   11760
catgggaggc agagaggcag cagtcacaga gatgggaggc aaagcagaac tttcaactag   11820
gagagggtgg cgagtgggct aagtgctgca gagtggtcta ggaggagcca gaggagtagc   11880
tgcggagtct gggcgcctgt ggagggcagc tccaggtggt gcaggacga cggacccccat   11940 cttccccatc agcaacatgc cgctgcagag gcctccaccc atcctccggg tgaggggct   12000 caggaaggcc acggcagcct ggccgtgcat ccccagactc tcgnnnnnnn nnnnnnnnn   12060 nnnnnnnnnn nnnnnnnnnn nnnnnnnnnn nnnnnnnnnn nnnnnnnnnn nnnnnnnnnn   12120
nnnnnnnnnn nnnnnnnnnn nnnnnnnnnn nnnnnnnnnn nnnnnnnnct tattagaatt   12180
gcagtcttca ataaccaggc tctttctctg cgccttggag tgcgcacaac aacaccccct   12240
```

```
catttcatct tcaccacaat cctacaatgc agttttgtt actcctttca cagataagaa    12300
aactaaggtt cacagctctt aggcaactga cgttgccata gctagagacc cagagctaga    12360
gtccttacgc agactgtcag gcaccaaacc tgtgccctc actacttcac ccttcctgag    12420
cctcacagtg cccttggggg cagagaaaac catgaaagtt catgcttacc tccctgatcc    12480
tgtctataaa caccagtcct tgctccttag ccagagggtc ctagaggtaa caggagacag    12540
cgagtaacca ccaaggtttt ctcaatacgt tgcaatttac aaagctcttt gatgtctgtg    12600
atcttgtcat ctttccttga ccccctgaa tgagccccat gaatgatttt tttaaaataa    12660
agacttcagc cgggcacgat ggctcacgcc tgtaatccca gcactttggg aggccaaggt    12720
gggcagatca cctaacgtca ggtgtttgag accagcctgg ccaacatggt gaaaccccat    12780
ctctactaaa aatacaaaaa ttatccgggc atagtggcgg gctcctgtaa tcccagctac    12840
tagggaggct gaggctggag aatcgcctga acccaggagg tggaggttgc aatgatccga    12900
gatcgtgcca tcacactcca gcctgggtga caggagcaaa actccatctc aaaaaactaa    12960
taataataaa agcaaaaaaa ataaagactt cactatgtcc ttgagagaac atcttcaccc    13020
tgtcccctag ccctcactcc agctccctca tccctcctac ccccaagcca gaaacctggg    13080
cattatcccc agctccttc tcttctgtac ccctctagcc aacacagcag ggtcaaagag    13140
gctgccctct agatgtttct caaaccgtgt tcctcaccat tgctgctgct cctctagttc    13200
aggcctcatt ttctcacctg ggccatttca ttagctattt aatggaccac atagaacatg    13260
cccatccttt cctaccacca tgcttttgca tgtgacattt cccccaccac gcgtgccctt    13320
tcccacccct tcctctctgt gtgtcaaggc tctcgatttc ctcctctcac ccagagatca    13380
ccccatctgc tcccccagcc ataaccctg acgactgtcc cccacagtct tccaccaaga    13440
gcctgcggac cactatcggc gaggccttcg agcggctgca ccggctgctg cgtgaacgcc    13500
agaaggccat gctagaggag ctggaggcgg acacggcccg cacgctgacc gacatcgagc    13560
agaaagtcca gcgctacagc cagcagctgc gcaaggtcca ggagggagcc cagatcctgc    13620
aggagcggct ggctgaaacc gaccggcaca ccttcctggc tggggtggcc tcactgtccg    13680
agcggtaagt gccaccacgg ggccctcccc ggctgaccat cccctcctcg acccatgctg    13740
ggcagtggga gtggaggcag atgggatcct tagcagagaa ttctttcatt caaatcttca    13800
tcaaacattt acgggacatc tgctatgggt aggagcatga agccttgagt atgaagccag    13860
tgaggcttga actagaggag cagcagcaat ggtgaggaac acagtctgaa aaccgcctag    13920
agggcagcca ccccgaccct tgttgtcttgg ctctagggt gcaggagaga aaggatctgg    13980
gaataaagac cacataaatt tacttttta tatatgtaat atattctgta tacattatag    14040
atagtaggta gcatttaata gtgtttacaa tcataatata aatatatggg gatcctccan    14100
nnnnnnnnnn nnnnnnnnnn nnnnnnnnnn nnnnnnnnnn nnnnnnnnnn nnnnnnttta    14160
tgataatgtt ggcattacgt gttactatat aaaggcttta tattactgta accctctcag    14220 tcccttgaa agtagttacc actgtcatca tcatttcatg catgtagaaa ctgaggctcc    14280
tgctgggcac ggtggctcac acctgtaatc ccagcacttt gggaggccga ggcaggtgga    14340
ttacctgagg tcaggagttc aggaccagcc tgactaacat ggtgaaaccc cgtctctact    14400
aaaaaaaaat acaaaaatta gccgggcgtg gtggcaggca cctgtagtcc cagctattca    14460
ggaggctgag gcaggagaat tgcttgaacc caggaggcag aggttgcagt gagctgagat    14520
cgcgccattg cacttcagcc tgggcaataa gagcgaaact ctgtctcaaa aaaaaaaga    14580
```

```
aaaaaaagaa aaaaactgag gctctgaaaa gctacatcag ttggccaagg ccccccatct    14640
ggtaactggt aagccaggat tcaagcctag gtctctgtga ccccaaatct tcccttagta    14700
gtaataacac ttagtcattg gtttgttggt gatcaatact gattgctaag atcatgaatt    14760
tggcattgac cgtgaccgag cactgtgctg agcatctgta tatgttatgc catgtaattc    14820
tcacaaaaag cctagaaggt gnatgctagc atagcaccca ttttaaagat gagaagactg    14880
agggaatggt tagagaggcc agaagcagca caagcaggca cttgaatctg agtcccacag    14940
acttctcact catgaccaca tcctatgcca gctgccctga aggtggctgc ggggcccctg    15000
gcattgggc aggaatccag tccctggtgc agcccccttt cctgctctcc ttccaggctc     15060
aagggaaaaa tccatgagac caacctcaca tatgaagact tcccgacctc caagtacaca    15120
ggcccctgc agtacaccat ctggaagtcc ctgttccagg acatccaccc aggtaaggca     15180
tgggttatca tggtccagag ctaggtgggg catgtcccag cacagcccag cccctgtcc     15240
taaacacagc atgggggcagt tggggtgaat gagcagagtg ccttgctgag cacctagtgt   15300
gttccaggac ctgtcctggg cacctgcaca atcactcagc tcagtggacc ttcataacac    15360
cccaggagat ggctgggcgt ggtggctcac acctgtaatc ccagcacttt gggaggctga    15420
ggtgggtgga tcatgaggtc aggagttcga gaccagcctg gtcaacatgg tgaaaccctg    15480
tctctattaa aaatacaaaa attagctggg catggtggcg tgcacctgta atcccagcta    15540
ctcgagaggc tgaggcagga gaattgcttg aacccaggag gcagaggttg cagtgagctg    15600
agactgagcc actgcactcc agcctgggca acagagcaag actccatctc ggaaaaaaag    15660
gaagaaaaaa aaaaacatg agataggttc cattagcaaa cccattctcc agatgaaatg     15720
actgaggcct ggacacttca tagactcctt ctatacaaca gggtacataa gagttcacat    15780
caggaactgt tctaggtgct ggagatacca tagtaagcaa aacaggcaaa aatccctgcc    15840
ctcacgcatc ttacatccta gggtgtgaga tagaaagtag acaaaagtaa atcagaaaaa    15900
tacagagcat attagatact gacaaagaat aaggaagggg gctgggaaag gtgagacagg    15960
atggagattt tagacaggtg gtccaggaac cagcccgcac tgagaaggaa gcattagagt    16020
caagggctga agaagagtga gccacgtagg tatctggagg aagagtgctc ctggcatggg    16080
gacagcaagt gcaaaggacc tgaggcagga gcacatctca ctctcaccag tctccctctg    16140
tttcccaggc aggaagagca aggaggttaa cgtggctgga gggagatgag tgagaaggag    16200
ggtcaaggtg aagagactga gaaggtagca gtgccagac accacgaggg tctgtaggcc     16260
attgtgagaa cttttggattt tatgctgagt gagatgagag ccagtggagg gcttggagcc    16320
atgaagtgac gtgaactggt ttaagttttt taaggatccc tttggctagt gggttgagaa    16380
tagaccgaag ggggtgaagg atggggggctg ggaaatgggt taggagacca ctgcataatc   16440
caggcaagag gtgatgtggg cgtgaagcag ggtggtggta gtggagggggg tgggaagggg   16500
tgggatttag gacatatttt gtaaggacag ccaacaggat ttgctagcgg attagcaaat    16560
ccaggtgtga aagaaagaag acgagggaga tagtaattat ttcagccaaa gtgactaaaa    16620
ggatgaagtt gtaagcctgt aaggtttgtg atgccaatta gttatctcag cactgatgct    16680
gaaaaggcag tagggatgac aagccagcaa tacaaaagga aggtcagcac cagcatcatt    16740
agcatatgga cagcttttaa tgagcctgga caagatcacc taggaagtgg gggcggatag    16800
aaaagacaga gggctgccct aacatcagga gccccggaac actcctagaa gtcagggaca    16860
agaggggacc cagccaagga gaccgagaag gagcagtcag agggataagga gtgcaaccca   16920
ggtatgtcct ggaagcctgg aggaagcatt tccaggagag agtggctaac agtgacaaag    16980
```

```
gctgctgagc caagcatggg agaacccaga agagactatt ctccagattt agcaacaggg    17040
aagtcattgg tggccttgat gagagctggt tgggtggagc agtaggggcc aaagcctggt    17100
tggagctggt ccaagagagg tggaggcaat gctttaaagg agttttcaag cgaaggagag    17160
agagtgtggc agtgctgttt tttatgatag aagaaataca gcatatctgt gagatgattg    17220
gaaagatcca gtagagggga cagaattaag gatgtaggag aggaagttgc aggagtgaca    17280
gtcttgactg cagcccagcc ttgactgcga tctgctgcat ggctgagagc cagcttctgc    17340
tgggagccca gacagttcat cttcaggagc ccagagaaag tagaataagt gggcaccaaa    17400
gccagtgggg cagtggtggg cgcttggggg attctcttct gatggcttca cctttctcag    17460
taaagcagga agcaagatca tcagcggaga tgggagcaag ggatgagagg tttgcagata    17520
gagaagaagg tctgaaacag gtttctagta gacttatcag gtgttgggac tgggaaatca    17580
gtgccttccc aaaatcacag atccccccca agggcagatt caaactgact ggcagcagag    17640
aaccctgtgt gttcctgagt caggcacgat gtcctttaga ggagagacct ggatagagaa    17700
gtgaattctc cctgagaagt gggaagtgtt attatcctca ttttttcaga ataagtaacg    17760
gaggcacaga gctgttagga acttgtcctt ggtcacgact tggaaatgct acagccagga    17820
cttaaacccc aacgtcgggc cccagagcct gtgcccttcc ttacctacta agctcactgg    17880
ccattctctg acctcacaca caccaggaag gaggctgggg agaccaaggc tcaggagac    17940
tcactgactc cctcaggtca cacagggtc agagtttctt ccatctggct ggattcattc    18000
ttctgttcca caaacatcaa aagtccctca aggcacgttc aagagtcagg ggaggccggg    18060
catggtggct catgcctgta attccagcac tttgggaggc aaggcaggcg gatcacttga    18120
ggtcaggagt tcgagaccag cctggccaac atggtgaaac cccgtctcta ctaaaaatac    18180
aaaaattagc caggcatggt ggtacacgcc tgtaatccca attactcggg aggctgaggt    18240
gggagaatgg cttgaaccca ggcggtgaag gctgcaatga ccgagatcg cgccactgca    18300
nnnnnnnnnn nnnnnnnnnn nnnnnnnnnn nnnnnnnnnn nnnnnnnnnn nnnnnnnnnn    18360
nnnnnnnnnn nnnnnnnnnn nnnnnnnnnn nnnnnnnnnn nnnnnnnnnn nnnnnnnnnn    18420
nnnnnnnnnn nnnnnnnnnn nnnnnnnnnn nnnnnnnnnn nnnnnnnnnn nnnnnnnnnn    18480
nnnnnnnnnn nnnnnnnnnn nnnnnnnnnn nnntgtttat tgttattatc atcatgaatc    18540
gacagatggt ccccagtctt tttttttttt ttttttcttt ttgagacgga gtttcactct    18600
tgttgcccag gctggagtgc aatggcacaa tcttggctca ccacaacctc cgcctcccag    18660
attcaagcga ttctcctgcc tcagcctccc aagtagctgg gattacaggc atgtgccacc    18720
atgcgccgct aattttttgt attttttagta gagacagggt ttctacatgt tggccaggct    18780
gatctcgaac tccggacctc aggtgatccg cctgcctcgg cctcccaaag tgctggaatt    18840
acgggcgtga gccaccaagc ccagcctccc cagtcttgct gaacaggctt ctgggccca    18900
catgctggga agagcatgat gtgaaaagac ctcagctgaa gttccaactc tgcttcctct    18960
ccaagtggca gcttgagcaa gccacttacc tcagagttgt ctccttggag cctcagtctc    19020
ctcttctgaa aaatggctag aacaatttgt gcccctgggt ctgtcgtggt gctcccatga    19080
gctagtgagt gtgagaatgt ttttgcacat gtctgccctg tacatctgag ggactgagga    19140
acctggtttt ttaaaggcct ggccagagga aaacgcttac agccagcctt tcatgttctg    19200
tcaggcctct gcatgttcga agcctctgtt cttgagaaca aagaaacaca atccactcac    19260
tgccaagcag ctgtgctggg ctgtgcccgg gagggctttc tccgctgctt gggcagaatg    19320
```

```
tgattgctca gtggtggccg ggaaacatct cctgggacct ccacagtcca tgatccttcc   19380
tgaatgcctt tgacctcaag gtctcagaga tgcttaaatg aatggacaac acacctggag   19440
accagacggg ctgcctcagt gtctggcttg tttttataaa tcttggtgtc ccgggactta   19500
gaaatgagct ctgacctgta aatagtgag ccccagggga ctgcgcttgt tttgctgggc   19560
ctgtcacctc ctggggatga gggacagatg gaggaactga cttctcagag ggggaagggg   19620
tgttgccatg ccccttctag gtccctttct ggtctgaagg ttgttactcc tgttagccct   19680
agcctcgggg agggagcccc aggagccaag accctgtgtt aatgattcgt gcaaggcctt   19740
ggaggtggct tcagcagagg tgccacaccc tgccccagcc tcacccttg ggtgatagaa    19800 gtctcctaag agtcaggcca caccccgcc taagagagtg gcaggcccct gccctaggc     19860 cggcccagtg agtggcaggc cctgtaccca tcctgtcccc tgggcttcaa gcagcacagg   19920
tccgctcgcc agggctggca ttcactgggt caggatttcc tccaatctgc aggcttatct   19980
ttgtctactg gtctcagacc cacggagagc cccttgtct ccctcctagg gtgccctccc    20040
actcatcagt ggcaccacaa gtggctcaca ttgtcctaca taagctacaa gtctgaagct   20100
gagcccttat acctgcttga gggtatcccc cgccccgcac cagtctttct gccgtgagcc   20160
tcggttgctg cctgttgctg gtctcaaatc acccaggcgc cttagatatc atgcctaggt   20220
tcccccagca ctctgaactg ctgctgttca tgcctgggca ctgtgcatcg ctcttctgcc   20280
cctccactgt cacacctgag tgtgatccac atcccactgt catagggtgg cccacctatg   20340
tctgattagg ttcctcttct caatctagct cttcccccta ccacacactc ctcctacagc   20400
tccctcccac tcccacctcc cgaccccact gtgggaattg cccacattcc accaggncag   20460 gggcccctg gttctgacaa gctgcctgtg gccagtcaga ccacagggtg aaacatccag    20520
ccaccaactc agtggccgtc ctctcttggt tccccgtctt ctatgtccct ggacagagga   20580 ttgtgttcc attgacccct ctattcacaa ggctaattac ttccatacag ccctctaagt    20640
ccaaaggaca gaaacaaaga gggtaaaatg caaaactaaa cttactcctg gcaaagatca   20700
tggaaggaac ttgatatagg tcactggtcc agtgggtata tgaacagagg cacagttcag   20760
ggactggctg tagctccctg ttggggacag tccccatcat tgaggcatct tatttctgca   20820
catcagtgca gccaacagag gcaactgaag tagggagaat gctccagcca agcataacca   20880
tgtccccact tcgccagtaa aggaaagagc cagagagctg gatgtccaag accccaagga   20940
acagaggcaa ttccttcttc ccacttttcc tcatctctgt cttgctgttg cctggaaatg   21000
gtcattcagg ctaaggaaag ccaatcccag tttcctcctt ctcctctggc cagttatcag   21060
ctccctcagg gagcagagag taaacagagg tcttaacaag ggttcatgaa attttagtc    21120 agacctgcta agccggtgtg ccagcccag agccaggtga tgcagcccat gccacctgcc    21180
caacacaaac atggccagtt taatttggtg agtctttccg gaaatgtgcc acaagccagg   21240
ccctgggctg ggctctggac acacaaggga gagccccatt agacagtaca cggtccttgc   21300
cctcttggtg caaatgggga aatagggcaa aatgtgatca cagaagataa taccccacgc   21360
cagtatcagg gcacaaataa agctaaagaa tttcaggcca ggtgcagtgg ctcacaccta   21420
taatcccagc actgtgagag gctgaggcag caggatcact tgaggccagg agttcgagac   21480
cagcctggcc aacattgcga aacctcatct ctatgaaaaa tttaaaaatt agctgcgcat   21540
agtgatgcat gcctatagtc tcagctactc aagaggctga agcaggagga tcacttaagc   21600
ctaggagttg gaggctccaa tgagctatga tgacactact gcactccagc ctgggtggca   21660
gagtgagacc ctgtctgtat ttttttttt taaaagaatc cagcacagtg gctcatgcct   21720
```

```
gtaatcccag aactttggga ggccgaggtg ggcagatcac ttgaggccag gagttcaaga   21780
ccagcctggc caacatgacg aaaccctgtc tctactaaaa atacaaaaaa ttagccaggc   21840
gtggtggcgc gtgcctataa tcccaactac tcgagaggct gaggcatgag aatcacttga   21900
acctgggagg tggaggttgc agtgggccaa gatcatgcca ctgcattccc gcctggggga   21960
taaagcaaga ctctgtctcc aataaataaa taagaaaaag aagaggcaaa aggaatttca   22020
gaggacagaa cgagcacatc tgctgggtga ccaggaaggc ttcccaaagg gtgggccttt   22080
tgaattgagc ctctgggggt ggttgcaaca agcagagagg aggaggtgga gggaaccgtg   22140
taagcagagg ctttggacct aagtgggggta gggggcagaa gtgagaggtt ggctgggaga   22200
aaggactggc gctagattgc agacgacctt ggttagtcct ggctctgcca atatttgcag   22260
gatgacctaa gtttgtcatg tctcccctct gggtctcagt ttcctcatct gtcaaatgga   22320
agagttggcc tagaattcat ggttttcaat cttttcagac ccattgtcta cttttcataa   22380
caaatcatgt gtaatatctc aaagataata taacctttt ataatttcaa gtgtaacctt   22440
ttcacaattt caagtgttgt gtgtgtatat gtacatagat acatactctg actattaata   22500
tgaaggaaaa tagaaggaaa ttattaataa taaaatattt tgtatgtcaa catgtagatg   22560
ctcacccaca atcacactag aaaacctaac aaagcagcca ggtcctctcg tcataggtaa   22620
aacaccatcc tgcctcaaat gcctatacag gtaggttgtc tcagtcagtg gtgttgccct   22680
tagggatgta ttttccaaca aagcaaacag ttcttaggga agttccaaac aaaacaaatg   22740
cagccttccc ttcatttaca cagtggttgc attctgaaat attcagtata tattaaaact   22800
gcaaaaaaaa tttcatgttt atacatgaaa tggagttagg ttatagtttc ttatccttat   22860 aaaaagatt tttcatccac atgaatgtct gctgggacac gtgaaaatca ctgggagtcg   22920
gggaaggtgt ggggcagaac ttccctttgc agaactgtcc tgtccatttc gtggtcttta   22980
gcatccctgg atcccagctg ttgttaagac aacctgaaca cactcaccaa tttcccatt   23040 cccctaggg ggcagtagca actggatcat ctggaagctc ccttccagct ctaaaattcc   23100
ccaattctag gcctcattct ggttaattca acaaacattt gccagtgccc actatgtgct   23160 ccgcctggg catcaggcag tgaacaagca gctgtagccc ctgctcccct gcagacaata   23220
tctggaagga ccttaaccac caccctccca ttctacagag gaggaagatg aggcccagag   23280
agggcagact tgtattcaag gtcacacagc aggtcagagg cctcctgcgt accaaccaga   23340
actctgccct caggaaggca ctgcatggtg ggtccacagc cttctcccca ctcatcttct   23400
ctccctcctc caacccccac agtgccagcc gccctaaccc tggacccggg cacagcccac   23460
cagcgcctga tcctgtcgga cgactgcacc attgtggctt acggcaactt gcacccacag   23520
ccactgcagg actcgccaaa gcgcttcgat gtggaggtgt cggtgctggg ttctgaagcc   23580
ttcagtagtg gcgtccacta ctgggaggtg gtggtggcgg agaagaccca gtgggtgatc   23640
gggctggcac acgaagccgc aagccgcaag gcagcatcca gatccagccc agccgcggct   23700
tctactgcat cgtgatgcac gatggcaacc agtacagcgc ctgcacggag ccctggacgc   23760
ggcttaacgt ccgggacaag cttgacaagg tgggtgtctt cctggactat gaccaaggct   23820
tgctcatctt ctacaatgct gatgacatgt cctggctcta caccttccgc gagaagttcc   23880
ctggcaagct ctgctcttac ttcagccctg gccagagcca cgccaatggc aagaacgttc   23940
agccgctgcg gatcaacacc gtccgcatct agtccaggca gaaggagacc acaacctcct   24000
gggaccactg ccacctgcaa gagccctgcc caggagatag aagacctgga ctccagccca   24060
```

-continued

```
ccgtggccac tggagacctc aggccagttg tttaccctcc agcctccagt ctgtaaaatg   24120
gaggttgcat tccctacttc ctaaactctc ttccagcatc gatgttctgt agctctgacc   24180
ttgatgggga tacagctttg atccaaggat gtgacatggc ttctcctcag ggcaacccct   24240
gcccaaccct catcccatc ttctcagggg caggggacta ccttccagtg tctccctcca    24300
gcccagccct gacctcagga agtgtcagag catggccagt agttggcagc ccgaaagaca   24360
cacagcaccc tcttatgtcc catggcctaa gacttacccc tgaccaagct agtgatgggc   24420
catttaccct tgaccccagt ccacagtggt cacaggtagt acctggtcct agggttgcct   24480
gagagccaac ctctcctgcc accccacac caagaactat atggttccta cttctcccac    24540
tgatctgctg gtcagtgatg atgctgtggc ctgtggaagg cacctggtag ttgagtccac   24600
acattatagt catgtgccac caccttcctg cccacaggcc gagggacagg gtgagggtat   24660
acccaaagct gatgcagagc ccattagcct aaaagcaact gcaggacaag cctccctgga   24720
tgatcgaggt ccccagtagc tctgaacaag agtccagcca accctcttca gccaggcctc   24780
tgtgacctgc tagggtgcag gaggcttcca gaagcagttg ttgtaattag gacccaagca   24840
ctgggagggg ctgttggctg gaccccttgt cagacttggc atctatctca gttaggatcc   24900
tgctgcagaa aacaagagcc acttgtagct ggtttaatta gacaaggatt tactacctgg   24960
cccctggtgg cttgcaaaat tgttggaaga gctggagaag cagactctgc tgaatttcca   25020
ggaactccca gcgccagatt catcatgtct gttgtgacca ggaaagctgc ccccatctgc   25080
aggaagccac tatgccagaa agctgctgac tgcagaacta ggctccctct gccacggtcc   25140
gtgccagcca atagatgtcc tgaggcctgc ccctctccca cttcactcag ttcccaaatc   25200 taaatttta caagagattc tgtttggggg aacttaagtc agatccagaa ccttggctgc    25260
aagggagtct gggaaatgtc atttccctag aaggaagtta gggtgggtgg agcaagcccc   25320
acctgcgttt ttctgccaca gcatccaatc gtgaagaact cgggagaggg tggagtccac   25380
atctagggtt gtcctgcccc ttggctctat ccctgcccag aggtgggaac tggaggagtg   25440
ggctgcaaga ctgagcctaa atgtctcccc ggccttgact tttctttcta gtcctggggc   25500
ctagattctg cacttggggt ctctgacaca acacaccatc ccaaagtagc cggaagagct   25560
aaacacaggg ggttcttaaa atggctgccc ccgccacccg ggcctccctt gggcaaaagg   25620
aattgtcagc cctaccccaa cccttcaact accagaatct gggccacccc agcagtattt   25680
ttatttaaaa tgttgcccat tttatgagtt atgatcaatt tgtattaaat taaagttaca   25740
gatgtcagta gccagttcca ttcattttga caaacacaca ggcccaccca gctctgtccc   25800
aggcagtgca cacacatgag catagctaat ccacaaagca gcccggctgg gtaaatggta   25860
ttatgctcat tttacagagg aggaaaattg aggttcagag agaagccaag acttacctgg   25920
ggtcccatat cccatgctgg caagtgccac accacaaacc tgtccaaaaa cttaccagcc   25980
agggaaggct gtcagtcttt acctggagga gaggtggtgg tagtcttggg agcaggcagc   26040
aggcagctca tggggcagtg gcaagagcct ggtctcggga accacacaga cctcagctca   26100
aatccaggct ccatcactgt gtgactttag aaaaatgacc ccctctctg ggactcagtt    26160 ttcccacatg gaagatgagg ataccaattt cacataattt attggtaagc tgtaaagtgc   26220
agtgcactta aggaggccct accctatccc cccagctgcc tccagagtc agtgcctgga    26280 gctgtatggg tttcctgaac ctctgggctg gctctgaccc aagaagtctg tctttctcct   26340
tatgggctgt gacgggtatg gaaccaccta gaccaggacc atcctgaggt ccatcccacc   26400
tctgactgat gaggaagcat cctggctggg agttaggaca ggctctgcat gtggacacac   26460
```

```
aggctgtgca cacttaagtg gaaaagactg tcgactaaag aagaaatatc aagcttttaa   26520
agaattaaag ttcactttac ttagaagtct tactgagtac tatagacagg cctagagccc   26580
agcagcggcc ctttagagag gttctatcag tcgggcccag acagtattt tagcccactg    26640 cttatataca ggtggtggag gtttagtaca cgcaaaatca catcacactt gctcagaagt   26700
aacattaaag ccaccgggcg cagtggctca tgcctgtaat cccaacactt tgggaggcca   26760
aggcaggcgg atcacctgag gttgggagtt caaaaccgcc ctgaccaacg tggagaaacc   26820
ccgtctctac taaaaatac aaaattagcc gggtgtggtg gcacatgcct gtaatcccag    26880
ctgctcggga ggctgaggca ggagaatctc ttgaacccgg gaggcggagg ttgcggtgag   26940
ctggagatcg cgccattgca ctccagcctg ggcaaagagc gaaactccgt ctcaaaaaaa   27000
aaaaaaaaaa aagaagtaa cattaaagcg gaatcatata tcaacgtttg catgtaagag    27060
tgtgtctggg ctatagatta cagaggcata atcatgaatg ccatcagaca ctatcttctg   27120
tacaggaaaa ggcaaggact aggtttattt atcttttaag gaacgtagtg actcaggcaa   27180
gagacatggg gccatgccca ctattctgtc ttgtctccaa agtatccctc cacagagccg   27240
cacatggtca cagagtcaga ggcttgtgaa attatgctgg caaacagaaa tgagggaagt   27300
agcttcttcc atttgctact gtgtctccca ggccactggg tgctctctgc agtgtgcaag   27360
ggagtacagc acccctggga gcccaggact ggtgttggct ttctgttaag tcattttcac   27420
cctaagccat tcttggcctc ctcacccaca gaatgaggga ggttaggctg caggccacag   27480
gtggatcttc atctacagcc tggagctggg gagagggaac caccccagtc attgactcgc   27540
ctgggtttct aggaagagga atgagaacga ggatgggaga ggggctgttg gcaggggtgg   27600
gtggagaggt ctctgattgt ctgatggaga gcagcccagt tcacagggaa gtgactgggg   27660
tgattctgag actagagtat cccaagccct cccccatcct ctcagatccc tgtgactgct   27720
ctaaaaccac gccctctcat tttggctcag tggatctgtc tttgctcagc cttctccctc   27780
tggggtcgga gcaccccctc catggcgcat tccaccttct ccccactcag cctcagcagc   27840
agctccaaga aatgctggcc acttcccagg ctttactcac agtttccacg tgtgtggaag   27900
taactataga ggccaaattt gcattatcaa ctggggactc ctggaaatgg gggtgtctcc   27960
aagagatata tttgatacac gtccagagaa ttcctgaagg aaagaatctg ggggttgtcag  28020 gctgatatca tgaaccccac atttaacaca ttaagtgaag agaggggaca aaggccaggc   28080
ttgggaagga aggagggatc aacaaagccc ttacccagga cagataaaaa tgatagaatg   28140
gcagtaaccc catttggagc ccccatttgt agtcagcaag caaagtactg gtccttttta   28200
caccttatct aaccatcgag acacgcccct gtggttggta tcattatctc agtgtttgag   28260
cagggaaacg tcacttccca gaggacccac agccagtact cggcagagct ggaaatcaaa   28320
cccggtccat ccaaagctaa agccagatgt ctctttactg gacctctctg gaaatgcttc   28380
tcaactttga tgatggctcc agtgacaggc agcagccacc aggactgtga tctccctggg   28440
atttaaagtg ggaggttaaa ccaggctcca cgccactgcg gaattgtgca attgtaagtc   28500
aagtctcaat tgtgagccaa gcttctccca gggtcagagg tggagttaga aaggcccat    28560 gtgaccctga gcaagtctct ctccttccct ggtcctcagt ttccccatct ctattgggga   28620
agggttaggt atctattcta gttgattaat tgccaggc tgagctctga tggtccagga     28680
ttctgtaagt ctaacgttag gtcccacggc ttgccctgct cagcacctaa taaggccatt   28740
agctctggct ccttctctct ggggtggcag cagggacaga aaacaacaga gatacattct   28800
```

| | | | | |
|---|---|---|---|---|
| cttggcagca | cagaactcag | ctcaagggtt | ctggggatgg | ggccttccct cctgccaggg | 28860 |
| aggccatctc | gagaggctga | ctgctcacac | ctgggcagca | ctctgtctcc tcccctcctg | 28920 |
| cctgggtccc | agctctgttc | accacccaa | agcacatcac | acaaggtca gttgcaaagg | 28980 |
| cccggtatca | caggcttaaa | tacagagggc | taggagggag | gtgggaggtg ggagaggaag | 29040 |
| gtggagtact | aacaaaggtg | ttgaattatc | actgcccatc | aggacacggt tatttcccct | 29100 |
| tactctggga | caccaaagat | tctacacaat | cttcctataa | tcctgaacca caaaggggag | 29160 |
| gcacagctca | caaaaaaagt | aggagagggg | agggggaag | tactttttatt ttgaaatgtg | 29220 |
| ttcattttc | tttgttttat | tttctatctt | gatgaaaaga | atatatttt aaacctaaat | 29280 |
| acaaaatagt | acagttttct | atttttttttt | aagttccagg | atacatgtgc aggacgtgca | 29340 |
| ggtttgttac | ataggtaaat | gtgtgctatg | gtggtttgct | gcacctatca acctatcaga | 29400 |
| acagttttct | atctgcttta | aaaatttcaa | cagttctatc | atatttctat tacaaaatgc | 29460 |
| tcccccctcc | cttgaaatta | gatgaagagg | gggaagggtt | gacactgtgg accagagacc | 29520 |
| cagggacttc | ctaccctgat | gtcatgataa | gggctgggga | agggctttca ggaagctggc | 29580 |
| atcagaggca | caaagcttca | ggtcctggtg | agcttcccaa | aactgtgaga ctagatgtga | 29640 |
| tcgaatctga | atgctggaag | ggtctgagtg | atcctccagt | ctaacctgaa gcccagagag | 29700 |
| ggttagtttc | tagctccaca | tcacacagca | tatggtggag | ctgagatgag tactcaagtg | 29760 |
| tcctggttcc | cagtcagcac | ataggggagg | gagattgact | aactgagagg gccccagccc | 29820 |
| aggcaaagaa | aaggaacaca | ggccaggctg | gaagggacag | ggccagagct taggagggag | 29880 |
| gtgctcagag | gagaagggtc | cacatctaag | aaggtctgcg | ggggtacaag agggcctatc | 29940 |
| agagttgggg | gctgcagctc | ctccgagagg | agaaggaggg | ggcaaaaggg tgatcaaatc | 30000 |
| aggaagtcct | ccctgggtg | tgcatgccag | tcagcatcac | gggccccaac atggctgatg | 30060 |
| agagacccct | gatctcagcc | ctgccatta | catagaagaa | aactgagaca cagatgcaaa | 30120 |
| gacagcagcc | tgcagggcac | agtcagggcc | agatccaagt | ctcctgactc ccagccatcg | 30180 |
| gctcttttca | tgcaaacttc | agtctccctc | ttgtggattc | tggtgtctcc tcctacccc | 30240 |
| tgggaacctg | gagcctgagc | agaaggagaa | ggggagagag | gagggttcca acaacccag | 30300 |
| gcaccaggag | ctgggtgcct | tcctctgttg | tcctctccaa | ggagaagaga gagctggcct | 30360 |
| ggacctccag | ggcagagcca | cttcatacct | gcccacacct | ggtcctcctt tgctggcaac | 30420 |
| agagttcaga | gctagcacca | gccacagcaa | ggacaaagcc | cagcccaggc agctgctgga | 30480 |
| gctgcaggga | gtcccaggta | agtgaaagca | ttgggactga | tggccaaggg ggttcctgat | 30540 |
| ttcatggcac | tagagaaann | nnnnnnnnn | nnnnnnnnn | nnnnnnnnn nnnnnnnnn | 30600 |
| nnnnnnnnnn | nnnnnnnnnn | nnnnnnnnnn | nnnnnnnnnn | nnnnnnnnnn nnnnnnnnnn | 30660 |
| nnnnnnnnnn | nnnnn | | | | 30676 |

<210> SEQ ID NO 9
<211> LENGTH: 369
<212> TYPE: DNA
<213> ORGANISM: Human

<400> SEQUENCE: 9

| | | | | |
|---|---|---|---|---|
| gttgcccagg | ctggagtgca | gtggtgcaat | atcagttcag | tgcaacttcc acttcccagg | 60 |
| ttcaagggat | tttttttggga | ggcttcagct | tcccaaatac | ctggaaaaca ggcgcccgcc | 120 |
| accatgcctg | gaaagatggg | tagagatggg | gttcaccgt | gttaaccagg atggtgtgga | 180 |
| cctcctgacc | tcatgatctg | cctacctctg | cctcccaaag | tgttgggatt ccaggcgtga | 240 |

```
                                        -continued
gccaccgcgc  ccagctggtt  ttattatttt  tttattgttt  tatttgaata  agtattactg      300
tggcccaagt  acatccaaga  atgtaatagc  ttaatgcttt  cactactatt  gtgagtgaaa      360
acttttccc                                                                   369
```